United States Patent
Hironaka et al.

(10) Patent No.: US 11,635,405 B2
(45) Date of Patent: Apr. 25, 2023

(54) METHOD FOR MEASURING COMPONENTS OF BIOLOGICAL SAMPLE

(71) Applicant: PHC Holdings Corporation, Tokyo (JP)

(72) Inventors: Shouko Hironaka, Ehime (JP); Eriko Yoshioka, Ehime (JP); Daiki Mizuoka, Ehime (JP); Suguru Sasaki, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 107 days.

(21) Appl. No.: 17/220,522

(22) Filed: Apr. 1, 2021

(65) Prior Publication Data

US 2021/0247346 A1 Aug. 12, 2021

Related U.S. Application Data

(63) Continuation of application No. 16/345,981, filed as application No. PCT/JP2017/042113 on Nov. 22, 2017, now Pat. No. 10,996,186.

(30) Foreign Application Priority Data

Nov. 25, 2016 (JP) .................................. 2016-229287

(51) Int. Cl.
*G01N 27/327* (2006.01)
*C12Q 1/00* (2006.01)
(Continued)

(52) U.S. Cl.
CPC ......... *G01N 27/3274* (2013.01); *C12Q 1/006* (2013.01); *G01N 27/307* (2013.01); *G01N 27/4166* (2013.01)

(58) Field of Classification Search
CPC ......................................... G01N 27/327–3274
See application file for complete search history.

(56) References Cited

U.S. PATENT DOCUMENTS

| 5,385,846 A | 1/1995 | Kuhn et al. |
|---|---|---|
| 6,287,451 B1 | 9/2001 | Winarta et al. |

(Continued)

FOREIGN PATENT DOCUMENTS

| CN | 1839313 | 9/2006 |
|---|---|---|
| CN | 103348239 | 10/2013 |

(Continued)

OTHER PUBLICATIONS

Office Action issued in corresponding Japanese Patent Application No. 2019-173152, dated Nov. 25, 2021, 3 pages.
(Continued)

*Primary Examiner* — Alexander S Noguerola
(74) *Attorney, Agent, or Firm* — Hamre, Schumann, Mueller & Larson, P.C.

(57) ABSTRACT

Provided is a method for measuring a component of a biological sample with a biosensor provided with: a capillary for introducing the biological sample; an electrode part including a first electrode system that includes a first working electrode and a first counter electrode in the capillary; and a reagent part disposed so as to be in contact with the electrode part, the reagent part containing an enzyme and a mediator, and the method including a step of starting voltage application for a duration longer than 0 second and up to 0.7 second to the first electrode system within 0 second to 0.5 second after detection of the introduction of the biological sample to obtain a hematocrit value based on a current value obtained thereby.

9 Claims, 150 Drawing Sheets

(51) Int. Cl.
*G01N 27/30* (2006.01)
*G01N 27/416* (2006.01)

(56) References Cited

U.S. PATENT DOCUMENTS

| | | | |
|---|---|---|---|
| 9,625,442 | B2 | 4/2017 | Shinno et al. |
| 2005/0023152 | A1 | 2/2005 | Surridge et al. |
| 2007/0131565 | A1 | 6/2007 | Fujiwara et al. |
| 2009/0177406 | A1 | 7/2009 | Wu |
| 2009/0184004 | A1 | 7/2009 | Chatelier et al. |
| 2010/0170807 | A1 | 7/2010 | Diebold et al. |
| 2011/0155584 | A1 | 6/2011 | Chatelier et al. |
| 2011/0272294 | A1 | 11/2011 | Fujiwara |
| 2013/0306474 | A1 | 11/2013 | Yoshioka et al. |
| 2013/0334064 | A1 | 12/2013 | Nien et al. |
| 2014/0090988 | A1 | 4/2014 | Malecha |
| 2014/0326601 | A1 | 11/2014 | Sato |
| 2015/0059448 | A1 | 3/2015 | Shinno et al. |
| 2015/0087940 | A1 | 3/2015 | Tatemoto et al. |
| 2015/0153298 | A1 | 6/2015 | Chen et al. |
| 2015/0323489 | A1 | 11/2015 | Fujiwara et al. |
| 2016/0025674 | A1 | 1/2016 | Fujiwara et al. |
| 2016/0273017 | A1 | 9/2016 | Fujiwara et al. |

FOREIGN PATENT DOCUMENTS

| | | |
|---|---|---|
| CN | 103487475 | 1/2014 |
| CN | 105158309 | 12/2015 |
| EP | 2 919 000 | 9/2015 |
| JP | 3369183 B | 1/2003 |
| JP | 4060078 B | 3/2008 |
| JP | 2011-506966 | 3/2011 |
| JP | 5066108 B | 11/2012 |
| JP | 2014-232101 | 12/2014 |
| JP | 5788857 B | 10/2015 |
| JP | 5801479 B | 10/2015 |
| WO | 2004/113910 | 12/2004 |
| WO | 2005/054840 | 6/2005 |
| WO | 2010/087191 | 8/2010 |
| WO | 2013/157263 | 10/2013 |
| WO | 2013/168390 | 11/2013 |
| WO | 2014/091682 | 6/2014 |
| WO | 2014/174815 | 10/2014 |
| WO | 2015/079635 | 6/2015 |

OTHER PUBLICATIONS

International Search Report issued in International Application No. PCT/JP2017/042113, dated Feb. 27, 2018, 8 pages.
Office Action issued corresponding Japanese Patent Application No. 2018-552954, dated Jun. 13, 2019, 6 pages with translation.
Extended European Search report issued in corresponding European Patent Application No. 17873348.1, dated Oct. 21, 2019, 7 pages.
Office Action issued in corresponding Chinese Patent Application No. 201780067463.1, dated Dec. 30, 2020, 12 pages w/translation.

(a)

(b)

(a)

(b)

(a)

(b)

METHOD FOR MEASURING COMPONENTS OF BIOLOGICAL SAMPLE

TECHNICAL FIELD

The present invention relates to a method for measuring a component of a biological sample.

BACKGROUND ART

Sensors for measuring a component of a biological sample have been conventionally used in, for example, clinical examinations and self-measurement of blood glucose levels of diabetic patients. Such sensors have a configuration in which, for example, a cover is disposed on an insulating substrate, which has a working electrode and a counter electrode formed on its surface, with a spacer being interposed therebetween. A reagent containing, for example, an oxidoreductase and a mediator (an electron mediator) is placed on the working electrode and the counter electrode, and this part serves as an analysis section. One end of a channel for introducing blood communicates with the analysis section, and the other end of the channel is open toward the outside, which serves as a biological sample supply port. Analysis of components (for example, blood glucose, ketone, HbA1c, etc.) of a biological sample (for example, blood) using such a sensor is performed as follows, for example. That is, firstly, the sensor is set in a dedicated measuring apparatus (a meter). Then, for example, a fingertip is pricked with a lancet to cause bleeding, and the biological sample supply port of the sensor is brought into contact therewith. The blood is drawn into the channel of the sensor by a capillary phenomenon to be introduced into the analysis section through the channel and then comes into contact with the reagent there. Then, the components of the blood react with the oxidoreductase to cause an oxidation-reduction reaction, and thereby a current flows through the mediator. This current is detected and based on the current value, the amounts of the blood components are calculated in the measuring apparatus to be displayed.

Although blood components can be measured using a sensor in such a manner as described above, the measured values may be affected by hematocrit (Hct). Therefore, in order to obtain correct measured values, it is necessary to measure the Hct value to correct the values of the amounts of the blood components based on the Hct value. For example, there is a known method in which a reagent layer containing an oxidoreductase and a mediator is disposed above a working electrode and a counter electrode, blood is supplied onto the reagent layer, thereby blood containing the reagent is obtained, and with the blood being supplied to the working electrode and the counter electrode, a voltage is applied to measure the Hct value (see Patent Document 1). Furthermore, there is a known method in which in a biosensor that includes two working electrodes W1 and W2 and a reference electrode R, with a mediator being disposed on the working electrode W1 and the reference electrode R and with the mediator and an oxidoreductase being disposed on the working electrode W2, a voltage is applied to these electrodes to measure the Hct value (see Patent Document 2). Furthermore, there is a known method in which using a sensor, which is an electrode system including a working electrode and a counter electrode, having a reagent layer containing an oxidoreductase and a mediator disposed only on the working electrode, a current value is measured while the polarities of the electrodes are switched (see Patent Document 3). In this method, the Hct value is obtained based on a plurality of current values.

There is also a known Hct measuring method characterized by a method of applying a voltage to electrodes. For example, there is a method in which in a sensor having a reagent layer containing an oxidoreductase and a mediator disposed on a working electrode and a counter electrode, immediately after blood is supplied to the working electrode and the counter electrode, a voltage is applied at 0.35 V for 2.5 seconds to measure the Hct value (see Patent Document 4). There is also a known method in which a whole blood sample is supplied to a sample analysis device having capillary pores, the initial current in the sample within at least part of the capillary pores is measured, and the Hct value of the sample is determined from the initial current (see Patent Document 5). Furthermore, there is also a known method in which in a sensor having a reagent layer containing an oxidoreductase and a mediator disposed only on the counter electrode for measuring the Hct value, a high voltage is applied to both electrodes multiple times to obtain the Hct value based on the current values obtained thereby (see Patent Document 6). However, for example, in the method described in Patent Document 3, it takes time to obtain the Hct value. Therefore, a method of obtaining the Hct value in a short time has been desired.

PRIOR ART DOCUMENTS

Patent Documents

[Patent Document 1] JP3369183B
[Patent Document 2] JP4060078B
[Patent Document 3] JP5066108B
[Patent Document 4] JP5801479B
[Patent Document 5] JP5788857B
[Patent Document 6] WO2014/174815

SUMMARY OF THE INVENTION

Problems to be Solved by the Invention

Therefore, the present invention is intended to provide a method of measuring the Hct value of a biological sample in a short time.

Means for Solving the Problem

The present invention is:
a method for measuring a component of a biological sample with a biosensor provided with:
a capillary for introducing the biological sample;
an electrode part including a first electrode system that includes a first working electrode and a first counter electrode in the capillary; and
a reagent part disposed so as to be in contact with the electrode part,
the reagent part containing an enzyme and a mediator, and
the method including a step of starting voltage application for a duration longer than 0 second and up to 0.7 second to the first electrode system within 0 second to 0.5 second after detection of introduction of the biological sample to obtain a Hct value based on a current value obtained thereby (this method may be referred to as a "first method for measuring a component of a biological sample" in the description).

Furthermore, the present invention is the first method for measuring a component of a biological sample, wherein the component is glucose (Glu), and the method further includes:

a step of applying a voltage to the first electrode system after the step to obtain a Hct value, to obtain a current value that depends on Glu, and a step of using the current value that depends on Glu and the Hct value to obtain a Glu value (this method may be referred to as a "second method for measuring a component of a biological sample" in the description).

Moreover, the present invention is the first method for measuring a component of a biological sample, wherein the component is Glu, the electrode part is further provided with a second electrode system that includes a second working electrode and a second counter electrode, and the method further includes:

a step of applying a voltage to the second electrode system after the step to obtain a Hct value, to obtain a current value that depends on Glu; and a step of using the current value that depends on Glu and the Hct value to obtain a Glu value (this method may be referred to as a "third method for measuring a component of a biological sample" in the description).

Furthermore, the present invention is:

a method for measuring a component of a biological sample with a biosensor provided with:

a capillary for introducing the biological sample;

an electrode part including a first electrode system that includes a first working electrode and a first counter electrode in the capillary; and a reagent part disposed so as to be in contact with the electrode part, the component being Glu, the reagent part containing an enzyme and a mediator, and the method including:

a step of starting voltage application for a duration longer than 0 second and up to 0.7 second to the first electrode system within 0 second to 0.5 second after detection of introduction of the biological sample to obtain a current value that depends on Hct;

a step of applying a voltage to the first electrode system after the step to obtain a current value that depends on Hct, to obtain a current value that depends on Glu; and a step of using the current value that depends on Glu and the current value that depends on Hct to obtain a Glu value (this method may be referred to as a "fourth method for measuring a component of a biological sample" in the description).

Moreover, the present invention is a method for measuring a component of a biological sample with a biosensor provided with:

a capillary for introducing the biological sample;

an electrode part including, in the capillary, a first electrode system that includes a first working electrode and a first counter electrode as well as a second electrode system that includes a second working electrode and a second counter electrode; and a reagent part disposed so as to be in contact with the electrode part, the component being Glu, the reagent part containing an enzyme and a mediator, and the method including:

a step of starting voltage application for a duration longer than 0 second and up to 0.7 second to the first electrode system within 0 second to 0.5 second after detection of introduction of the biological sample to obtain a current value that depends on Hct;

a step of applying a voltage to the second electrode system after the step to obtain a current value that depends on Hct, to obtain a current value that depends on Glu; and a step of using the current value that depends on Glu and the current value that depends on Hct to obtain a Glu value (this method may be referred to as a "fifth method for measuring a component of a biological sample" in the description).

Furthermore, the present invention is a biosensor including:

a capillary for introducing a biological sample;

a reagent part containing an enzyme and a mediator in the capillary;

a first Hct measurement system for measuring a Hct value that is disposed so as to be in contact with the reagent part in the capillary and includes a third working electrode and a third counter electrode; and a second Hct measurement system for measuring a Hct value that includes a fifth working electrode arranged at a place where the reagent part is not disposed and a fifth counter electrode disposed so as to be in contact with the reagent part (this biosensor may be referred to as a "first biosensor A" in the description).

Moreover, the present invention is the first biosensor, further being provided with; an electrode system for obtaining a current value that depends on Glu, the electrode system including a fourth working electrode and a fourth counter electrode disposed in the capillary so as to be in contact with the reagent part (this biosensor may be referred to as a "first biosensor B" in the description).

When simply referred to as a "first biosensor", it includes the first biosensor A and the first biosensor B.

Furthermore, the present invention is the first A biosensor, further being provided with:

an electrode system for obtaining a current value that depends on Glu, the electrode system including the sixth working electrode and the sixth counter electrode; and an electrode system for obtaining a current value that depends on Glu, the electrode system including the fourth working electrode and the fourth counter electrode (this biosensor may be referred to as a "second biosensor" in the description).

Moreover, the present invention is the second biosensor, further being provided with: an additional electrode system for obtaining a current value that depends on Glu, the additional electrode system including a fourth working electrode and a fourth counter electrode disposed in the capillary so as to be in contact with the reagent part (this biosensor may be referred to as a "third biosensor A" in the description).

Furthermore, the present invention is the third biosensor A, further being provided with an electrode system for obtaining a current value that depends on Int (an interfering substance), the electrode system including, in the capillary, a seventh working electrode disposed so as not to be in contact with the reagent part and a seventh counter electrode that is in contact with the reagent part (this biosensor may be referred to as a "third biosensor B").

When simply referred to as a "third biosensor", it includes the third biosensor A and the third biosensor B.

Moreover, the present invention is a method for measuring a component of a biological sample, including a step of using a first biosensor to obtain a Hct value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value; and a step of obtaining the Hct value of the biological sample based on the first current value and the second current value (this method may be referred to as a "sixth method for measuring a component of a biological sample" in the description).

Furthermore, the present invention is the sixth method for measuring a component of a biological sample, further including:

a step of applying a voltage to the first Hct measurement system after the step to obtain a first current value, to obtain a current value that depends on Glu; and a step of obtaining a Glu value of the biological sample based on the current value that depends on Glu and the Hct value of the biological sample (this method may be referred to as a "seventh method for measuring a component of a biological sample" in the description).

Moreover, the present invention is a method for measuring a component of a biological sample, including a step of using a second biosensor to obtain a Hct value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value; and a step of obtaining the Hct value of the biological sample based on the first current value and the second current value (this method may be referred to as an "eighth method for measuring a component of a biological sample" in the description).

Furthermore, the present invention is the eighth method for measuring a component of a biological sample, further including:

a step of applying a voltage to the electrode system for obtaining a current value that depends on Glu after the step to obtain a first current value, to obtain a current value that depends on Glu; and a step of obtaining a Glu value of the biological sample based on the current value that depends on Glu and the Hct value of the biological sample (this method may be referred to as a "ninth method for measuring a component of a biological sample" in the description).

Moreover, the present invention is a method for measuring a component of a biological sample, including a step of using a first biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of applying a voltage to the first Hct measurement system after the step to obtain a first current value, to obtain a current value that depends on Glu; and a step of using the current value that depends on Glu, the first current value, and the second current value to obtain a Glu value of the biological sample (this method may be referred to as a "tenth method for measuring a component of a biological sample" in the description).

Furthermore, the present invention is a method for measuring a component of a biological sample, including a step of using a second biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of applying a voltage to the electrode system for obtaining a current value that depends on Glu after the step to obtain a first current value, to obtain a current value that depends on Glu; and a step of using the current value that depends on Glu, the first current value, and the second current value to obtain a Glu value of the biological sample (this method may be referred to as an "eleventh method for measuring a component of a biological sample" in the description).

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a current value that depends on Glu; and a step of obtaining the Glu value of the biological sample based on the current value that depends on Glu and the Hct value of the biological sample (this method may be referred to as a "twelfth method for measuring a component of a biological sample" in the description).

Furthermore, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the electrode system for obtaining a current value that depends on Glu after the step to obtain a first current value, to obtain a current value that depends on Glu; and a step of obtaining the Glu value of the biological sample based on the current value that depends on Glu and the Hct value of the biological sample (this method may be referred to as a "thirteenth method for measuring a component of a biological sample" in the description).

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a current value that depends on Glu;

a step of applying a voltage to an electrode system for obtaining a current value that depends on Int after the step to obtain a current value that depends on Glu, to obtain a current value that depends on an Int value of the biological sample; and a step of obtaining the Glu value of the biological sample based on the current value that depends on Glu, the Hct value of the biological sample, and the current value that depends on an Int value of the biological sample (this method may be referred to as a "fourteenth method for measuring a component of a biological sample" in the description).

Furthermore, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the electrode system for obtaining a current value that depends on Glu after the step to obtain s first current value, to obtain a current value that depends on Glu;

a step of applying a voltage to an electrode system for obtaining a current value that depends on Int after the step to obtain a current value that depends on Glu, to obtain a current value that depends on an Int value of the biological sample; and a step of obtaining the Glu value of the biological sample based on the current value that depends on Glu, the Hct value of the biological sample, and the current value that depends on an Int value of the biological sample (this method may be referred to as a "fifteenth method for measuring a component of a biological sample" in the description).

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a first current value that depends on Glu;

a step of applying a voltage to the electrode system for obtaining a second current value that depends on Glu after the step to obtain a first current value that depends on Glu, to obtain a second current value that depends on Glu;

a step of applying a voltage to an electrode system for obtaining a current value that depends on Int after the step to obtain a second current value that depends on Glu, to obtain a current value that depends on an Int value of the biological sample; and a step of obtaining the Glu value of the biological sample based on the first current value that depends on Glu, the second current value that depends on Glu, the Hct value of the biological sample, and the current value that depends on an Int value of the biological sample (this method may be referred to as a "sixteenth method for measuring a component of a biological sample" in the description).

Furthermore, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the electrode system for obtaining a first current value that depends on Glu after the step to obtain a first current value, to obtain a first current value that depends on Glu;

a step of applying a voltage to the electrode system for obtaining a second current value that depends on Glu after the step to obtain a first current value that depends on Glu, to obtain a second current value that depends on Glu;

a step of applying a voltage to an electrode system for obtaining a current value that depends on Int after the step to obtain a second current value that depends on Glu, to obtain a current value that depends on an Int value of the biological sample; and a step of obtaining the Glu value of the biological sample based on the first current value that depends on Glu, the second current value that depends on Glu, the Hct value of the biological sample, and the current value that depends on an Int value of the biological sample (this method may be referred to as a "seventeenth method for measuring a component of a biological sample" in the description).

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a first current value that depends on Glu;

a step of applying a voltage to the electrode system for obtaining a current value that depends on Glu after the step to obtain a first current value, to obtain a second current value that depends on Glu; and a step of obtaining the Glu value of the biological sample based on the first current value that depends on Glu, the second current value that depends on Glu, and the Hct value of the biological sample (this method may be referred to as an "eighteenth method for measuring a component of a biological sample" in the description).

Effects of Invention

As described above, the method for measuring a component of a biological sample of the present invention is characterized in that the biological sample is measured with a biosensor in which a reagent layer containing an enzyme and a mediator is in contact with an electrode system including a working electrode and a counter electrode, and voltage application to the electrode system for a duration longer than 0 second and up to 0.7 second is started within 0 second to 0.5 second after detection of introduction of the biological sample to obtain a Hct value based on the current value obtained thereby (the first method for measuring a component of a biological sample). That is, in the biosensor in which the reagent layer is in contact with both the working electrode and the counter electrode, a voltage is applied for a very short time after detection of the biological sample, and the Hct value is obtained based on the current value obtained thereby. According to such a method, the Hct value can be measured in a short time.

Furthermore, such a method for measuring a component of a biological sample is characterized in that a voltage is applied to the electrode system to obtain a current value that depends on Glu and then the current value and the resultant Hct value are used to obtain a Glu value (the second method for measuring a component of a biological sample). That is, since the current value that depends on Glu in the vicinity of the electrodes that are in contact with the reagent layer and the Hct value in the vicinity of the same electrodes are used to obtain a Glu value, the Glu value can be measured, with the properties of the biological sample in the vicinity of the electrodes being reflected with higher accuracy. Moreover, according to such a method, the Hct value can be measured in a short time in the first electrode system, and the Glu value corrected using the Hct value can be obtained with high accuracy.

Moreover, such a method for measuring a component of a biological sample is characterized in that a voltage is applied to an electrode system different from the above-mentioned electrode system to obtain a current value that depends on Glu and then the current value and the resultant Hct value are used to obtain a Glu value (the third method for measuring a component of a biological sample). According to such a method, the Hct value can be measured in a short time in the first electrode system, and the Glu value corrected using the Hct value can be obtained with high accuracy.

Furthermore, a method for measuring a component of a biological sample of the present invention is characterized in that the biological sample is measured with a biosensor in which a reagent layer containing an enzyme and a mediator is in contact with an electrode system including a working electrode and a counter electrode, and voltage application to the electrode system for a duration longer than 0 second and up to 0.7 second is started within 0 second to 0.5 second after detection of introduction of the biological sample to obtain a current value that depends on Hct, a voltage is applied to the electrode system to obtain a current value that depends on Glu, and the current value that depends on Hct and the current value that depends on Glu are used to obtain a Glu value (the fourth method for measuring a component of a biological sample). That is, since the current value that depends on Glu in the vicinity of the electrodes that are in contact with the reagent layer and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the current value that depends on Hct can be measured in a short time in the first electrode system, and the Glu value corrected using the current value that depends on Hct can be obtained with high accuracy.

Moreover, a method for measuring a component of a biological sample of the present invention is characterized in that the biological sample is measured with a biosensor in which a reagent layer containing an enzyme and a mediator is in contact with an electrode system including a working electrode and a counter electrode, and voltage application to the electrode system for a duration longer than 0 second and up to 0.7 second is started within 0 second to 0.5 second after detection of introduction of the biological sample to obtain a current value that depends on Hct, a voltage is applied to an electrode system different from the above-mentioned electrode system to obtain a current value that depends on Glu, and the current value that depends on Hct and the current value that depends on Glu are used to obtain a Glu value (the fifth method for measuring a component of a biological sample). Furthermore, according to such a method, the current value that depends on Hct can be measured in a short time in the first electrode system, and the Glu value corrected using the current value that depends on Hct can be obtained with high accuracy.

Furthermore, a biosensor of the present invention has a first Hct measurement system that is in contact with a reagent part and a second Hct measurement system in a place where the reagent part is not disposed (the first biosensor). According to such a biosensor, measurement can be carried out in systems having different environments (the measurement place and the presence or absence of a reagent)

for measurement of a biological sample (for example, blood) applied as a spot in a capillary. With the biosensor of the present invention, particularly a hematocrit value and a current value that depends thereon can be measured in a plurality of systems in the capillary and thereby the measurement accuracy in determining the Glu value can be further improved.

Moreover, a method for measuring a component of a biological sample of the present invention is characterized in that the biological sample is measured with the first biosensor, and voltage application to the first Hct measurement system for a duration longer than 0 second and up to 0.7 second is started within 0 second to 0.5 second after detection of introduction of the biological sample to obtain a first current value, then a voltage is applied to the second Hct measurement system to obtain a second current value, and the first current value and the second current value are used to obtain a Hct value (the sixth method for measuring a component of a biological sample). According to such a method, in the first Hct measurement system with a reagent disposed thereon, particularly, the first current value (a Hct value or a current value that depends on a Hct value) can be measured in a short time, and the first current value and the second current value (a Hct value or a current value that depends on a Hct value) measured in the second Hct measurement system are used and thereby a measurement accuracy in determining a corrected Glu value can be improved. Furthermore, the method is characterized by further including a step of applying a voltage to the first Hct measurement system after the step to obtain a first current value, to obtain a current value that depends on Glu and a step of obtaining a Glu value of the biological sample based on the current value that depends on Glu and the Hct value of the biological sample (the seventh method for measuring a component of a biological sample). According to such a method, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Moreover, according to such a method, the Hct value can be measured in a short time in the first Hct measurement system, and the Glu value corrected using the Hct value can be obtained with high accuracy.

Furthermore, a method for measuring a component of a biological sample of the present invention is characterized in that the biological sample is measured with the first biosensor, and voltage application to the first Hct measurement system for a duration longer than 0 second and up to 0.7 second is started within 0 second to 0.5 second after detection of introduction of the biological sample to obtain a first current value then a voltage is applied to the second Hct measurement system to obtain a second current value, and after the step to obtain a first current value, the method further includes a step of applying a voltage to the first Hct measurement system to obtain a current value that depends on Glu and a step of obtaining a Glu value of the biological sample based on the current value that depends on Glu, the first current value, and the second current value (the tenth method for measuring a component of a biological sample). According to such a method, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Moreover, according to such a method, the current value that depends on Hct can be measured in a short time in the first Hct measurement system, and the Glu value corrected using the current value that depends on Hct can be obtained with high accuracy.

Moreover, the biosensor of the present invention further includes an electrode system for obtaining a current value that depends on Glu, the electrode system being in contact with the reagent part, for obtaining a current value that depends on Glu (the second biosensor). According to such a biosensor, since it includes the fifth working electrode and the fifth counter electrode disposed so as to be in contact with the reagent part, it is possible to measure more current values that depend on Glu and therefore a corrected Glu value can be obtained with higher accuracy.

Furthermore, a method for measuring a component of a biological sample of the present invention is characterized in that the biological sample is measured with the second biosensor, and voltage application to the first Hct measurement system for a duration longer than 0 second and up to 0.7 second is started within 0 second to 0.5 second after detection of introduction of the biological sample to obtain a first current value, then a voltage is applied to the second Hct measurement system to obtain a second current value, and the first current value and the second current value are used to obtain a Hct value (the eighth method for measuring a component of a biological sample). According to such a method, the first current value (a Hct value) can be measured in a short time in the first Hct measurement system and the Glu value corrected using the Hct value can be obtained with high accuracy.

Moreover, a method for measuring a component of a biological sample is characterized by further including, in the eighth method for measuring a component of a biological sample, a step of applying a voltage to the electrode system for obtaining a current value that depends on Glu after the step to obtain a first current value, to obtain a current value that depends on Glu, and a step of obtaining a Glu value of the biological sample based on the current value that depends on Glu and the Hct value of the biological sample (the ninth method for measuring a component of a biological sample). According to such a method, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy.

Furthermore, a method for measuring a component of a biological sample of the present invention is characterized in that the biological sample is measured with the second biosensor, and voltage application to the first Hct measurement system for a duration longer than 0 second and up to 0.7 second is started within 0 second to 0.5 second after detection of introduction of the biological sample to obtain a first current value, then a voltage is applied to the second Hct measurement system to obtain a second current value, and after the step to obtain a first current value, the method further includes a step of applying a voltage to the electrode system for obtaining a current value that depends on Glu to obtain a current value that depends on Glu and a step of obtaining a Glu value of the biological sample based on the current value that depends on Glu, the first current value, and the second current value (the eleventh method for measuring a component of a biological sample). According to such a method, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the first current value can be measured in a short time in the first Hct measurement system, and the Glu value corrected using the first current value can be obtained with high accuracy.

In the description, when simply referring to a "method for measuring a component of a biological sample," it refers to all of the "first method for measuring a component of a biological sample," "second method for measuring a component of a biological sample," "third method for measuring a component of a biological sample," "fourth method for measuring a component of a biological sample," "fifth method for measuring a component of a biological sample," "sixth method for measuring a component of a biological sample," "seventh method for measuring a component of a biological sample," "eighth method for measuring a component of a biological sample," "ninth method for measuring a component of a biological sample," "tenth method for measuring a component of a biological sample," "eleventh method for measuring a component of a biological sample," "twelfth method for measuring a component of a biological sample," "thirteenth method for measuring a component of a biological sample," "fourteenth method for measuring a component of a biological sample," "fifteenth method for measuring a component of a biological sample," "sixteenth method for measuring a component of a biological sample," "seventeenth method for measuring a component of a biological sample," and "eighteenth method for measuring a component of a biological sample." Furthermore, in the description, when simply referring to a "biosensor," it refers to all of the "first biosensor," "second biosensor," and "third biosensor."

BRIEF DESCRIPTION OF DRAWINGS

FIG. 52b is a graph showing the sensitivity difference (%) in each case of Hct values of 0%, 42%, and 70% with reference to Glu 45 mg/dl in Example 30.

FIG. 53a is a graph showing the sensitivity difference (%) in each case of Glu values of 45 mg/dl and 550 mg/dl with reference to Hct 42% in Example 31.

FIG. 53b is a graph showing the sensitivity difference (%) in each case of Hct values of 0%, 42%, and 70% with reference to Glu 45 mg/dl in Example 31.

FIG. 54a is a graph showing the sensitivity difference (%) in each case of Glu values of 45 mg/dl and 550 mg/dl with reference to Hct 42% in Example 32.

FIG. 54b is a graph showing the sensitivity difference (%) in each case of Hct values of 0%, 42%, and 70% with reference to Glu 45 mg/dl in Example 32.

FIG. 55a is a graph showing the sensitivity difference (%) in each case of Glu values of 45 mg/dl and 550 mg/dl with reference to Hct 42% in Comparative Example 4.

FIG. 55b is a graph showing the sensitivity difference (%) in each case of Hct values of 0%, 42%, and 70% with reference to Glu 45 mg/dl in Comparative Example 4.

FIG. 56a is a graph showing the sensitivity difference (%) in each case of Glu values of 45 mg/dl and 550 mg/dl with reference to Hct 42% in Comparative Example 5.

FIG. 56b is a graph showing the sensitivity difference (%) in each case of Hct values of 0%, 42%, and 70% with reference to Glu 45 mg/dl in Comparative Example 5.

FIG. 57a is a graph showing the sensitivity difference (%) in each case of Glu values of 45 mg/dl and 550 mg/dl with reference to Hct 42% in Comparative Example 6.

FIG. 57b is a graph showing the sensitivity difference (%) in each case of Hct values of 0%, 42%, and 70% with reference to Glu 45 mg/dl in Comparative Example 6.

FIG. 58a is a graph showing the change with time in the response current value relative to an applied voltage with respect to each blood sample with a Glu concentration of 45 mg/dl (Hct value: 0%, 42%, and 70%) in Example 33.

Figure 58A:
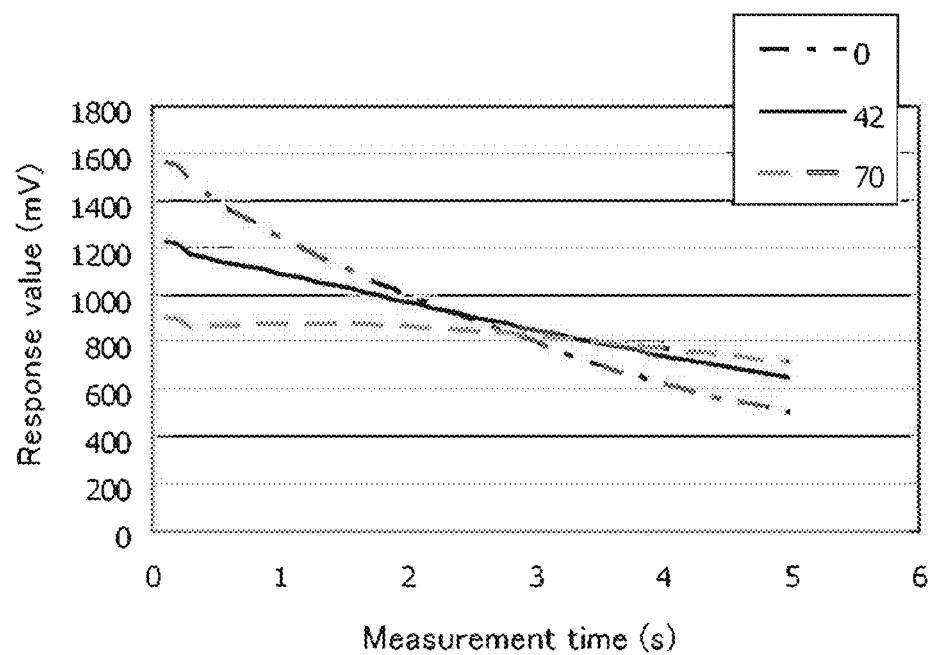
Figure 58B:
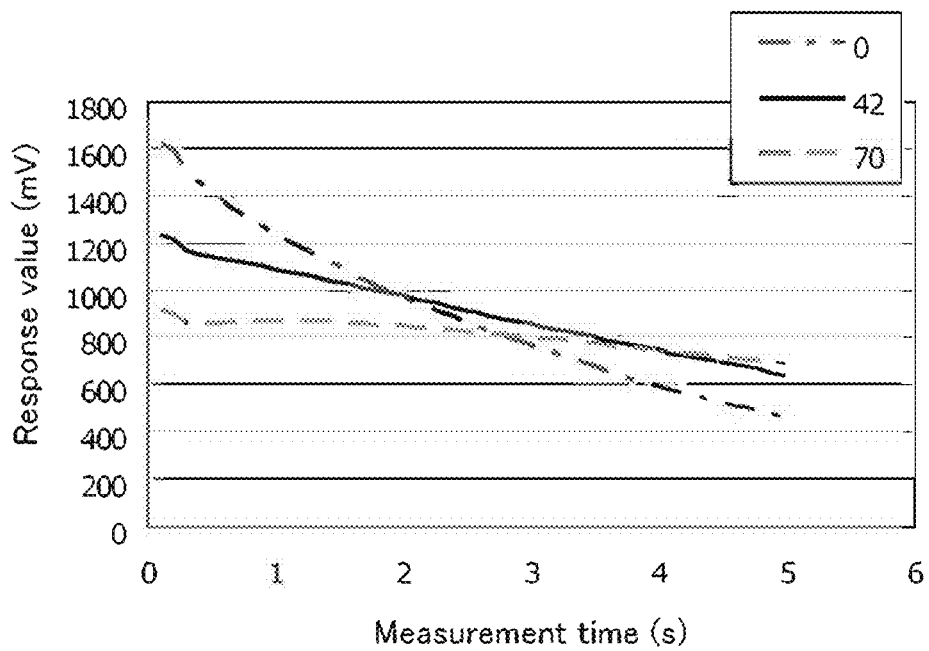

FIG. 58b is a graph showing the change with time in the response current value relative to an applied voltage with respect to each blood sample with a Glu concentration of 550 mg/dl (Hct value: 0%, 42%, and 70%) in Example 33.

Figure 58C:
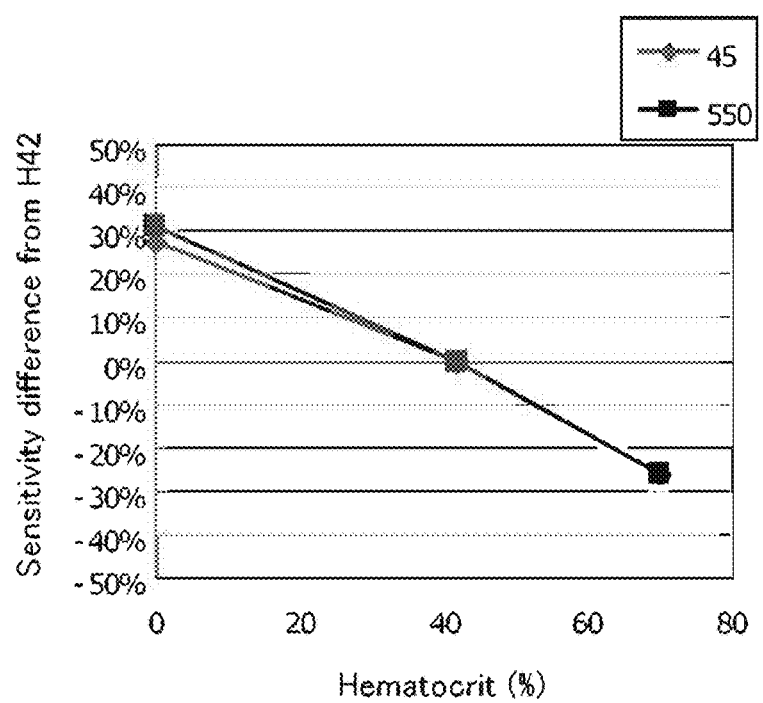

FIG. 58c is a graph showing the sensitivity difference (%) in each case of Glu values of 45 mg/dl and 550 mg/dl with reference to Hct 42% in Example 33.

Figure 58D:
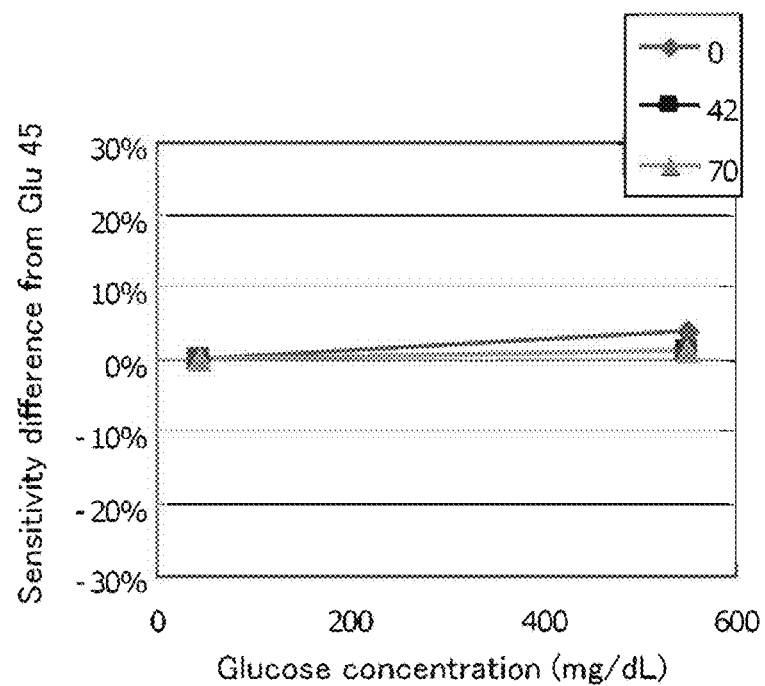

FIG. 58d is a graph showing the sensitivity difference (%) in each case of Hct values of 0%, 42%, and 70% with reference to Glu 45 mg/dl in Example 33.

Figure 59A:
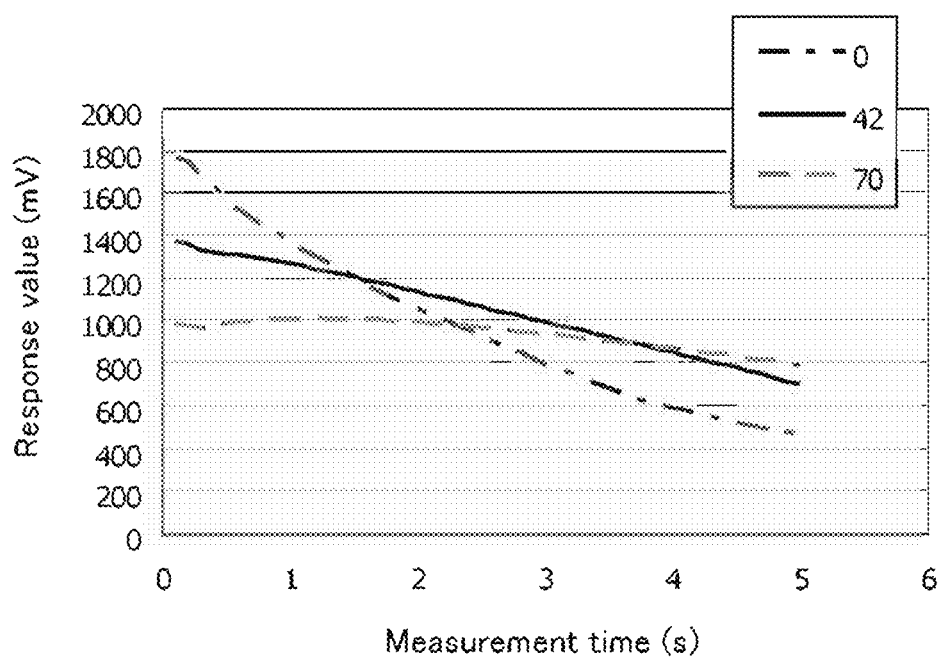

FIG. 59a is a graph showing the change with time in the response current value relative to an applied voltage with respect to each blood sample with a Glu concentration of 45 mg/dl (Hct value: 0%, 42%, and 70%) in Example 34.

Figure 59B:
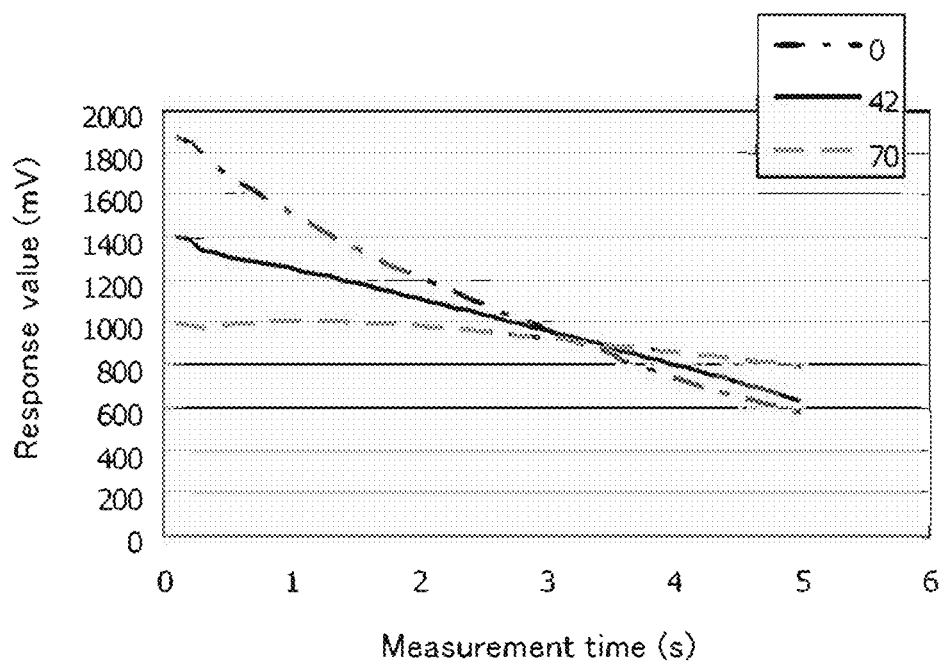

FIG. 59b is a graph showing the change with time in the response current value relative to an applied voltage with respect to each blood sample with a Glu concentration of 550 mg/dl (Hct value: 0%, 42%, and 70%) in Example 34.

Figure 59C:
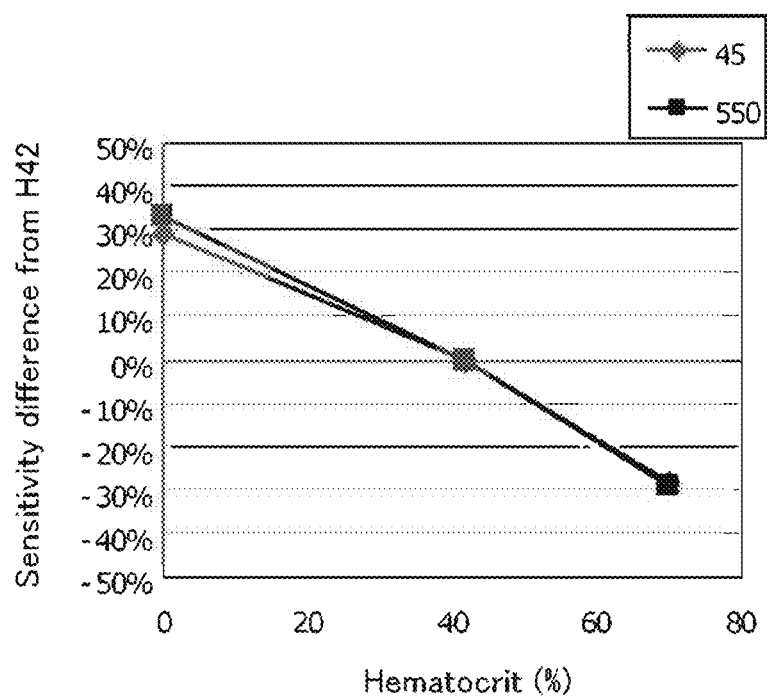

FIG. 59c is a graph showing the sensitivity difference (%) in each case of Glu values of 45 mg/dl and 550 mg/dl with reference to Hct 42% in Example 34.

Figure 59D:
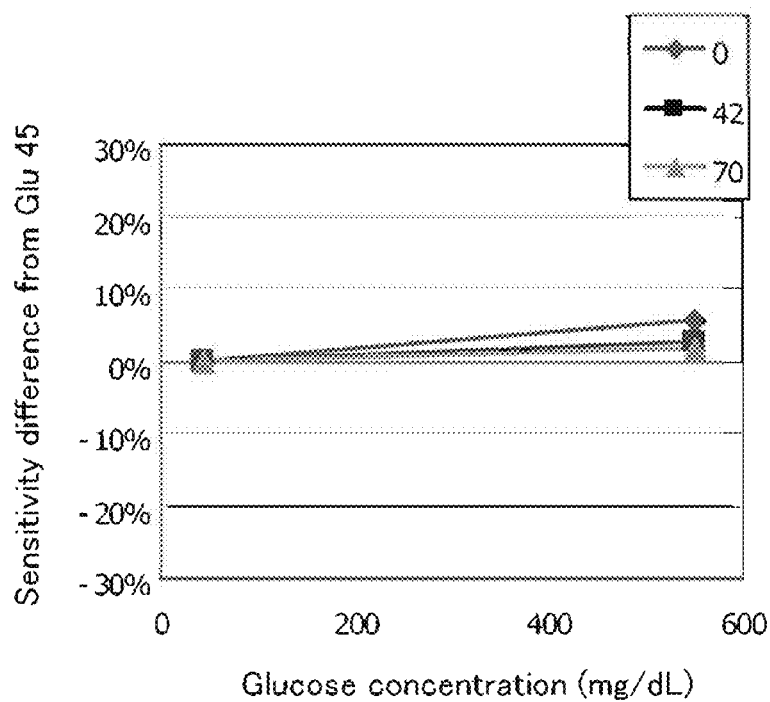

FIG. 59d is a graph showing the sensitivity difference (%) in each case of Hct values of 0%, 42%, and 70% with reference to Glu 45 mg/dl in Example 34.

Figure 60A:
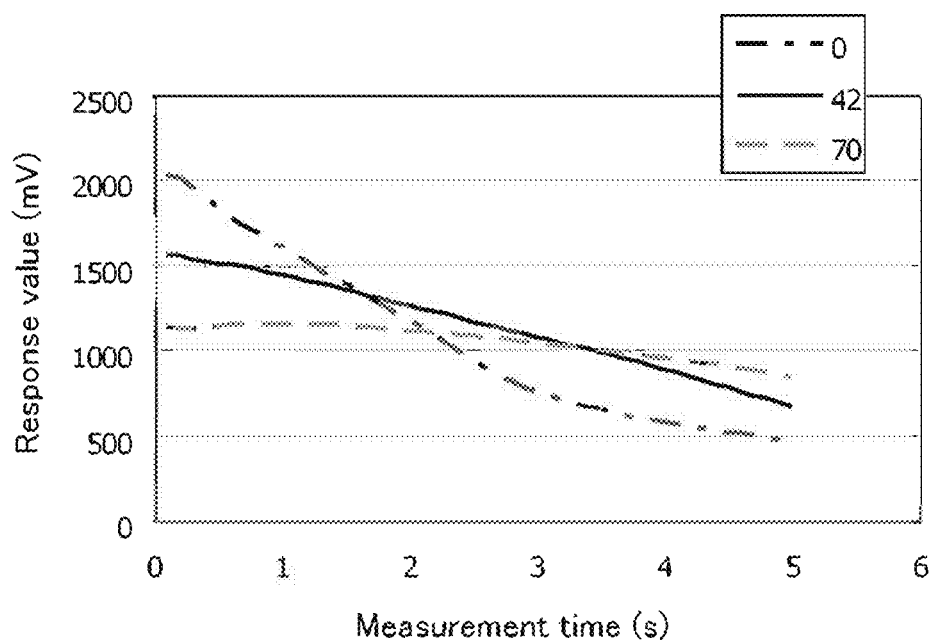

FIG. 60a is a graph showing the change with time in the response current value relative to an applied voltage with respect to each blood sample with a Glu concentration of 45 mg/dl (Hct value: 0%, 42%, and 70%) in Example 35.

Figure 60B:
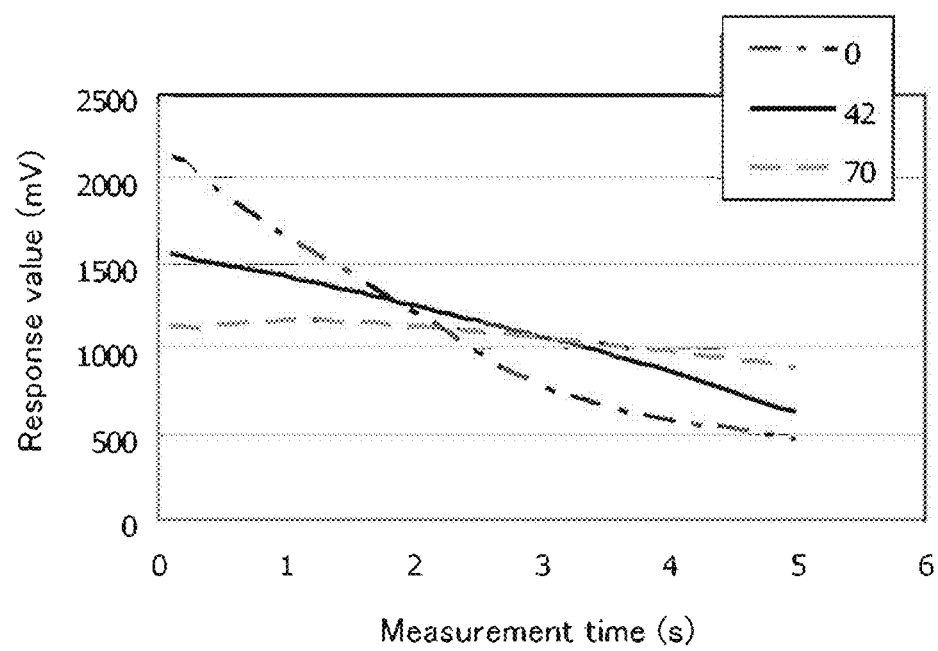

FIG. 60b is a graph showing the change with time in the response current value relative to an applied voltage with respect to each blood sample with a Glu concentration of 550 mg/dl (Hct value: 0%, 42%, and 70%) in Example 35.

Figure 60C:
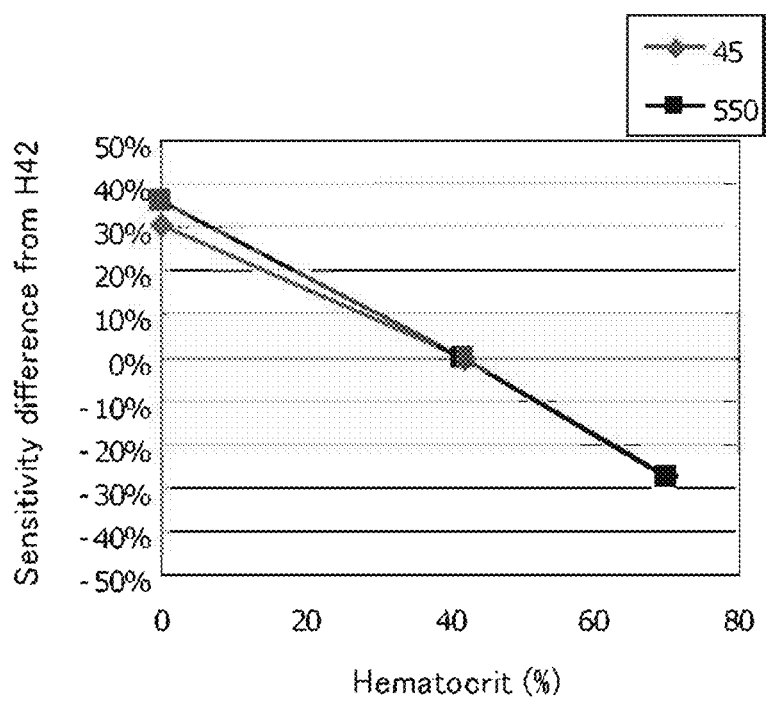

FIG. 60c is a graph showing the sensitivity difference (%) in each case of Glu values of 45 mg/dl and 550 mg/dl with reference to Hct 42% in Example 35.

Figure 60D:
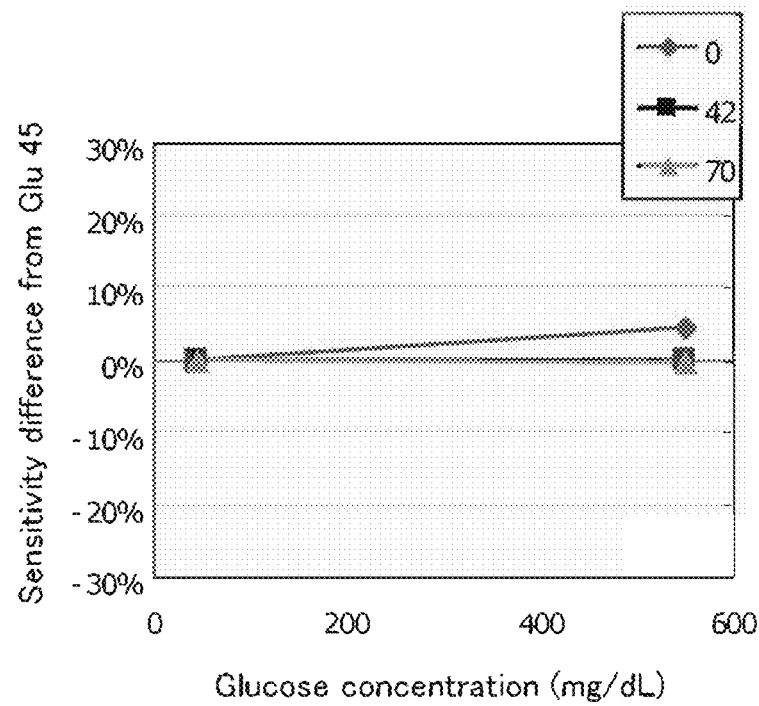

FIG. 60d is a graph showing the sensitivity difference (%) in each case of Hct values of 0%, 42%, and 70% with reference to Glu 45 mg/dl in Example 35.

Figure 61A:
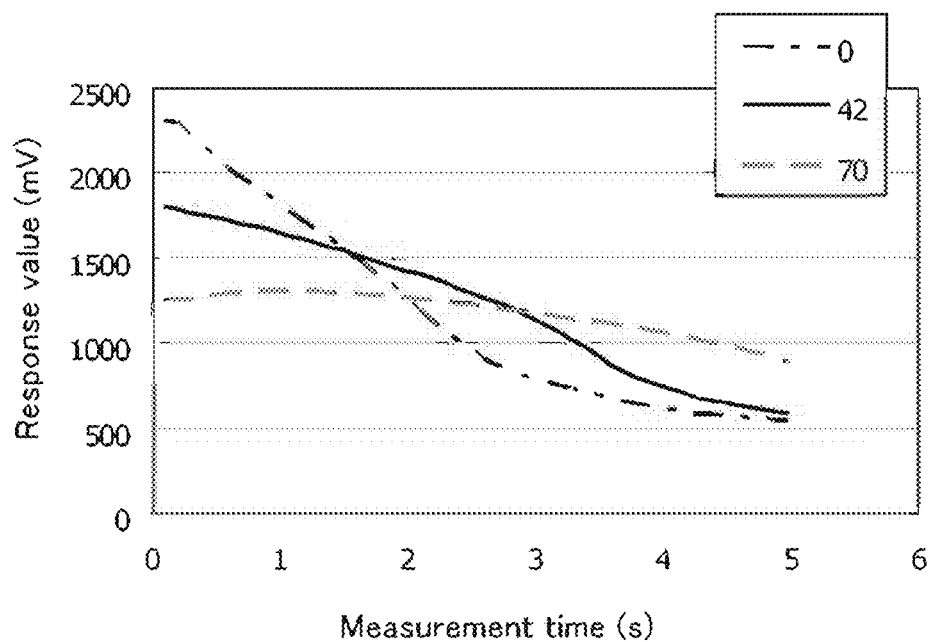

FIG. 61a is a graph showing the change with time in the response current value relative to an applied voltage with respect to each blood sample with a Glu concentration of 45 mg/dl (Hct value: 0%, 42%, and 70%) in Example 36.

Figure 61B:
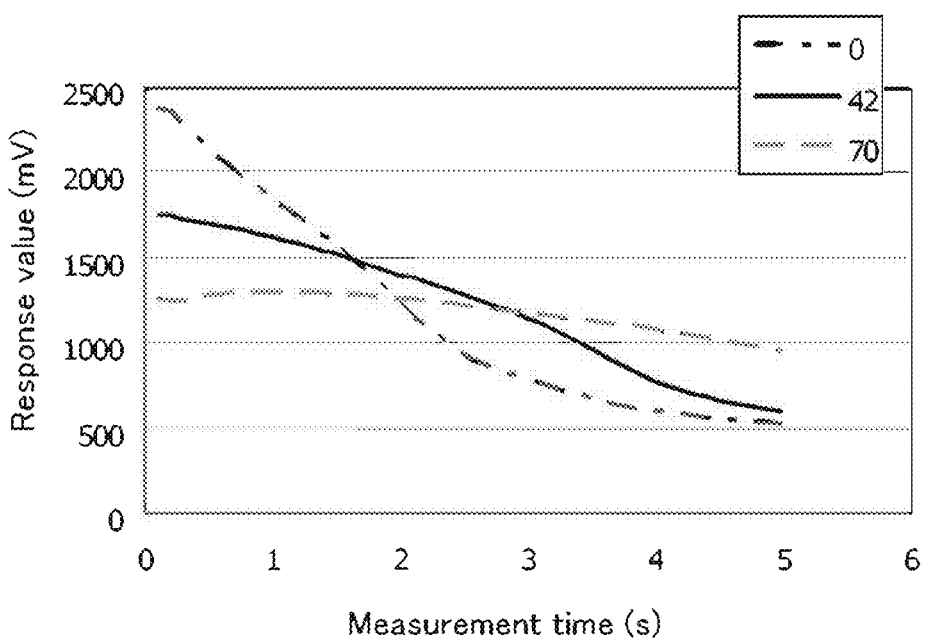

FIG. 61b is a graph showing the change with time in the response current value relative to an applied voltage with respect to each blood sample with a Glu concentration of 550 mg/dl (Hct value: 0%, 42%, and 70%) in Example 36.

Figure 61C:
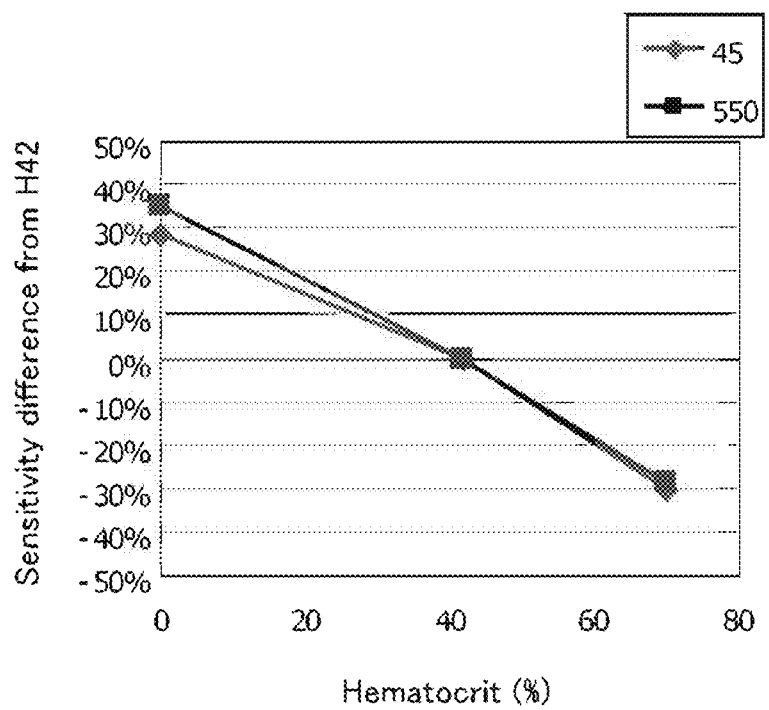

FIG. 61c is a graph showing the sensitivity difference (%) in each case of Glu values of 45 mg/dl and 550 mg/dl with reference to Hct 42% in Example 36.

Figure 61D:
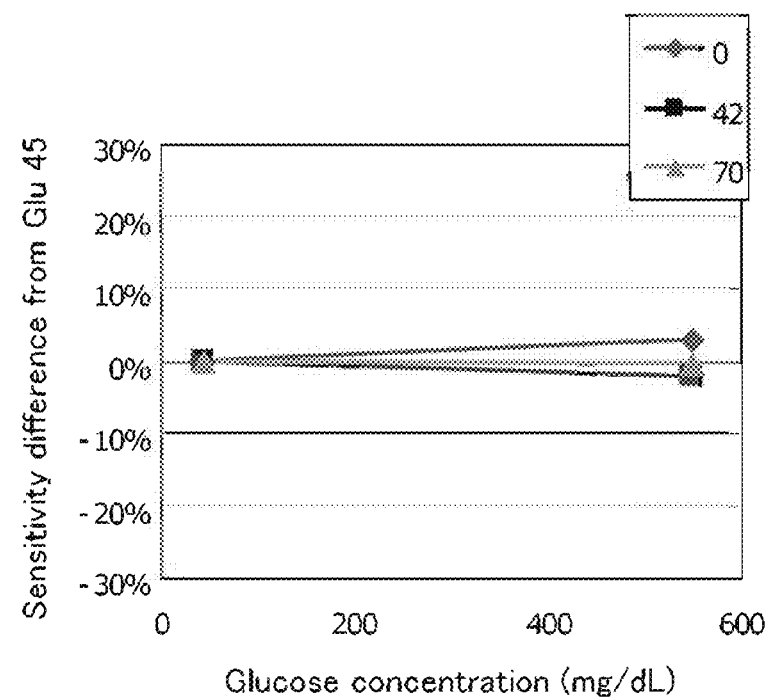

FIG. 61d is a graph showing the sensitivity difference (%) in each case of Hct values of 0%, 42%, and 70% with reference to Glu 45 mg/dl in Example 36.

Figure 62A:
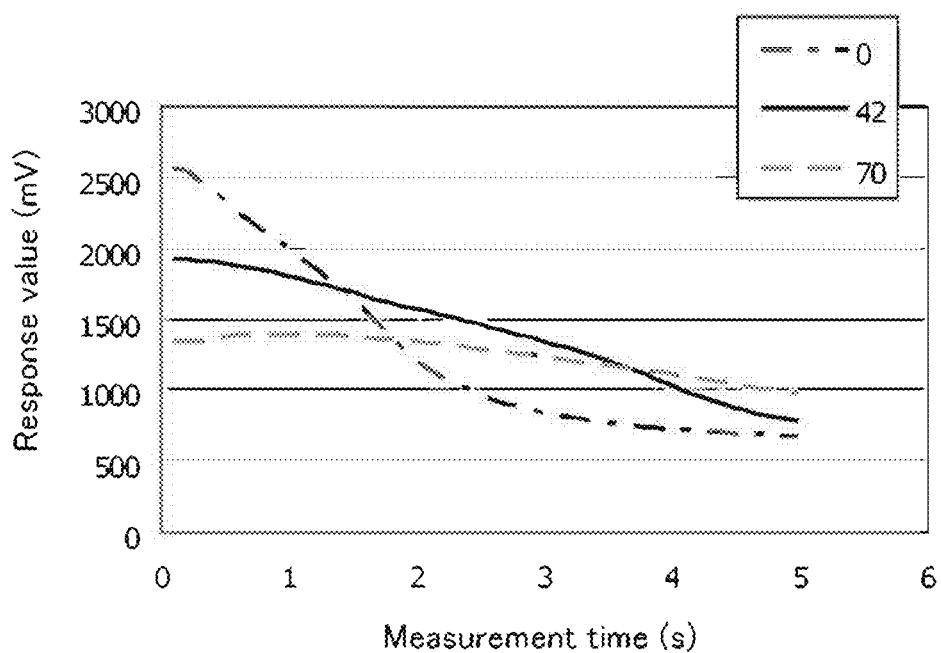

FIG. 62a is a graph showing the change with time in the response current value relative to an applied voltage with respect to each blood sample with a Glu concentration of 45 mg/dl (Hct value: 0%, 42%, and 70%) in Example 37.

Figure 62B:
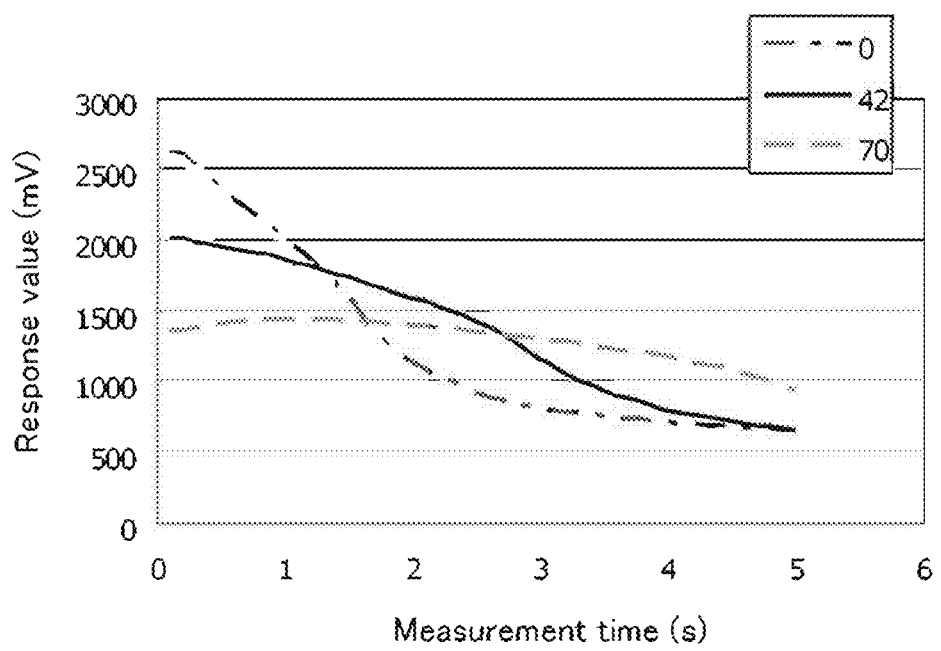

FIG. 62b is a graph showing the change with time in the response current value relative to an applied voltage with respect to each blood sample with a Glu concentration of 550 mg/dl (Hct value: 0%, 42%, and 70%) in Example 37.

Figure 62C:
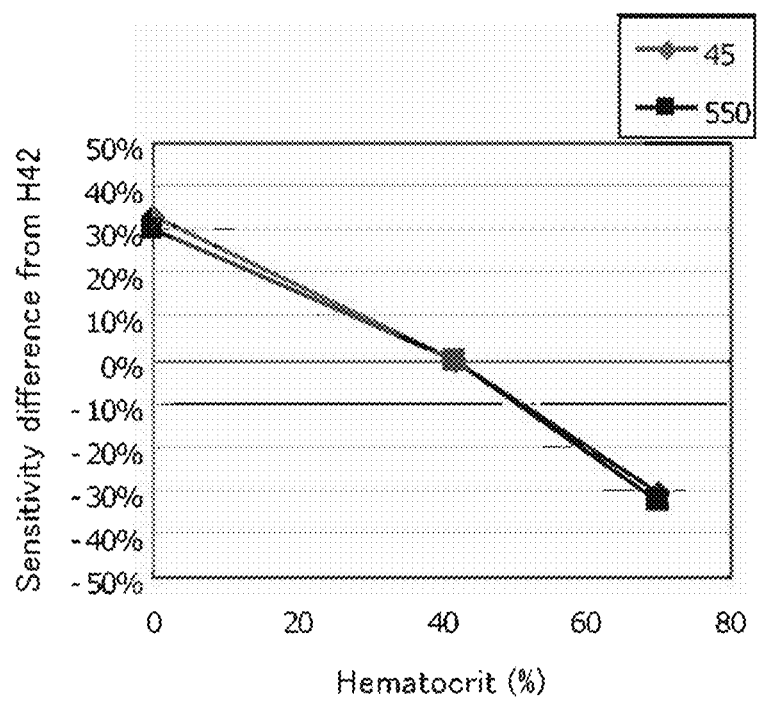

FIG. 62c is a graph showing the sensitivity difference (%) in each case of Glu values of 45 mg/dl and 550 mg/dl with reference to Hct 42% in Example 37.

Figure 62D:
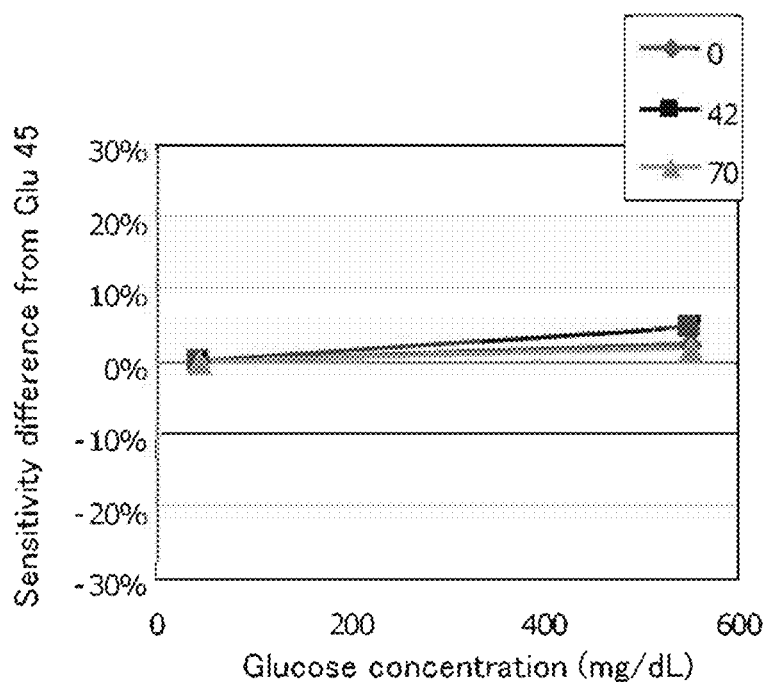

FIG. 62d is a graph showing the sensitivity difference (%) in each case of Hct values of 0%, 42%, and 70% with reference to Glu 45 mg/dl in Example 37.

Figure 63A:
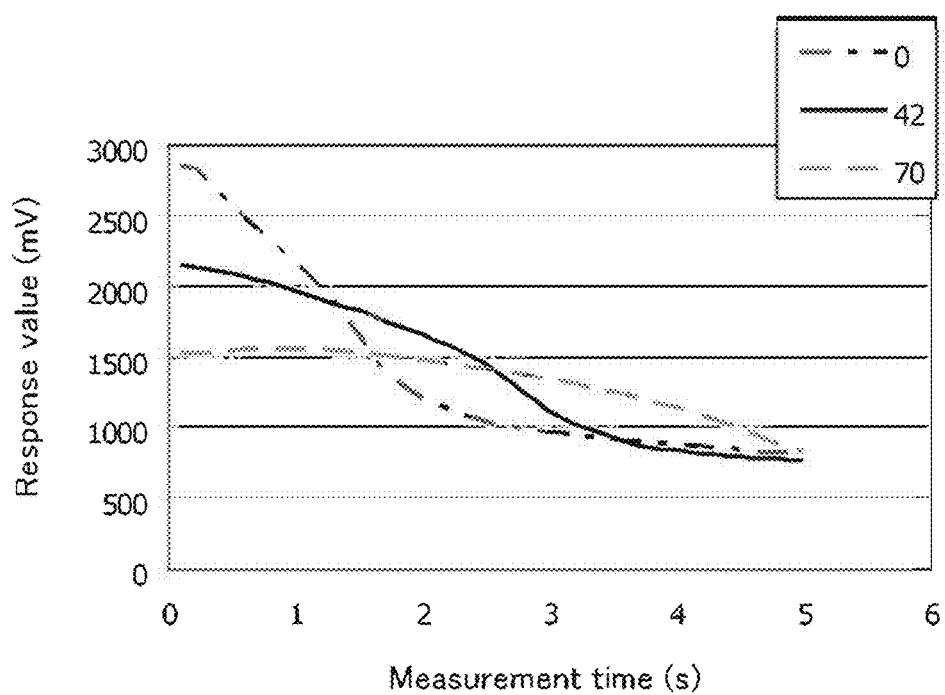

FIG. 63a is a graph showing the change with time in the response current value relative to an applied voltage with respect to each blood sample with a Glu concentration of 45 mg/dl (Hct value: 0%, 42%, and 70%) in Example 38.

Figure 63B:
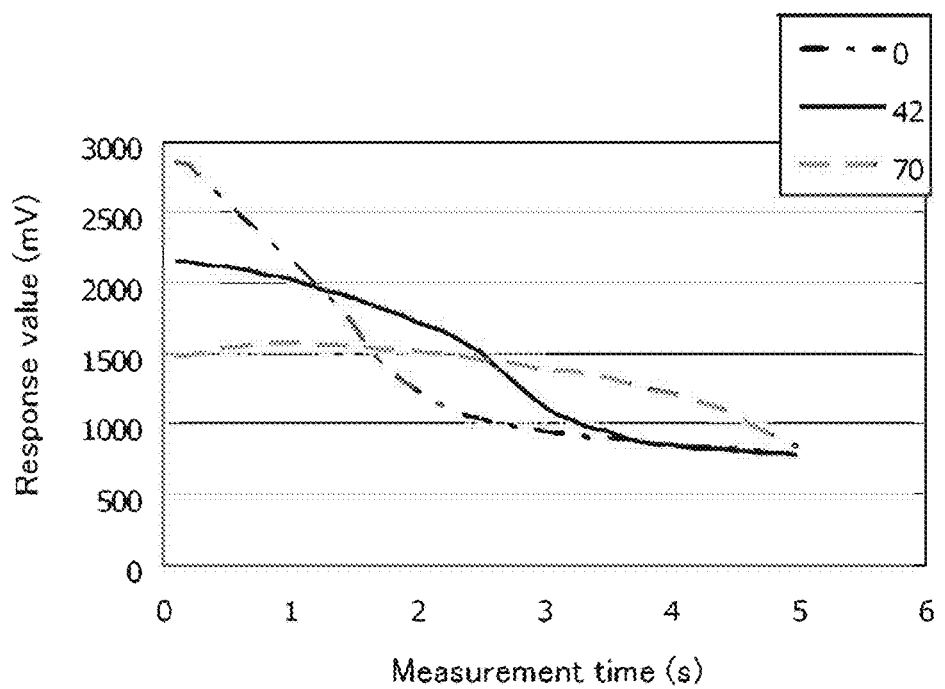

FIG. 63b is a graph showing the change with time in the response current value relative to an applied voltage with respect to each blood sample with a Glu concentration of 550 mg/dl (Hct value: 0%, 42%, and 70%) in Example 38.

Figure 63C:
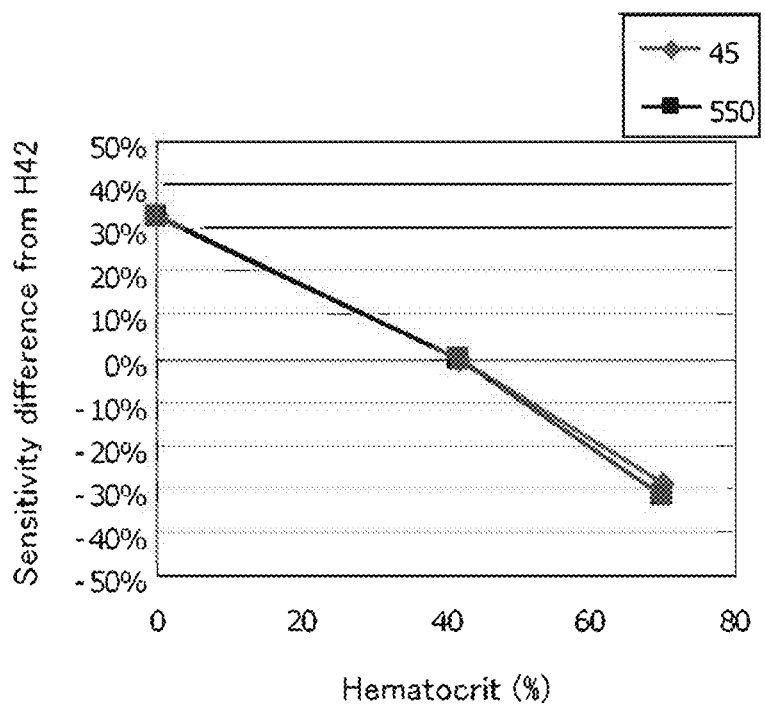

FIG. 63c is a graph showing the sensitivity difference (%) in each case of Glu values of 45 mg/dl and 550 mg/dl with reference to Hct 42% in Example 38.

Figure 63D:
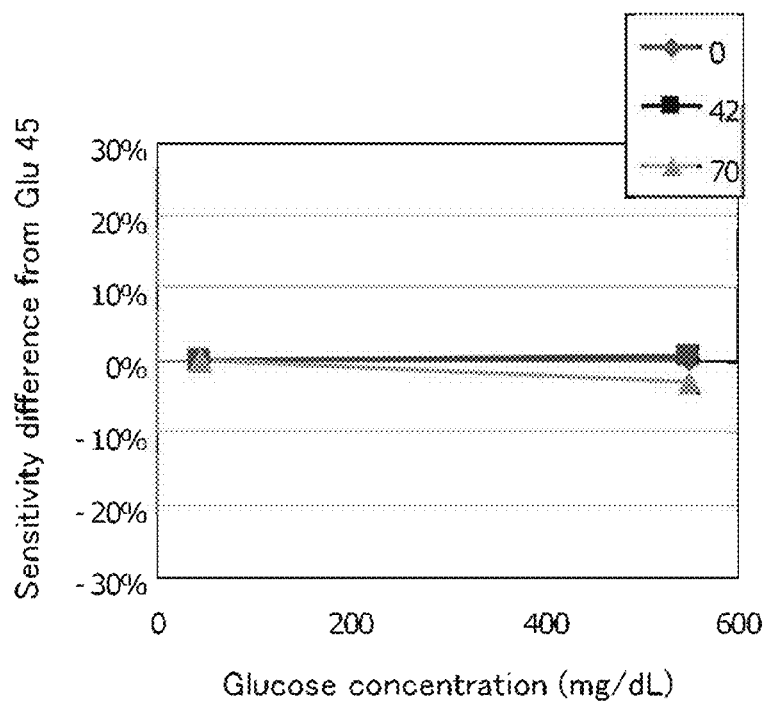

FIG. 63d is a graph showing the sensitivity difference (%) in each case of Hct values of 0%, 42%, and 70% with reference to Glu 45 mg/dl in Example 38.

Figure 64A:
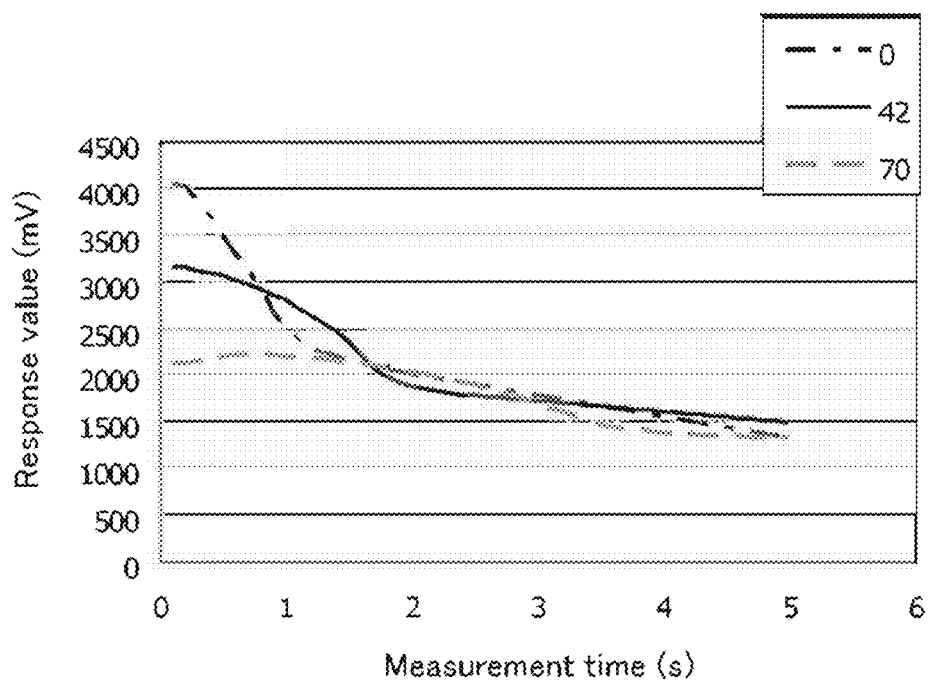

FIG. 64a is a graph showing the change with time in the response current value relative to an applied voltage with respect to each blood sample with a Glu concentration of 45 mg/dl (Hct value: 0%, 42%, and 70%) in Example 39.

Figure 64B:
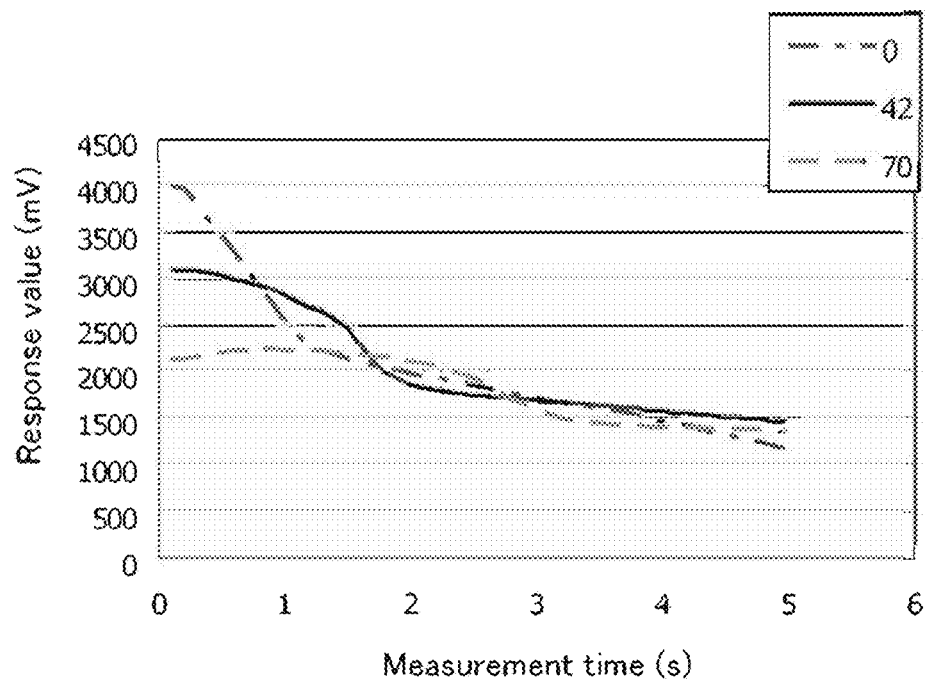

FIG. 64b is a graph showing the change with time in the response current value relative to an applied voltage with respect to each blood sample with a Glu concentration of 550 mg/dl (Hct value: 0%, 42%, and 70%) in Example 39.

Figure 64C:
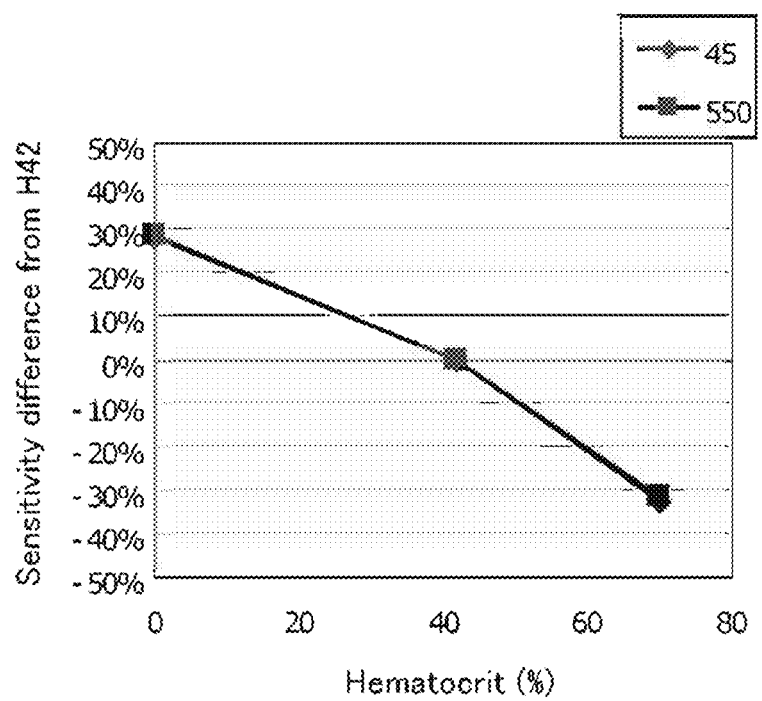

FIG. 64c is a graph showing the sensitivity difference (%) in each case of Glu values of 45 mg/dl and 550 mg/dl with reference to Hct 42% in Example 39.

Figure 64D:
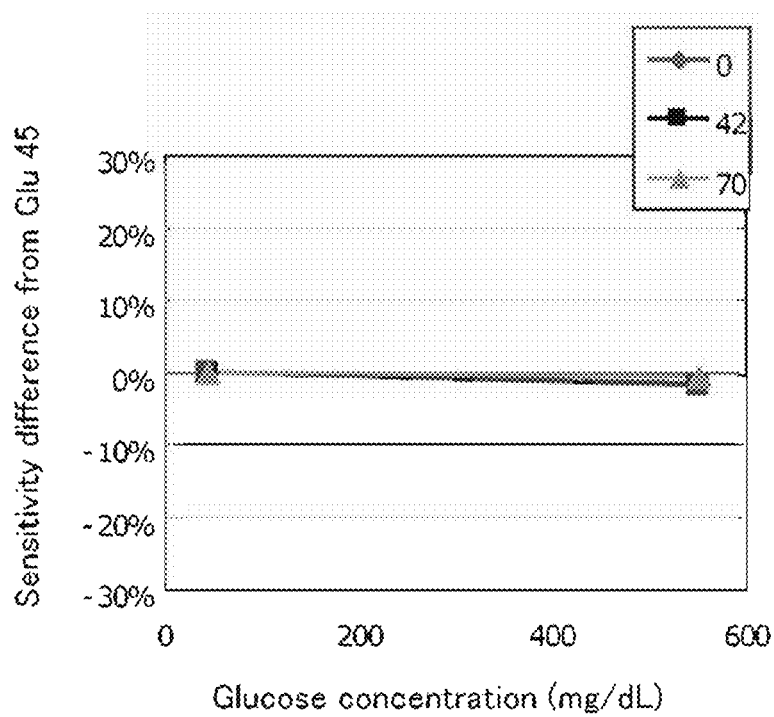

FIG. 64d is a graph showing the sensitivity difference (%) in each case of Hct values of 0%, 42%, and 70% with reference to Glu 45 mg/dl in Example 39.

Figure 65A:
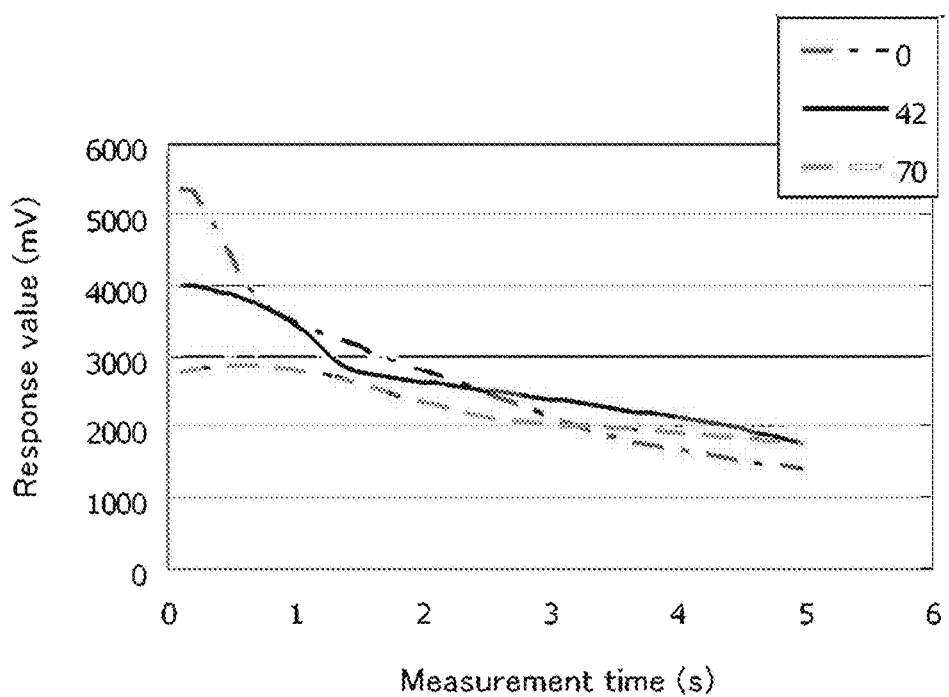

FIG. 65a is a graph showing the change with time in the response current value relative to an applied voltage with respect to each blood sample with a Glu concentration of 45 mg/dl (Hct value: 0%, 42%, and 70%) in Example 40.

Figure 65B:
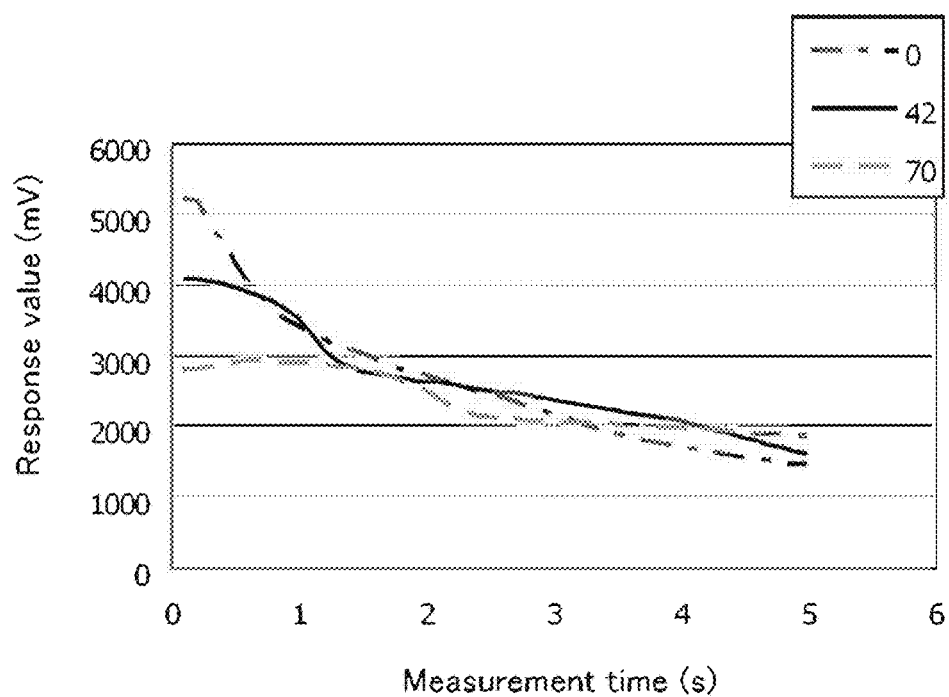

FIG. 65b is a graph showing the change with time in the response current value relative to an applied voltage with respect to each blood sample with a Glu concentration of 550 mg/dl (Hct value: 0%, 42%, and 70%) in Example 40.

Figure 65C:
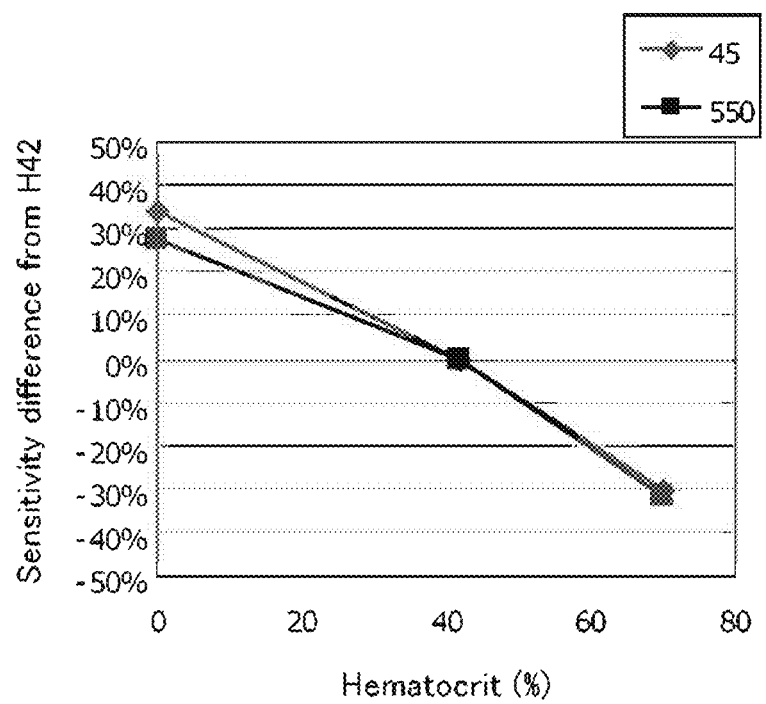

FIG. 65c is a graph showing the sensitivity difference (%) in each case of Glu values of 45 mg/dl and 550 mg/dl with reference to Hct 42% in Example 40.

Figure 65D:
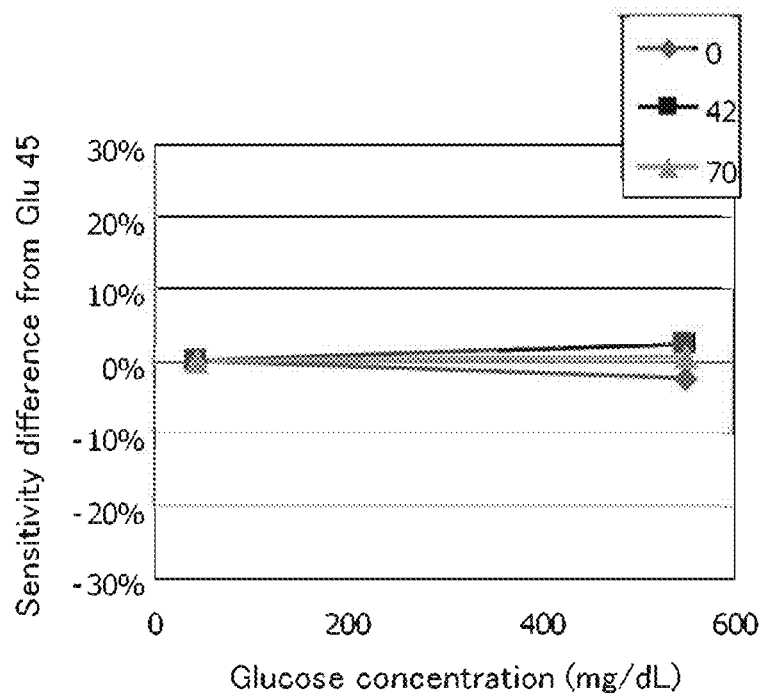

FIG. 65d is a graph showing the sensitivity difference (%) in each case of Hct values of 0%, 42%, and 70% with reference to Glu 45 mg/dl in Example 40.

Figure 66A:
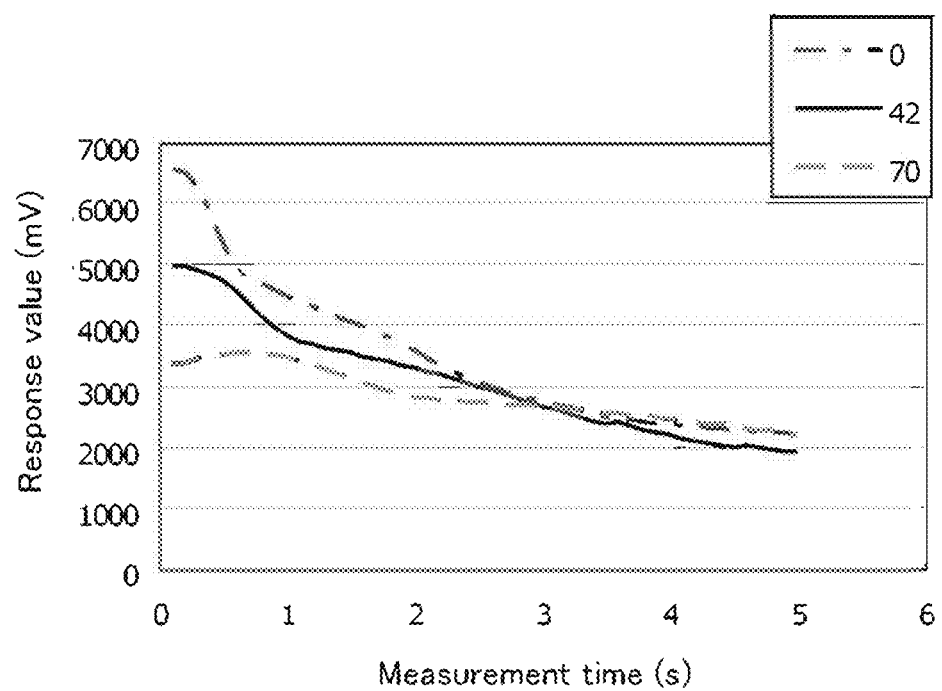

FIG. 66a is a graph showing the change with time in the response current value relative to an applied voltage with respect to each blood sample with a Glu concentration of 45 mg/dl (Hct value: 0%, 42%, and 70%) in Example 41.

Figure 66B:
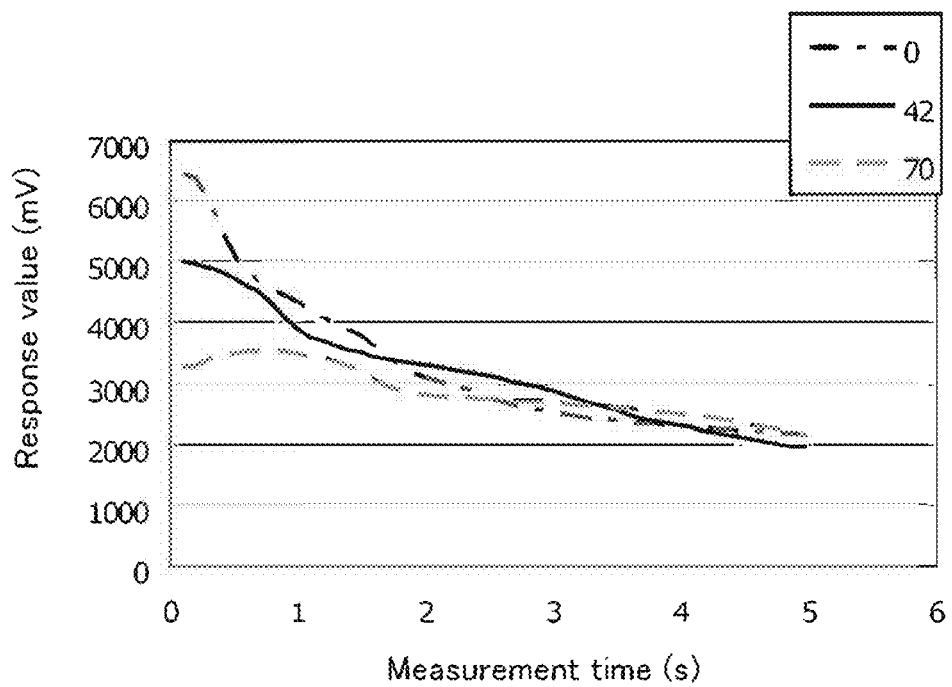

FIG. 66b is a graph showing the change with time in the response current value relative to an applied voltage with respect to each blood sample with a Glu concentration of 550 mg/dl (Hct value: 0%, 42%, and 70%) in Example 41.

Figure 66C:
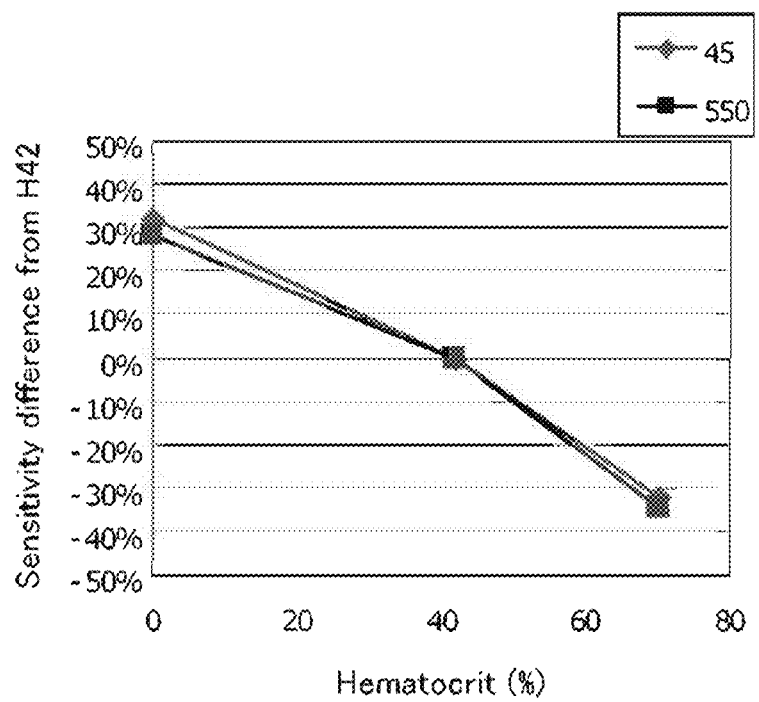

FIG. 66c is a graph showing the sensitivity difference (%) in each case of Glu values of 45 mg/dl and 550 mg/dl with reference to Hct 42% in Example 41.

Figure 66D:
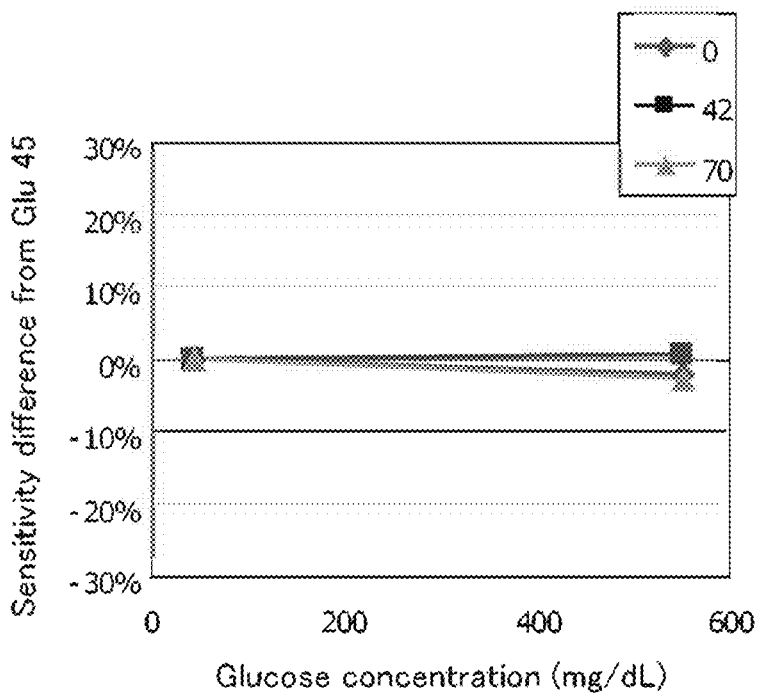

FIG. 66d is a graph showing the sensitivity difference (%) in each case of Hct values of 0%, 42%, and 70% with reference to Glu 45 mg/dl in Example 41.

Figure 67A:
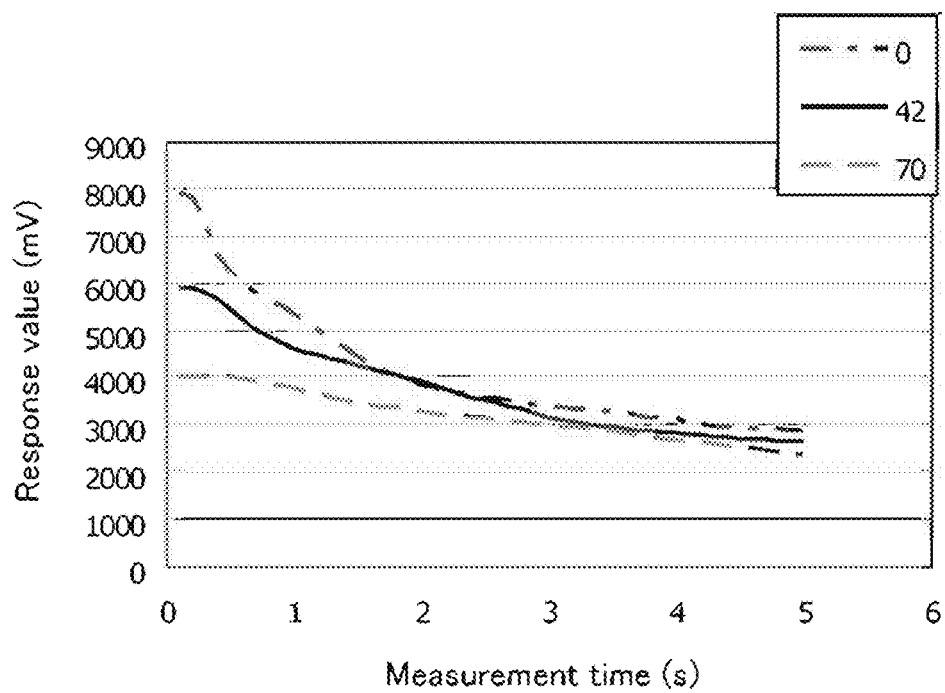

FIG. 67a is a graph showing the change with time in the response current value relative to an applied voltage with respect to each blood sample with a Glu concentration of 45 mg/dl (Hct value: 0%, 42%, and 70%) in Example 42.

Figure 67B:
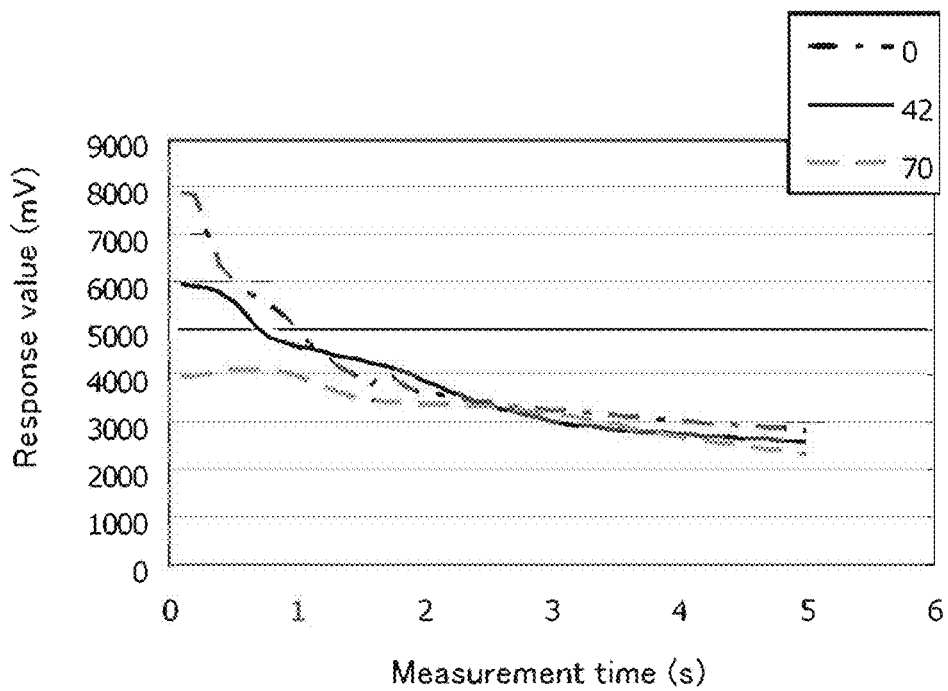

FIG. 67b is a graph showing the change with time in the response current value relative to an applied voltage with respect to each blood sample with a Glu concentration of 550 mg/dl (Hct value: 0%, 42%, and 70%) in Example 42.

Figure 67C:
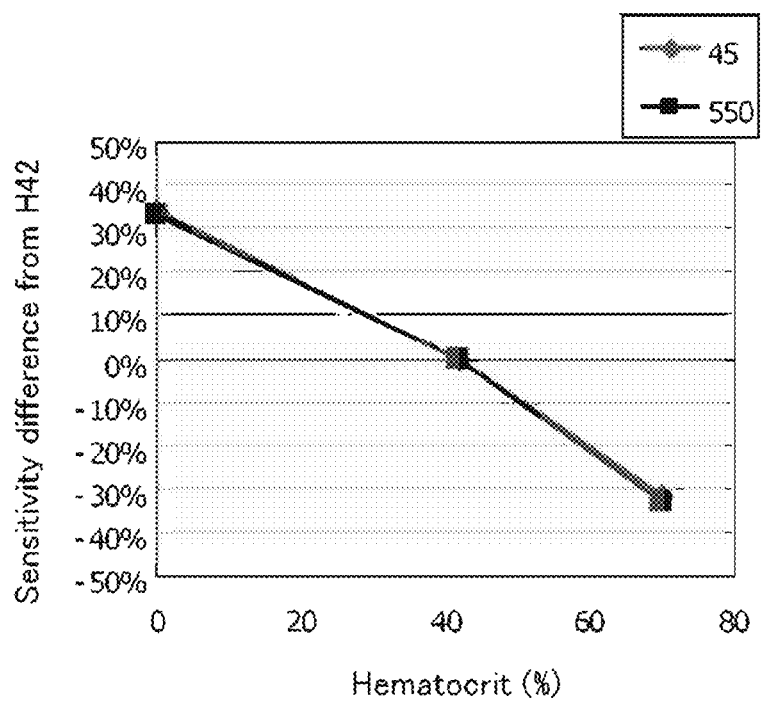

FIG. 67c is a graph showing the sensitivity difference (%) in each case of Glu values of 45 mg/dl and 550 mg/dl with reference to Hct 42% in Example 42.

Figure 67D:
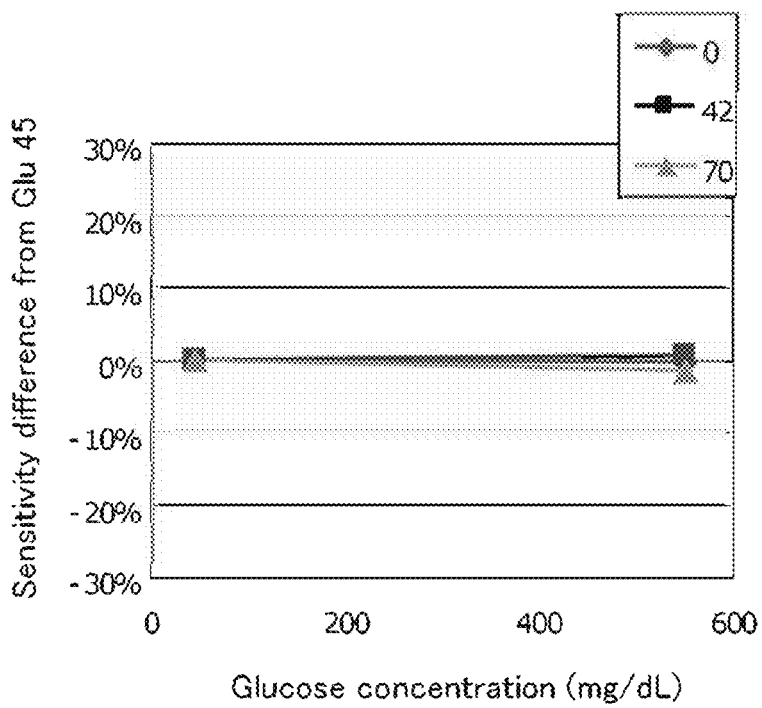

FIG. 67d is a graph showing the sensitivity difference (%) in each case of Hct values of 0%, 42%, and 70% with reference to Glu 45 mg/dl in Example 42.

Figure 68A:
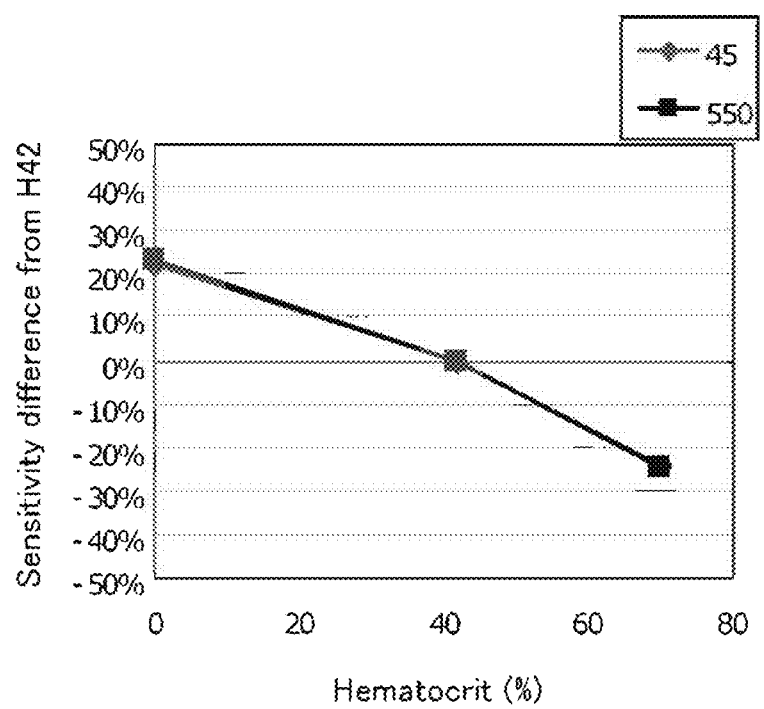

FIG. 68a is a graph showing the sensitivity difference (%) in each case of Glu values of 45 mg/dl and 550 mg/dl with reference to Hct 42% in Example 43.

Figure 68B:
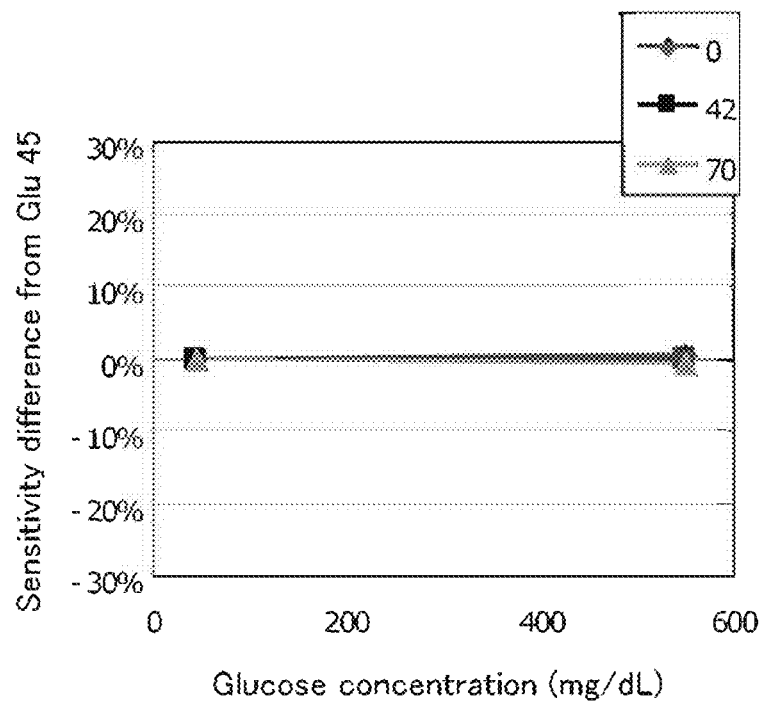

FIG. 68b is a graph showing the sensitivity difference (%) in each case of Hct values of 0%, 42%, and 70% with reference to Glu 45 mg/dl in Example 43.

Figure 69A:
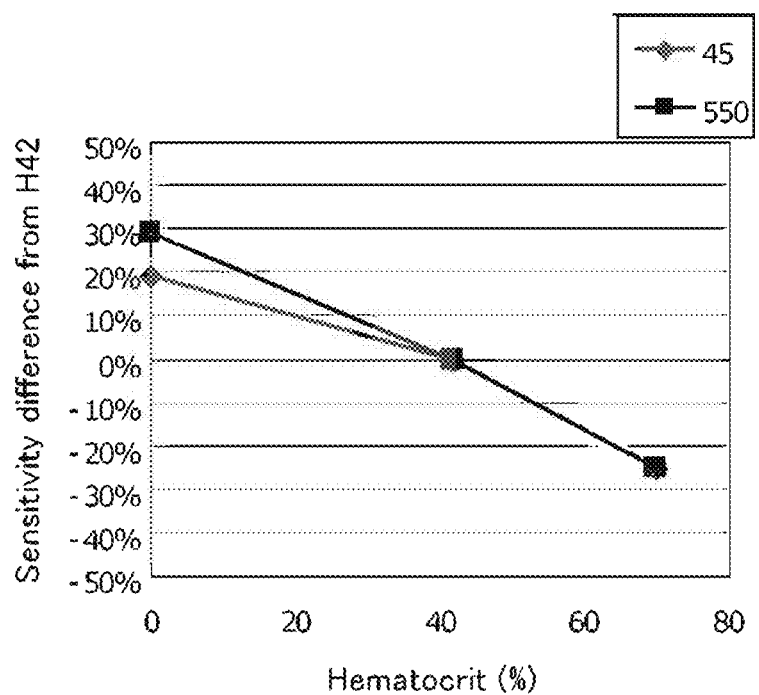

FIG. 69a is a graph showing the sensitivity difference (%) in each case of Glu values of 45 mg/dl and 550 mg/dl with reference to Hct 42% in Example 44.

Figure 69B:
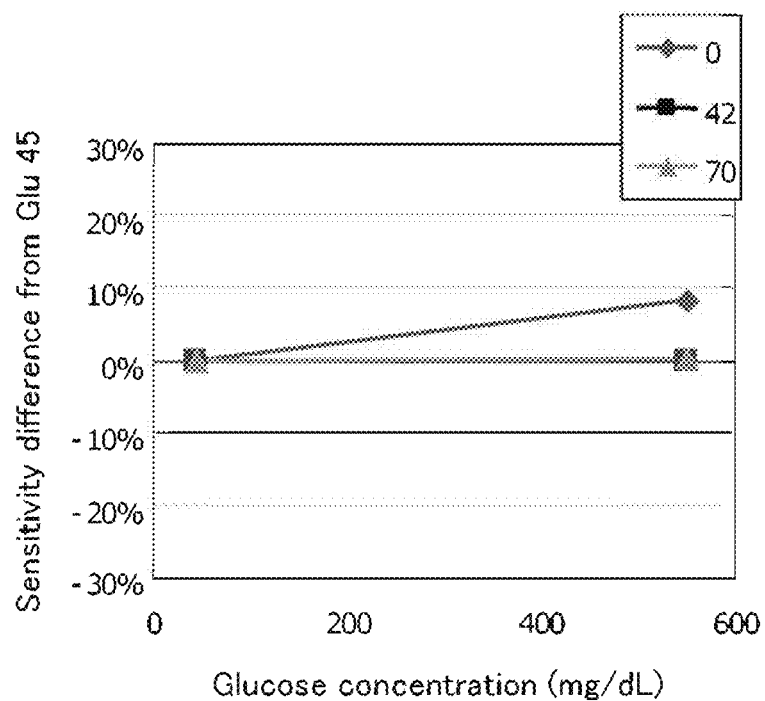

FIG. 69b is a graph showing the sensitivity difference (%) in each case of Hct values of 0%, 42%, and 70% with reference to Glu 45 mg/dl in Example 44.

Figure 70A:
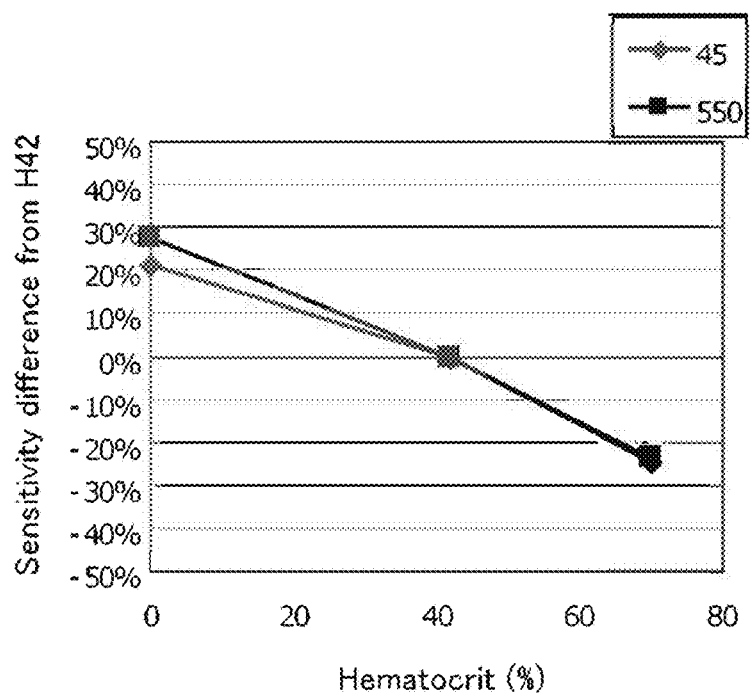

FIG. 70a is a graph showing the sensitivity difference (%) in each case of Glu values of 45 mg/dl and 550 mg/dl with reference to Hct 42% in Example 45.

Figure 70B:
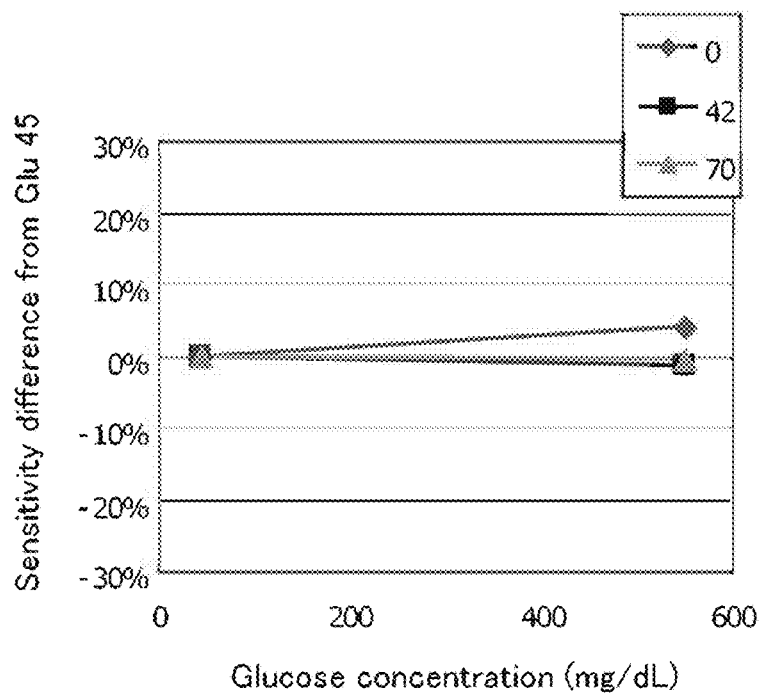

FIG. 70b is a graph showing the sensitivity difference (%) in each case of Hct values of 0%, 42%, and 70% with reference to Glu 45 mg/dl in Example 45.

Figure 71A:
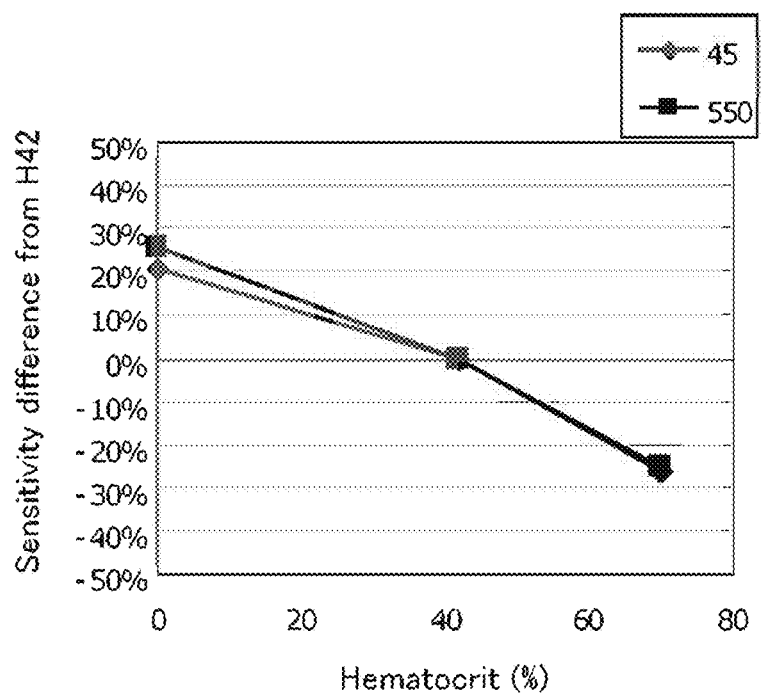

FIG. 71a is a graph showing the sensitivity difference (%) in each case of Glu values of 45 mg/dl and 550 mg/dl with reference to Hct 42% in Example 46.

Figure 71B:
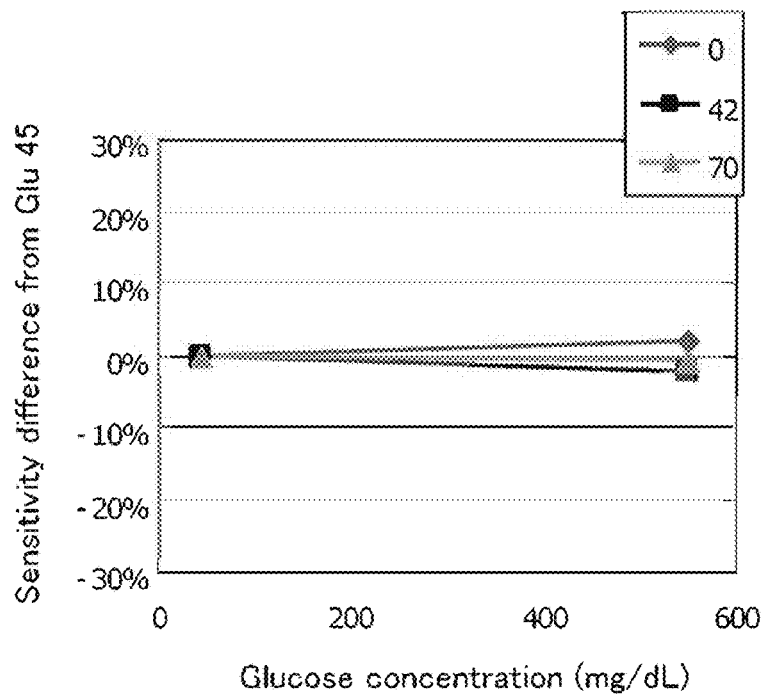

FIG. 71b is a graph showing the sensitivity difference (%) in each case of Hct values of 0%, 42%, and 70% with reference to Glu 45 mg/dl in Example 46.

Figure 72A:
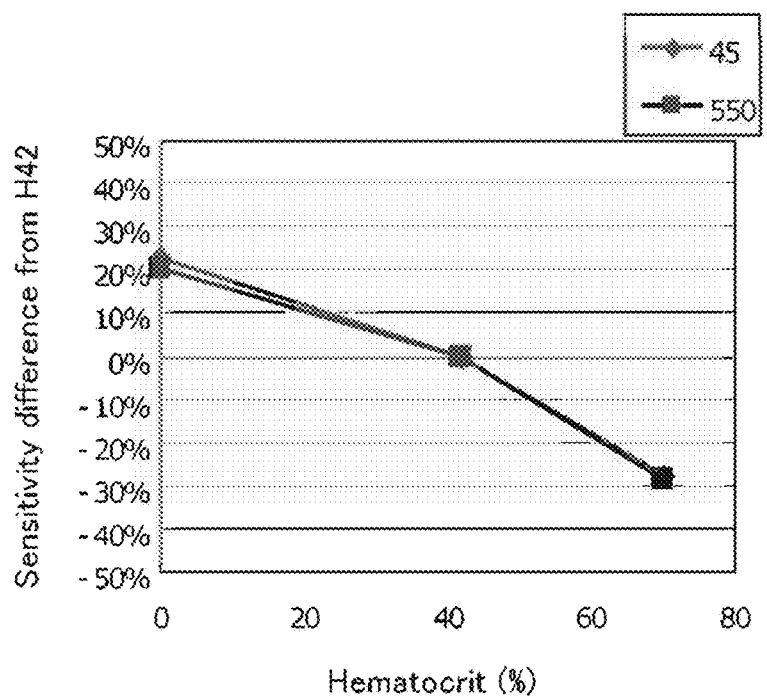

FIG. 72a is a graph showing the sensitivity difference (%) in each case of Glu values of 45 mg/dl and 550 mg/dl with reference to Hct 42% in Example 47.

Figure 72B:
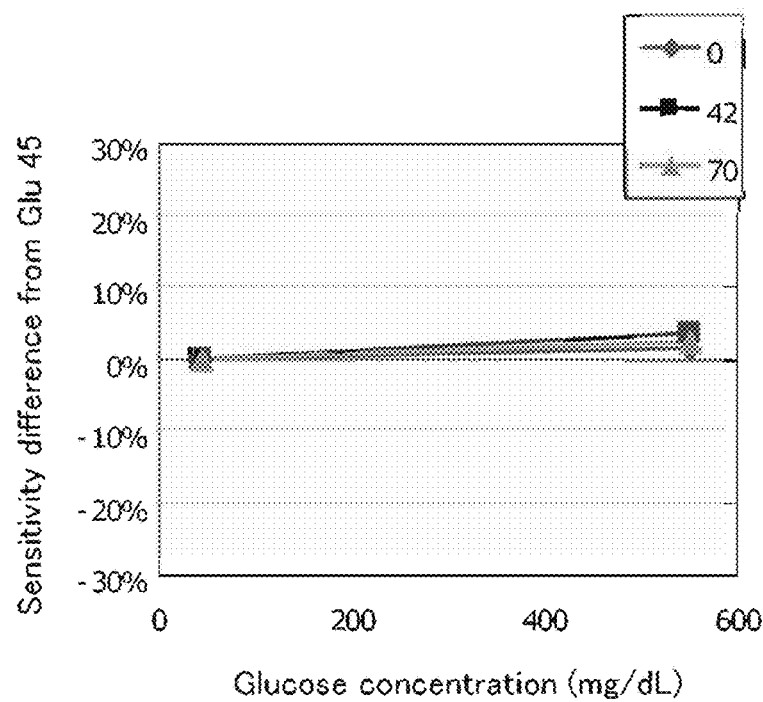

FIG. 72b is a graph showing the sensitivity difference (%) in each case of Hct values of 0%, 42%, and 70% with reference to Glu 45 mg/dl in Example 47.

Figure 73A:
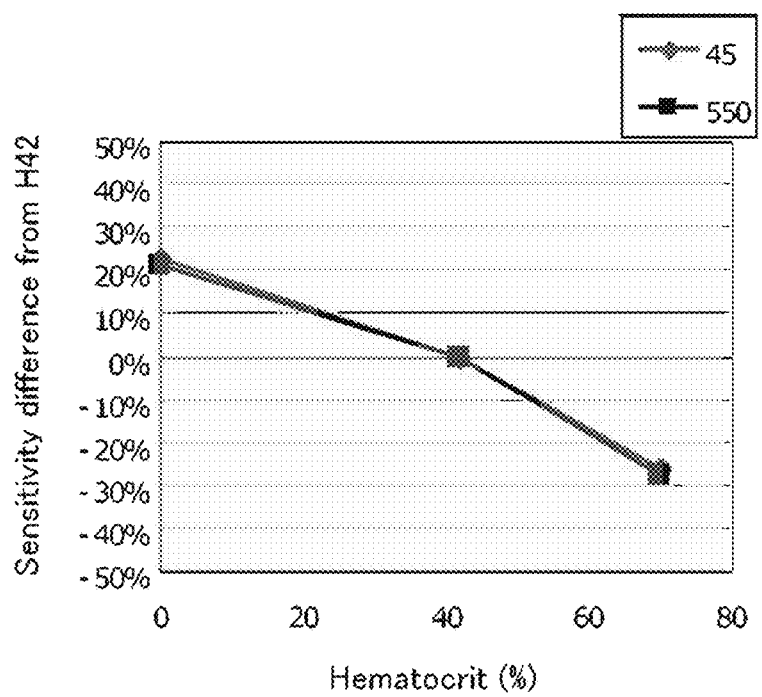

FIG. 73a is a graph showing the sensitivity difference (%) in each case of Glu values of 45 mg/dl and 550 mg/dl with reference to Hct 42% in Example 48.

Figure 73B:
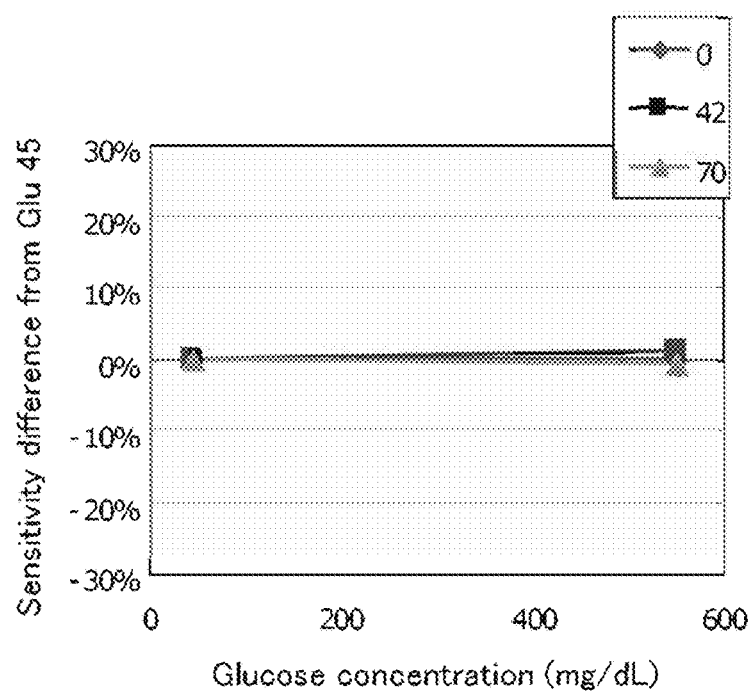

FIG. 73b is a graph showing the sensitivity difference (%) in each case of Hct values of 0%, 42%, and 70% with reference to Glu 45 mg/dl in Example 48.

Figure 74A:
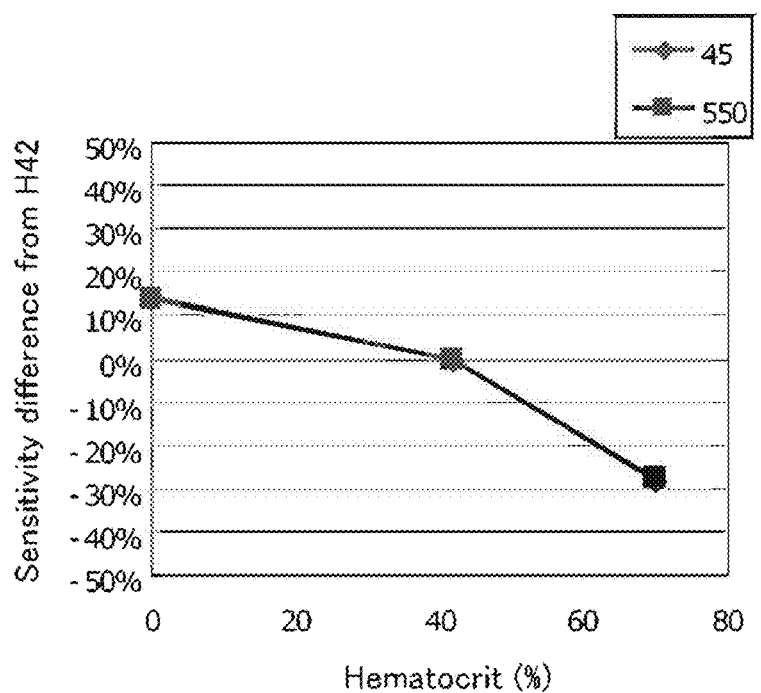

FIG. 74a is a graph showing the sensitivity difference (%) in each case of Glu values of 45 mg/dl and 550 mg/dl with reference to Hct 42% in Example 49.

Figure 74B:
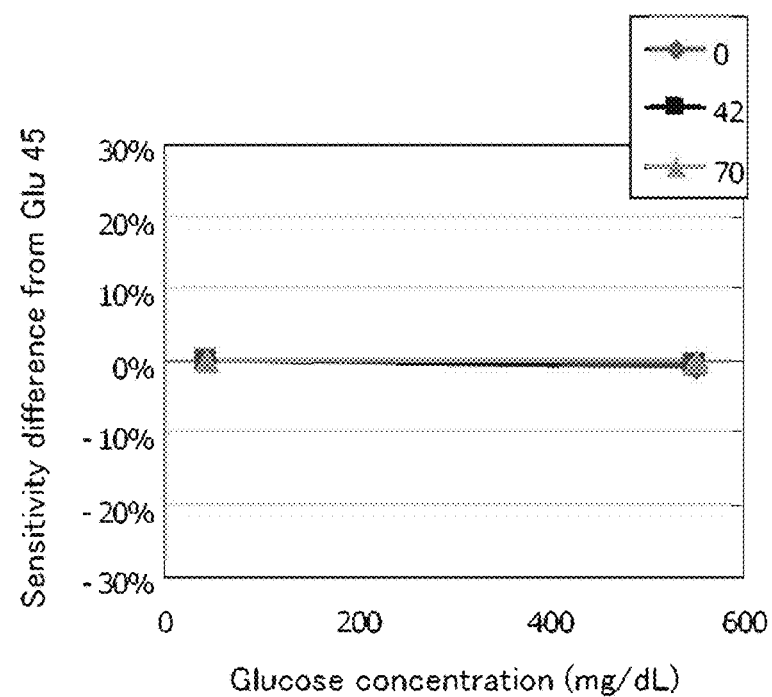

FIG. 74b is a graph showing the sensitivity difference (%) in each case of Hct values of 0%, 42%, and 70% with reference to Glu 45 mg/dl in Example 49.

Figure 75A:
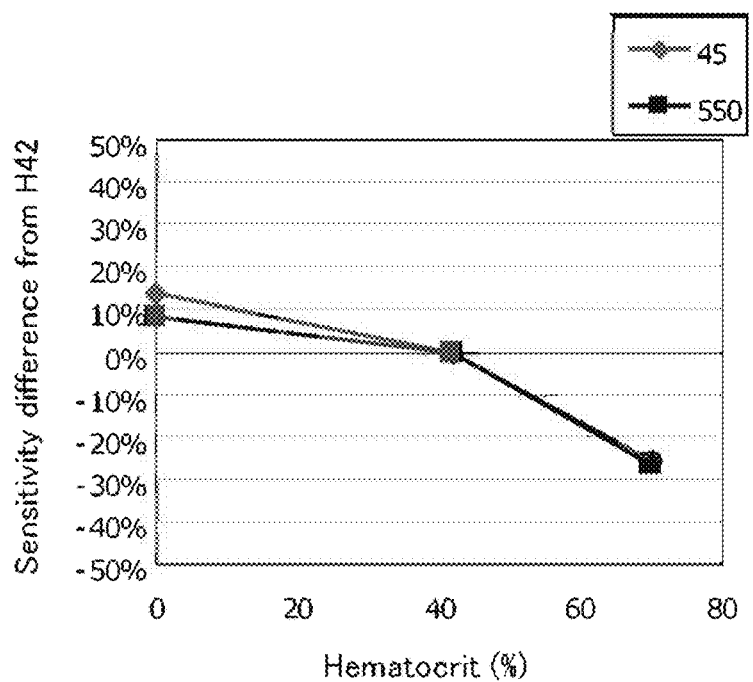

FIG. 75a is a graph showing the sensitivity difference (%) in each case of Glu values of 45 mg/dl and 550 mg/dl with reference to Hct 42% in Example 50.

Figure 75B:
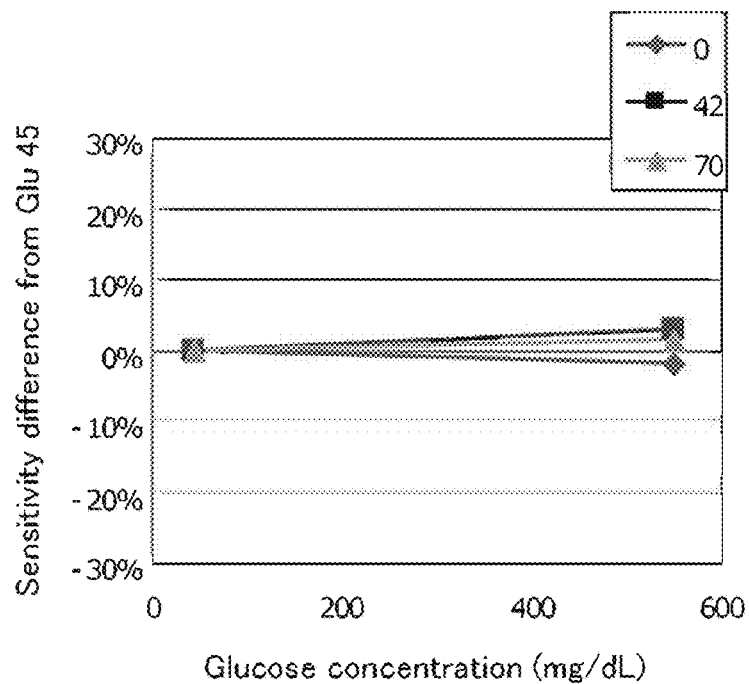

FIG. 75b is a graph showing the sensitivity difference (%) in each case of Hct values of 0%, 42%, and 70% with reference to Glu 45 mg/dl in Example 50.

Figure 76A:
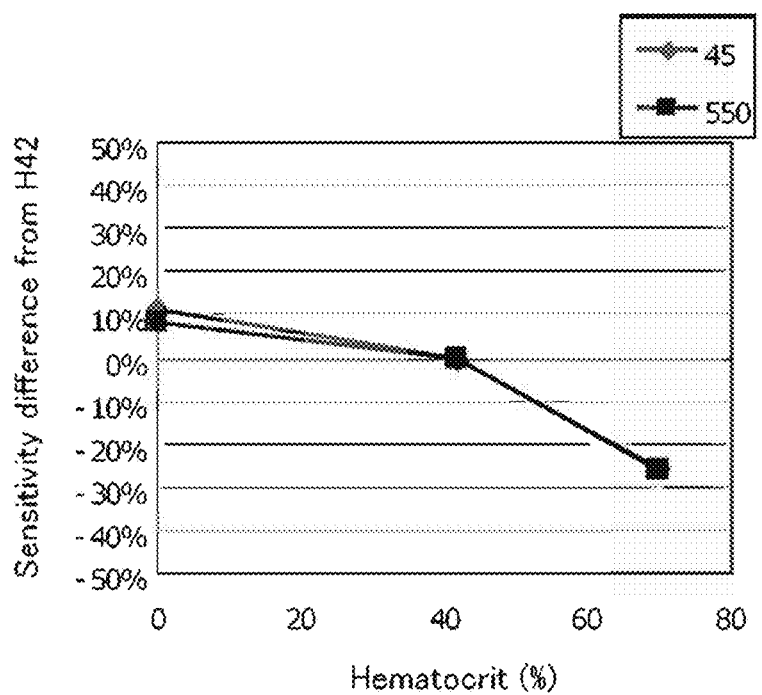

FIG. 76a is a graph showing the sensitivity difference (%) in each case of Glu values of 45 mg/dl and 550 mg/dl with reference to Hct 42% in Example 51.

Figure 76B:
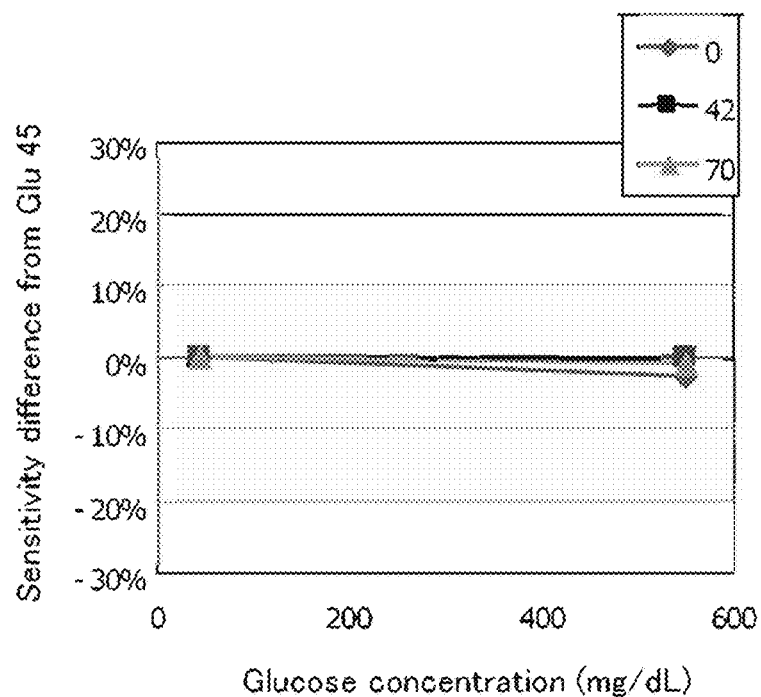

FIG. 76b is a graph showing the sensitivity difference (%) in each case of Hct values of 0%, 42%, and 70% with reference to Glu 45 mg/dl in Example 51.

Figure 77A:
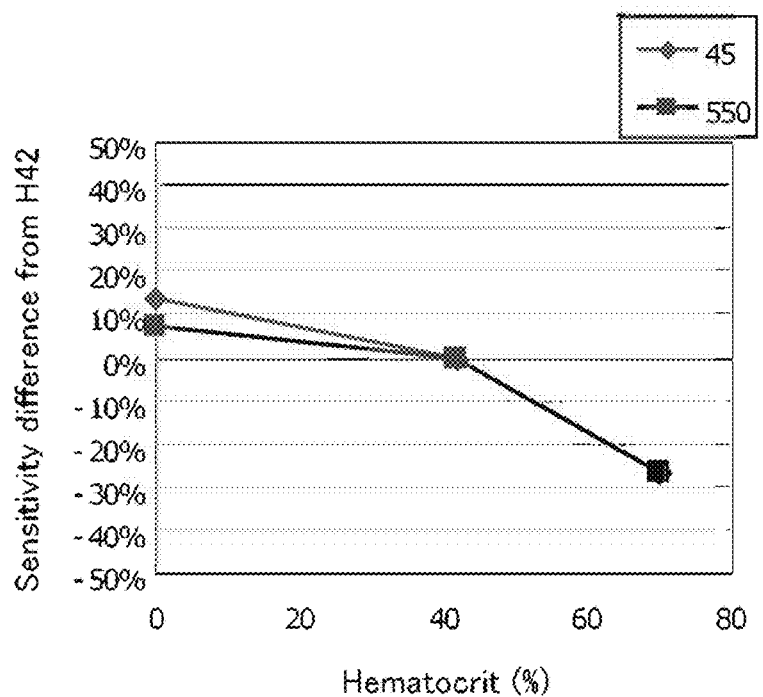

FIG. 77a is a graph showing the sensitivity difference (%) in each case of Glu values of 45 mg/dl and 550 mg/dl with reference to Hct 42% in Example 52.

Figure 77B:
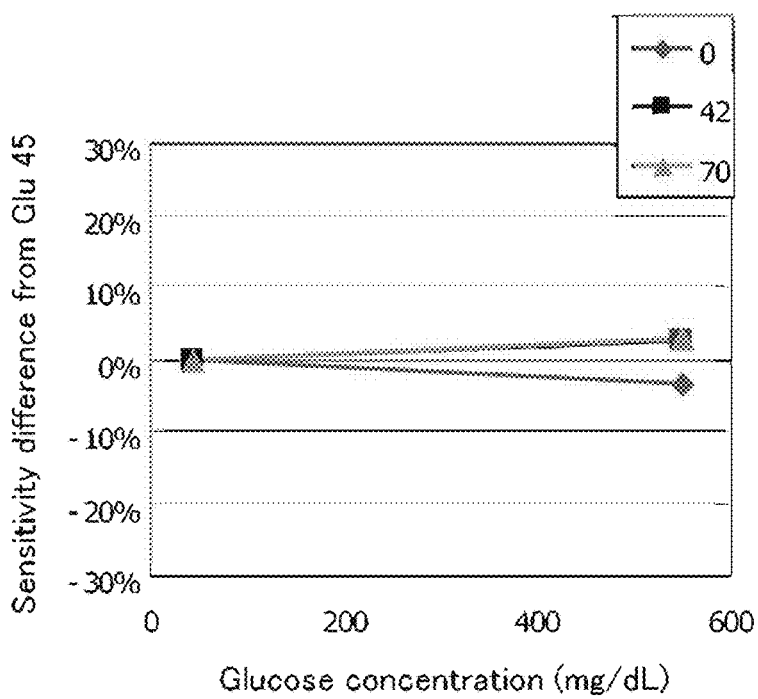

FIG. 77b is a graph showing the sensitivity difference (%) in each case of Hct values of 0%, 42%, and 70% with reference to Glu 45 mg/dl in Example 52.

Figure 78A:
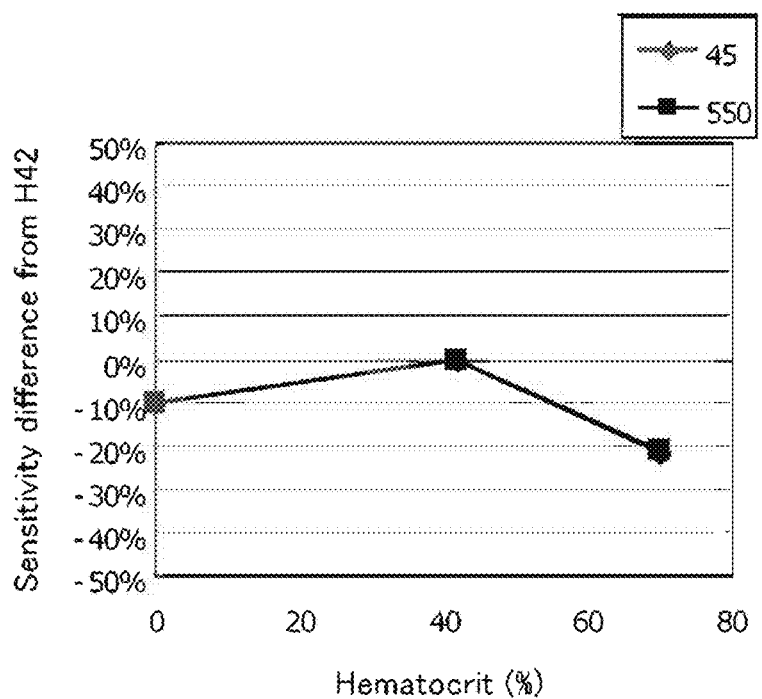

FIG. 78a is a graph showing the sensitivity difference (%) in each case of Glu values of 45 mg/dl and 550 mg/dl with reference to Hct 42% in Comparative Example 7.

Figure 78B:
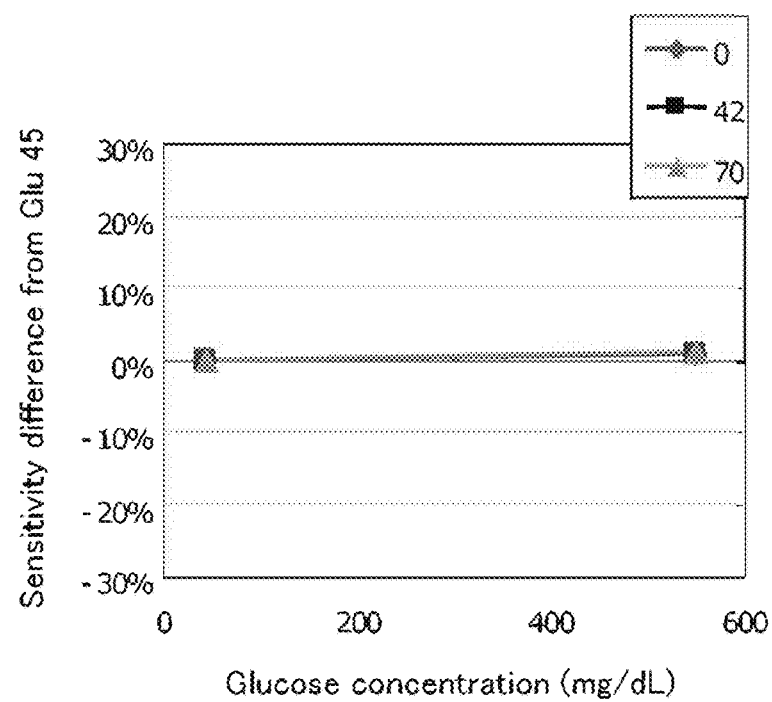

FIG. 78b is a graph showing the sensitivity difference (%) in each case of Hct values of 0%, 42%, and 70% with reference to Glu 45 mg/dl in Comparative Example 7.

Figure 79A:
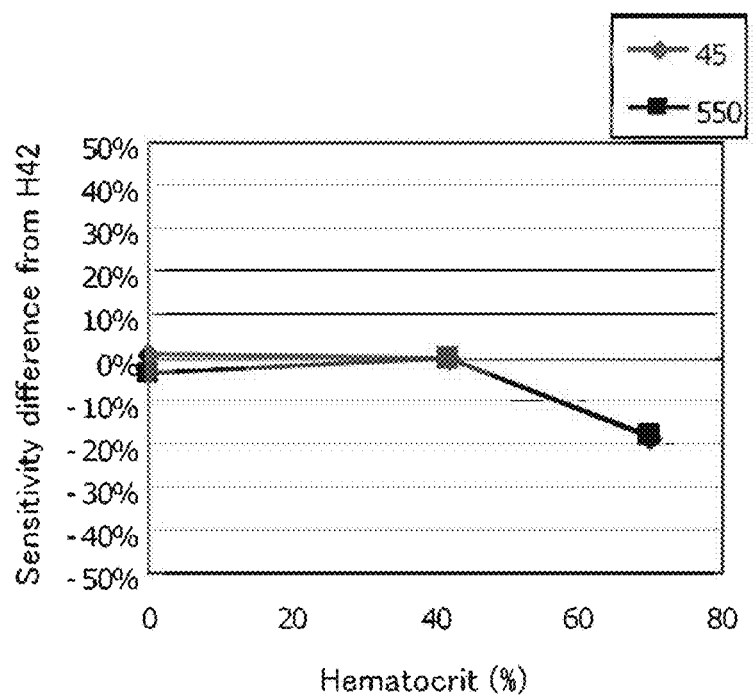

FIG. 79a is a graph showing the sensitivity difference (%) in each case of Glu values of 45 mg/dl and 550 mg/dl with reference to Hct 42% in Comparative Example 8.

Figure 79B:
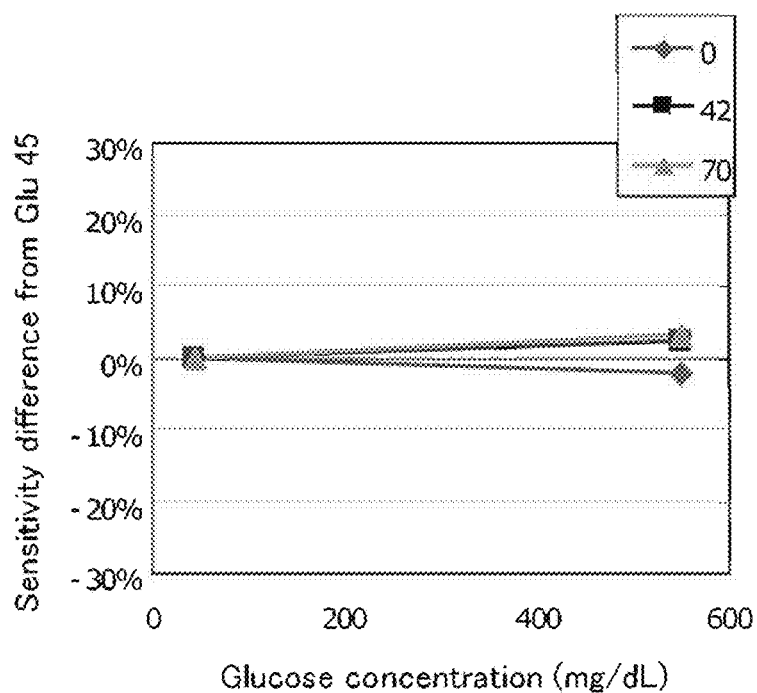

FIG. 79b is a graph showing the sensitivity difference (%) in each case of Hct values of 0%, 42%, and 70% with reference to Glu 45 mg/dl in Comparative Example 8.

Figure 80:
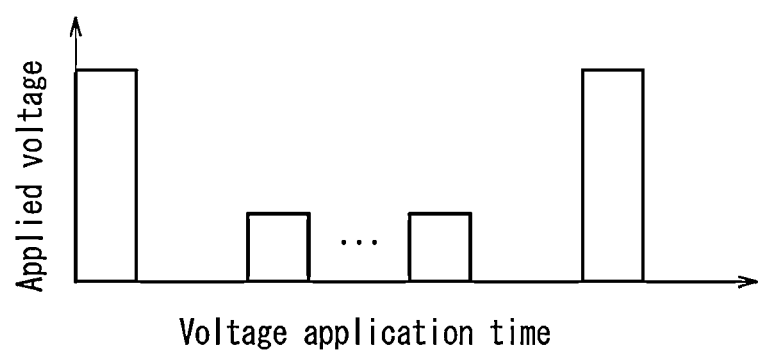
Figure 80:
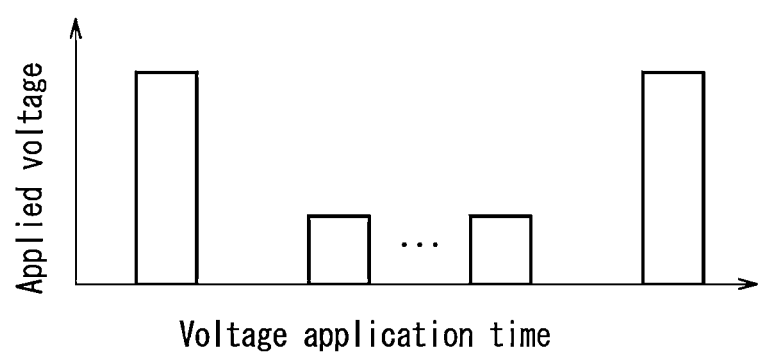

FIG. 80 (a) shows the relationship between voltage application time and applied voltage in Examples 53 to 73 of Embodiment 3 and Comparative Examples 9 to 13. Furthermore, (b) shows the relationship between voltage application time and applied voltage in Examples 74 to 93 of Embodiment 3 and Comparative Example 14.

Figure 81A:
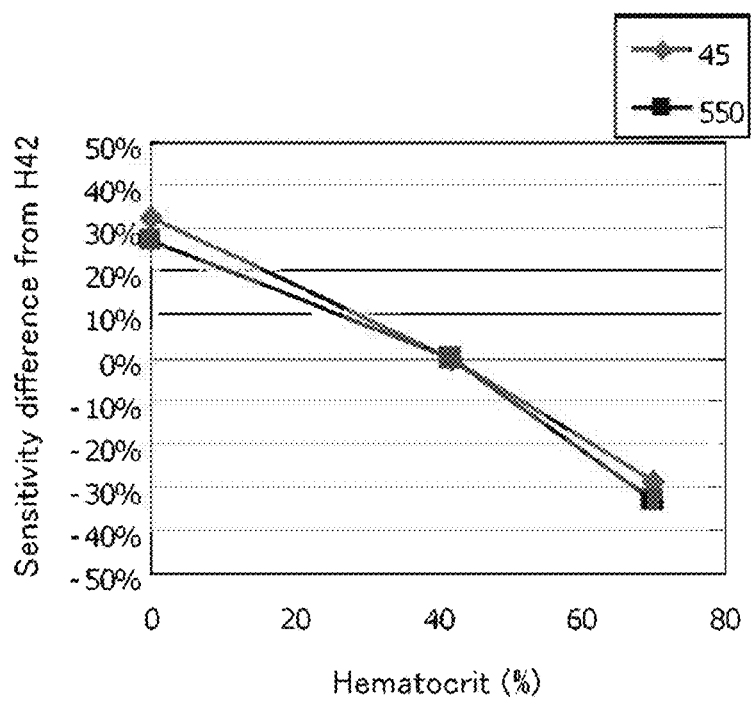

FIG. 81a is a graph showing the sensitivity difference (%) in each case of Glu values of 45 mg/dl and 550 mg/dl with reference to Hct 42% in Example 53.

Figure 81B:
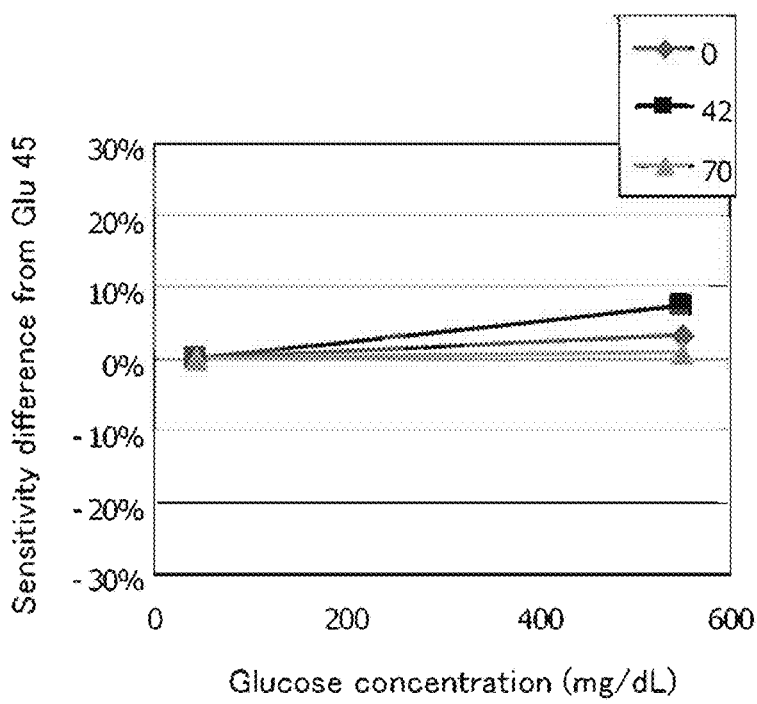

FIG. 81b is a graph showing the sensitivity difference (%) in each case of Hct values of 0%, 42%, and 70% with reference to Glu 45 mg/dl in Example 53.

Figure 82A:
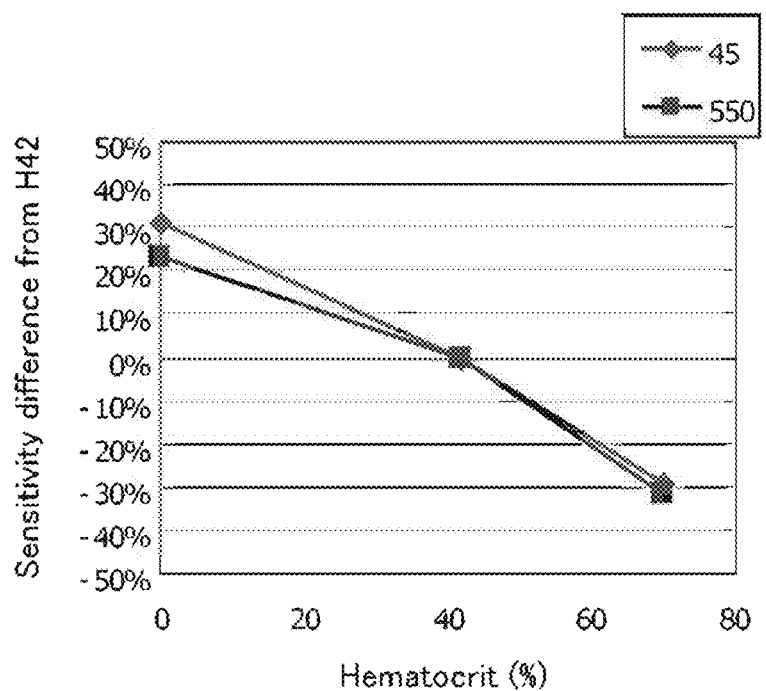

FIG. 82a is a graph showing the sensitivity difference (%) in each case of Glu values of 45 mg/dl and 550 mg/dl with reference to Hct 42% in Example 54.

Figure 82B:
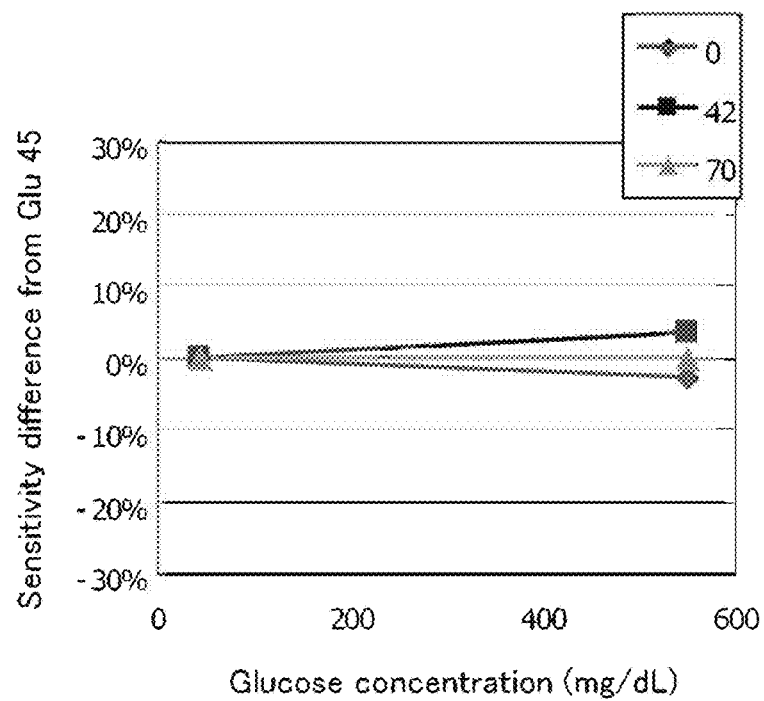

FIG. 82b is a graph showing the sensitivity difference (%) in each case of Hct values of 0%, 42%, and 70% with reference to Glu 45 mg/dl in Example 54.

Figure 83A:
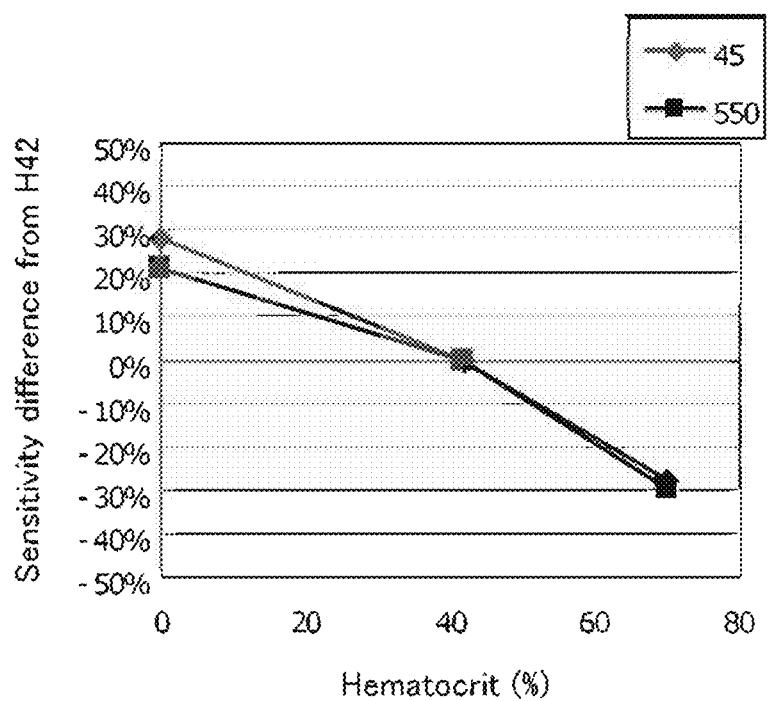

FIG. 83a is a graph showing the sensitivity difference (%) in each case of Glu values of 45 mg/dl and 550 mg/dl with reference to Hct 42% in Example 55.

Figure 83B:
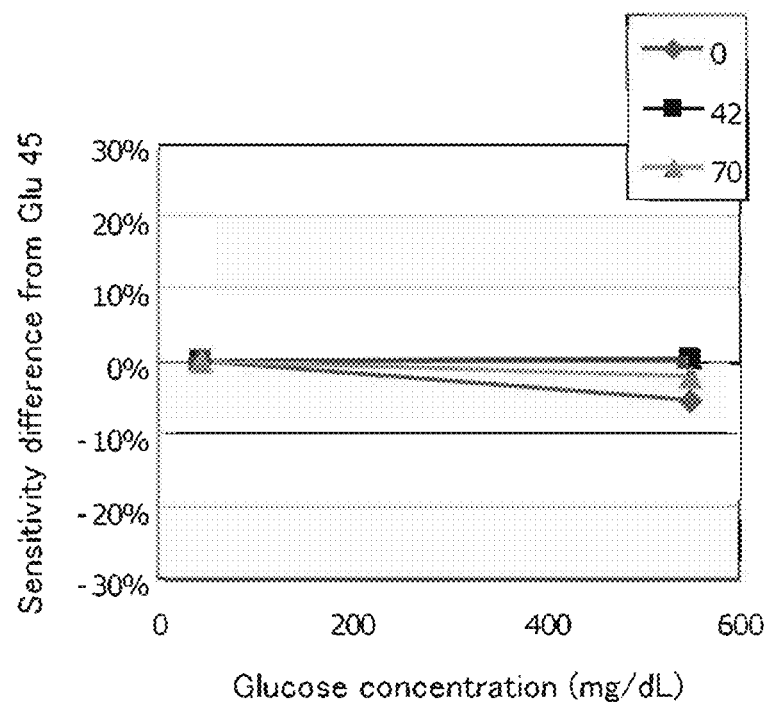

FIG. 83b is a graph showing the sensitivity difference (%) in each case of Hct values of 0%, 42%, and 70% with reference to Glu 45 mg/dl in Example 55.

Figure 84A:
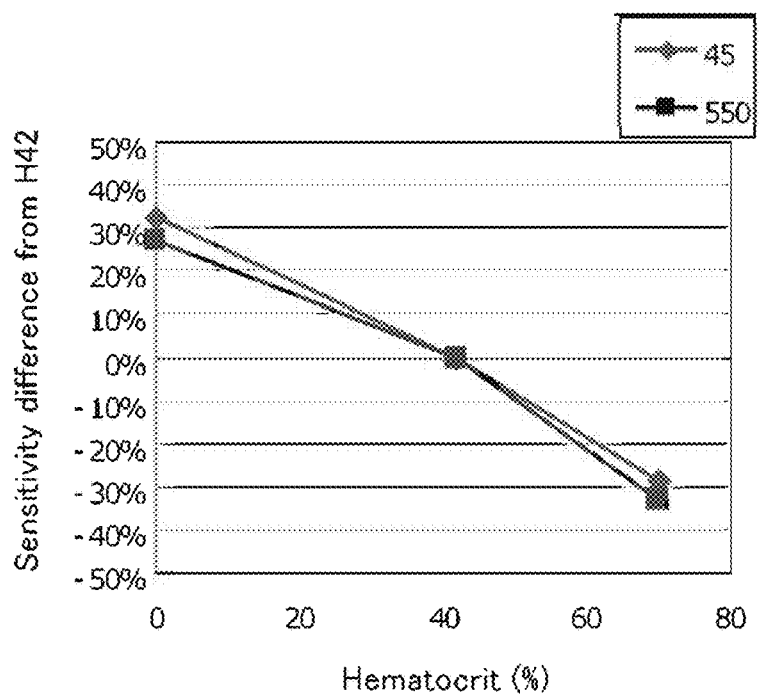

FIG. 84a is a graph showing the sensitivity difference (%) in each case of Glu values of 45 mg/dl and 550 mg/dl with reference to Hct 42% in Example 56.

Figure 84B:
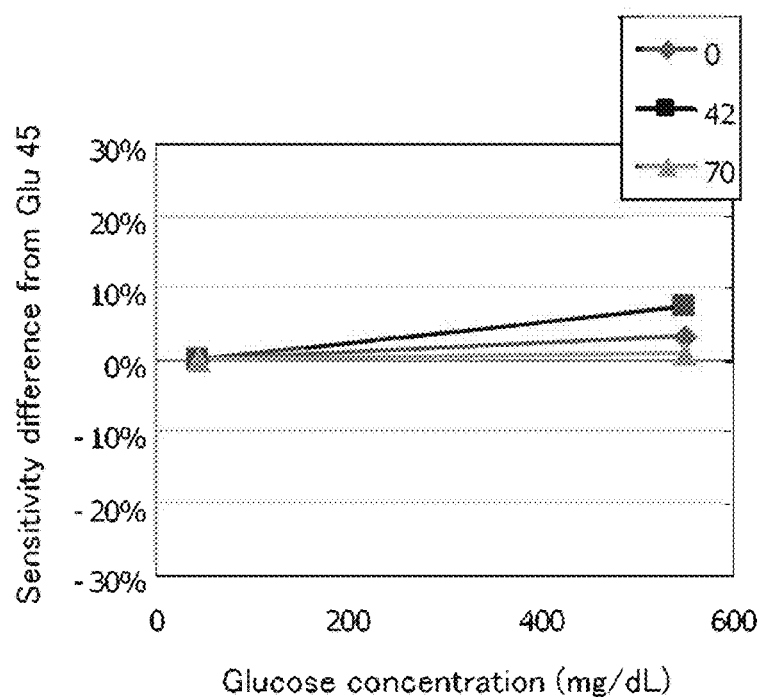

FIG. 84b is a graph showing the sensitivity difference (%) in each case of Hct values of 0%, 42%, and 70% with reference to Glu 45 mg/dl in Example 56.

Figure 85A:
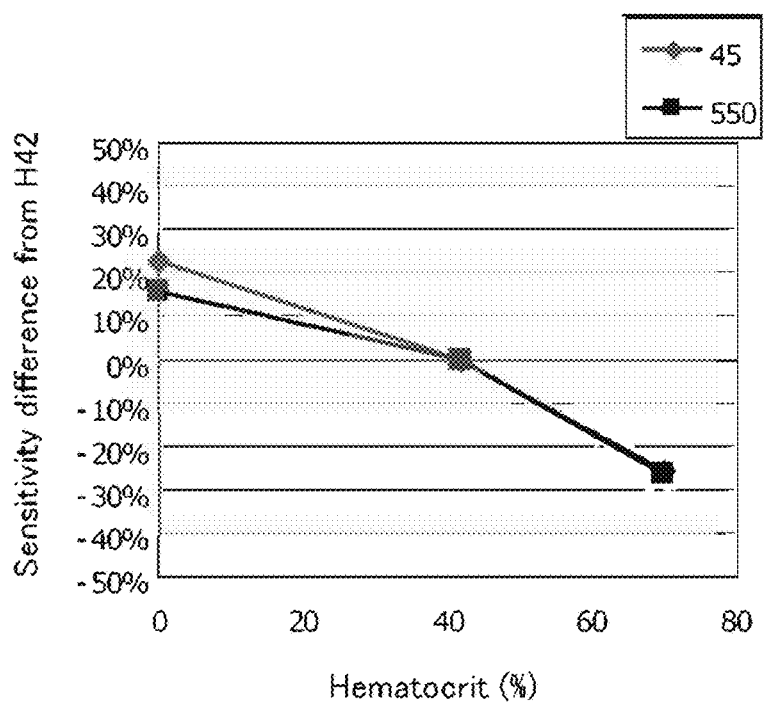

FIG. 85a is a graph showing the sensitivity difference (%) in each case of Glu values of 45 mg/dl and 550 mg/dl with reference to Hct 42% in Example 57.

Figure 85B:
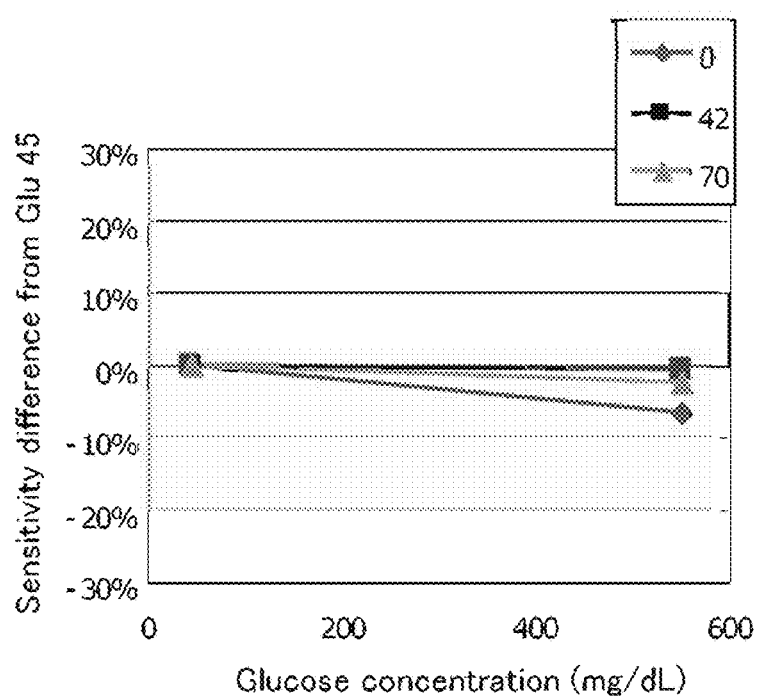

FIG. 85b is a graph showing the sensitivity difference (%) in each case of Hct values of 0%, 42%, and 70% with reference to Glu 45 mg/dl in Example 57.

Figure 86A:
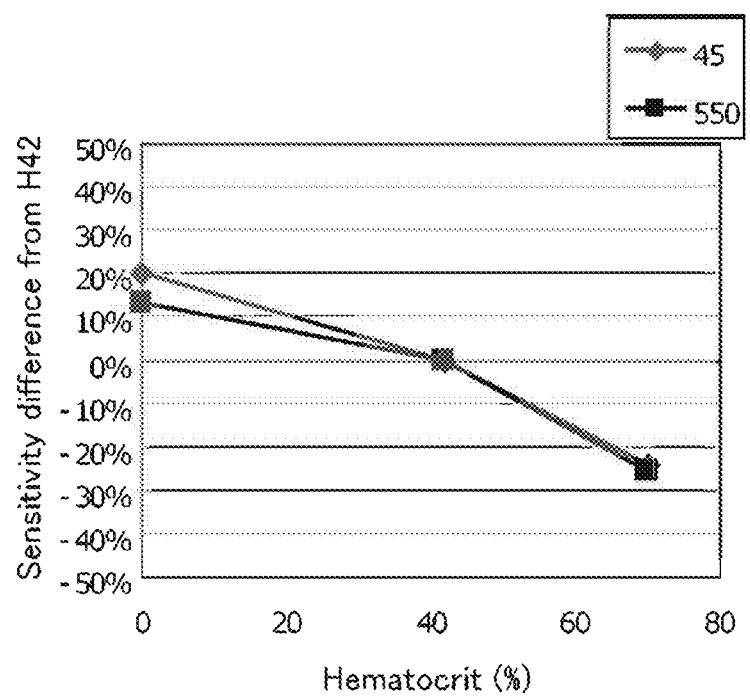

FIG. 86a is a graph showing the sensitivity difference (%) in each case of Glu values of 45 mg/dl and 550 mg/dl with reference to Hct 42% in Example 58.

Figure 86B:
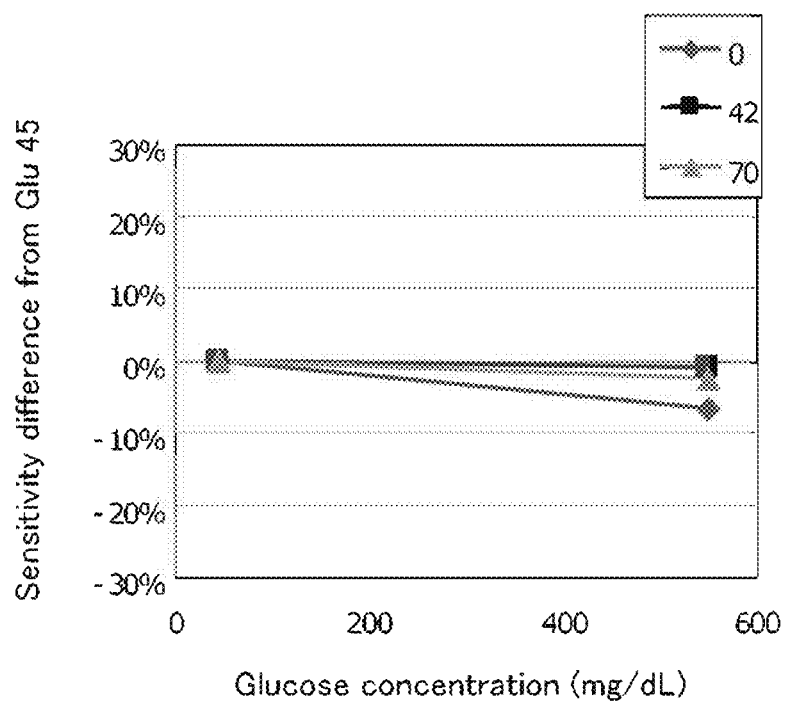

FIG. 86b is a graph showing the sensitivity difference (%) in each case of Hct values of 0%, 42%, and 70% with reference to Glu 45 mg/dl in Example 58.

Figure 87A:
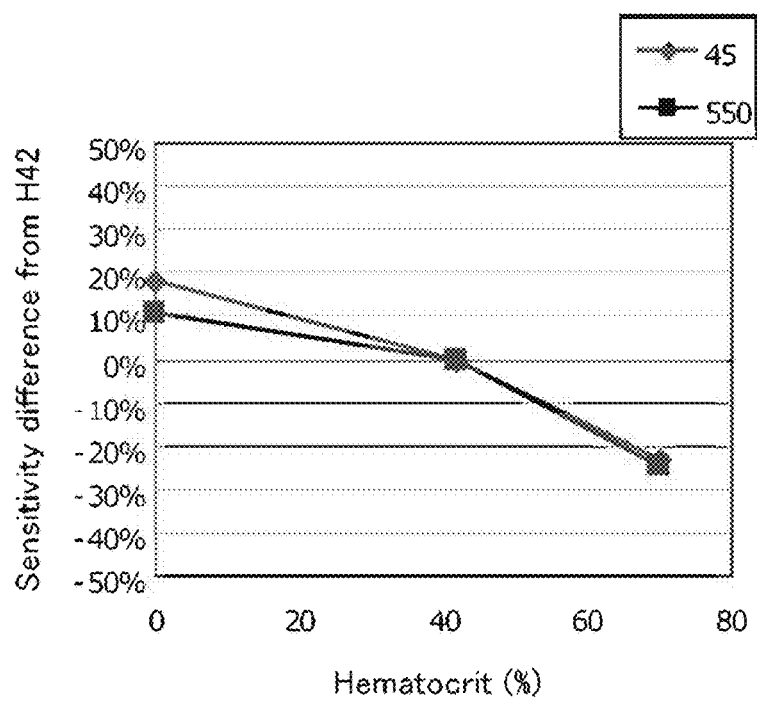

FIG. 87a is a graph showing the sensitivity difference (%) in each case of Glu values of 45 mg/dl and 550 mg/dl with reference to Hct 42% in Example 59.

Figure 87B:
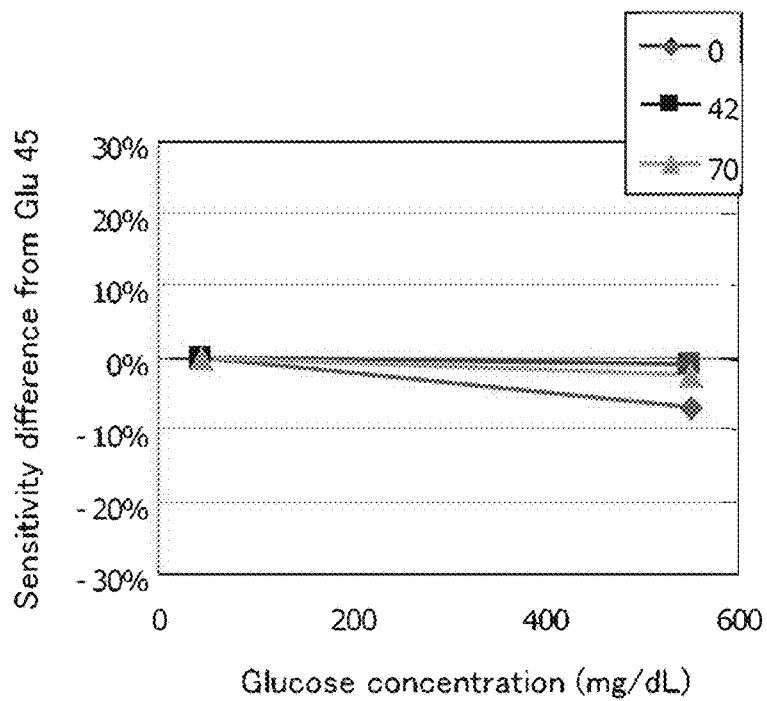

FIG. 87b is a graph showing the sensitivity difference (%) in each case of Hct values of 0%, 42%, and 70% with reference to Glu 45 mg/dl in Example 59.

Figure 88A:
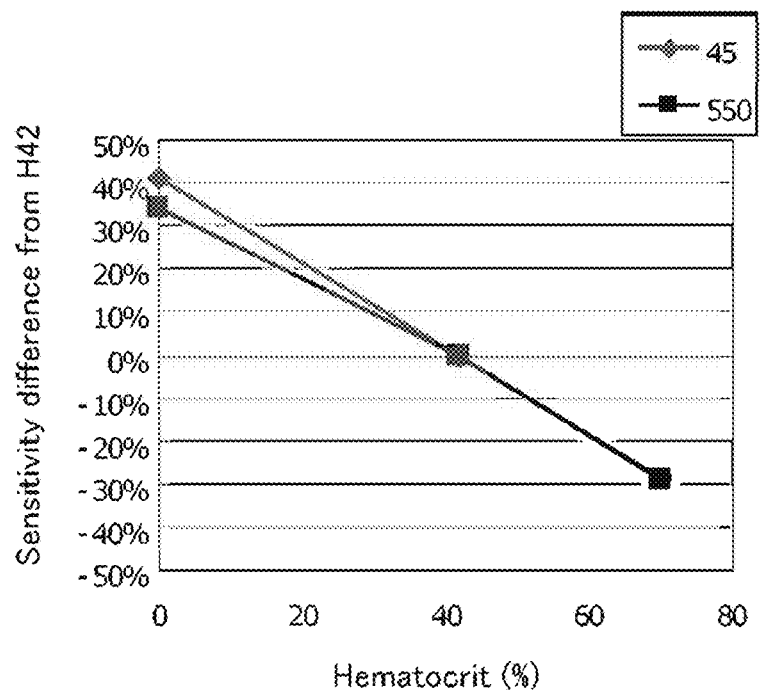

FIG. 88a is a graph showing the sensitivity difference (%) in each case of Glu values of 45 mg/dl and 550 mg/dl with reference to Hct 42% in Example 60.

Figure 88B:
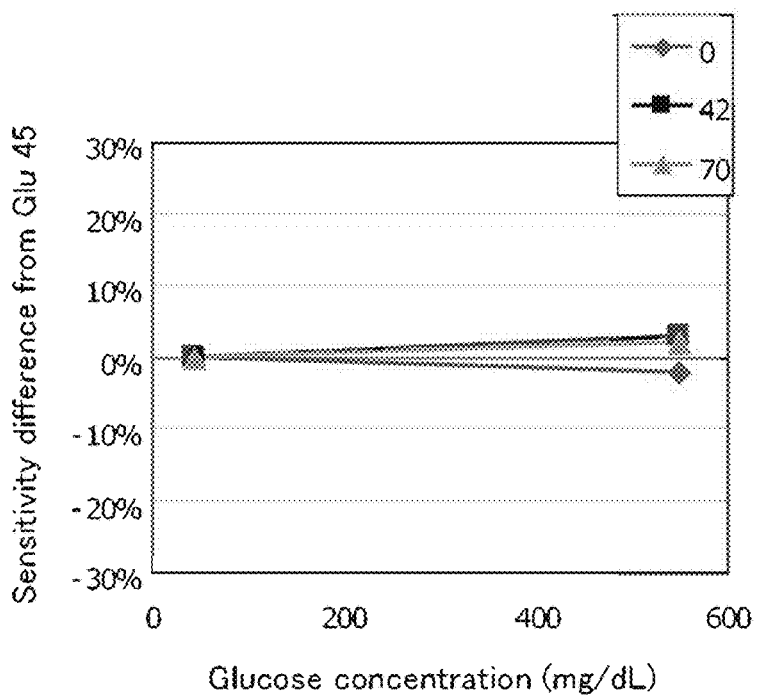

FIG. 88b is a graph showing the sensitivity difference (%) in each case of Hct values of 0%, 42%, and 70% with reference to Glu 45 mg/dl in Example 60.

Figure 89A:
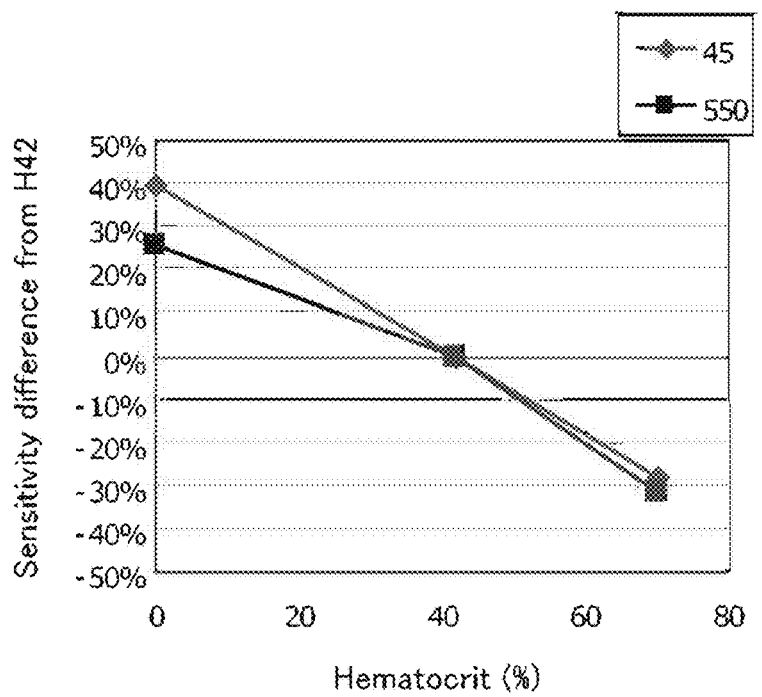

FIG. 89a is a graph showing the sensitivity difference (%) in each case of Glu values of 45 mg/dl and 550 mg/dl with reference to Hct 42% in Example 61.

Figure 89B:
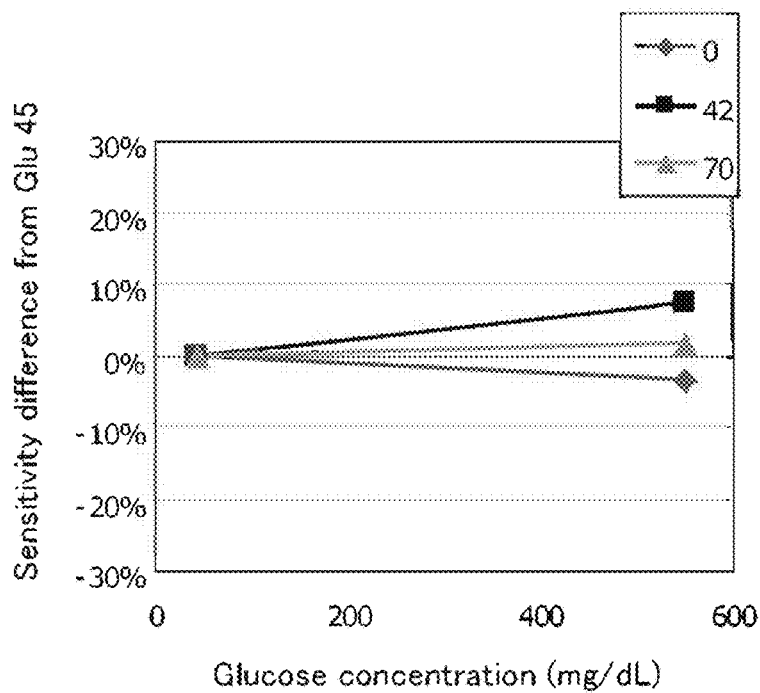

FIG. 89b is a graph showing the sensitivity difference (%) in each case of Hct values of 0%, 42%, and 70% with reference to Glu 45 mg/dl in Example 61.

Figure 90A:
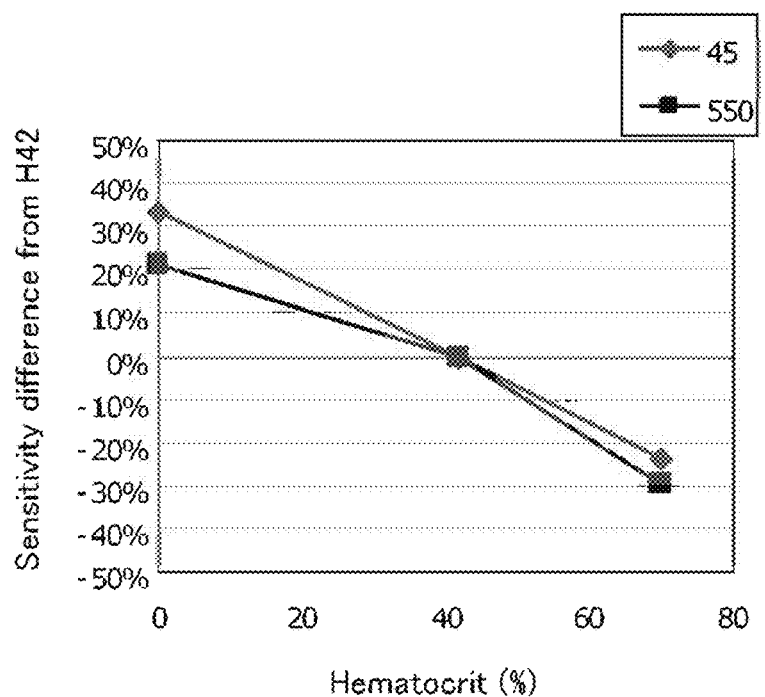

FIG. 90a is a graph showing the sensitivity difference (%) in each case of Glu values of 45 mg/dl and 550 mg/dl with reference to Hct 42% in Example 62.

Figure 90B:
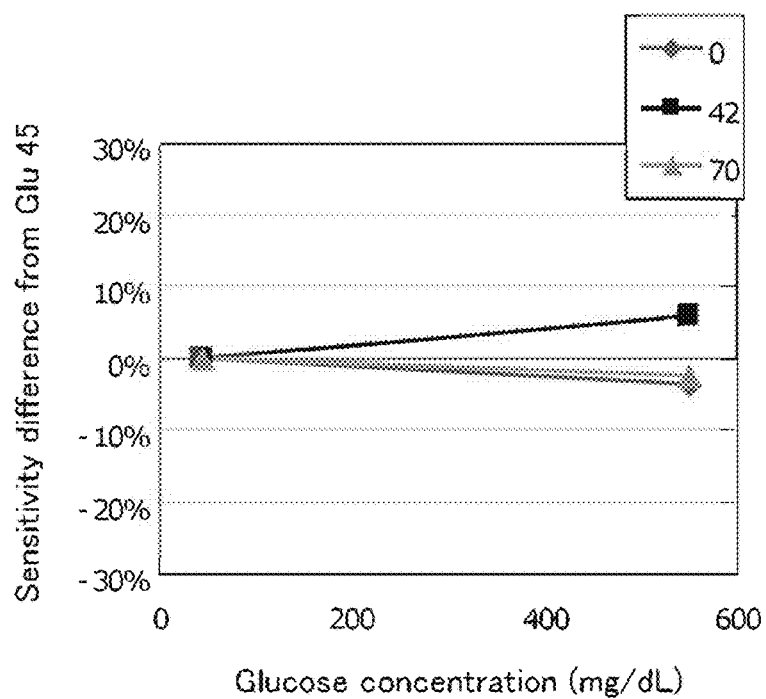

FIG. 90b is a graph showing the sensitivity difference (%) in each case of Hct values of 0%, 42%, and 70% with reference to Glu 45 mg/dl in Example 62.

Figure 91A:
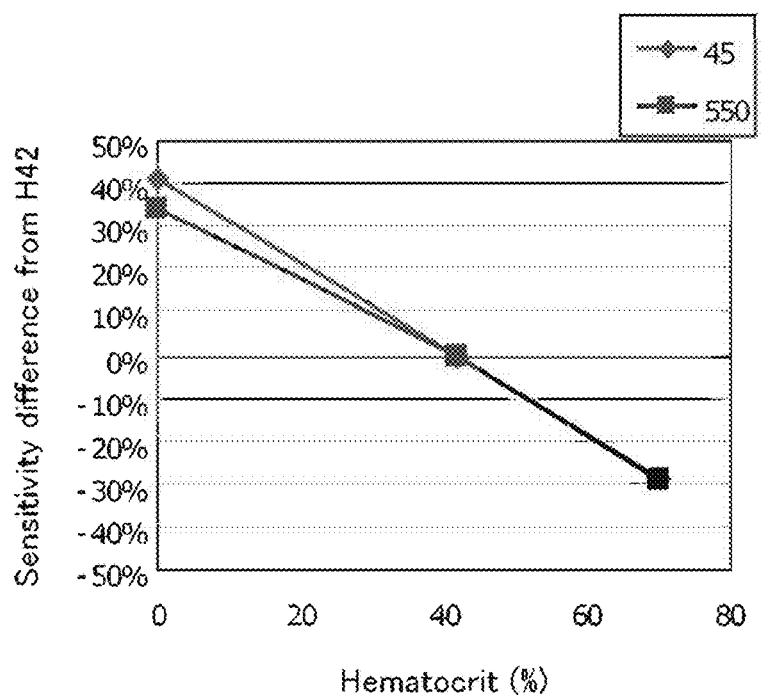

FIG. 91a is a graph showing the sensitivity difference (%) in each case of Glu values of 45 mg/dl and 550 mg/dl with reference to Hct 42% in Example 63.

Figure 91B:
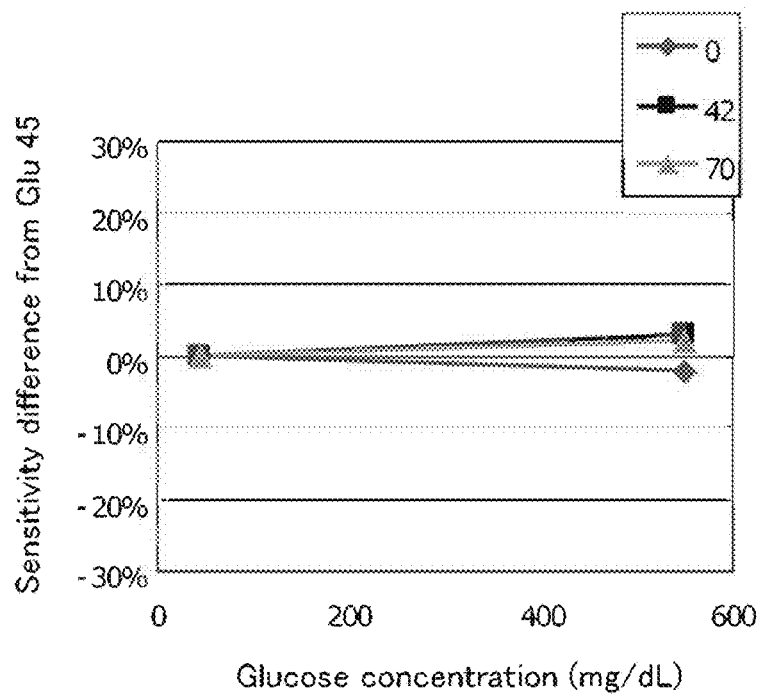

FIG. 91b is a graph showing the sensitivity difference (%) in each case of Hct values of 0%, 42%, and 70% with reference to Glu 45 mg/dl in Example 63.

Figure 92A:
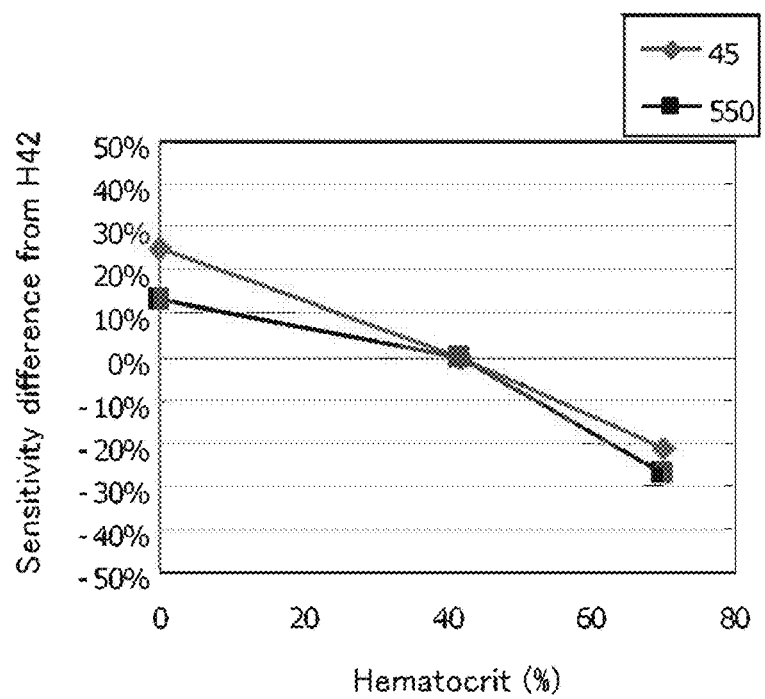

FIG. 92a is a graph showing the sensitivity difference (%) in each case of Glu values of 45 mg/dl and 550 mg/dl with reference to Hct 42% in Example 64.

Figure 92B:
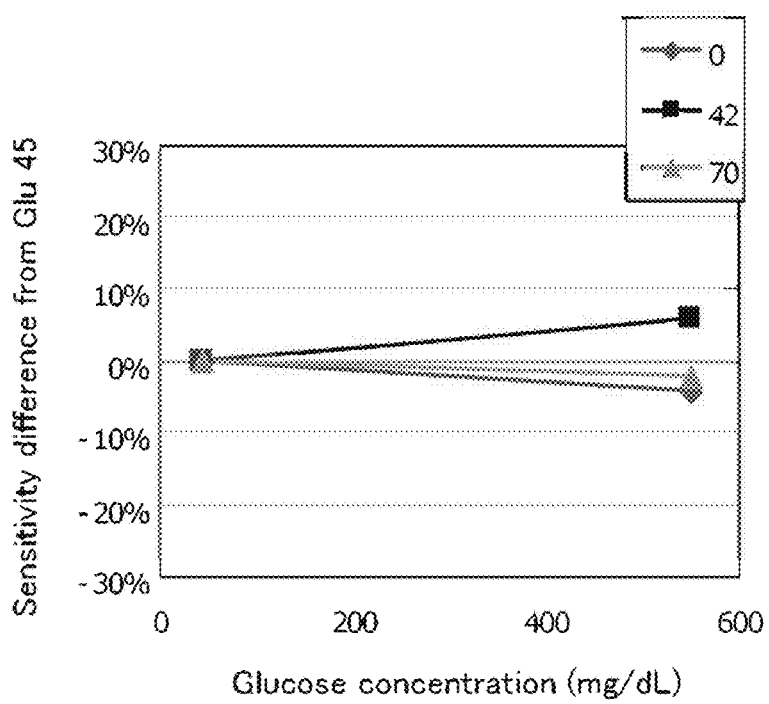

FIG. 92b is a graph showing the sensitivity difference (%) in each case of Hct values of 0%, 42%, and 70% with reference to Glu 45 mg/dl in Example 64.

Figure 93A:
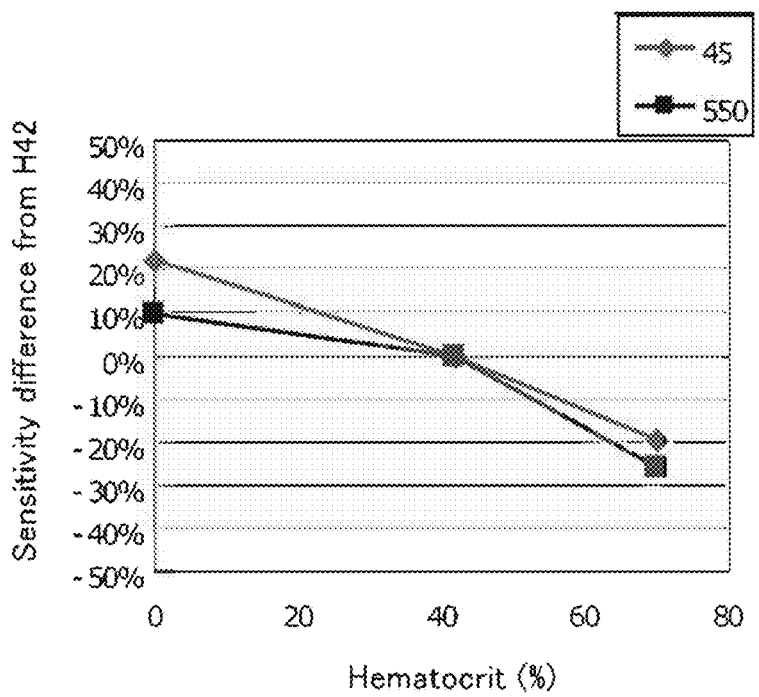

FIG. 93a is a graph showing the sensitivity difference (%) in each case of Glu values of 45 mg/dl and 550 mg/dl with reference to Hct 42% in Example 65.

Figure 93B:
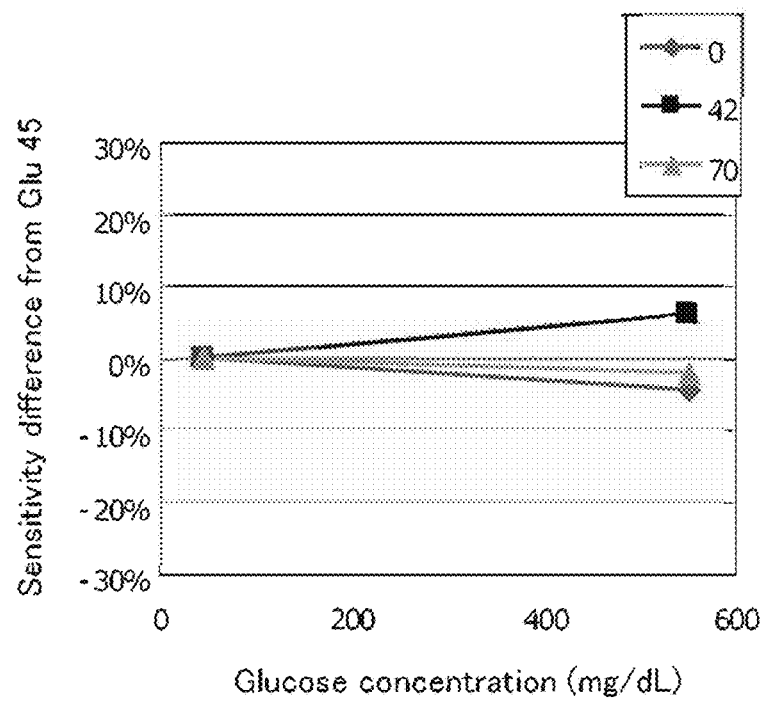

FIG. 93b is a graph showing the sensitivity difference (%) in each case of Hct values of 0%, 42%, and 70% with reference to Glu 45 mg/dl in Example 65.

Figure 94A:
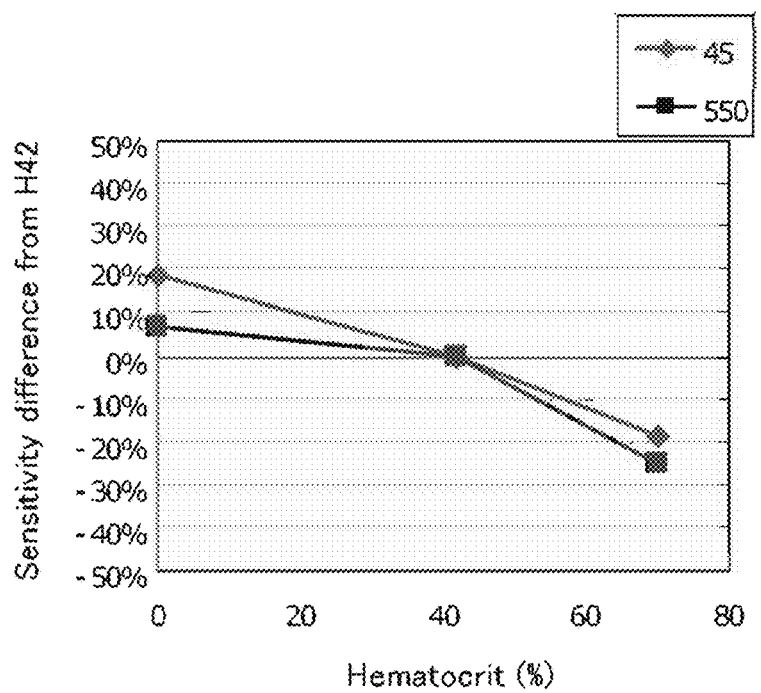

FIG. 94a is a graph showing the sensitivity difference (%) in each case of Glu values of 45 mg/dl and 550 mg/dl with reference to Hct 42% in Example 66.

Figure 94B:
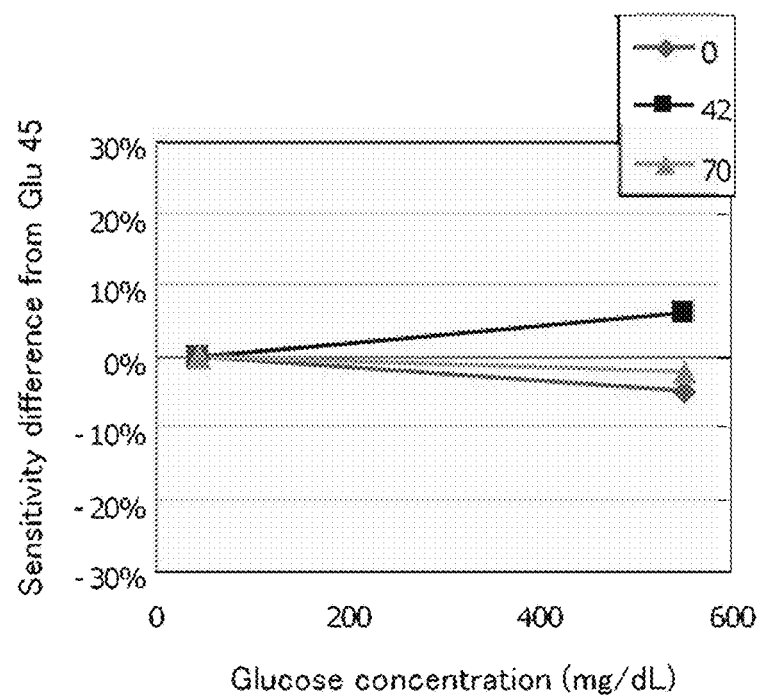

FIG. 94b is a graph showing the sensitivity difference (%) in each case of Hct values of 0%, 42%, and 70% with reference to Glu 45 mg/dl in Example 66.

Figure 95A:
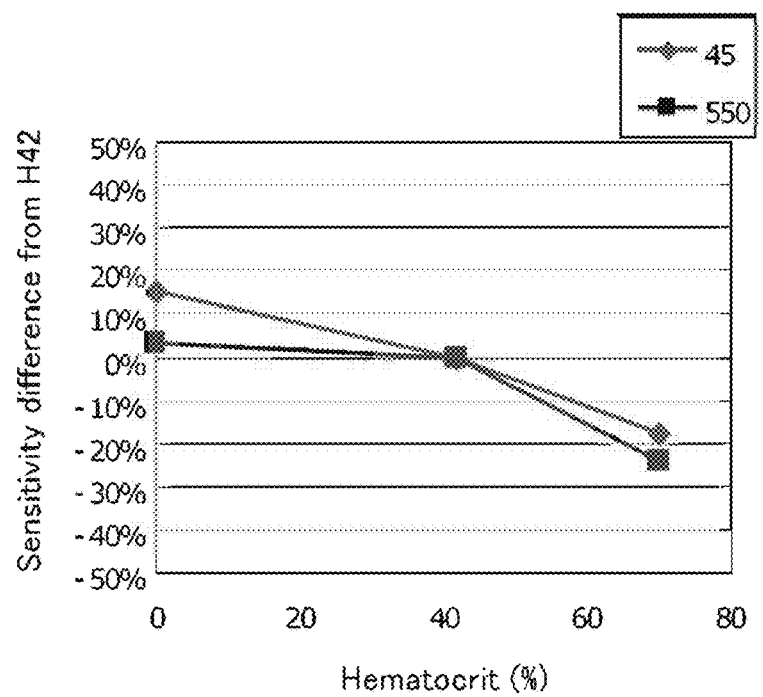

FIG. 95a is a graph showing the sensitivity difference (%) in each case of Glu values of 45 mg/dl and 550 mg/dl with reference to Hct 42% in Comparative Example 9.

Figure 95B:
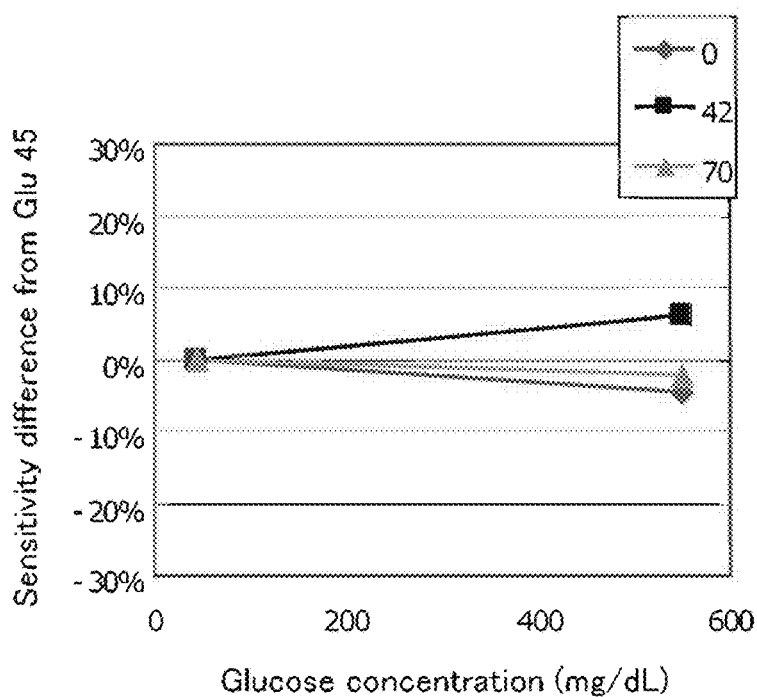

FIG. 95b is a graph showing the sensitivity difference (%) in each case of Hct values of 0%, 42%, and 70% with reference to Glu 45 mg/dl in Comparative Example 9.

Figure 96A:
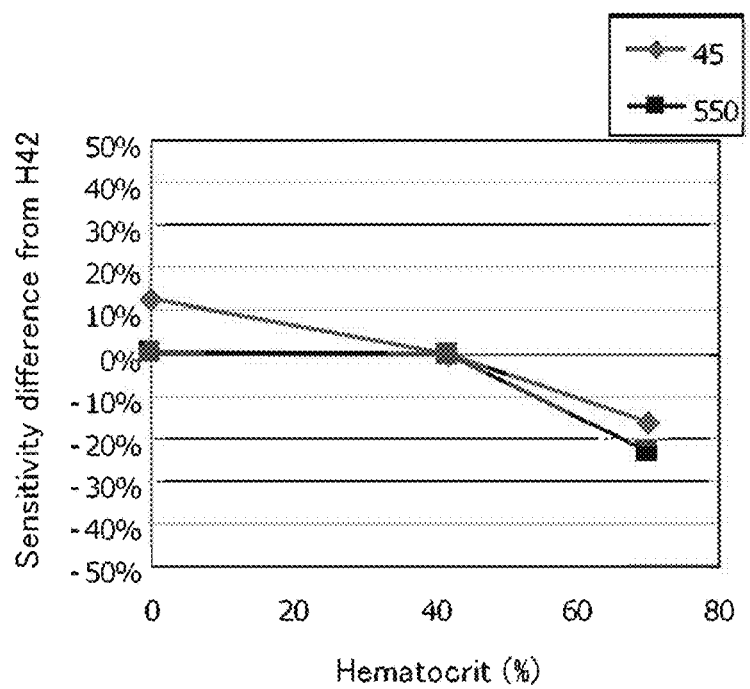

FIG. 96a is a graph showing the sensitivity difference (%) in each case of Glu values of 45 mg/dl and 550 mg/dl with reference to Hct 42% in Comparative Example 10.

Figure 96B:
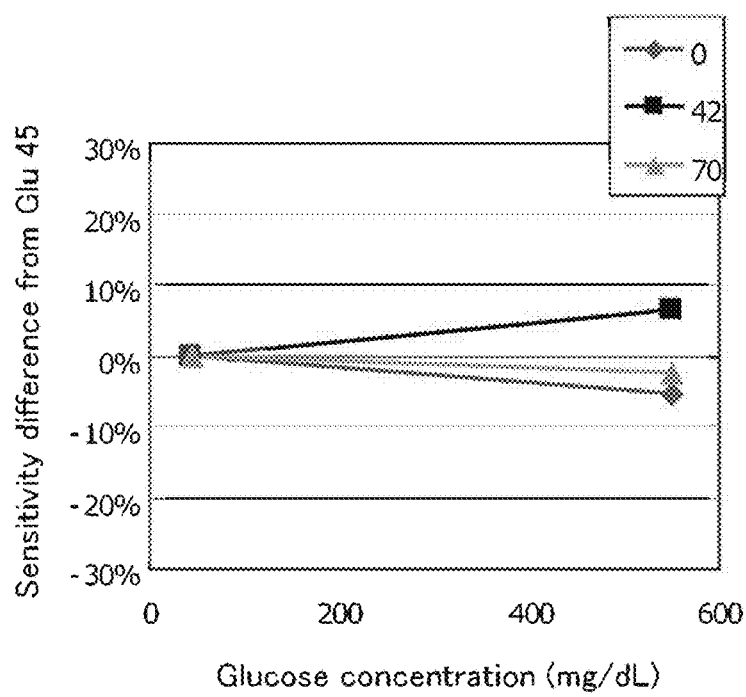

FIG. 96b is a graph showing the sensitivity difference (%) in each case of Hct values of 0%, 42%, and 70% with reference to Glu 45 mg/dl in Comparative Example 10.

Figure 97A:
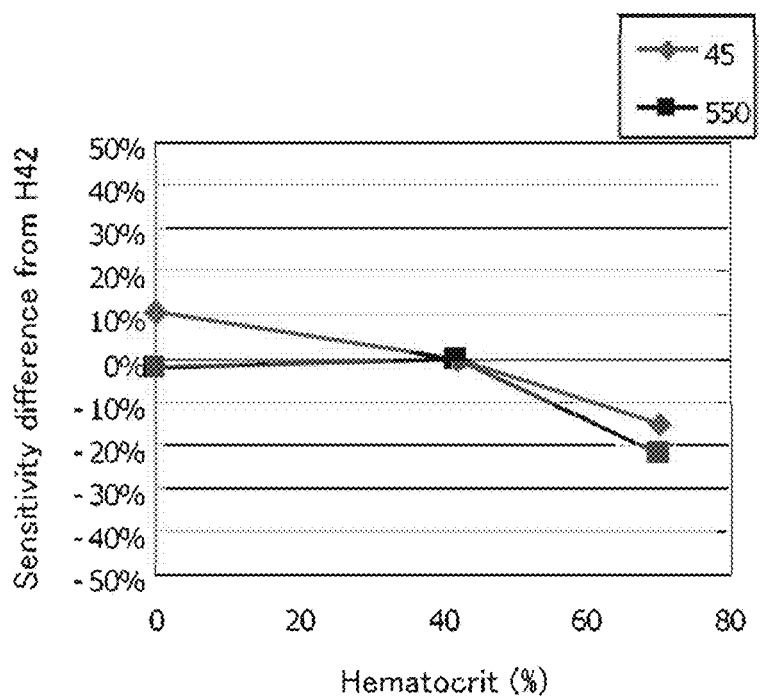

FIG. 97a is a graph showing the sensitivity difference (%) in each case of Glu values of 45 mg/dl and 550 mg/dl with reference to Hct 42% in Comparative Example 11.

Figure 97B:
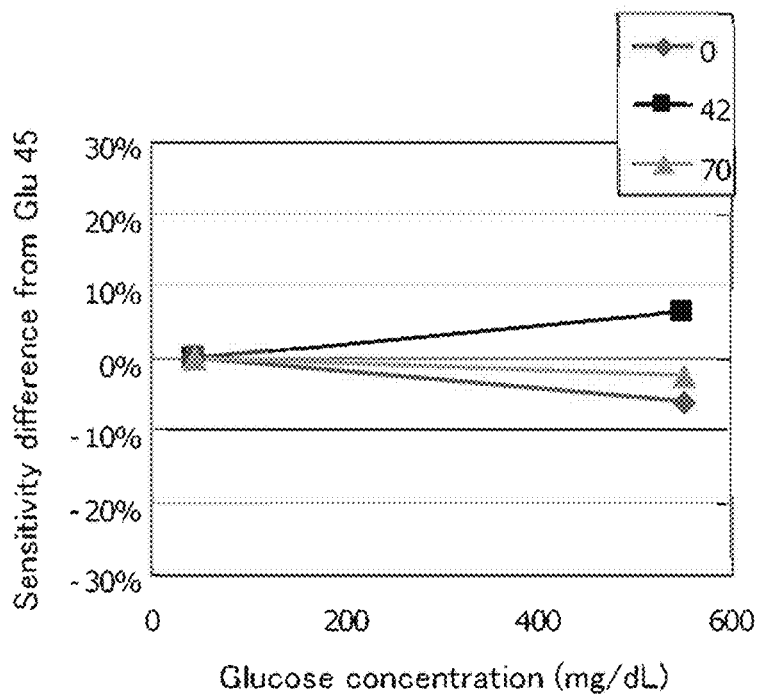

FIG. 97b is a graph showing the sensitivity difference (%) in each case of Hct values of 0%, 42%, and 70% with reference to Glu 45 mg/dl in Comparative Example 11.

Figure 98A:
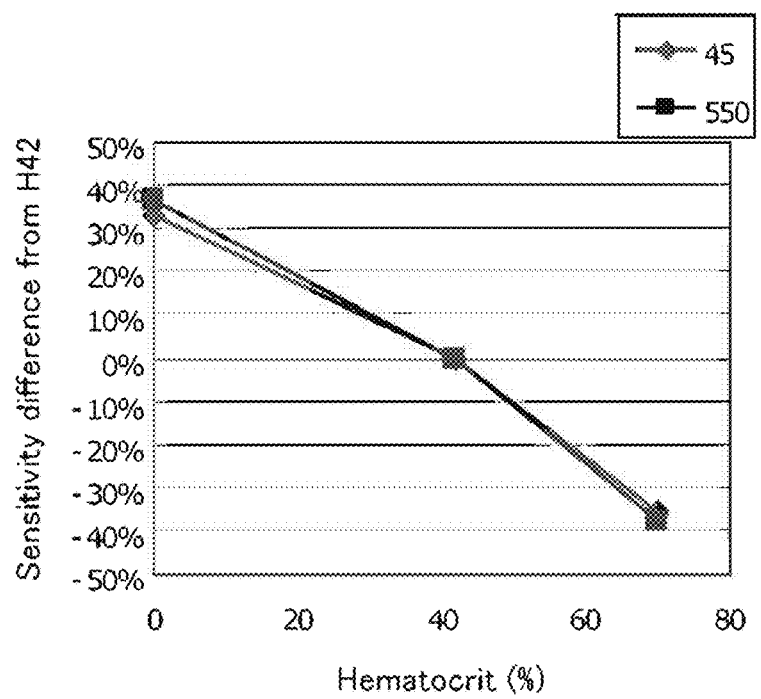

FIG. 98a is a graph showing the sensitivity difference (%) in each case of Glu values of 45 mg/dl and 550 mg/dl with reference to Hct 42% in Example 67.

Figure 98B:
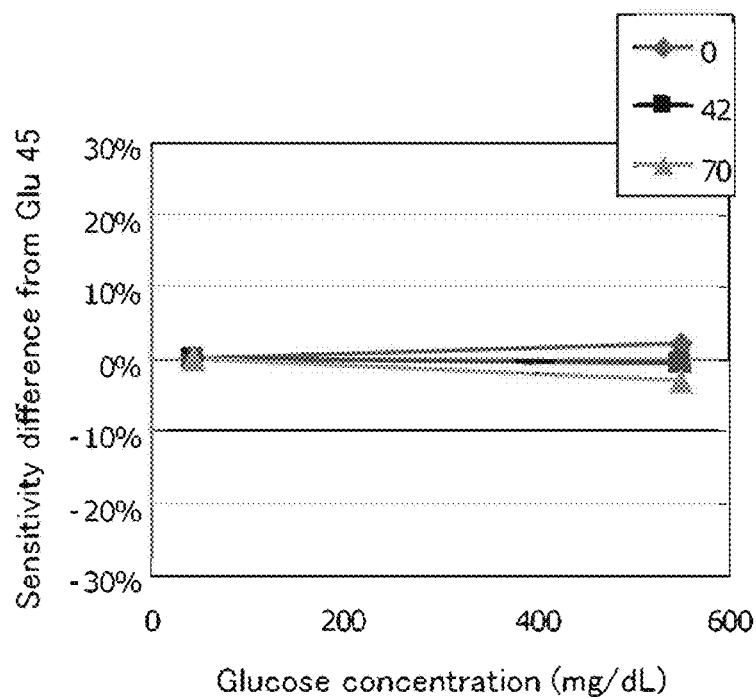

FIG. 98b is a graph showing the sensitivity difference (%) in each case of Hct values of 0%, 42%, and 70% with reference to Glu 45 mg/dl in Example 67.

Figure 99A:
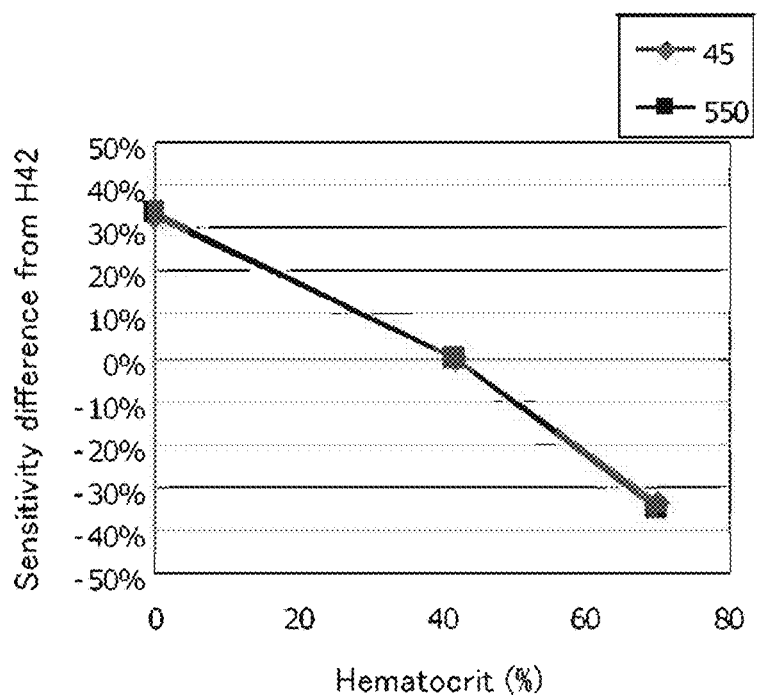

FIG. 99a is a graph showing the sensitivity difference (%) in each case of Glu values of 45 mg/dl and 550 mg/dl with reference to Hct 42% in Example 68.

Figure 99B:
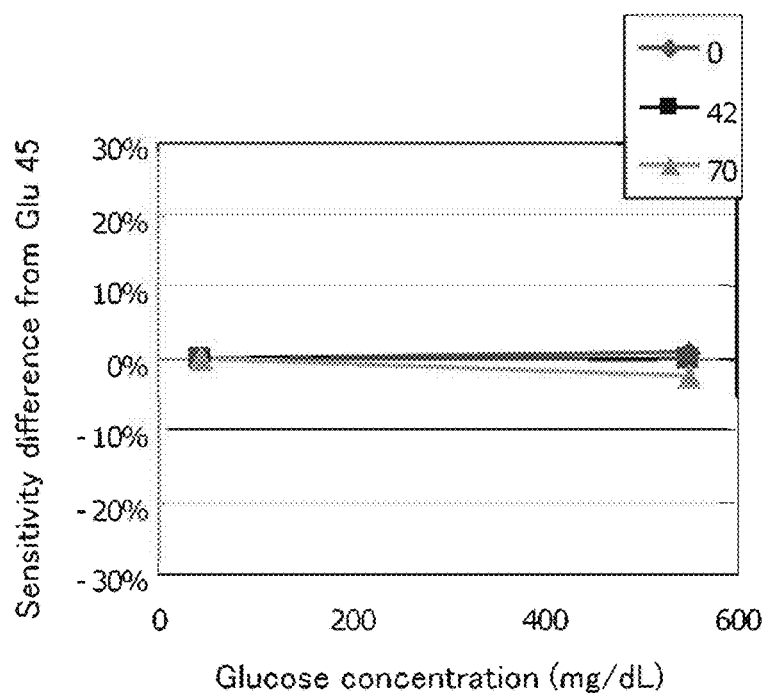

FIG. 99b is a graph showing the sensitivity difference (%) in each case of Hct values of 0%, 42%, and 70% with reference to Glu 45 mg/dl in Example 68.

Figure 100A:
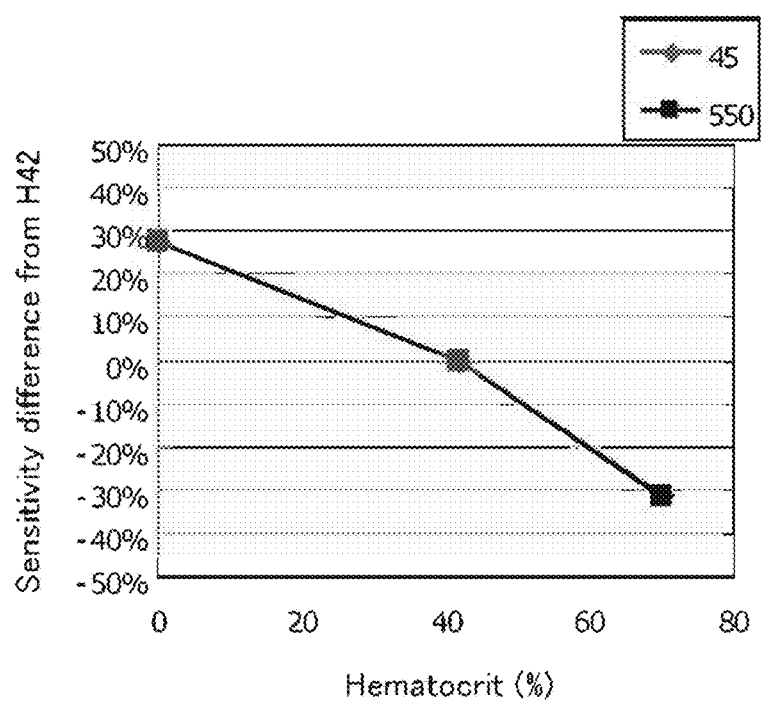

FIG. 100a is a graph showing the sensitivity difference (%) in each case of Glu values of 45 mg/dl and 550 mg/dl with reference to Hct 42% in Example 69.

Figure 100B:
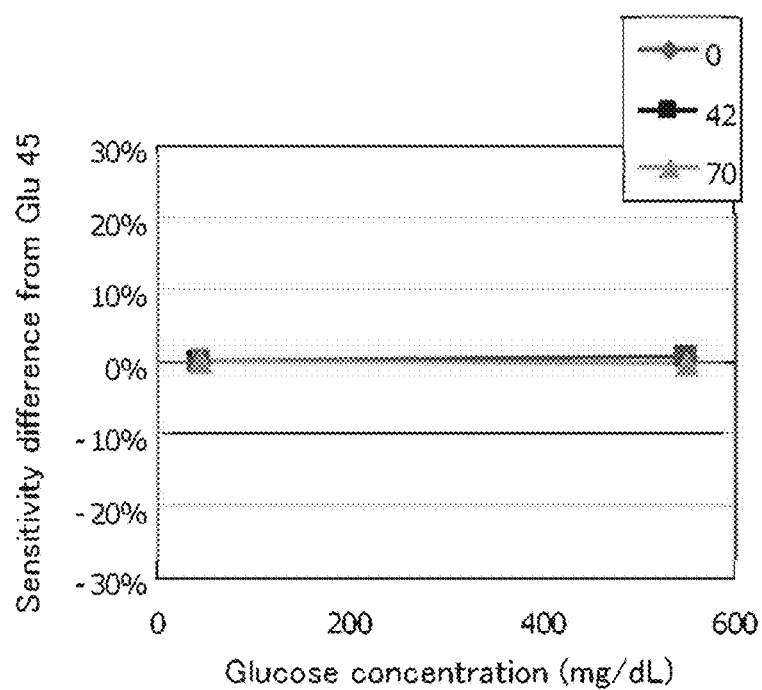

FIG. 100b is a graph showing the sensitivity difference (%) in each case of Hct values of 0%, 42%, and 70% with reference to Glu 45 mg/dl in Example 69.

Figure 101A:
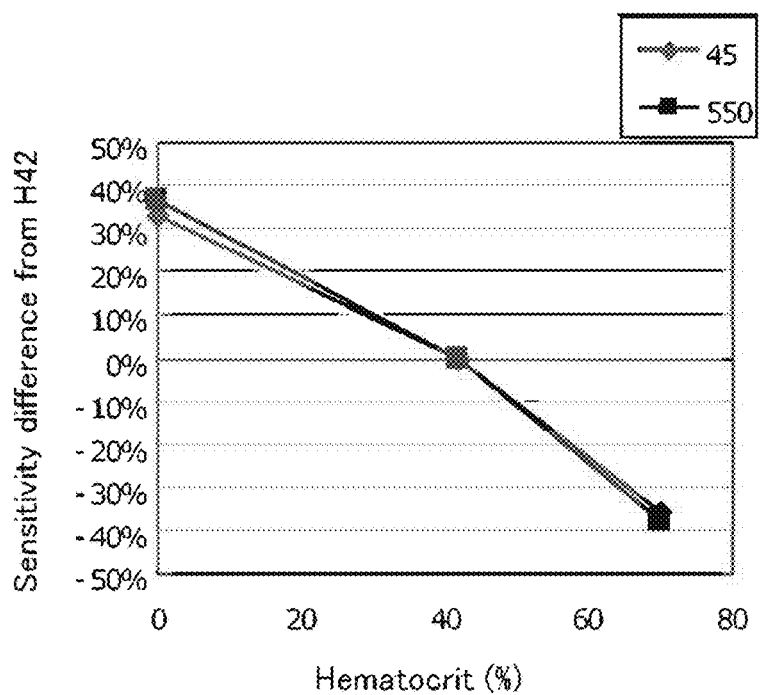

FIG. 101a is a graph showing the sensitivity difference (%) in each case of Glu values of 45 mg/dl and 550 mg/dl with reference to Hct 42% in Example 70.

Figure 101B:
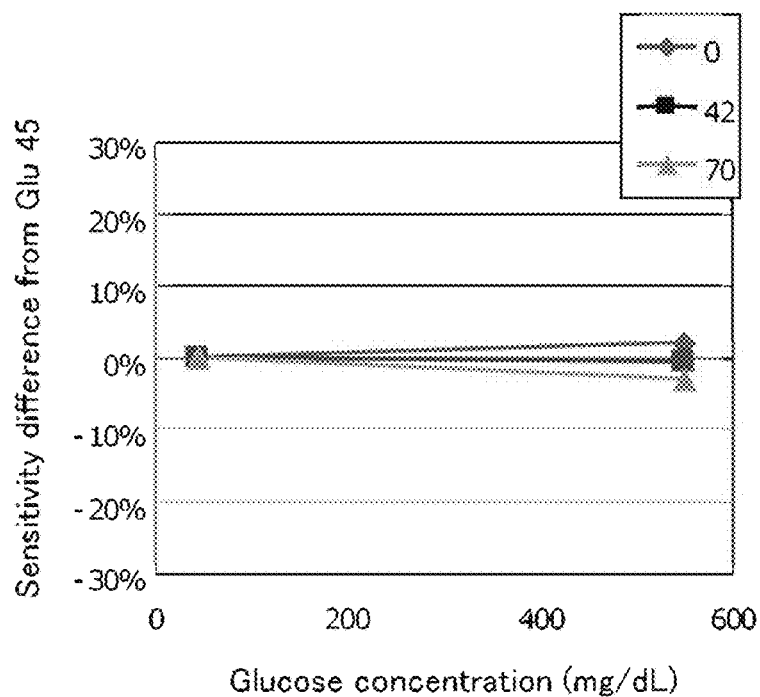

FIG. 101b is a graph showing the sensitivity difference (%) in each case of Hct values of 0%, 42%, and 70% with reference to Glu 45 mg/dl in Example 70.

Figure 102A:
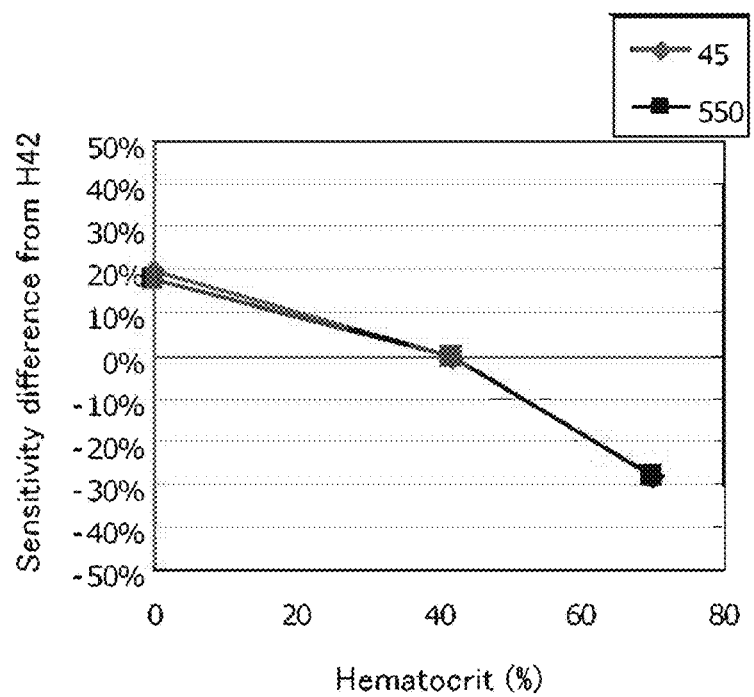

FIG. 102a is a graph showing the sensitivity difference (%) in each case of Glu values of 45 mg/dl and 550 mg/dl with reference to Hct 42% in Example 71.

Figure 102B:
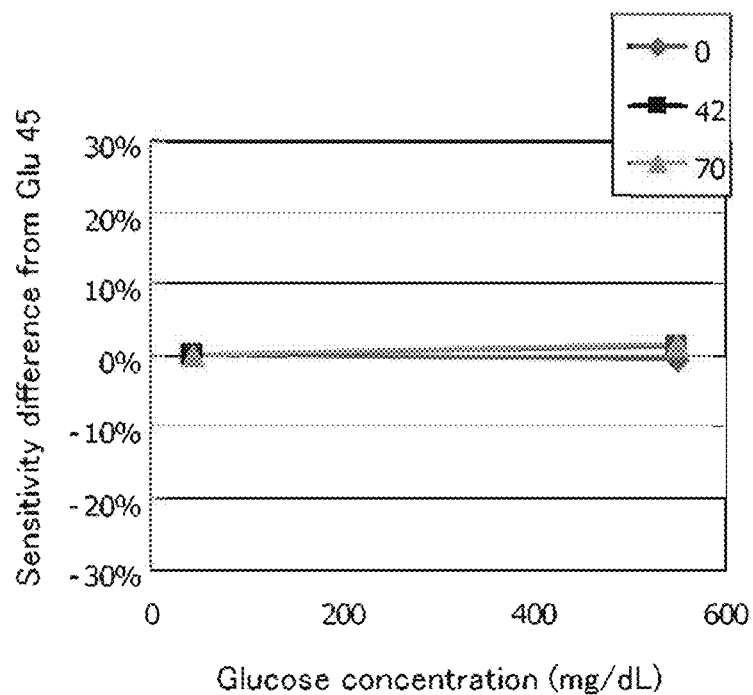

FIG. 102b is a graph showing the sensitivity difference (%) in each case of Hct values of 0%, 42%, and 70% with reference to Glu 45 mg/dl in Example 71.

Figure 103A:
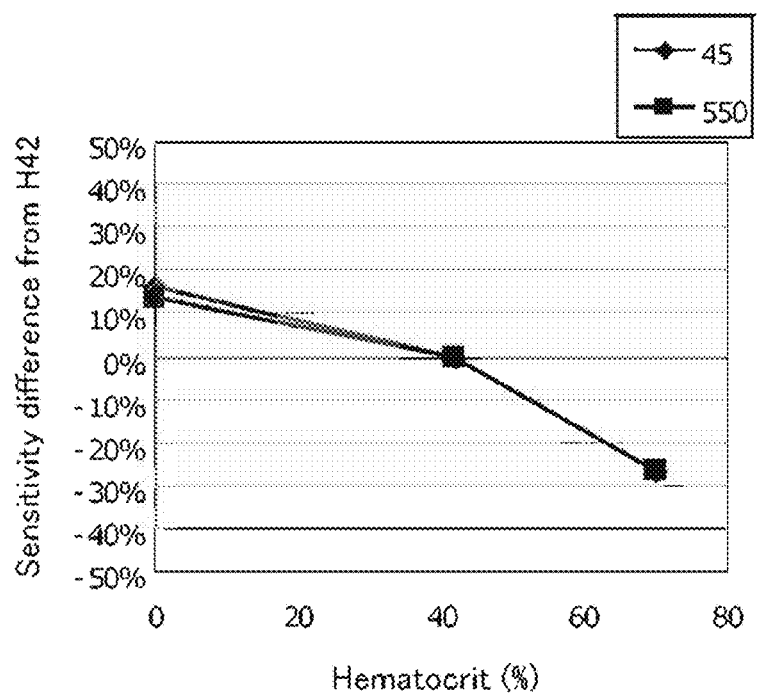

FIG. 103a is a graph showing the sensitivity difference (%) in each case of Glu values of 45 mg/dl and 550 mg/dl with reference to Hct 42% in Example 72.

Figure 103B:
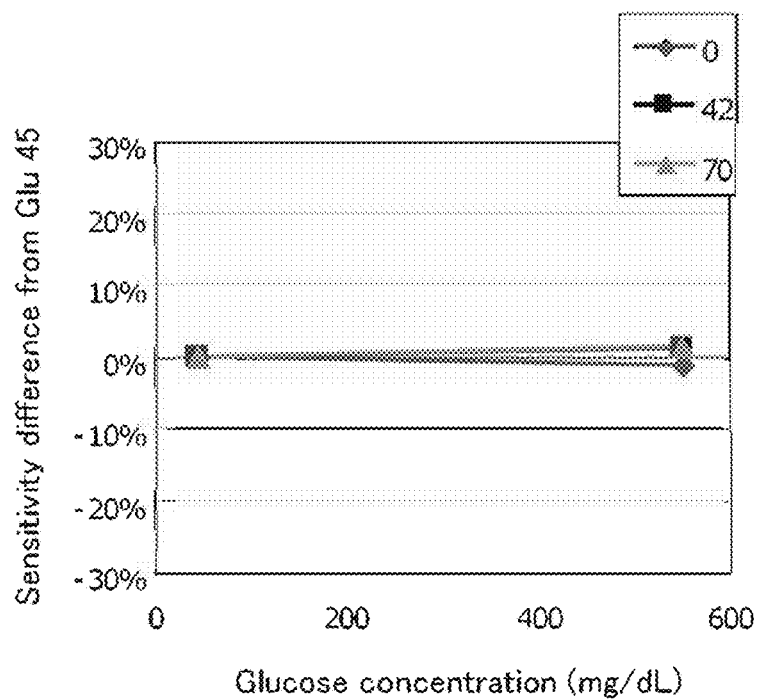

FIG. 103b is a graph showing the sensitivity difference (%) in each case of Hct values of 0%, 42%, and 70% with reference to Glu 45 mg/dl in Example 72.

Figure 104A:
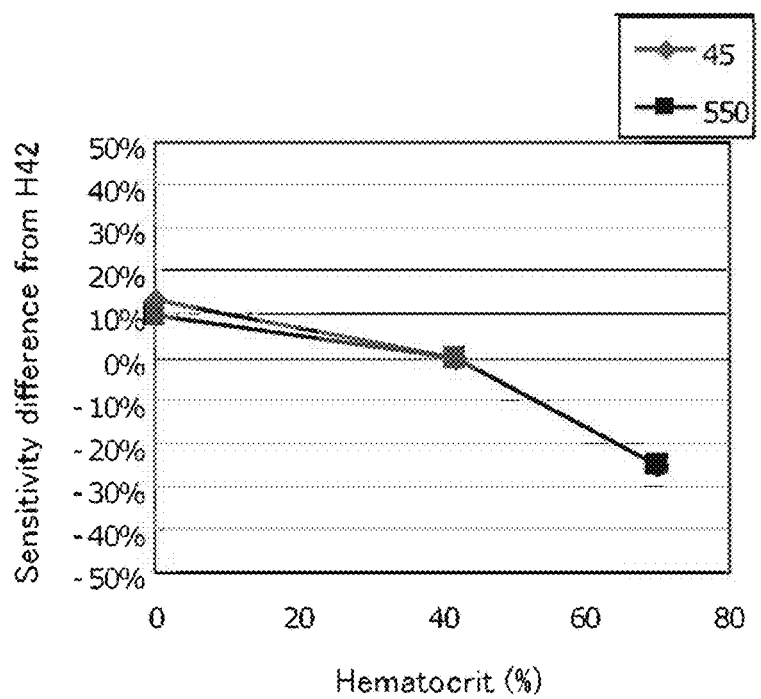

FIG. 104a is a graph showing the sensitivity difference (%) in each case of Glu values of 45 mg/dl and 550 mg/dl with reference to Hct 42% in Example 73.

Figure 104B:
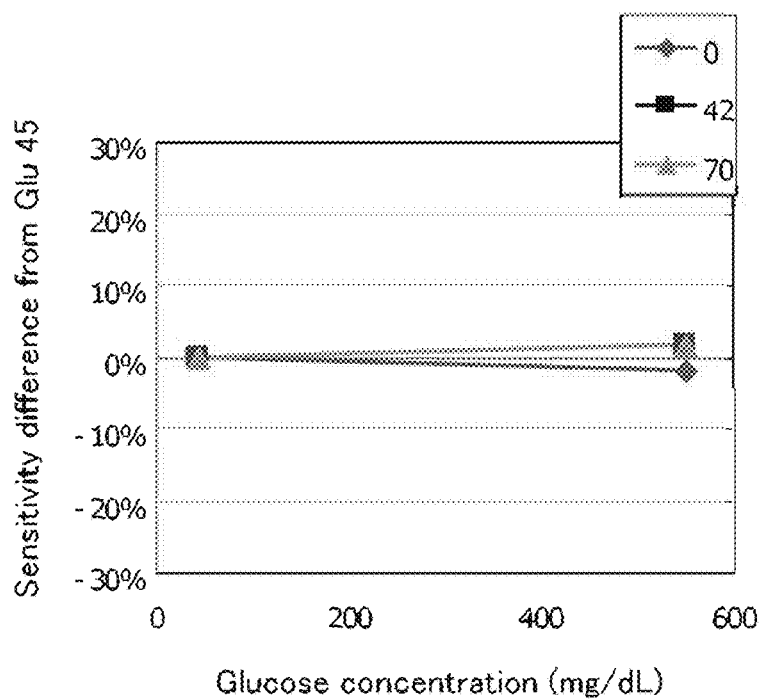

FIG. 104b is a graph showing the sensitivity difference (%) in each case of Hct values of 0%, 42%, and 70% with reference to Glu 45 mg/dl in Example 73.

Figure 105A:
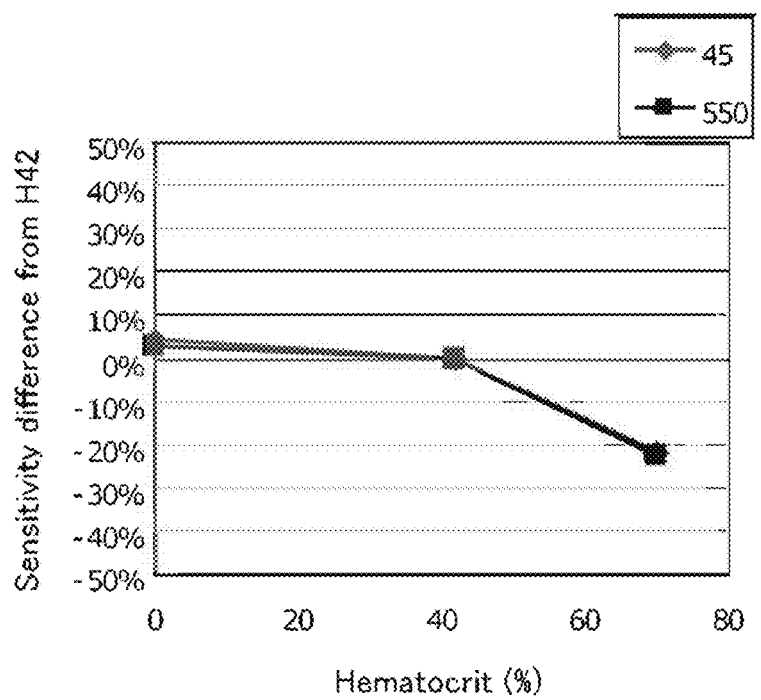

FIG. 105a is a graph showing the sensitivity difference (%) in each case of Glu values of 45 mg/dl and 550 mg/dl with reference to Hct 42% in Comparative Example 12.

Figure 105B:
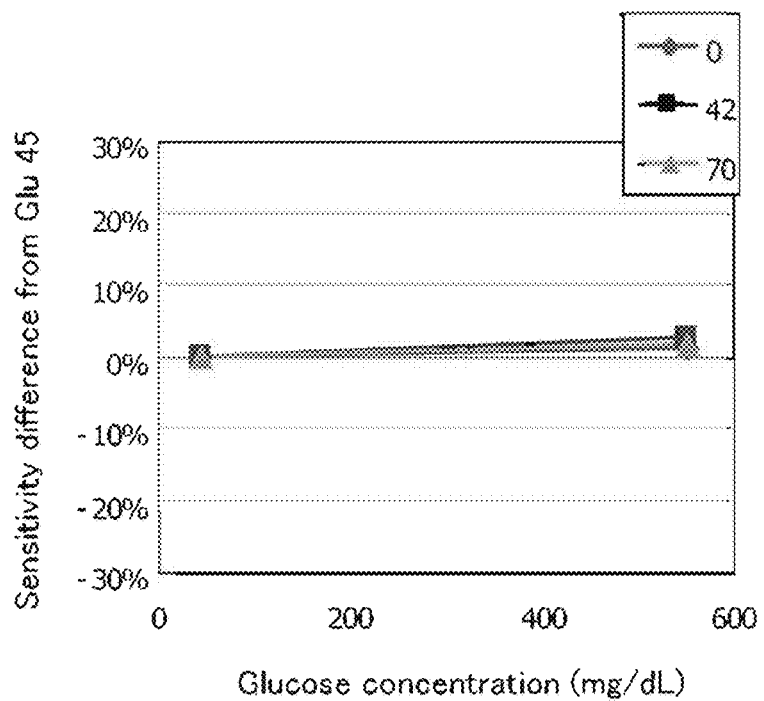

FIG. 105b is a graph showing the sensitivity difference (%) in each case of Hct values of 0%, 42%, and 70% with reference to Glu 45 mg/dl in Comparative Example 12.

Figure 106A:
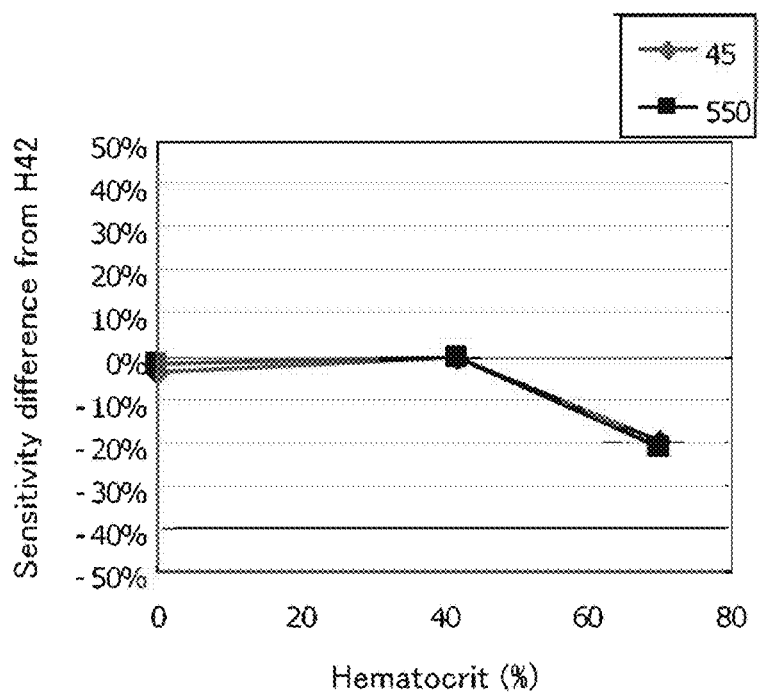

FIG. 106a is a graph showing the sensitivity difference (%) in each case of Glu values of 45 mg/dl and 550 mg/dl with reference to Hct 42% in Comparative Example 13.

Figure 106B:
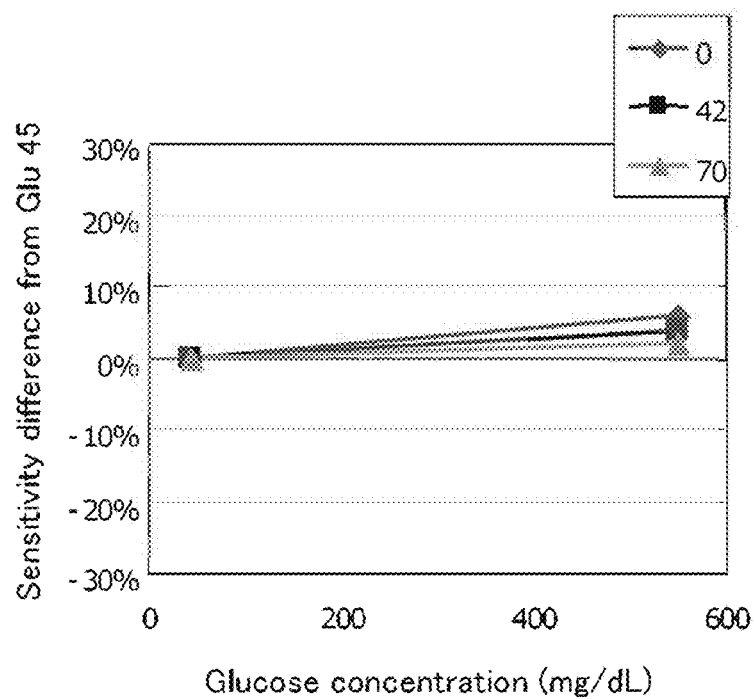

FIG. 106b is a graph showing the sensitivity difference (%) in each case of Hct values of 0%, 42%, and 70% with reference to Glu 45 mg/dl in Comparative Example 13.

Figure 107A:
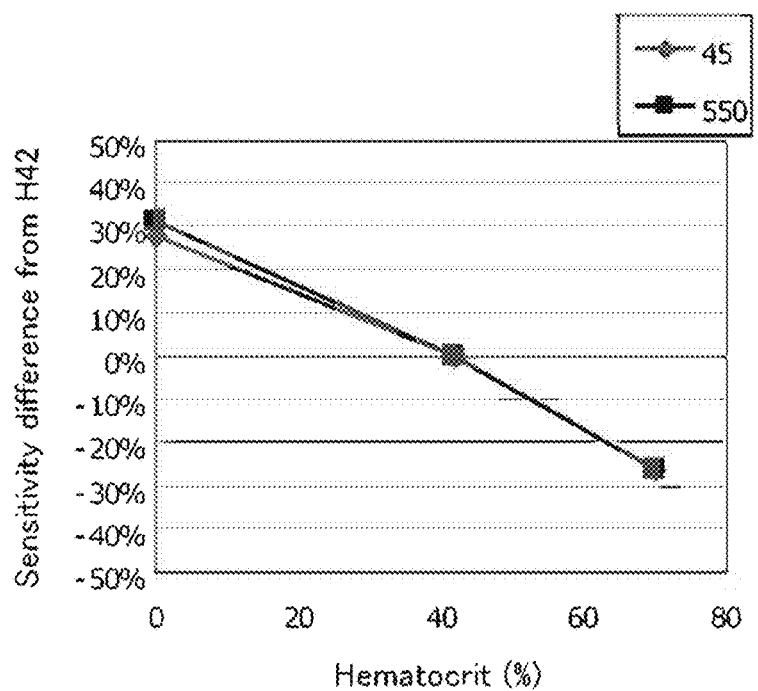

FIG. 107a is a graph showing the sensitivity difference (%) in each case of Glu values of 45 mg/dl and 550 mg/dl with reference to Hct 42% in Example 74.

Figure 107B:
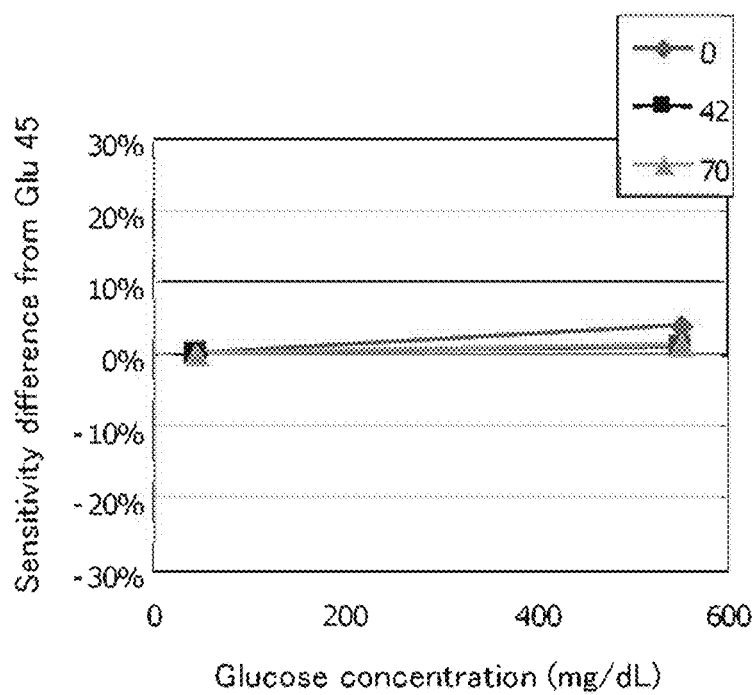

FIG. 107b is a graph showing the sensitivity difference (%) in each case of Hct values of 0%, 42%, and 70% with reference to Glu 45 mg/dl in Example 74.

Figure 108A:
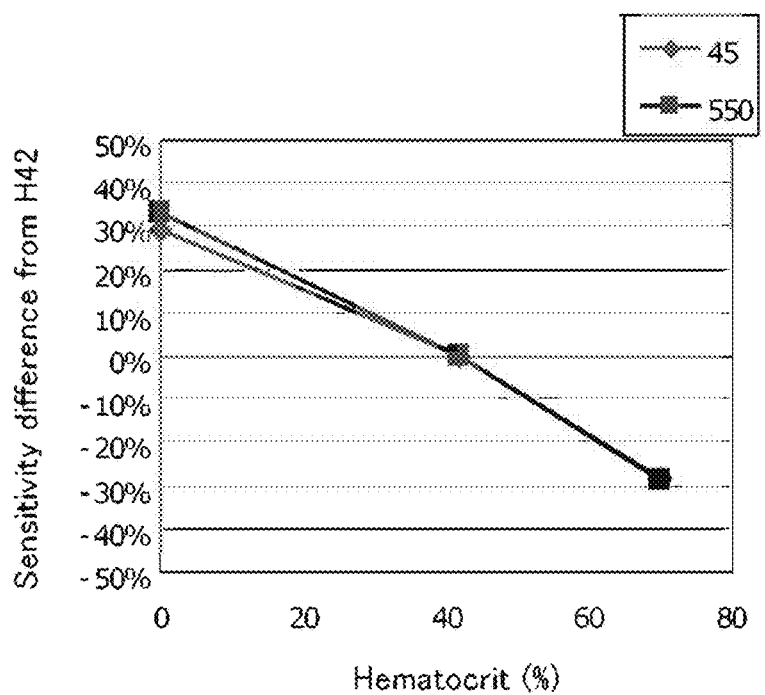

FIG. 108a is a graph showing the sensitivity difference (%) in each case of Glu values of 45 mg/dl and 550 mg/dl with reference to Hct 42% in Example 75.

Figure 108B:
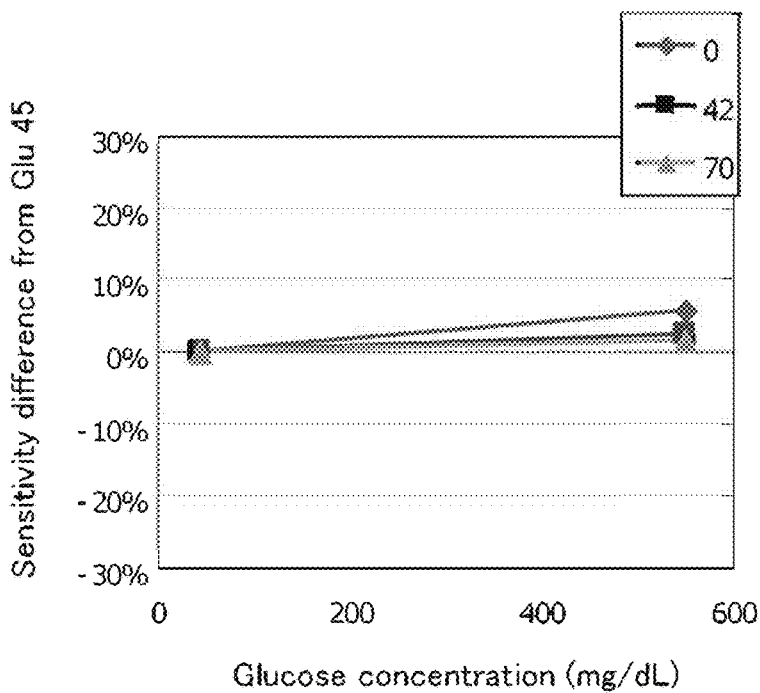

FIG. 108b is a graph showing the sensitivity difference (%) in each case of Hct values of 0%, 42%, and 70% with reference to Glu 45 mg/dl in Example 75.

Figure 109A:
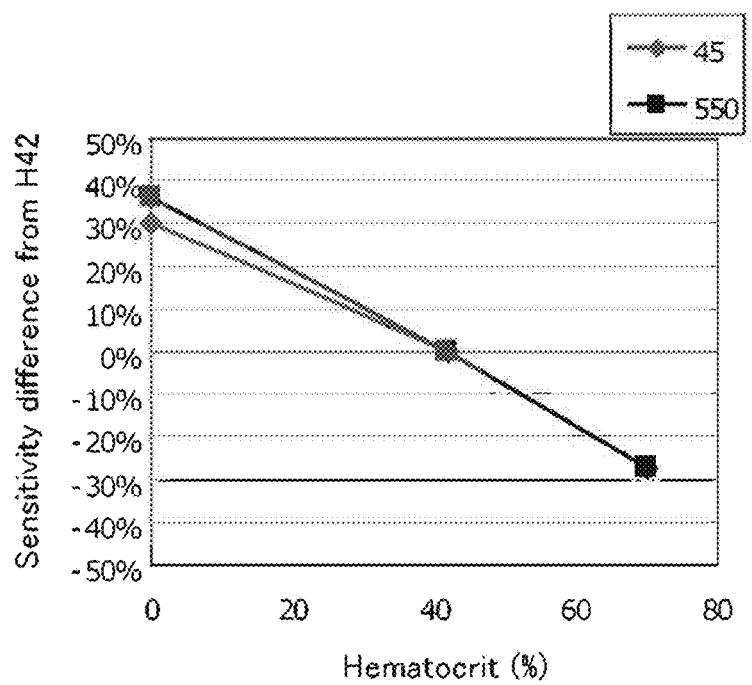

FIG. 109a is a graph showing the sensitivity difference (%) in each case of Glu values of 45 mg/dl and 550 mg/dl with reference to Hct 42% in Example 76.

Figure 109B:
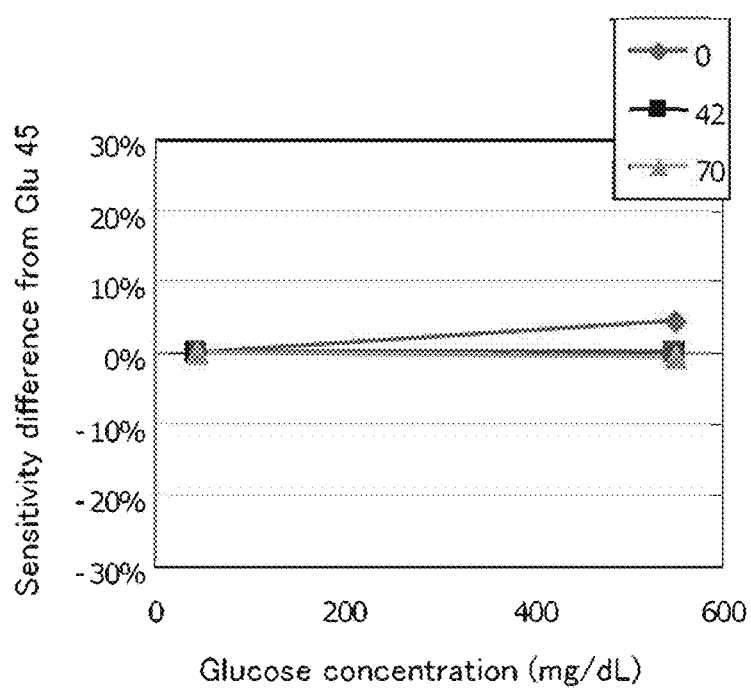

FIG. 109b is a graph showing the sensitivity difference (%) in each case of Hct values of 0%, 42%, and 70% with reference to Glu 45 mg/dl in Example 76.

Figure 110A:
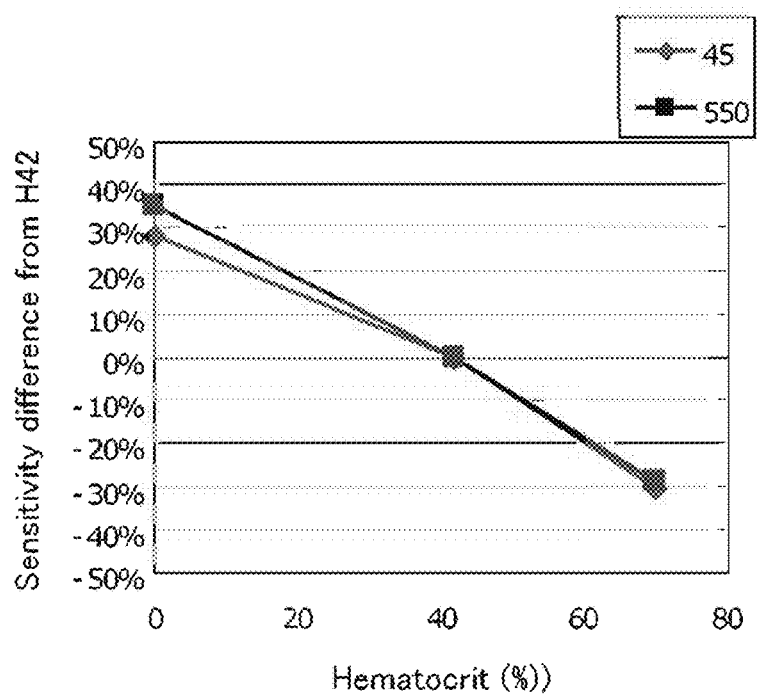

FIG. 110a is a graph showing the sensitivity difference (%) in each case of Glu values of 45 mg/dl and 550 mg/dl with reference to Hct 42% in Example 77.

Figure 110B:
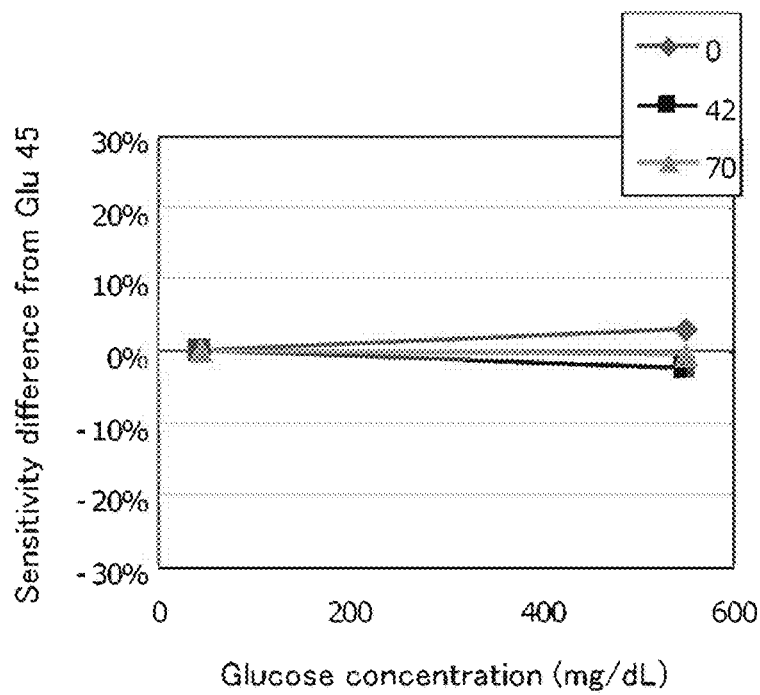

FIG. 110b is a graph showing the sensitivity difference (%) in each case of Hct values of 0%, 42%, and 70% with reference to Glu 45 mg/dl in Example 77.

Figure 111A:
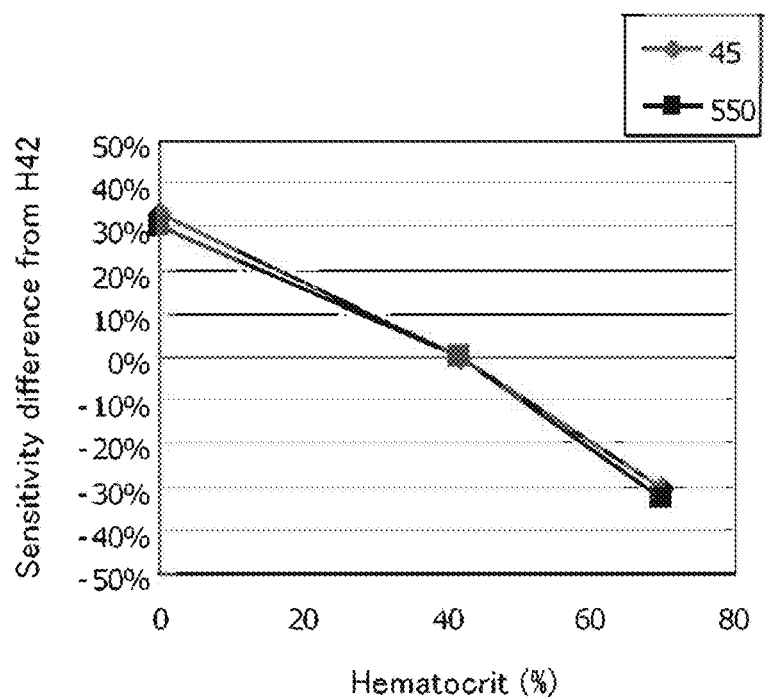

FIG. 111a is a graph showing the sensitivity difference (%) in each case of Glu values of 45 mg/dl and 550 mg/dl with reference to Hct 42% in Example 78.

Figure 111B:
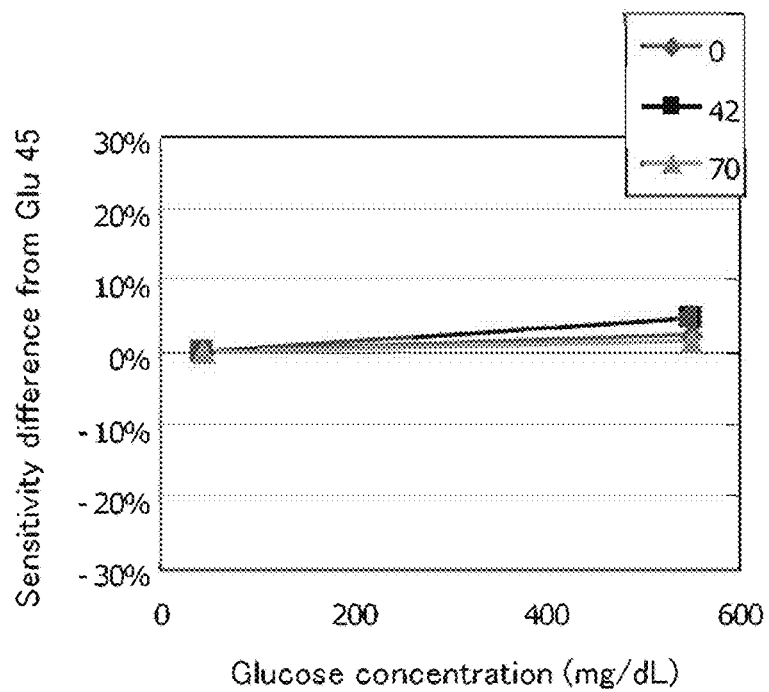

FIG. 111b is a graph showing the sensitivity difference (%) in each case of Hct values of 0%, 42%, and 70% with reference to Glu 45 mg/dl in Example 78.

Figure 112A:
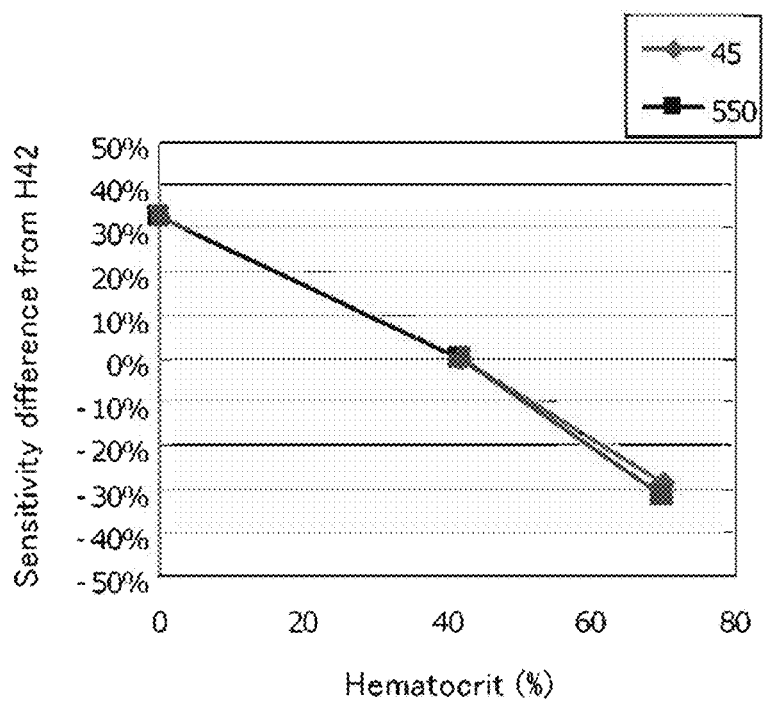

FIG. 112a is a graph showing the sensitivity difference (%) in each case of Glu values of 45 mg/dl and 550 mg/dl with reference to Hct 42% in Example 79.

Figure 112B:
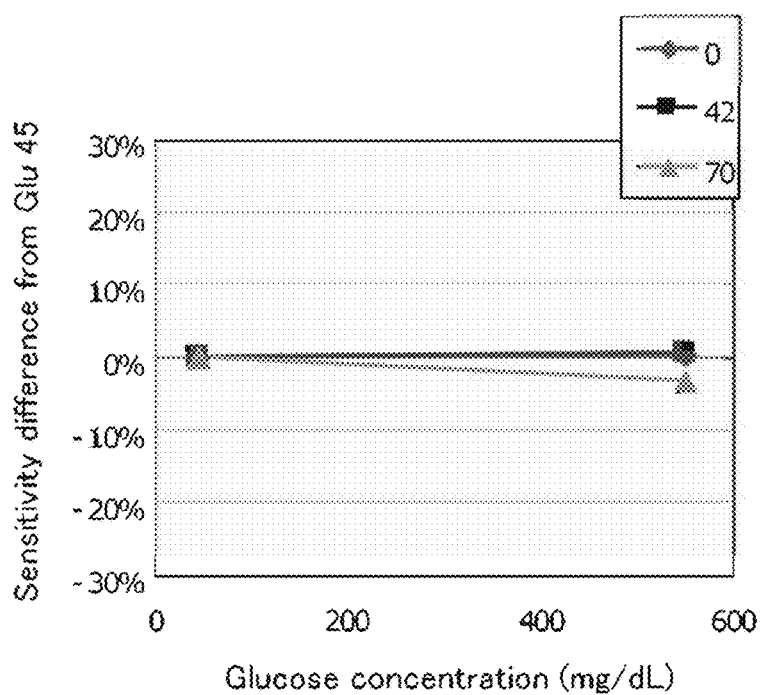

FIG. 112b is a graph showing the sensitivity difference (%) in each case of Hct values of 0%, 42%, and 70% with reference to Glu 45 mg/dl in Example 79.

Figure 113A:
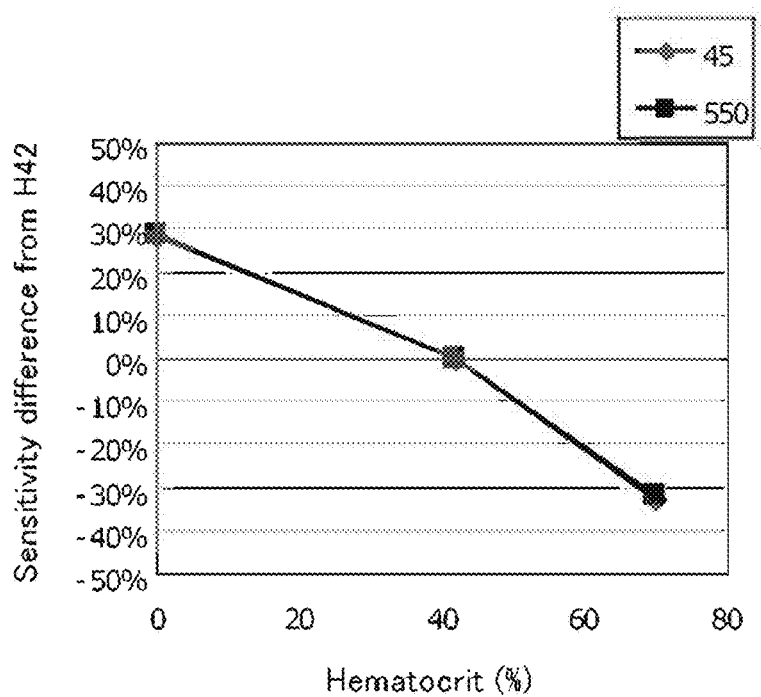

FIG. 113a is a graph showing the sensitivity difference (%) in each case of Glu values of 45 mg/dl and 550 mg/dl with reference to Hct 42% in Example 80.

Figure 113B:
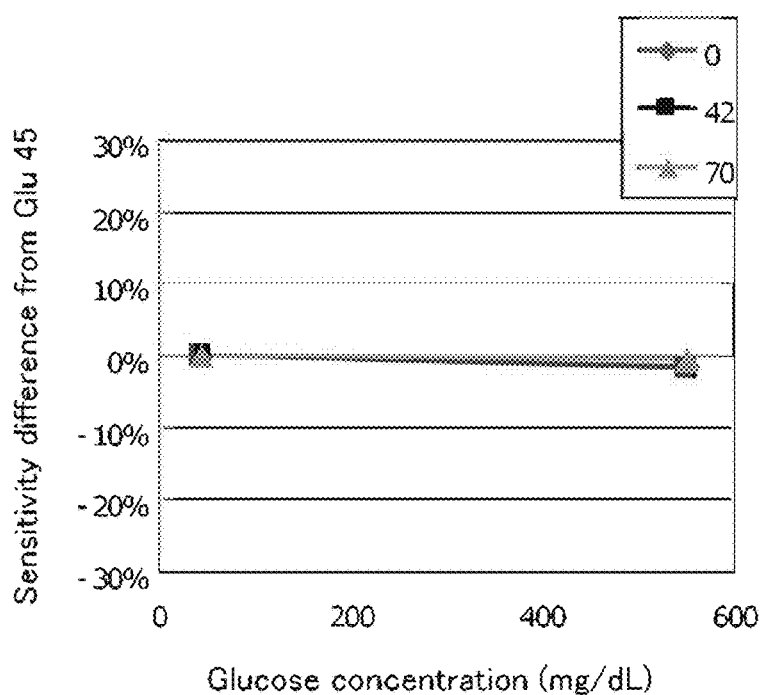

FIG. 113b is a graph showing the sensitivity difference (%) in each case of Hct values of 0%, 42%, and 70% with reference to Glu 45 mg/dl in Example 80.

Figure 114A:
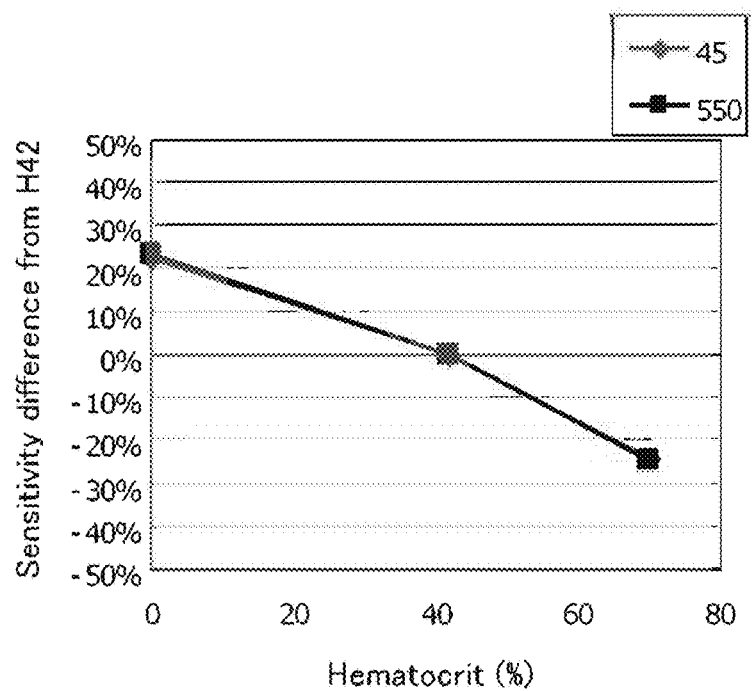

FIG. 114a is a graph showing the sensitivity difference (%) in each case of Glu values of 45 mg/dl and 550 mg/dl with reference to Hct 42% in Example 81.

Figure 114B:
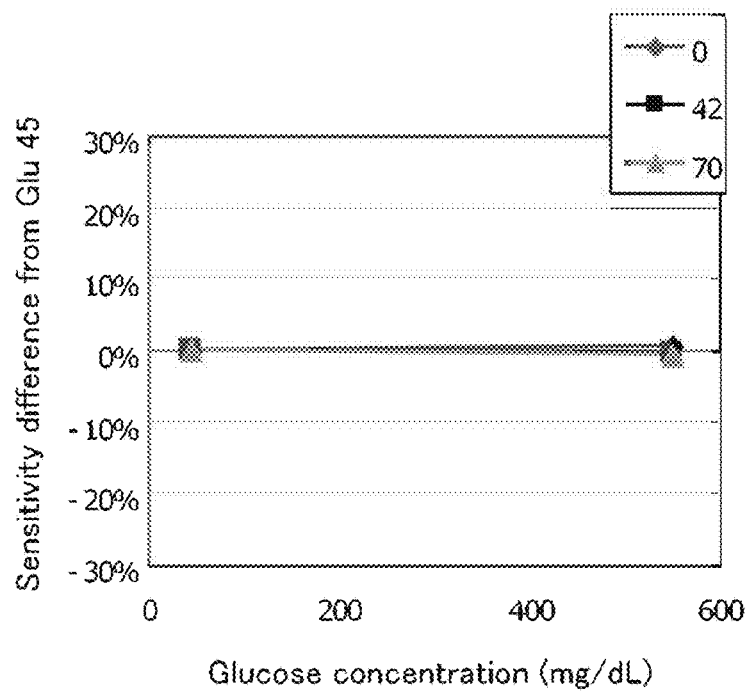

FIG. 114b is a graph showing the sensitivity difference (%) in each case of Hct values of 0%, 42%, and 70% with reference to Glu 45 mg/dl in Example 81.

Figure 115A:
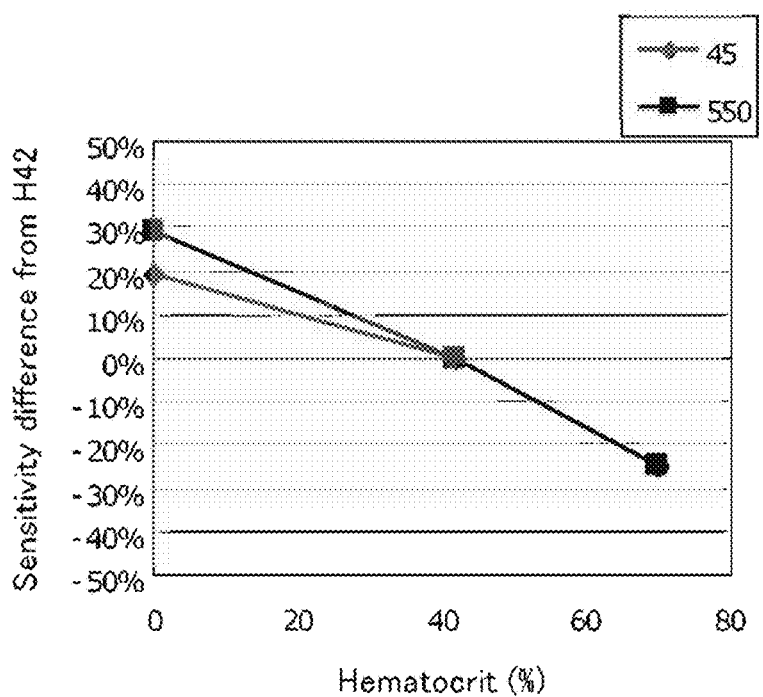

FIG. 115a is a graph showing the sensitivity difference (%) in each case of Glu values of 45 mg/dl and 550 mg/dl with reference to Hct 42% in Example 82.

Figure 115B:
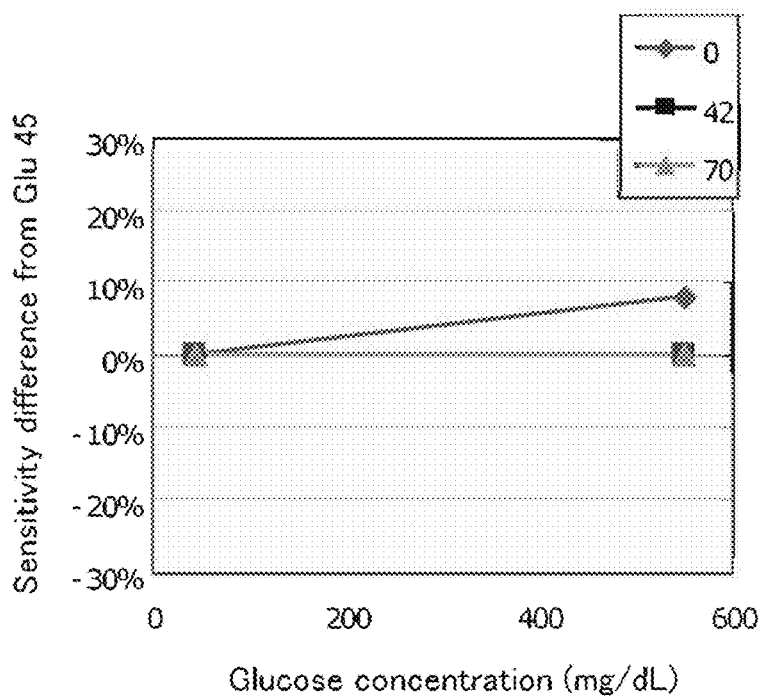

FIG. 115b is a graph showing the sensitivity difference (%) in each case of Hct values of 0%, 42%, and 70% with reference to Glu 45 mg/dl in Example 82.

Figure 116A:
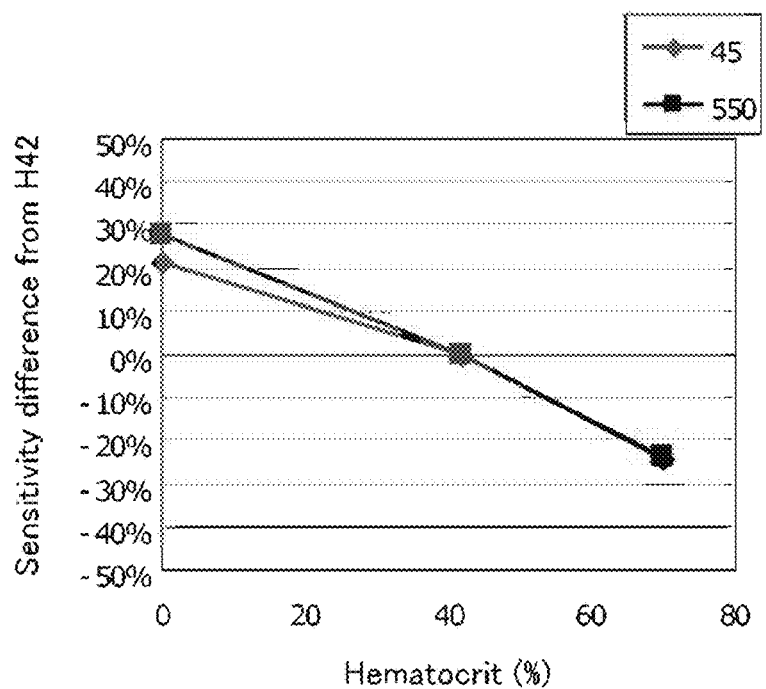

FIG. 116a is a graph showing the sensitivity difference (%) in each case of Glu values of 45 mg/dl and 550 mg/dl with reference to Hct 42% in Example 83.

Figure 116B:
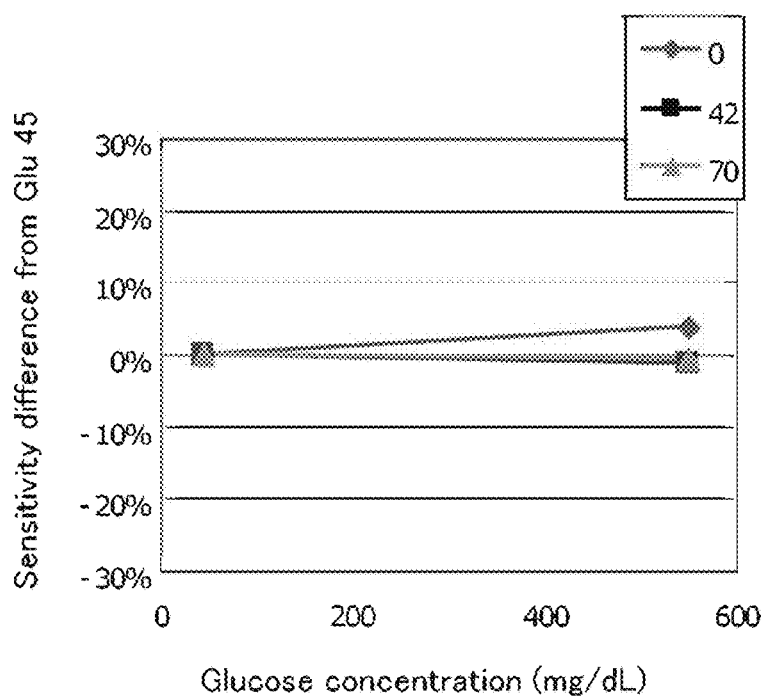

FIG. 116b is a graph showing the sensitivity difference (%) in each case of Hct values of 0%, 42%, and 70% with reference to Glu 45 mg/dl in Example 83.

Figure 117A:
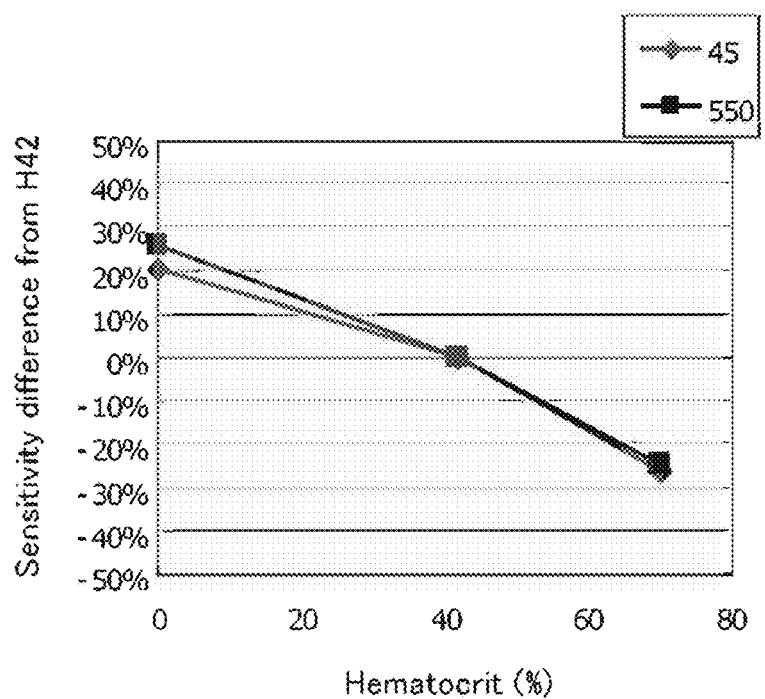

FIG. 117a is a graph showing the sensitivity difference (%) in each case of Glu values of 45 mg/dl and 550 mg/dl with reference to Hct 42% in Example 84.

Figure 117B:
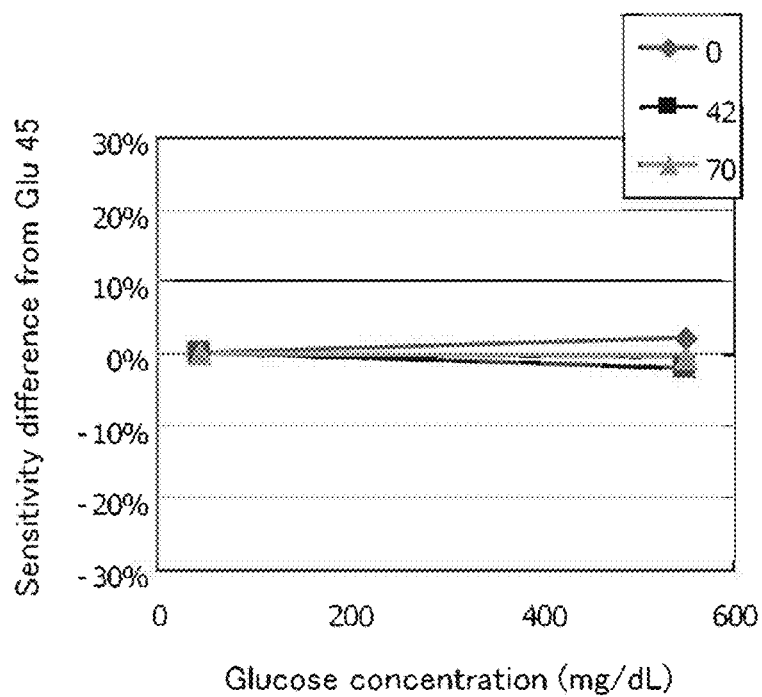

FIG. 117b is a graph showing the sensitivity difference (%) in each case of Hct values of 0%, 42%, and 70% with reference to Glu 45 mg/dl in Example 84.

Figure 118A:
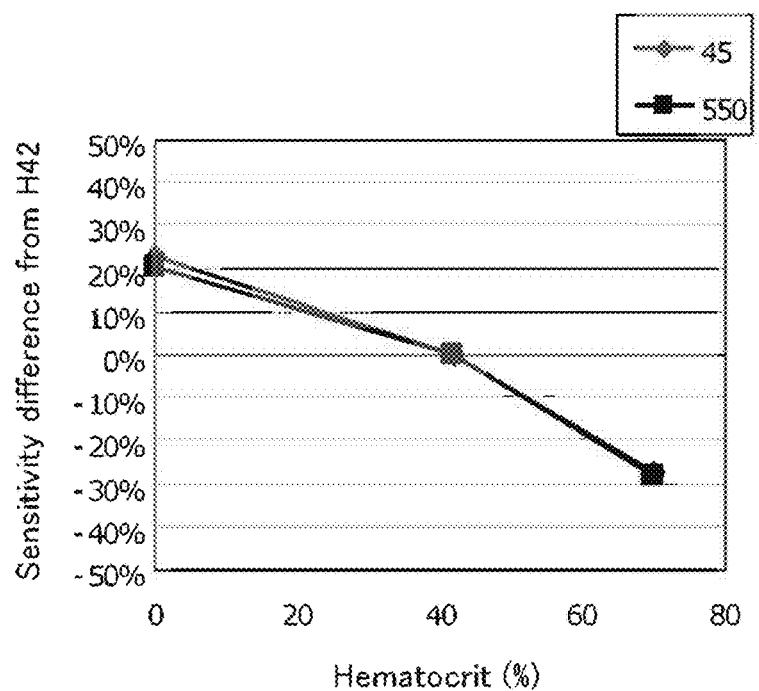

FIG. 118a is a graph showing the sensitivity difference (%) in each case of Glu values of 45 mg/dl and 550 mg/dl with reference to Hct 42% in Example 85.

Figure 118B:
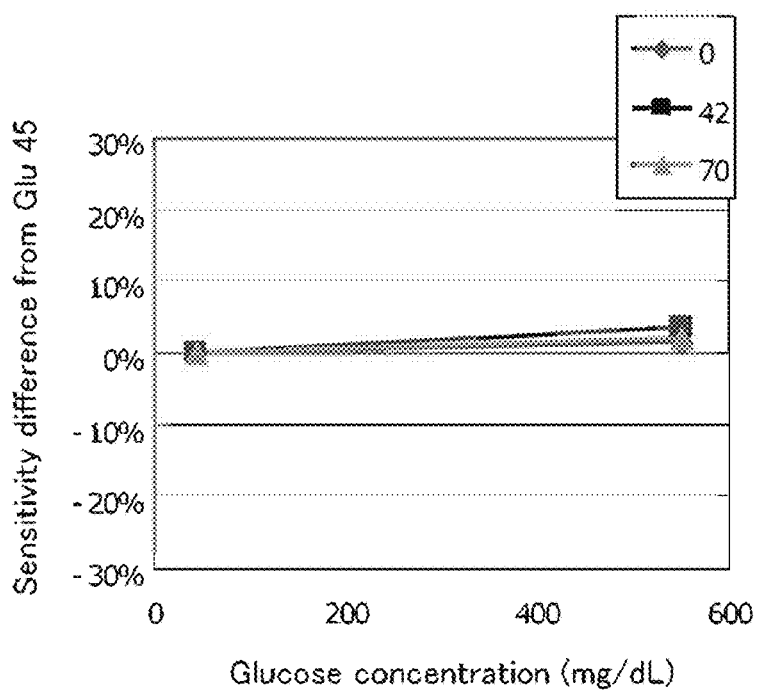

FIG. 118b is a graph showing the sensitivity difference (%) in each case of Hct values of 0%, 42%, and 70% with reference to Glu 45 mg/dl in Example 85.

Figure 119A:
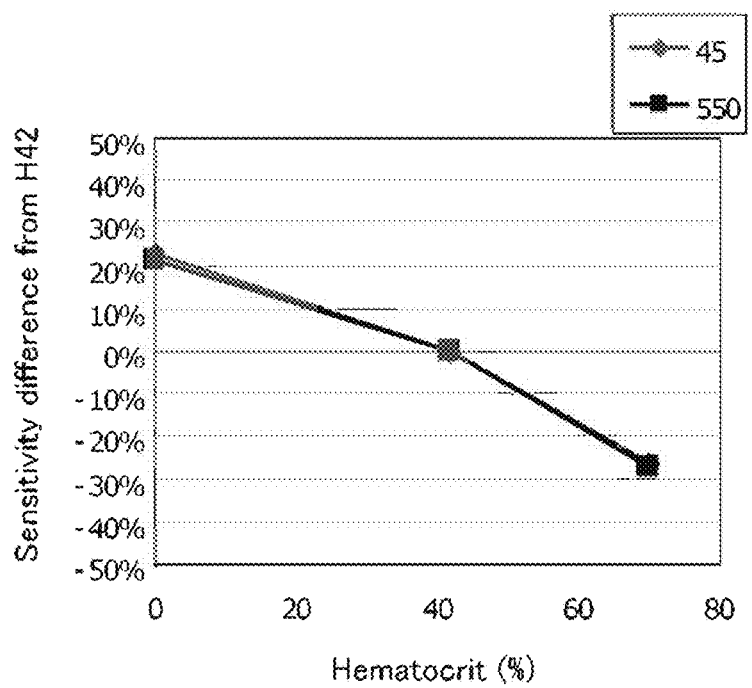

FIG. 119a is a graph showing the sensitivity difference (%) in each case of Glu values of 45 mg/dl and 550 mg/dl with reference to Hct 42% in Example 86.

Figure 119B:
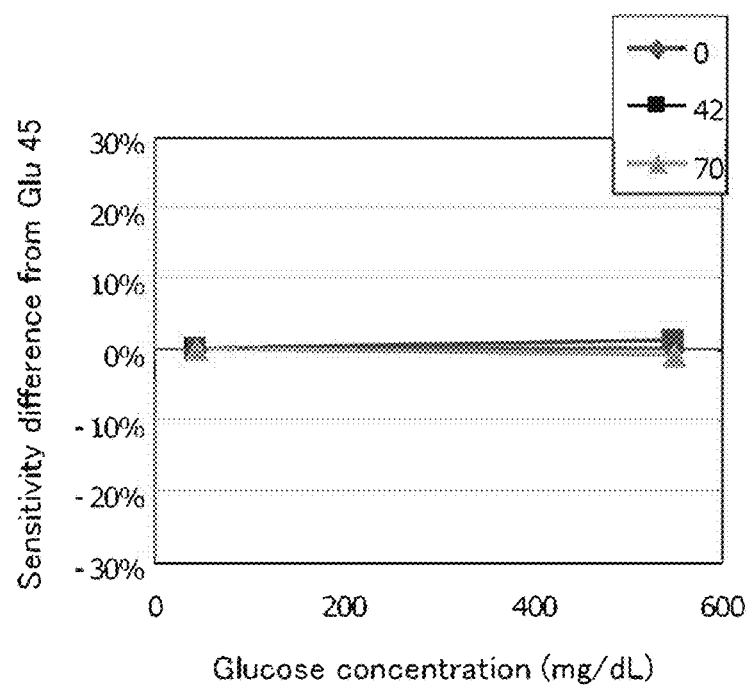

FIG. 119b is a graph showing the sensitivity difference (%) in each case of Hct values of 0%, 42%, and 70% with reference to Glu 45 mg/dl in Example 86.

Figure 120A:
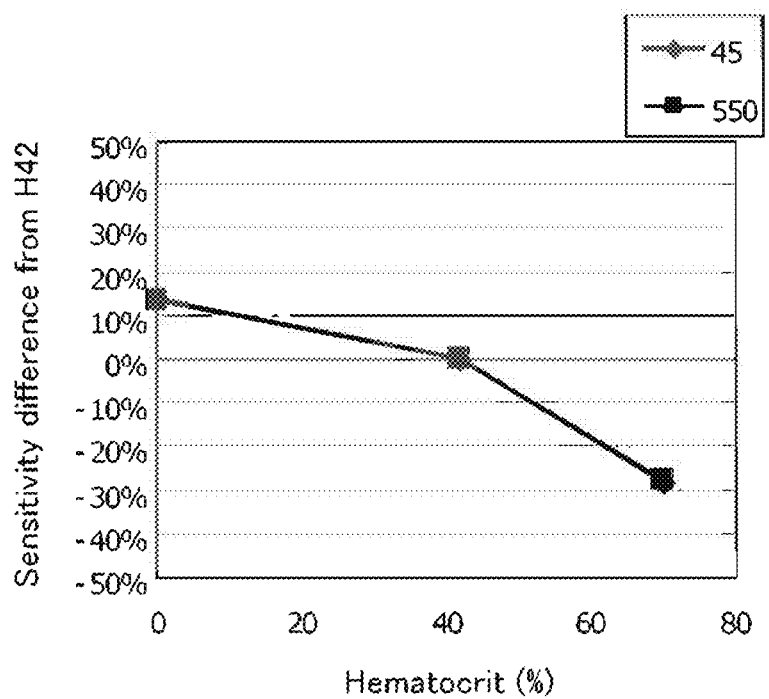

FIG. 120a is a graph showing the sensitivity difference (%) in each case of Glu values of 45 mg/dl and 550 mg/dl with reference to Hct 42% in Example 87.

Figure 120B:
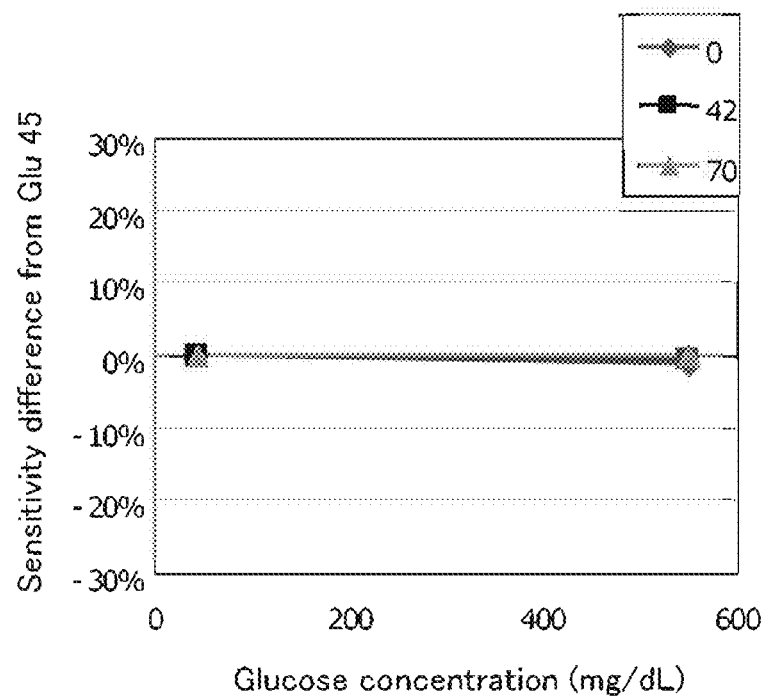

FIG. 120b is a graph showing the sensitivity difference (%) in each case of Hct values of 0%, 42%, and 70% with reference to Glu 45 mg/dl in Example 87.

Figure 121A:
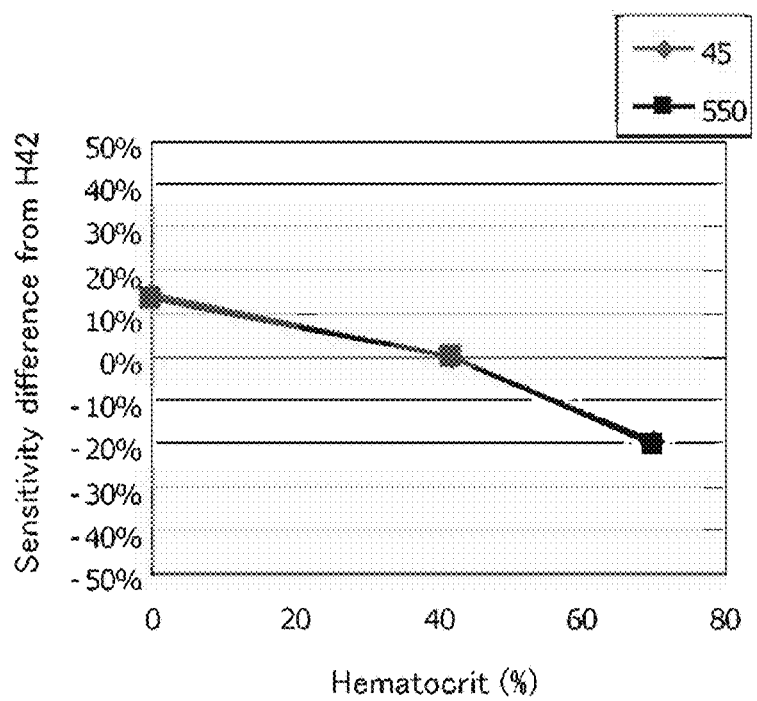

FIG. 121a is a graph showing the sensitivity difference (%) in each case of Glu values of 45 mg/dl and 550 mg/dl with reference to Hct 42% in Example 88.

Figure 121B:
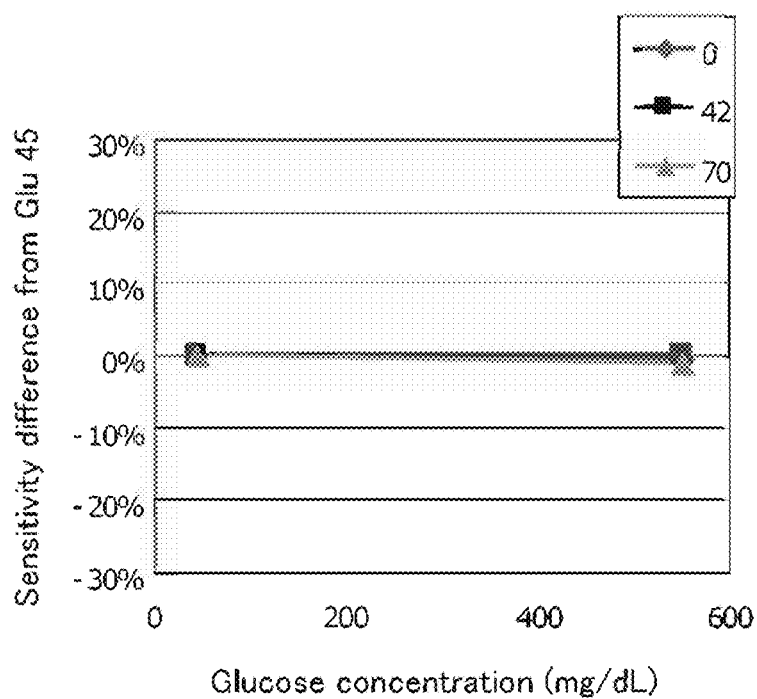

FIG. 121b is a graph showing the sensitivity difference (%) in each case of Hct values of 0%, 42%, and 70% with reference to Glu 45 mg/dl in Example 88.

Figure 122A:
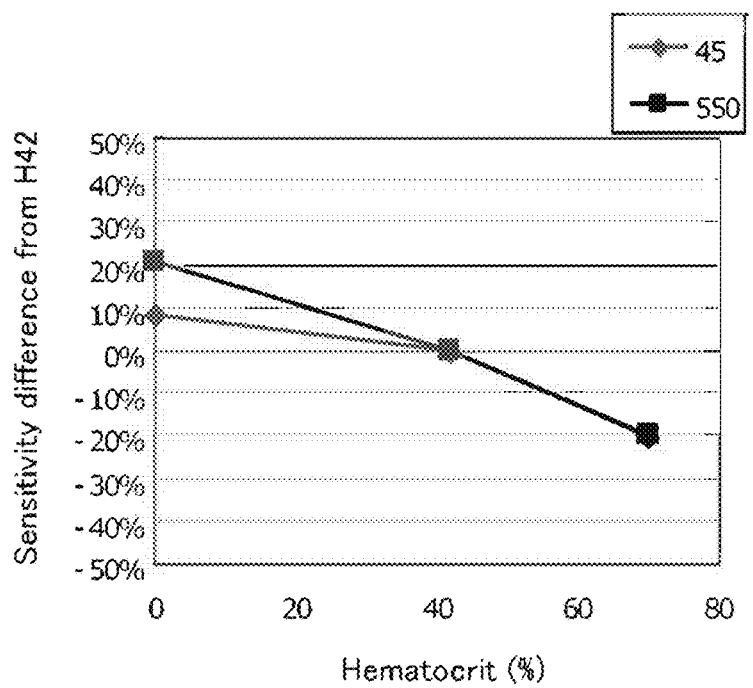

FIG. 122a is a graph showing the sensitivity difference (%) in each case of Glu values of 45 mg/dl and 550 mg/dl with reference to Hct 42% in Example 89.

Figure 122B:
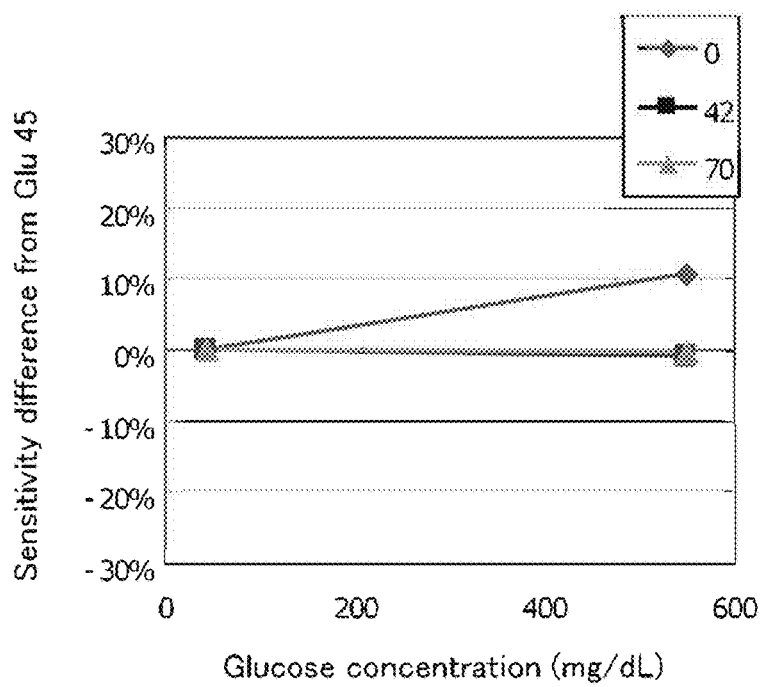

FIG. 122b is a graph showing the sensitivity difference (%) in each case of Hct values of 0%, 42%, and 70% with reference to Glu 45 mg/dl in Example 89.

Figure 123A:
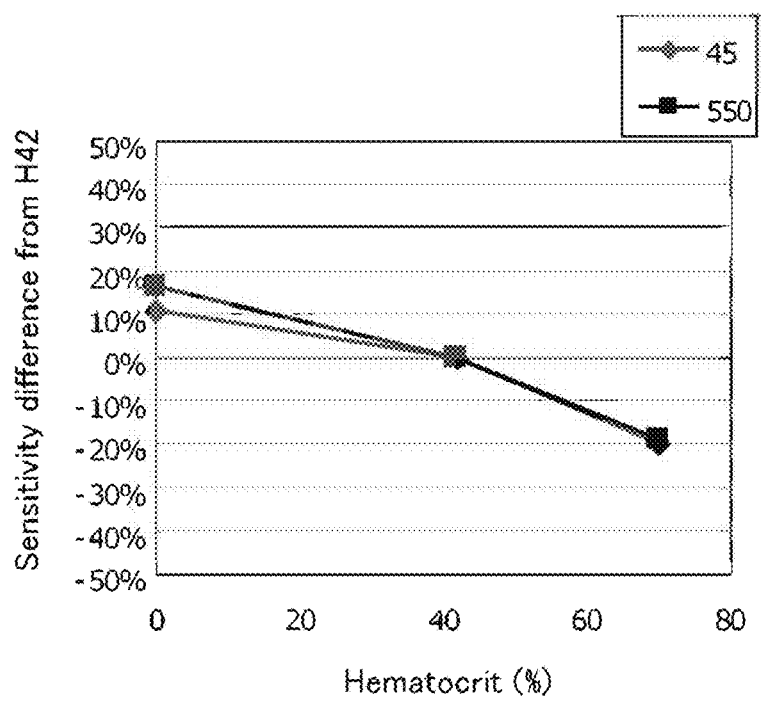

FIG. 123a is a graph showing the sensitivity difference (%) in each case of Glu values of 45 mg/dl and 550 mg/dl with reference to Hct 42% in Example 90.

Figure 123B:
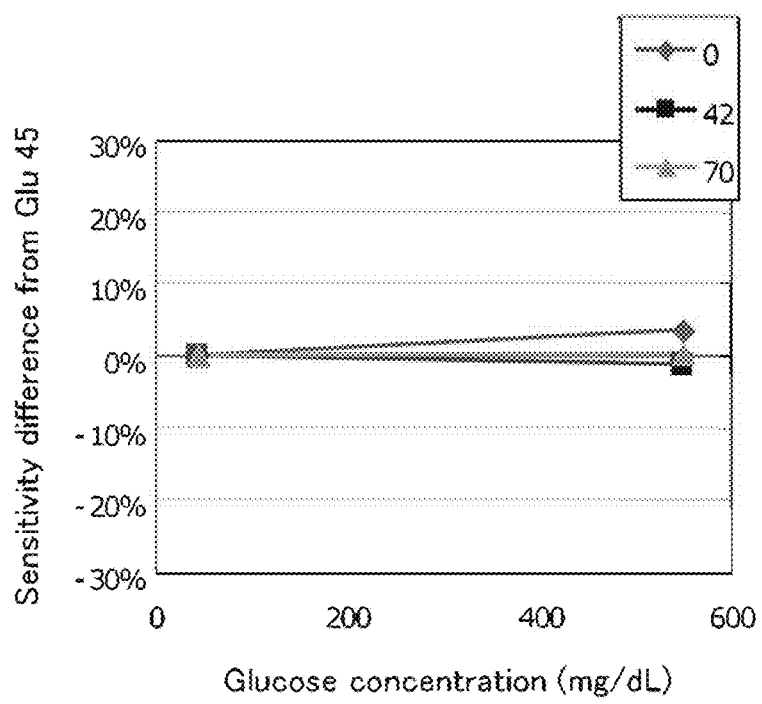

FIG. 123b is a graph showing the sensitivity difference (%) in each case of Hct values of 0%, 42%, and 70% with reference to Glu 45 mg/dl in Example 90.

Figure 124A:
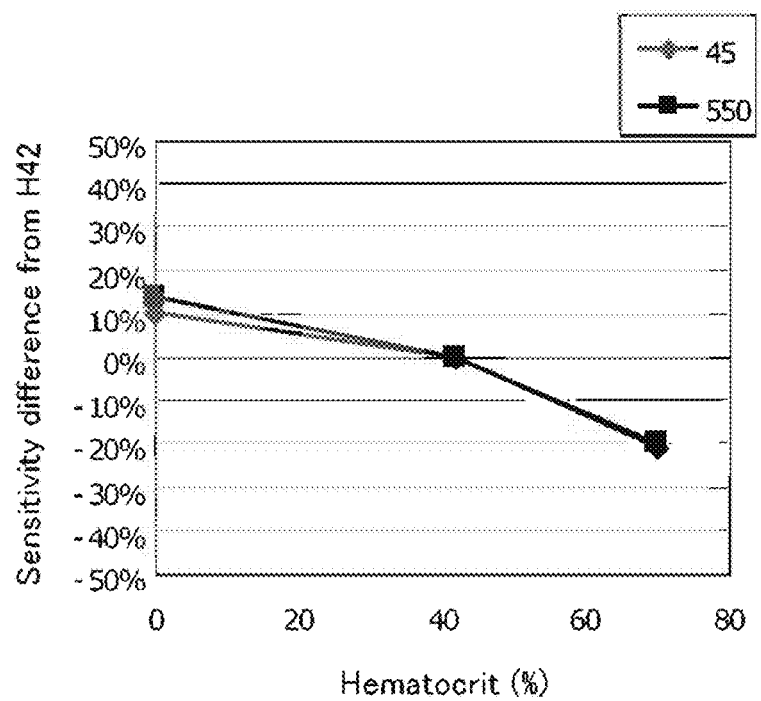

FIG. 124a is a graph showing the sensitivity difference (%) in each case of Glu values of 45 mg/dl and 550 mg/dl with reference to Hct 42% in Example 91.

Figure 124B:
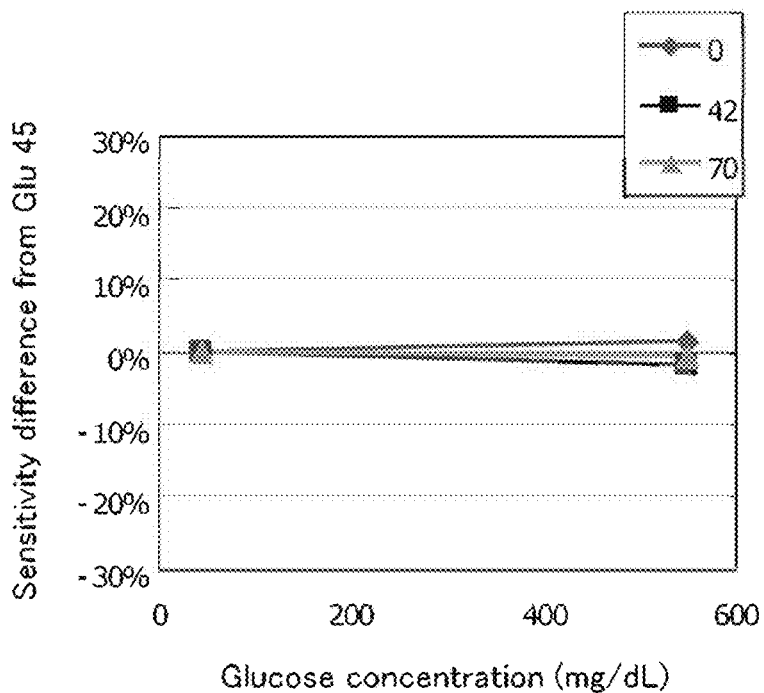

FIG. 124b is a graph showing the sensitivity difference (%) in each case of Hct values of 0%, 42%, and 70% with reference to Glu 45 mg/dl in Example 91.

Figure 125A:
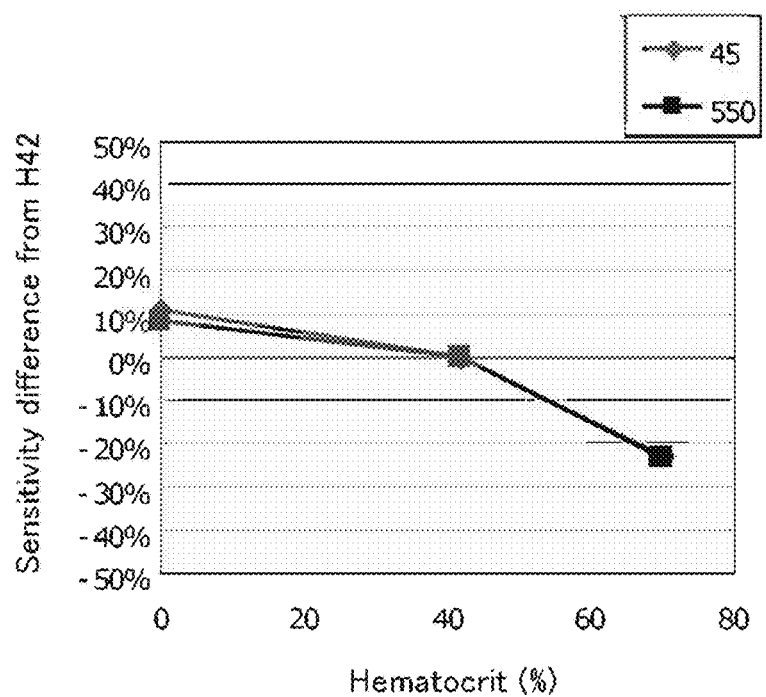

FIG. 125a is a graph showing the sensitivity difference (%) in each case of Glu values of 45 mg/dl and 550 mg/dl with reference to Hct 42% in Example 92.

Figure 125B:
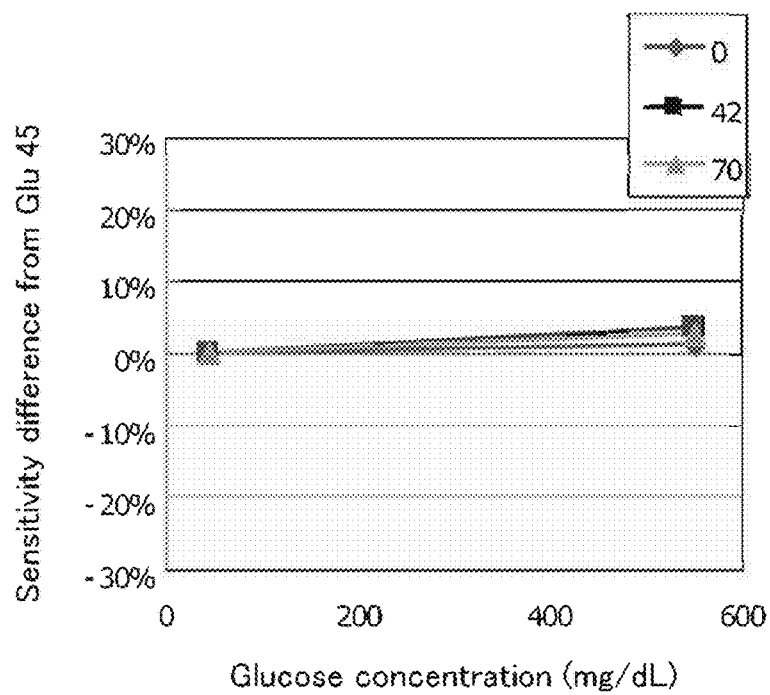

FIG. 125b is a graph showing the sensitivity difference (%) in each case of Hct values of 0%, 42%, and 70% with reference to Glu 45 mg/dl in Example 92.

Figure 126A:
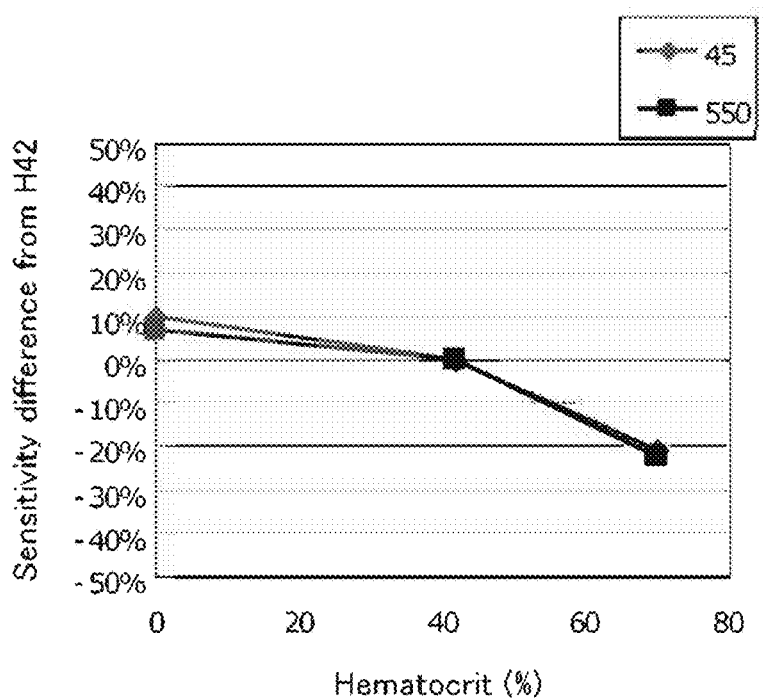

FIG. 126a is a graph showing the sensitivity difference (%) in each case of Glu values of 45 mg/dl and 550 mg/dl with reference to Hct 42% in Example 93.

Figure 126B:
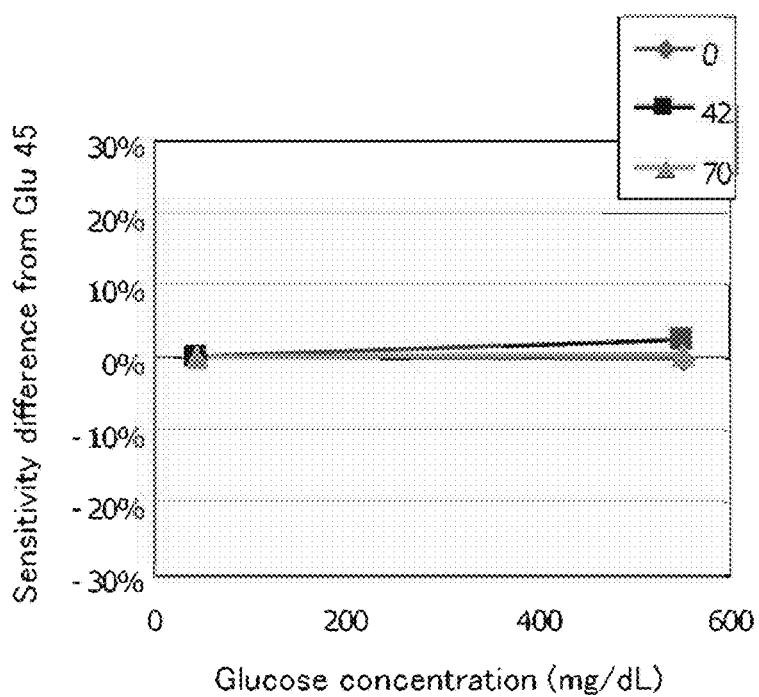

FIG. 126b is a graph showing the sensitivity difference (%) in each case of Hct values of 0%, 42%, and 70% with reference to Glu 45 mg/dl in Example 93.

Figure 127A:
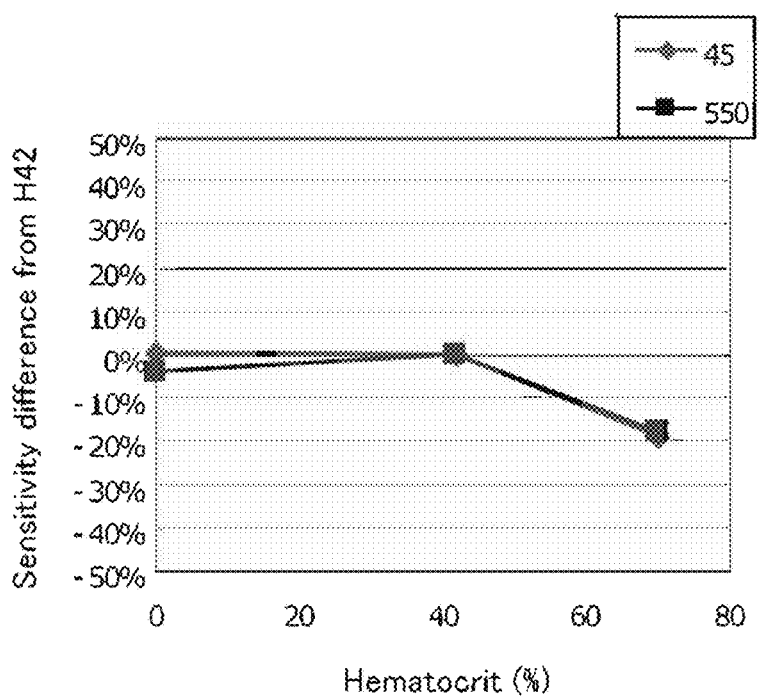

FIG. 127a is a graph showing the sensitivity difference (%) in each case of Glu values of 45 mg/dl and 550 mg/dl with reference to Hct 42% in Comparative Example 14.

Figure 127B:
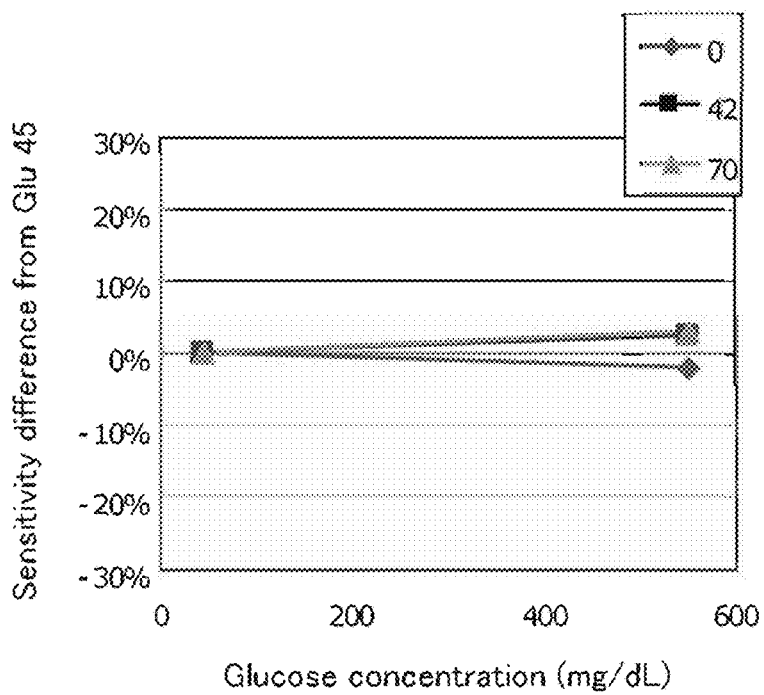

FIG. 127b is a graph showing the sensitivity difference (%) in each case of Hct values of 0%, 42%, and 70% with reference to Glu 45 mg/dl in Comparative Example 14.

DESCRIPTION OF PREFERRED EMBODIMENTS

Next, the present invention will be described in detail.

In the method for measuring a component of a biological sample and the biosensor of the present invention, examples of the component to be measured include glucose, ketone, HbA1c, lactic acid, uric acid, bilirubin, and cholesterol. In the biosensor that is used in the method for measuring a component of a biological sample of the present invention, the enzyme contained in the reagent part is suitably selected according to the component of the biological sample to be measured.

<First Method for Measuring Component of Biological Sample>

The present invention is:

a method for measuring a component of a biological sample with a biosensor provided with:

a capillary for introducing the biological sample;

an electrode part including a first electrode system that includes a first working electrode and a first counter electrode in the capillary; and a reagent part disposed so as to be in contact with the electrode part, the reagent part containing an enzyme and a mediator, and the method including a step of starting voltage application for a duration longer than 0 second and up to 0.7 second to the first electrode system within 0 second to 0.5 second after detection of introduction of the biological sample to obtain a Hct value based on a current value obtained thereby (the first method for measuring a component of a biological sample).

In the first method for measuring a component of a biological sample, the duration of the voltage application to the first electrode system is any duration longer than 0 second and up to 0.7 second, preferably any duration longer than 0 second and up to 0.5 second, and further preferably any duration longer than 0 second and up to 0.1 second.

In the first method for measuring a component of a biological sample, it is preferable that the voltage application to the first electrode system be started at 0 second after detection of introduction of the biological sample. Furthermore, in the first method for measuring a component of a biological sample, the voltage application to the first electrode system is started at later than 0 second but within 0.5 second after detection of introduction of the biological sample, preferably later than 0 second but within 0.3 second, more preferably later than 0 second but within 0.1 second, and further preferably later than 0 second but within 0.05 second.

In the first method for measuring a component of a biological sample, the voltage to be applied to the first electrode system is preferably any voltage in the range of 1.5 to 4.0 V, more preferably any voltage in the range of 1.5 to 3.0 V, and further preferably any voltage in the range of 1.5 to 2.5 V.

In the first method for measuring a component of a biological sample, in a biosensor in which the reagent layer is in contact with both the working electrode and the counter electrode, a voltage is applied for a very short time after detection of the biological sample and a Hct value is obtained based on a current value obtained thereby. According to such a method, the Hct value can be measured in a short time.

<Second Method for Measuring Component of Biological Sample>

Furthermore, the present invention is a method for measuring a component of a biological sample, wherein in the first method for measuring a component of a biological sample, the component is Glu, and the method further includes;

a step of applying a voltage to the first electrode system after the step to obtain a Hct value, to obtain a current value that depends on Glu, and a step of using the current value that depends on Glu and the Hct value to obtain a Glu value (the second method for measuring a component of a biological sample).

In the second method for measuring a component of a biological sample, the duration of the voltage application to the first electrode system in the step to obtain a current value that depends on Glu is preferably any duration between 0.01 and 10.0 seconds, more preferably any duration between 0.1 and 7.0 seconds, and further preferably any duration between 0.1 and 5.0 seconds.

In the second method for measuring a component of a biological sample, the voltage to be applied to the first electrode system in the step to obtain a current value that depends on Glu is preferably any voltage in the range of 0.1 V to 1.4 V, more preferably any voltage in the range of 0.1 V to 1.0 V.

In the second method for measuring a component of a biological sample, since the current value that depends on Glu in the vicinity of the electrodes that are in contact with the reagent layer and the Hct value in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time.

In the second method for measuring a component of a biological sample, the step of applying a voltage to the first electrode system to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

<Third Method for Measuring Component of Biological Sample>

Moreover, the present invention is a method for measuring a component of a biological sample, wherein in the first method for measuring a component of a biological sample, the component is Glu, the electrode part is further provided with a second electrode system that includes a second working electrode and a second counter electrode, and the method further includes:

a step of applying a voltage to the second electrode system after the step to obtain a Hct value, to obtain a current value that depends on Glu; and a step of using the current value that depends on Glu and the Hct value to obtain a Glu value (the third method for measuring a component of a biological sample).

In the third method for measuring a component of a biological sample, the duration of the applying a voltage to the second electrode system is preferably any duration between 0.01 and 10.0 seconds, more preferably any duration between 0.1 and 7.0 seconds, and further preferably any duration between 0.1 and 5.0 seconds.

In the third method for measuring a component of a biological sample, the voltage to be applied to the second electrode system is preferably any voltage in the range of 0.1 V to 1.4 V, more preferably any voltage in the range of 0.1 V to 1.0 V.

According to the third method for measuring a component of a biological sample, the Hct value can be measured in a short time, and the Glu value corrected using the Hct value can be obtained in a short time.

In the third method for measuring a component of a biological sample, the step of applying a voltage to the second electrode system to obtain a current value that depends on Glu may be performed multiple times. In this case, a plurality of the current values that depend on Glu and the Hct value are used to obtain a Glu value.

<Fourth Method for Measuring Component of Biological Sample>

Furthermore, the present invention is:

a method for measuring a component of a biological sample with a biosensor provided with:

a capillary for introducing the biological sample;

an electrode part including a first electrode system that includes a first working electrode and a first counter electrode in the capillary; and a reagent part disposed so as to be in contact with the electrode part, the component being Glu, the reagent part containing an enzyme and a mediator, and the method including:

a step of starting voltage application for a duration longer than 0 second and up to 0.7 second to the first electrode system within 0 second to 0.5 second after detection of introduction of the biological sample to obtain a current value that depends on Hct;

a step of applying a voltage to the first electrode system after the step to obtain a current value that depends on Hct, to obtain a current value that depends on Glu; and a step of using the current value that depends on Glu and the current value that depends on Hct to obtain a Glu value (the fourth method for measuring a component of a biological sample).

In the fourth method for measuring a component of a biological sample, the duration of the voltage application to the first electrode system in the step to obtain a current value that depends on Hct is preferably any duration longer than 0 second and up to 0.5 second, further preferably any duration longer than 0 second and up to 0.1 second.

In the fourth method for measuring a component of a biological sample, it is preferable that the voltage application to the first electrode system in the step to obtain a current value that depends on Hct be started at 0 second after detection of introduction of the biological sample.

In the fourth method for measuring a component of a biological sample, the voltage application to the first electrode system in the step to obtain a current value that depends on Hct is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the fourth method for measuring a component of a biological sample, the voltage to be applied to the first electrode system in the step to obtain a current value that depends on Hct is preferably any voltage in the range of 1.5 to 4.0 V, more preferably any voltage in the range of 1.5 V to 3.0 V, and further preferably any voltage in the range of 1.5 V to 2.5 V.

In the fourth method for measuring a component of a biological sample, the duration of the voltage application to the first electrode system in the step to obtain a current value that depends on Glu is preferably any duration between 0.01 and 10.0 seconds, more preferably any duration between 0.1 and 7.0 seconds, and further preferably any duration between 0.1 and 5.0 seconds.

In the fourth method for measuring a component of a biological sample, the voltage to be applied to the first electrode system in the step to obtain a current value that depends on Glu is preferably any voltage in the range of 0.1 V to 1.4 V, more preferably any voltage in the range of 0.1 V to 1.0 V.

In the fourth method for measuring a component of a biological sample, since the current value that depends on Glu in the vicinity of the electrodes that are in contact with the reagent layer and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time, and the Glu value corrected using the Hct value can be obtained in a short time.

In the fourth method for measuring a component of a biological sample, the step of applying a voltage to the first electrode system to obtain a current value that depends on Glu may be performed multiple times. In this case, a plurality of the current values that depend on Glu and the current value that depends on Hct are used to obtain a Glu value. When the step to obtain a current value that depends on Glu is performed multiple times, the measurement accuracy can be further improved, which is preferable.

<Fifth Method for Measuring Component of Biological Sample>

Moreover, the present invention is:

a method for measuring a component of a biological sample with a biosensor provided with:

a capillary for introducing the biological sample;

an electrode part including, in the capillary, a first electrode system that includes a first working electrode and a first counter electrode as well as a second electrode system that includes a second working electrode and a second counter electrode; and a reagent part disposed so as to be in contact with the electrode part, the component being Glu, the reagent part containing an enzyme and a mediator, and the method including:

a step of starting voltage application for a duration longer than 0 second and up to 0.7 second to the first electrode system within 0 second to 0.5 second after detection of introduction of the biological sample to obtain a current value that depends on Hct;

a step of applying a voltage to the second electrode system after the step to obtain a current value that depends on Hct, to obtain a current value that depends on Glu; and a step of using the current value that depends on Glu and the current value that depends on Hct to obtain a Glu value (the fifth method for measuring a component of a biological sample).

In the fifth method for measuring a component of a biological sample, the duration of the voltage application to the first electrode system is preferably any duration longer than 0 second and up to 0.5 second, further preferably any duration longer than 0 second and up to 0.1 second.

In the fifth method for measuring a component of a biological sample, it is preferable that the voltage application to the first electrode system be started at 0 second after detection of introduction of the biological sample.

In the fifth method for measuring a component of a biological sample, the voltage application to the first electrode system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the fifth method for measuring a component of a biological sample, the voltage to be applied to the first electrode system is preferably any voltage in the range of 1.5 to 4.0 V, more preferably any voltage in the range of 1.5 V to 3.0 V, and further preferably any voltage in the range of 1.5 V to 2.5 V.

In the fifth method for measuring a component of a biological sample, the duration of applying a voltage to the second electrode system is preferably any duration between 0.01 and 10.0 seconds, more preferably any duration between 0.1 and 7.0 seconds, and further preferably any duration between 0.1 and 5.0 seconds.

In the fifth method for measuring a component of a biological sample, the voltage to be applied to the second electrode system is preferably any voltage in the range of 0.1 to 1.4 V, more preferably any voltage in the range of 0.1 V to 1.0 V.

According to the fifth method for measuring a component of a biological sample, the Hct value can be measured in a short time and the Glu value corrected using the Hct value can be obtained in a short time.

In the fifth method for measuring a component of a biological sample, the step of applying a voltage to the second electrode system to obtain a current value that depends on Glu may be performed multiple times. In this case, a plurality of the current values that depend on Glu and the current value that depends on Hct are used to obtain a Glu value. When the step to obtain a current value that depends on Glu is performed multiple times, the measurement accuracy can be further improved, which is preferable.

In the first method for measuring a component of a biological sample, the second method for measuring a component of a biological sample, the third method for measuring a component of a biological sample, the fourth method for measuring a component of a biological sample, or the fifth method for measuring a component of a biological sample, the biological sample is, for example, blood, sweat, or urine and is preferably blood.

<First Biosensor>

Furthermore, the present invention is:

a biosensor including:

a capillary for introducing a biological sample;

a reagent part containing an enzyme and a mediator in the capillary;

a first Hct measurement system for measuring a Hct value that is disposed so as to be in contact with the reagent part in the capillary and includes a third working electrode and a third counter electrode; and a second Hct measurement system for measuring a Hct value that includes a fifth working electrode arranged at a place where the reagent part is not disposed and a fifth counter electrode disposed so as to be in contact with the reagent part (the first biosensor A).

Moreover, in the present invention, it is preferable that in the first biosensor, an electrode system for obtaining a current value that depends on Glu be further provided, the electrode system including a fourth working electrode and a fourth counter electrode disposed in the capillary so as to be in contact with the reagent part.

Such a biosensor is referred to as a first biosensor B.

<Second Biosensor>

Furthermore, in the present invention, it is preferable that the first biosensor Abe further provided with:

an electrode system for obtaining a current value that depends on Glu, the electrode system including the sixth working electrode and the sixth counter electrode; and an electrode system for obtaining a current value that depends on Glu, the electrode system including the fourth working electrode and the fourth counter electrode. Such a biosensor is referred to as a second biosensor.

<Third Biosensor>

Moreover, in the present invention, it is preferable that the second biosensor be further provided with:

an additional electrode system for obtaining a current value that depends on Glu, the additional electrode system including a fourth working electrode and a fourth counter electrode disposed in the capillary so as to be in contact with the reagent part. Such a biosensor is referred to as a third biosensor A.

Furthermore, in the present invention, it is preferable that the third biosensor Abe further provided with;

an electrode system for obtaining a current value that depends on Int (an interfering substance), the electrode system including, in the capillary, a seventh working electrode disposed so as not to be in contact with the reagent part and a seventh counter electrode that is in contact with the reagent part. Such a biosensor is referred to as a third biosensor B.

In the biosensor used in the first method for measuring a component of a biological sample, the second method for measuring a component of a biological sample, the third method for measuring a component of a biological sample, the fourth method for measuring a component of a biological sample, or the fifth method for measuring a component of a biological sample, as well as the first biosensor, the second biosensor, and the third biosensor, for the purpose of, for example, preventing adhesion of impurities and preventing oxidation, it is preferable that the electrode on which the reagent part is not disposed be coated with a polymer material. Examples of the polymer material include carboxymethyl cellulose (CMC), hydroxyethyl cellulose, hydroxypropyl cellulose, methyl cellulose, ethyl cellulose, ethyl hydroxyethyl cellulose, carboxyethyl cellulose, polyvinyl alcohol, polyvinylpyrrolidone, polyamino acid such as polysine, polystyrene sulfonate, gelatin and derivatives thereof, polyacrylic acid and salts thereof, polymethacrylic acid and salts thereof, starch and derivatives thereof, maleic anhydride polymer and salts thereof, as well as agarose gel and derivatives thereof. They may be used individually or two or more of them may be used together. Among these, CMC is preferred. Coating of the electrode with a polymer material is not particularly limited. For example, a polymer material solution may be prepared to be applied to the electrode surface and then dried and thereby the solvent contained in the coating film may be removed. The proportion of the polymer material is, for example, 0.001 to 10% by weight, preferably 0.005 to 5% by weight, and more preferably 0.01 to 2% by weight relative to the entire reagent solution for producing the reagent part.

In the biosensor used in the first method for measuring a component of a biological sample, the second method for measuring a component of a biological sample, the third method for measuring a component of a biological sample, the fourth method for measuring a component of a biological sample, or the fifth method for measuring a component of a biological sample, as well as the first biosensor, the second biosensor, and the third biosensor, the closest distance between the working electrode and the counter electrode is preferably 0.1 mm or more. As described above, when the distance between the electrodes is 0.1 mm or more, the reliability of measured values is improved. The distance between the electrodes is more preferably 0.3 mm or more, further preferably 0.5 mm or more.

In the biosensor used in the first method for measuring a component of a biological sample, the second method for measuring a component of a biological sample, the third method for measuring a component of a biological sample, the fourth method for measuring a component of a biological sample, or the fifth method for measuring a component of a biological sample, as well as the first biosensor, the second biosensor, and the third biosensor, the enzyme contained in the reagent part is preferably an oxidoreductase. The oxidoreductase is suitably selected according to the blood component to be measured. Examples of the oxidoreductase include glucose oxidase, lactate oxidase, cholesterol oxidase, bilirubin oxidase, glucose dehydrogenase, and lactate dehydrogenase. The amount of the oxidoreductase is, for example, 0.01 to 100 U, preferably 0.05 to 10 U, and more preferably 0.1 To 5 U, for example, per sensor or per measurement. Particularly, glucose is preferably to be measured, and in this case the oxidoreductase is preferably glucose oxidase and glucose dehydrogenase.

In the biosensor used in the first method for measuring a component of a biological sample, the second method for measuring a component of a biological sample, the third method for measuring a component of a biological sample, the fourth method for measuring a component of a biological sample, or the fifth method for measuring a component of a biological sample, as well as the first biosensor, the second biosensor, and the third biosensor, the mediator (an electron acceptor) contained in the reagent part is not particularly limited. Examples thereof include ferricyanides, p-benzoquinone, p-benzoquinone derivatives, phenazine methosulfate, methylene blue, ferrocene, ferrocene derivatives, phenothiazine derivatives, phenoxazine derivatives, and phenanthrenequinone derivatives. Among these, phenanthrenequinone (9,10-phenanthrenequinone), 3-phenylimino-3H-phenothiazine, or ferricyanide (potassium ferricyanide) is preferred. The amount of the mediator to be mixed is not particularly limited and is, for example, 0.1 to 1000 mM, preferably 1 to 500 mM, and more preferably 10 to 300 mM per measurement or per sensor. For example, when a glucose value (a component) in blood (a biological sample) is to be measured, in the case of a biosensor in which glucose dehydrogenase (oxidoreductase) is used as an enzyme and potassium ferricyanide is used as a mediator, a current value that depends on Glu is obtained, for example, as follows. In the biosensor, the oxidoreductase and the mediator come into contact with the blood, and these are dissolved in the blood. Then, an enzymatic reaction progresses between Glu, which is a substrate in the blood, and the oxidoreductase, and the mediator is reduced to produce ferrocyanide. After completion of this reaction, the mediator thus reduced is electrochemically oxidized, and from the current obtained thereby, a current value that depends on Glu in the blood is obtained.

In the biosensor used in the first method for measuring a component of a biological sample, the second method for measuring a component of a biological sample, the third method for measuring a component of a biological sample, the fourth method for measuring a component of a biological sample, or the fifth method for measuring a component of a biological sample, as well as the first biosensor, the second biosensor, and the third biosensor, the reagent part may further contain at least one of an enzyme stabilizer and a crystal homogenizing agent.

Examples of the enzyme stabilizer include sugar alcohol. Examples of the sugar alcohol include chain polyhydric alcohols and cyclic sugar alcohols, such as sorbitol, maltitol, xylitol, mannitol, lactitol, reduced palatinose, arabinitol, glycerol, ribitol, galactitol, sedoheptitol, perseitol, volemitol, styracitol, polygalitol, iditol, talitol, allitol, isylitol, and saccharified reduced starch. Furthermore, stereoisomers, substitution products, or derivatives of these sugar alcohols may be used. These sugar alcohols may be used individually or two or more of them may be used together. Among these, maltitol is preferred. The amount of the enzyme stabilizer to be mixed is, for example, in the range of 0.1 to 500 mM, preferably in the range of 0.5 to 100 mM, and more preferably in the range of 1 to 50 mM per measurement or per sensor.

The crystal homogenizing agent is used for homogenizing the crystal state of the reagent part, and examples thereof include amino acids. Examples of the amino acids include glycine, alanine, valine, leucine, isoleucine, serine, threonine, methionine, asparagine, glutamine, arginine, lysine, histidine, phenylalanine, tryptophan, proline, sarcosine, betaine, and taurine, as well as salts, substitution products, and derivatives thereof. These may be used individually or two or more of them may be used together. Among these, glycine, serine, proline, threonine, lysine, and taurine are preferable, and taurine is more preferable. The amount of the crystal homogenizing agent to be mixed is, for example, 0.1 to 1000 mM, preferably 10 to 500 mM, and more preferably 20 to 200 mM per measurement or per sensor.

Figure 1:
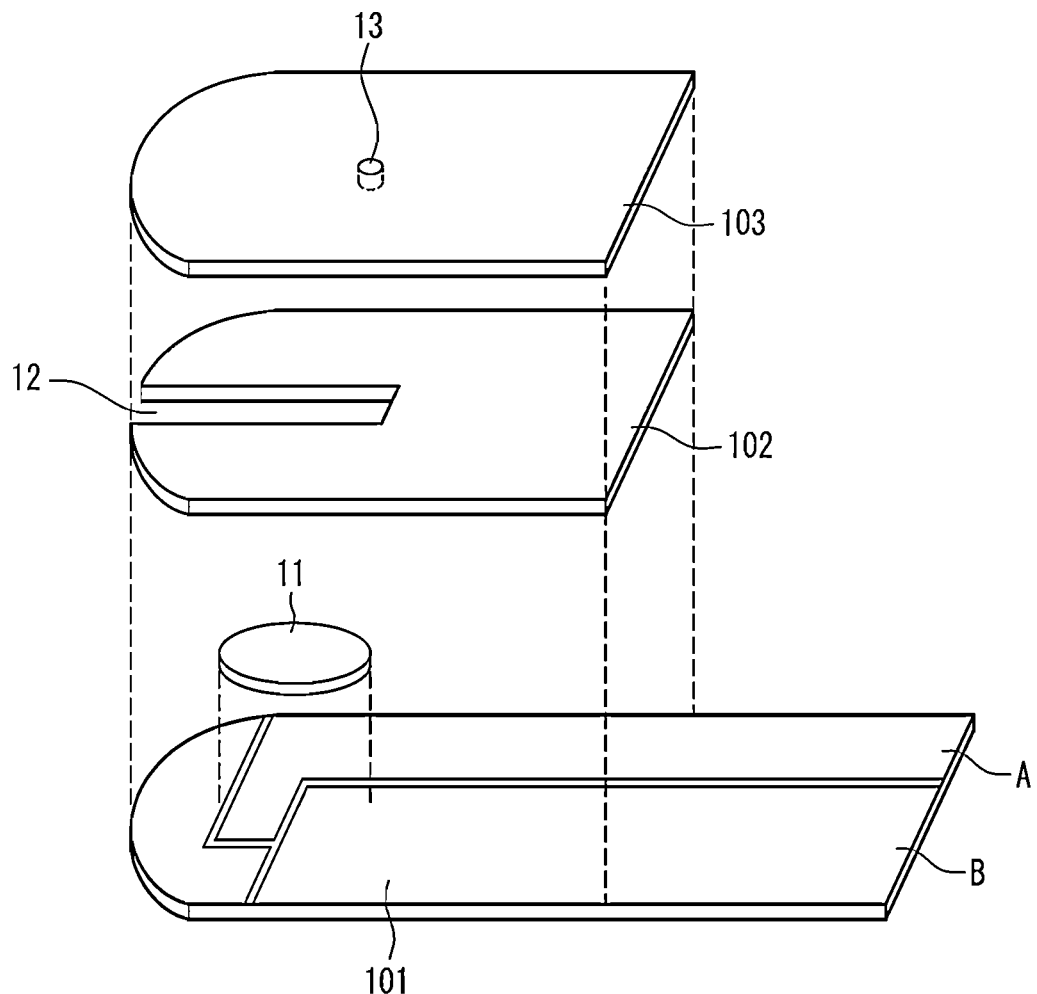
FIG. 1 is an exploded perspective view of a biosensor used in the present invention.
Figure 2:
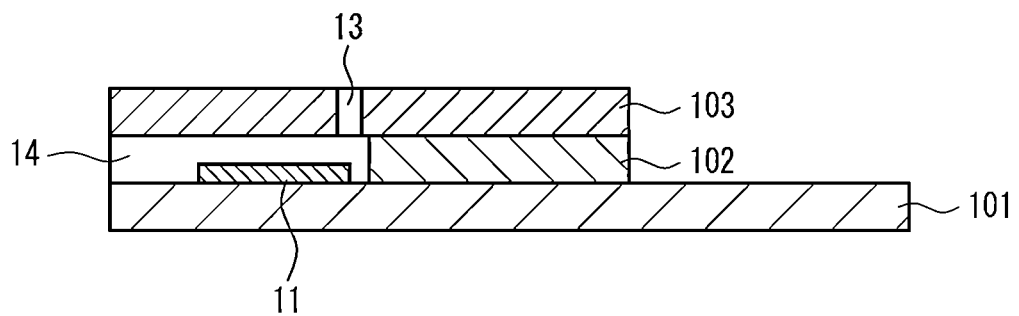
FIG. 2 is a sectional view of the biosensor used in the present invention.
Figure 3:
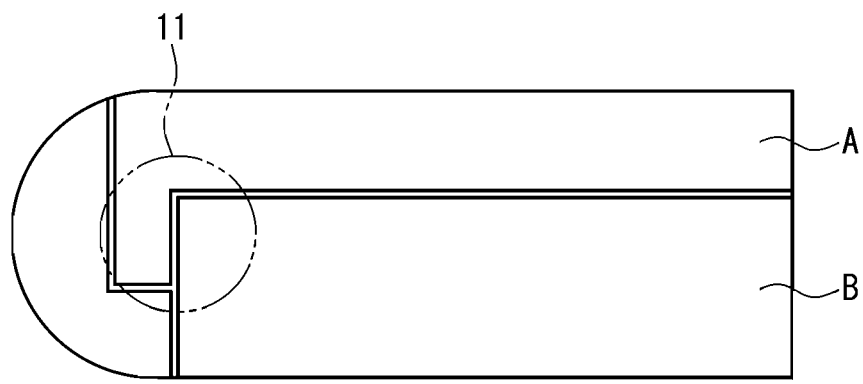
FIG. 3 is a plan view of an example of the biosensor used in the present invention.

FIGS. 1, 2, and 3 show an example of a biosensor that is used in the present invention. FIG. 1 is an exploded perspective view of the sensor, FIG. 2 is a sectional view, and FIG. 3 is a plan view. In the above-mentioned three drawings, the same parts are indicated with the same reference signs. This sensor is the biosensor used, as an example, in the first method for measuring a component of a biological sample, the second method for measuring a component of a biological sample, or the fourth method for measuring a component of a biological sample.

As shown in the drawings, in this sensor, two electrodes A and B are formed on an insulating substrate 101. These electrodes can be switched between a working electrode and a counter electrode. A reagent layer 11 is disposed so as to cover part of the electrodes A and B. The reagent layer 11 contains an oxidoreductase such as glucose dehydrogenase and a mediator such as phenanthrenequinone (9,10-phenanthrenequinone), 3-phenylimino-3H-phenothiazine, or potassium ferricyanide, as well as, as an optional component, an enzyme stabilizer, a crystal homogenizing agent, a polymer, etc. A cover 103 is disposed above the insulating substrate 101 with a spacer 102 interposed therebetween, with one end (the right end in the drawings) being left uncovered. In this sensor, in order to introduce blood to each electrode (A and B), a channel 14 is formed of the insulating substrate 101, the spacer 102, and the cover 103. The end of the channel 14 extends to the other end (the left end in the drawings) of the sensor and is open to the outside to serve as a biological sample supply port 12. The two electrodes (A and B) are connected to leads, respectively, and these leads extend to the one end side (the right end in the drawings), and the end of each lead is exposed without being covered with the cover. The cover 103 has an air hole 13 formed in a portion corresponding to the right end of the channel 14.

When this biosensor is used as the biosensor that is used in the first method for measuring a component of a biological sample, the second method for measuring a component of a biological sample, or the fourth method for measuring a component of a biological sample, the electrode A may function as the first working electrode and the electrode B may function as the first counter electrode.

In the present invention, the material for the insulating substrate 101 is not particularly limited. Examples of the material that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resin (PMMA), ABS resin (ABS), and glass Among these, polyethylene terephthalate (PET), polycarbonate (PC), and polyimide (PI) are preferable, and polyethylene terephthalate (PET) is more preferable. The size of the insulating substrate is not particularly limited and is, for example, an overall length of 5 to 100 mm, a width of 2 to 50 mm, and a thickness of 0.05 to 2 mm, preferably an overall length of 7 to 50 mm, a width of 3 to 20 mm, and a thickness of 0.1 to 1 mm, and more preferably an overall length of 10 to 30 mm, a width of 3 to 10 mm, and a thickness of 0.1 to 0.6 mm.

The electrodes and leads on the insulating substrate can be formed by forming a conductive layer by sputtering or vapor deposition using, for example, gold, platinum, palladium, or ruthenium as a material and processing it into a specific electrode pattern with a laser. Examples of the laser that can be used include YAG lasers, green lasers, $CO_2$ lasers, and excimer lasers.

The reagent layer 11 is formed as follows. For example, an aqueous solution containing 0.1 to 5 U/sensor of glucose dehydrogenase, 10 to 300 mM of phenanthrenequinone (9,10-phenanthrenequinone), 3-phenylimino-3H-phenothiazine, or potassium ferricyanide, which is used as a mediator, 1 to 50 mM of maltitol, 20 to 200 mM of taurine, and 0.1 to 2% by weight of polymer (also containing a surfactant as necessary) is applied dropwise to a circular slit portion (not shown in the drawings) and then is dried. With this slit portion being provided, spreading of the aqueous solution applied dropwise can be suppressed, and the reagent layer 11 can be disposed at a more accurate position. Thus, the reagent layer 11 is formed so as to cover part of the electrode part formed of the electrodes A and B. The drying may be, for example, natural drying or forced drying using warm air, but if the temperature is too high, the enzyme may be deactivated. Therefore, it is preferable to use warm air at around 50° C.

In the present invention, the material for the spacer 102 is not particularly limited and, for example, the same materials as those used for the insulating substrate can be used. Furthermore, the size of the spacer 102 is not particularly limited and, for example, is an overall length of 5 to 100 mm, a width of 2 to 50 mm, and a thickness of 0.01 to 1 mm, preferably an overall length of 7 to 50 mm, a width of 3 to 20 mm, and a thickness of 0.05 to 0.5 mm, and more preferably an overall length of 10 to 30 mm, a width of 3 to 10 mm, and a thickness of 0.05 to 0.25 mm. The spacer 102 of this example is formed with an I-shaped cutout portion that serves as a channel for blood introduction, and the size thereof is, for example, an overall length of 0.5 to 8 mm and a width of 0.1 to 5 mm, preferably an overall length of 1 to 10 mm and a width of 0.2 to 3 mm, and more preferably an overall length of 1 to 5 mm and a width of 0.5 to 2 mm. The cutout portion may be formed by cutting with, for example, a laser or a drill or may be formed using a mold that can form a cutout portion at the time of forming the spacer 102.

In the present invention, the material for the cover 103 is not particularly limited. For example, the same materials as those used for the insulating substrate can be used. It is further preferable that the portion corresponding to the ceiling portion of the channel for introducing a biological sample of the cover 103 be subjected to a hydrophilic treatment. Examples of the hydrophilic treatment include a method of applying a surfactant and a method of introducing a hydrophilic functional group such as a hydroxyl group, a carbonyl group, or a carboxyl group to the surface of the cover 103 by, for example, a plasma treatment. Furthermore, a layer composed of a surfactant such as lecithin may be formed on the reagent layer. The size of the cover 103 is not particularly limited. For example, the cover may have an overall length of 5 to 100 mm, a width of 3 to 50 mm, and a thickness of 0.01 to 0.5 mm, preferably an overall length of 10 to 50 mm, a width of 3 to 20 mm, and a thickness of 0.05 to 0.25 mm, and more preferably an overall length of 15 to 30 mm, a width of 5 to 10 mm, and a thickness of 0.05 to 0.1 mm. The cover 103 preferably has an air hole 13 formed therein, and the shape thereof is, for example, circular, oval, or polygonal. The size of the air hole 13 is, for example, a maximum diameter of 0.01 to 10 mm, preferably a maximum diameter of 0.05 to 5 mm, and more preferably a maximum diameter of 0.1 to 2 mm. The air hole may be formed by cutting with, for example, a laser or a drill or may be formed using a mold that can form an air vent portion at the time of forming the cover 103.

Moreover, this sensor can be produced by stacking the insulating substrate 101, the spacer 102, and the cover 103 in this order to form one body. The aforementioned three members are stuck together with an adhesive or by thermal fusion bonding to form one body. Examples of the adhesive that can be used herein include an epoxy adhesive, an acrylic adhesive, and a polyurethane adhesive, as well as a thermosetting adhesive (for example, a hot melt adhesive) and a UV curable adhesive.

When this biosensor is used in the first method for measuring a component of a biological sample, the second method for measuring a component of a biological sample, or the fourth method for measuring a component of a biological sample, the electrode A may function as the first working electrode and the electrode B may function as the first counter electrode. Furthermore, the electrode B may function as the first working electrode and the electrode A may function as the first counter electrode.

Figure 4:
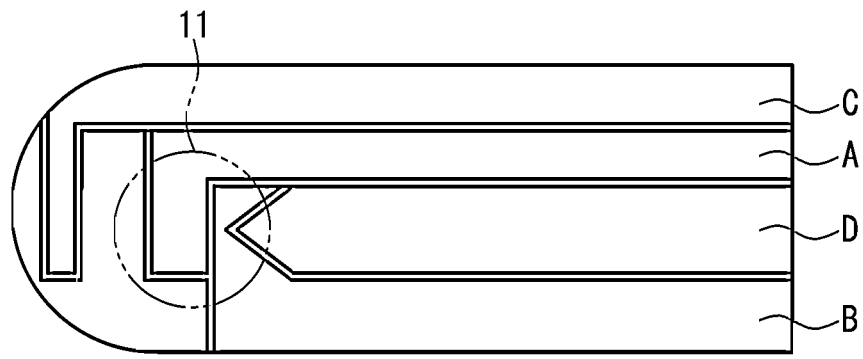
FIG. 4 show a plan view of another example (the first biosensor) of the biosensor used in the present invention.

FIG. 4 shows another example (the first biosensor) of the biosensor used in the present invention. The configuration thereof is the same as that shown in FIGS. 1 and 2 except that the plan view of an insulating substrate 101 shown in FIG. 4 is used instead of the plan view of the insulating substrate 101 shown in FIG. 2. This sensor is a biosensor used, as an example, in the first method for measuring a component of a biological sample, the second method for measuring a component of a biological sample, the third method for measuring a component of a biological sample, the fourth method for measuring a component of a biological sample, or the fifth method for measuring a component of a biological sample.

As shown in the drawing, the first biosensor has four electrodes A, B, C, and D formed on an insulating substrate 101. These electrodes can be switched between a working electrode and a counter electrode. A reagent layer 11 is disposed so as to cover part of the electrodes A, B and D. The four electrodes (A, B, C, and D) are connected to leads, respectively, and these leads extend to the one end side (the right end in the drawing), and the ends of the leads are exposed without being covered with a cover. In the cover 103, an air hole 13 is formed in a portion corresponding to the right end of the channel 14.

When the first biosensor is used as the biosensor that is used in the third method for measuring a component of a biological sample or the fifth method for measuring a component of a biological sample, the electrode A may function as the first working electrode and the second working electrode, the electrode B may function as the first counter electrode and the second counter electrode, and the electrode D may function as a detection electrode. The first working electrode and the first counter electrode correspond to the third working electrode and the third counter electrode of the first biosensor, and the second working electrode and the second counter electrode correspond to the fourth working electrode and the fourth counter electrode of the first biosensor.

TABLE 1

| | Working Electrode | Counter Electrode |
|---|---|---|
| First | A | B |
| Second | A | B |

Furthermore, when the first biosensor is used as the biosensor that is used in the fifth method for measuring a component of a biological sample, the electrode B may function as the first working electrode, the electrode A may function as the first counter electrode and the second counter electrode, and the electrode D may function as a detection electrode. The first working electrode and the first counter electrode correspond to the third working electrode and the third counter electrode of the first biosensor, and the second working electrode and the second counter electrode correspond to the fourth working electrode and the fourth counter electrode of the first biosensor.

TABLE 2

| | Working Electrode | Counter Electrode |
|---|---|---|
| First | B | A |
| Second | B | A |

Moreover, when the first biosensor is used as the biosensor that is used in the first method for measuring a component of a biological sample, the second method for measuring a component of a biological sample, or the fourth method for measuring a component of a biological sample, the electrode A may function as the first working electrode, and the electrode B may function as the first counter electrode.

When the first biosensor is used as the biosensor that is used in the sixth method for measuring a component of a biological sample described later, the electrode A may function as the third working electrode or the fifth working electrode, and the electrode B may function as the third counter electrode or the fifth counter electrode.

TABLE 3

| | Working Electrode | Counter Electrode |
|---|---|---|
| Third | A | B |
| Fifth | A | B |

Furthermore, when the first biosensor is used as the biosensor that is used in the seventh method for measuring a component of a biological sample or the tenth method for measuring a component of a biological sample described later, the electrode A may function as the third working electrode, the fourth working electrode, or the fifth counter, the electrode B may function as the third counter electrode, the fourth counter electrode, or the fifth counter electrode, and the electrode C may function as the fifth working electrode.

TABLE 4

| | Working Electrode | Counter Electrode |
|---|---|---|
| Third | A | B |
| Fourth | A | B |
| Fifth | C | A, B |

When the first biosensor is used as the biosensor that is used in the seventh method for measuring a component of a biological sample or the tenth method for measuring a component of a biological sample described later, the electrode A may function as the third counter electrode, the fourth counter electrode, or the fifth counter, the electrode B may function as the third working electrode, the fourth working electrode, or the fifth counter electrode, and the electrode C may function as the fifth working electrode.

TABLE 5

|  | Working Electrode | Counter Electrode |
| --- | --- | --- |
| Third | B | A |
| Fourth | B | A |
| Fifth | C | A, B |

Figure 5:
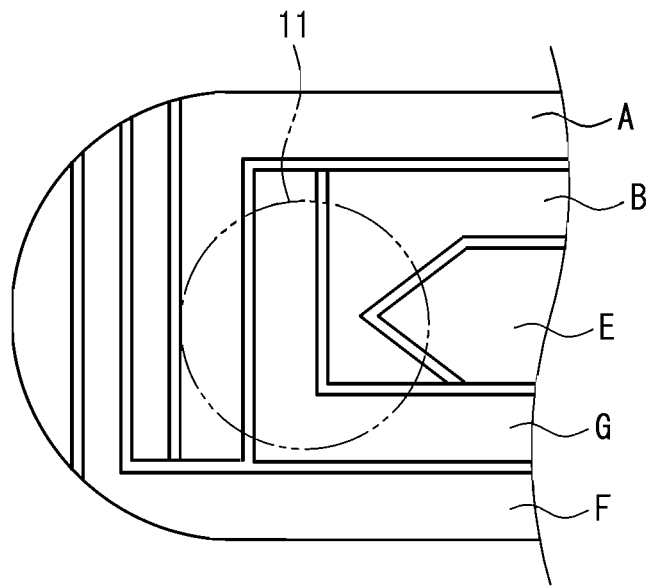
FIG. 5 shows a plan view of still another example (the second biosensor) of the biosensor used in the present invention.

FIG. 5 shows still another example (the second biosensor) of the biosensor used in the present invention. The configuration thereof is the same as that shown in FIGS. 1 and 2 except that the plan view of an insulating substrate 101 shown in FIG. 5 is used instead of the plan view of the insulating substrate 101 shown in FIG. 2. This sensor is a biosensor used, as an example, in the sixth method for measuring a component of a biological sample, the seventh method for measuring a component of a biological sample, the eighth method for measuring a component of a biological sample, the ninth method for measuring a component of a biological sample, the tenth method for measuring a component of a biological sample, or the eleventh method for measuring a component of a biological sample.

As shown in the drawing, the second biosensor has five electrodes A, B, E, F, and G formed on an insulating substrate 101. These electrodes can be switched between a working electrode and a counter electrode. A reagent layer 11 is disposed so as to cover part of the electrodes A, B, E, and G. The electrode A and the electrode B are placed at an interval. That is, another electrode may be provided between the electrode A and the electrode B. Furthermore, the electrode A and the electrode E also are placed at an interval. Moreover, the electrode F is spaced from the reagent layer 11 and placed on the side of a biological sample supply port 12 in a channel 14. The electrode A and the electrode F are placed at an interval. The five electrodes (A, B, E, F, and G) are connected to leads, respectively, and as shown in FIGS. 1 and 2, these leads extend to the one end side (the right end in the drawings), and the ends of the leads are exposed without being covered with a cover. In the cover 103, an air hole 13 is formed in a portion corresponding to the right end of the channel 14. In the third sensor, the electrode A and the electrode B are not adjacent to each other.

When the second biosensor is used as the biosensor that is used in the third method for measuring a component of a biological sample or the fifth method for measuring a component of a biological sample, the electrode A may function as the first working electrode or the second counter electrode, the electrode B may function as the first counter electrode or the second counter electrode, the electrode E may function as a detection electrode or the second counter electrode, and the electrode G may function as the second working electrode. The first working electrode and the first counter electrode correspond to the third working electrode and the third counter electrode of the second biosensor, and the second working electrode and the second counter electrode correspond to the sixth working electrode and the sixth counter electrode of the second biosensor.

TABLE 6

|  | Working Electrode | Counter Electrode |
| --- | --- | --- |
| First | A | B |
| Second | G | A, B, E |

Furthermore, when the second biosensor is used as the biosensor that is used in the third method for measuring a component of a biological sample or the fifth method for measuring a component of a biological sample, the electrode B may function as the first working electrode or the second counter electrode, the electrode A may function as the first counter electrode or the second counter electrode, the electrode E may function as a detection electrode or the second counter electrode, and the electrode G may function as the second working electrode. In the second biosensor, when the electrode A is used as a counter electrode and the electrode B is used as a working electrode in order to obtain a hematocrit value, the electrode A and the electrode B are placed at an interval. Also, when the electrode F is used as a working electrode and any one of the electrodes E, A, or B is used as a counter electrode, the electrode F and any one of the electrode E, A, or B are placed at an interval. The first working electrode and the first counter electrode correspond to the third working electrode and the third counter electrode of the second biosensor, and the second working electrode and the second counter electrode correspond to the sixth working electrode and the sixth counter electrode of the second biosensor.

TABLE 7

|  | Working Electrode | Counter Electrode |
| --- | --- | --- |
| First | B | A |
| Second | G | A, B, E |

When the second biosensor is used as the biosensor that is used in the first method for measuring a component of a biological sample, the second method for measuring a component of a biological sample, or the fourth method for measuring a component of a biological sample, the electrode B and the electrode E may function as the first counter electrode, and the electrode A may function as the first working electrode.

Furthermore, when the second biosensor is used as the biosensor that is used in the eighth method for measuring a component of a biological sample, the ninth method for measuring a component of a biological sample, or the eleventh method for measuring a component of a biological sample described later, the electrode A may function as the third working electrode, the fifth counter electrode, or the sixth counter electrode, the electrode B may function as the third counter electrode, the fifth counter electrode, or the sixth counter electrode, the electrode E may function as a detection electrode or the sixth counter electrode, the electrode F may function as the fifth working electrode, and the electrode G may function as the fifth counter electrode or the sixth working electrode.

TABLE 8

|       | Working Electrode | Counter Electrode |
|-------|-------------------|-------------------|
| Third | A                 | B                 |
| Fifth | F                 | A, B, G           |
| Sixth | G                 | A, B, E           |

Moreover, when the second biosensor is used as the biosensor that is used in the eighth method for measuring a component of a biological sample, the ninth method for measuring a component of a biological sample, or the eleventh method for measuring a component of a biological sample described later, the electrode A may function as the third counter electrode, the fifth counter electrode, or the sixth counter electrode, the electrode B may function as the third working electrode, the fifth counter electrode, or the sixth counter electrode, the electrode E may function as a detection electrode or the sixth counter electrode, the electrode F may function as the fifth working electrode, and the electrode G may function as the fifth counter electrode or the sixth working electrode.

TABLE 9

|       | Working Electrode | Counter Electrode |
|-------|-------------------|-------------------|
| Third | B                 | A                 |
| Fifth | F                 | A, B, G           |
| Sixth | G                 | A, B, E           |

It is preferable that the detection electrode be positioned behind at least one of the respective electrode systems from the biological sample supply 12 and that this blood detection electrode can detect that the biological sample has been reliably introduced into at least one of the respective electrode systems More preferably, the blood detection electrode is positioned behind all the respective electrode systems.

Figure 6:
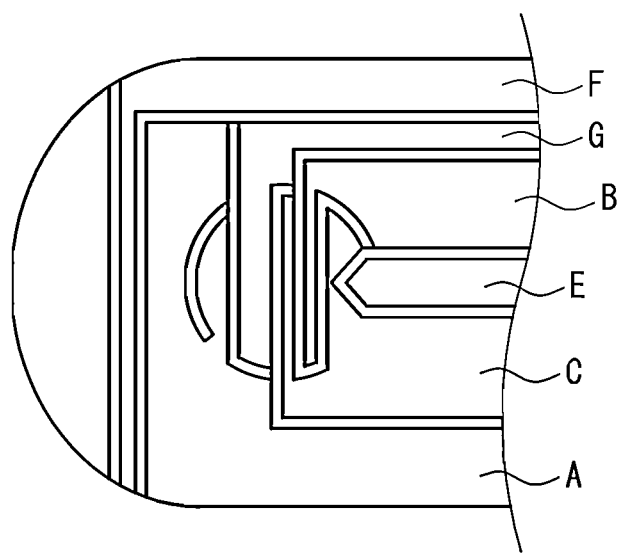
FIG. 6 shows a plan view of yet another example (the third biosensor) of the biosensor used in the present invention.

FIG. 6 shows yet another example (the third biosensor) of the biosensor used in the present invention. The configuration thereof is the same as that shown in FIGS. 1 and 2 except that the plan view of an insulating substrate 101 shown in FIG. 6 is used instead of the plan view of the insulating substrate 101 shown in FIG. 2. This sensor is a biosensor used, as an example, in the twelfth method for measuring a component of a biological sample, the thirteenth method for measuring a component of a biological sample, the fourteenth method for measuring a component of a biological sample, the fifteenth method for measuring a component of a biological sample, the sixteenth method for measuring a component of a biological sample, and the seventeenth method for measuring a component of a biological sample.

As shown in the drawing, the third biosensor has six electrodes A, B, C, E, F, and G formed on the insulating substrate 101. These electrodes can be switched between a working electrode and a counter electrode. A reagent layer 11 is disposed so as to cover part of the electrodes A, B, C, E, and G. The electrode A and the electrode B are placed at an interval. That is, another electrode may be provided between the electrode A and the electrode B. Furthermore, the electrode A and the electrode E also are placed at an interval. Moreover, the electrode F is spaced from the reagent layer 11 and placed on the side of a biological sample supply port 12 in a channel 14. The electrode A and the electrode F are placed at an interval. The six electrodes (A, B, C, E, F, and G) are connected to leads, respectively, and as shown in FIGS. 1 and 2, these leads extend to the one end side (the right end in the drawings), and the ends of the leads are exposed without being covered with a cover. In the cover 103, an air hole 13 is formed in a portion corresponding to the right end of the channel 14. In the fourth sensor, the electrode A and the electrode B are not adjacent to each other.

The electrode configurations shown in Tables 10 to 21 below can also be obtained by using the second biosensor instead of the third biosensor. However, as examples, the electrode configurations obtained in the case of using the third biosensor are described.

When the third biosensor is used as the biosensor that is used in the sixth method for measuring a component of a biological sample, the seventh method for measuring a component of a biological sample, or the tenth method for measuring a component of a biological sample described later, the electrode A may function as the third working electrode or the fourth working electrode, the electrode B may function as the third counter electrode or the fourth counter electrode, the electrode C may function as the fourth counter electrode, and the electrode E may function as a detection electrode.

TABLE 11

|        | Working Electrode | Counter Electrode |
|--------|-------------------|-------------------|
| Third  | B                 | A                 |
| Fourth | B                 | A, C              |

Furthermore, when the third biosensor is used as the biosensor that is used in the sixth method for measuring a component of a biological sample, the seventh method for measuring a component of a biological sample, or the tenth method for measuring a component of a biological sample described later, the electrode A may function as the third counter electrode or the fourth counter electrode, the electrode B may function as the third working electrode or the fourth working electrode, the electrode C may function as the fourth counter electrode, and the electrode E may function as a detection electrode.

TABLE 10

|        | Working Electrode | Counter Electrode |
|--------|-------------------|-------------------|
| Third  | A                 | B                 |
| Fourth | A                 | B, C              |

When the third biosensor is used as the biosensor that is used in the twelfth method for measuring a component of a biological sample described later, the electrode A may function as the third working electrode, the fourth working electrode, or the fifth counter electrode, the electrode B may function as the third counter electrode, the fourth counter electrode, or the fifth counter electrode, the electrode C may function as the fourth counter electrode or the fifth counter electrode, the electrode E may function as a detection electrode, the electrode F may function as the fifth working electrode, and the electrode G may function as the fifth counter electrode.

TABLE 12

| | Working Electrode | Counter Electrode |
|---|---|---|
| Third | A | B |
| Fourth | A | B, C |
| Fifth | F | A, B, C, G |

When the third biosensor is used as the biosensor that is used in the twelfth method for measuring a component of a biological sample described later, or the electrode B may function as the third working electrode, the fourth working electrode, or the fifth counter electrode, the electrode A may function as the third counter electrode, the fourth counter electrode, or the fifth counter electrode, the electrode C may function as the fourth counter electrode or the fifth counter electrode, the electrode E may function as a detection electrode, the electrode F may function as the fifth working electrode, and the electrode G may function as the fifth counter electrode. In the third biosensor, when the electrode A is used as a counter electrode and the electrode B is used as a working electrode in order to obtain a hematocrit value, the electrode A and the electrode B are placed at an interval. Also, when the electrode F is used as a working electrode and the electrode A, B, C, or G is used as a counter electrode, the electrode F and the electrode A, B, C, or G are placed at an interval.

TABLE 13

| | Working Electrode | Counter Electrode |
|---|---|---|
| Third | B | A |
| Fourth | B | A, C |
| Fifth | F | A, B, C, G |

Furthermore, when the third biosensor is used as the biosensor that is used in the thirteenth method for measuring a component of a biological sample described later, the electrode A may function as the third working electrode, the fourth counter electrode, or the fifth working electrode, the electrode B may function as the third counter electrode, the fourth counter electrode, or the fifth counter electrode, the electrode C may function as the third counter electrode, the fourth counter electrode, or the fifth counter electrode, the electrode E may function as a detection electrode, the electrode F may function as the fourth working electrode, and the electrode G may function as the fifth working electrode.

TABLE 14

| | Working Electrode | Counter Electrode |
|---|---|---|
| Third | A | B |
| Fifth | F | A, B, C, G |
| Sixth | G | B, C, E |

Furthermore, when the third biosensor is used as the biosensor that is used in the thirteenth method for measuring a component of a biological sample described later, the electrode B may function as the third working electrode or the fifth counter electrode, the electrode A may function as the third counter electrode, the fifth counter electrode, or the sixth counter electrode, the electrode C may function as the fifth counter electrode or the sixth counter electrode, the electrode E may function as a detection electrode, the electrode F may function as the fifth working electrode, and the electrode G may function as the fifth counter electrode or the fifth working electrode.

TABLE 15

| | Working Electrode | Counter Electrode |
|---|---|---|
| Third | B | A |
| Fifth | F | A, B, C, G |
| Sixth | G | A, C, E |

When the third biosensor is used as the biosensor that is used in the eighteenth method for measuring a component of a biological sample described later, the electrode A may function as the third working electrode, the fourth working electrode, or the fifth counter electrode, the electrode B may function as the third counter electrode, the fourth counter electrode, the fifth counter electrode, or the sixth counter electrode, the electrode C may function as the fourth counter electrode, the fifth counter electrode, or the sixth counter electrode, the electrode E may function as a detection electrode or the sixth counter electrode, the electrode F may function as the fifth working electrode, and the electrode G may function as the fifth counter electrode or the sixth working electrode.

TABLE 16

| | Working Electrode | Counter Electrode |
|---|---|---|
| Third | A | B |
| Fourth | A | B, C, E |
| Fifth | F | A, B, C, G |
| Sixth | G | B, C, E |

When the third biosensor is used as the biosensor that is used in the eighteenth method for measuring a component of a biological sample described later, the electrode A may function as the third counter electrode, the fourth counter electrode, the fifth counter electrode, or the sixth counter electrode, the electrode B may function as the third working electrode, the fourth working electrode, or the fifth working electrode, the electrode C may function as the fourth counter electrode, the fifth counter electrode, or the sixth counter electrode, the electrode E may function as a detection electrode or the sixth counter electrode, the electrode F may function as the fifth working electrode, and the electrode G may function as the fifth counter electrode or the sixth working electrode. In the third biosensor, when the electrode A is used as a counter electrode and the electrode B is used as a working electrode in order to obtain a hematocrit value, the electrode A and the electrode B are placed at an interval. Also, when the electrode F is used as a working electrode and the electrode A, B, C, or G is used as a counter electrode, the electrode F and the electrode A, B, C, or G are placed at an interval.

TABLE 17

| | Working Electrode | Counter Electrode |
|---|---|---|
| Third | B | A |
| Fourth | B | A, C, E |
| Fifth | F | A B, C, G |
| Sixth | G | A, C, E |

Furthermore, when the third biosensor is used as the biosensor that is used in the fourteenth method for measuring a component of a biological sample described later, the electrode A may function as the third working electrode, the fourth working electrode, or the fifth counter electrode, the electrode B may function as the third counter electrode, the fourth counter electrode, the fifth counter electrode, or the seventh counter electrode, the electrode C may function as the fourth counter electrode, the fifth counter electrode, or the seventh counter electrode, the electrode E may function as a detection electrode, the electrode F may function as the fifth working electrode or the seventh working electrode, and the electrode G may function as the sixth counter electrode.

TABLE 18

|  | Working Electrode | Counter Electrode |
| --- | --- | --- |
| Third | A | B |
| Fourth | A | B, C, E |
| Fifth | F | A, B, C, G |
| Seventh | F | B, C, E |

Furthermore, when the third biosensor is used as the biosensor that is used in the fourteenth method for measuring a component of a biological sample described later, the electrode B may function as the third working electrode, the fourth working electrode, or the fifth counter electrode, the electrode A may function as the third counter electrode, the fourth counter electrode, the fifth counter electrode, or the seventh working electrode, the electrode C may function as the fourth counter electrode, the fifth counter electrode, or the seventh counter electrode, the electrode F may function as the fifth working electrode or the seventh working electrode, and the electrode G may function as the fifth counter electrode. In the third biosensor, when the electrode A is used as a counter electrode and the electrode B is used as a working electrode in order to obtain a hematocrit value, the electrode A and the electrode B are placed at an interval. Also, when the electrode F is used as a working electrode and the electrode A, B, C, or G is used as a counter electrode, the electrode F and the electrode A, B, C, or G are placed at an interval.

TABLE 19

|  | Working Electrode | Counter Electrode |
| --- | --- | --- |
| Third | B | A |
| Fourth | B | A, C, E |
| Fifth | F | A, B, C, G |
| Seventh | F | A, C, E |

Furthermore, the third biosensor is used as the biosensor that is used in the sixteenth method for measuring a component of a biological sample described later, the electrode A may function as the third working electrode, the fourth working electrode, or the fifth counter electrode, the electrode B may function as the third counter electrode, the fourth counter electrode, the fifth counter electrode, or the seventh counter electrode, the electrode C may function as the fourth counter electrode, the fifth counter electrode, or the seventh counter electrode, the electrode E may function as a detection electrode, the electrode F may function as the fifth working electrode or the seventh working electrode, and the electrode G may function as the fifth counter electrode or the seventh working electrode.

TABLE 20

|  | Working Electrode | Counter Electrode |
| --- | --- | --- |
| Third | A | B |
| Fourth | A | B, C, E |
| Fifth | F | A, B, C, G |
| Seventh | F | B, C, E |

Furthermore, when the third biosensor is used as the biosensor that is used in the sixteenth method for measuring a component of a biological sample described later, the electrode B may function as the third working electrode, the fourth working electrode, or the fifth counter electrode, the electrode A may function as the third counter electrode, the fourth counter electrode, the fifth counter electrode, or the seventh counter electrode, the electrode C may function as the fourth counter electrode, the fifth counter electrode, or the seventh counter electrode, the electrode E may function as a detection electrode, the electrode F may function as the fifth working electrode or the seventh working electrode, and the electrode G may function as the fifth counter electrode. In the third biosensor, when the electrode A is used as a counter electrode and the electrode B is used as a working electrode in order to obtain a hematocrit value, the electrode A and the electrode B are placed at an interval. Also, when the electrode F is used as a working electrode and the electrode A, B, C, or G is used as a counter electrode, the electrode F and the electrode A, B, C, or G are placed at an interval.

TABLE 21

|  | Working Electrode | Counter Electrode |
| --- | --- | --- |
| Third | B | A |
| Fourth | B | A, C, E |
| Fifth | F | A, B, C, G |
| Seventh | F | A, C, E |

It is preferable that the detection electrode be positioned behind at least one of the respective electrode systems from the biological sample supply 12 and that this blood detection electrode can detect that the biological sample has been reliably introduced into at least one of the respective electrode systems More preferably, the blood detection electrode is positioned behind all the respective electrode systems.

Figure 7:
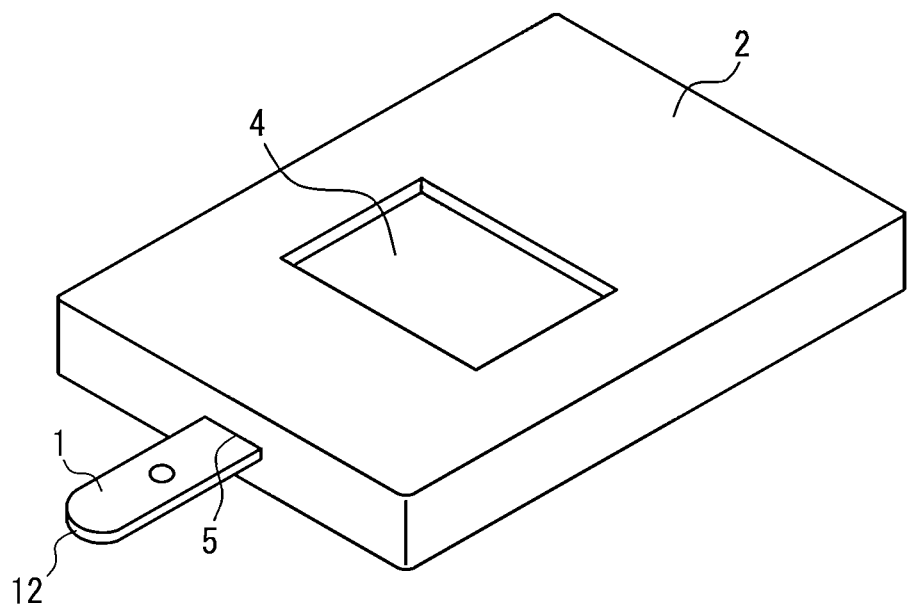
FIG. 7 shows a perspective view of an example of a measuring apparatus of the present invention, with a biosensor used in a measuring method of the present invention being inserted thereinto.

FIG. 7 shows a perspective view of an example of a measuring apparatus of the present invention, with a biosensor 1 used in the measuring method of the present invention being inserted thereinto. As shown in the drawing, the measuring apparatus 2 has an insertion port 5 for the sensor 1 at one end thereof, and the sensor 1 is inserted thereinto and held therein. Reference sign 12 denotes a biological sample supply port of the sensor 1. Furthermore, the measuring apparatus 2 has a display unit 4 substantially in the center thereof, and the measurement result is displayed here.

Figure 8:
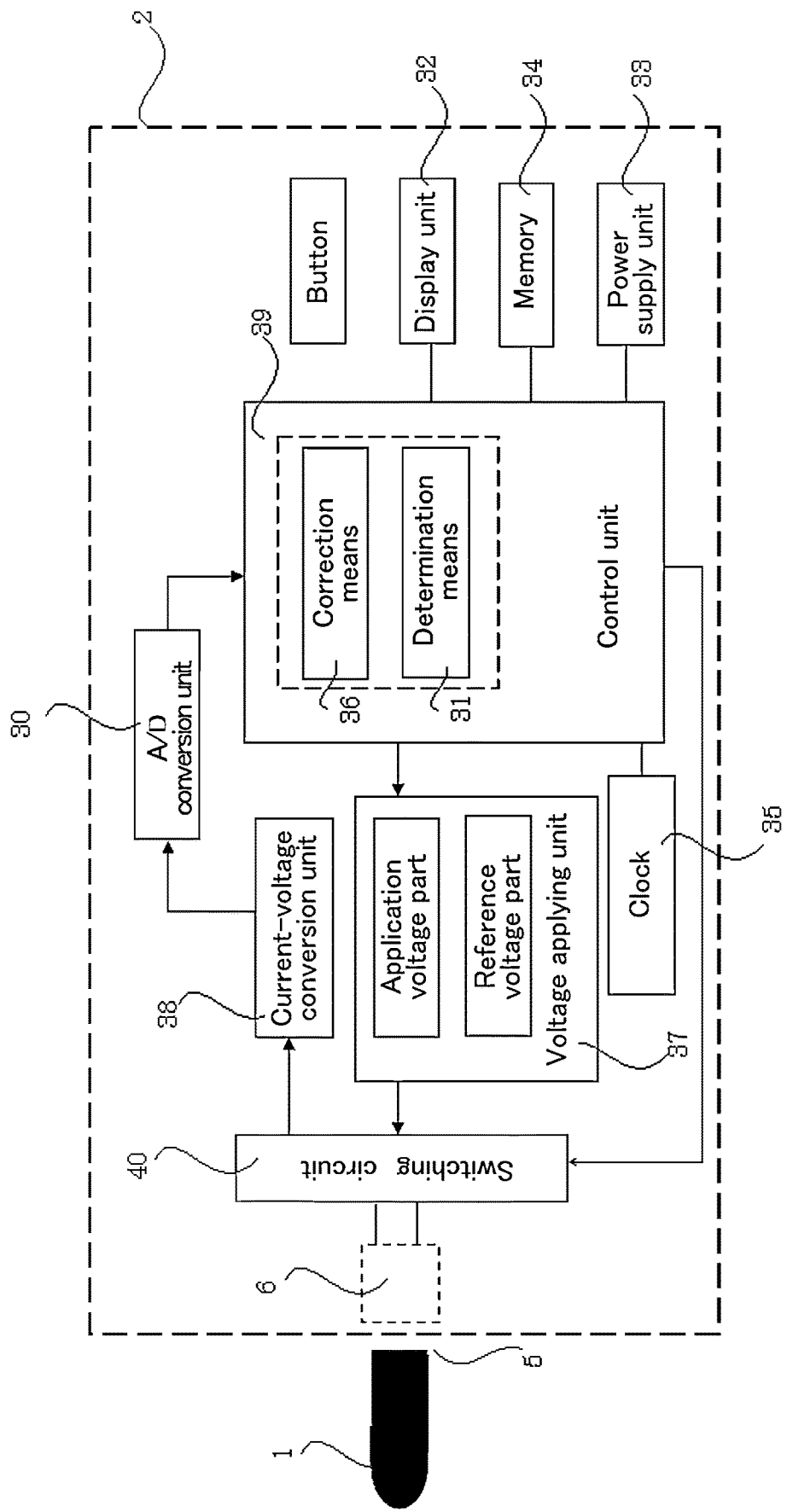
FIG. 8 shows an example of an electric block diagram of the measuring apparatus of the present invention, with the biosensor used in the measuring method of the present invention being inserted thereinto.

FIG. 8 shows an example of an electric block diagram of the measuring apparatus of the present invention, with the biosensor 1 used in the measuring method of the present invention being inserted thereinto. In the measuring apparatus of the present invention, a voltage applying unit 37 for applying a voltage and a current-voltage conversion unit 38 are connected to an input terminal section 6 of the measuring apparatus according to an embodiment of the present invention. A voltage is applied to the voltage applying unit 37 from a control unit 39 and this voltage is applied to a desired electrode selected from the electrodes of the biosensor 1 for a predetermined duration through the input terminal section 6. The current that flows between the electrodes in the biosensor 1 by the voltage application is converted into a voltage by a current-voltage conversion unit 38. Thereafter, the voltage is digitally converted by an A/D conversion unit 30, and the voltage thus digitally converted is compared with a threshold value by a determination means 31.

On the display unit 32 connected to the control unit 39, the value of the component detected by the biosensor 1 and the result of determination made by the determination means 31 are displayed. In FIG. 8, reference sign 33 denotes a power supply unit for supplying power to the respective parts. Reference sign 34 denotes a memory that is provided with a table including, for example, applied voltage and voltage application time used at the time of measurement of a Hct value and Glu, as well as a calibration curve and calibration table prepared in advance based on the environmental temperature.

A clock 35 is connected to the control unit 39, and the control unit 39 is configured to utilize the time shown and the time measured by the clock 35 to execute various control operations. Furthermore, a correction means 36 is provided in the control unit 39 to correct a measured Glu value with the Hct value and thereby the measurement accuracy of the Glu value is improved.

<Sixth Method for Measuring Component of Biological Sample>

Moreover, the present invention is:

a method for measuring a component of a biological sample, including a step of using the first biosensor to obtain a Hct value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value; and a step of obtaining a Hct value of the biological sample based on the first current value and the second current value (the sixth method for measuring a component of a biological sample).

In the sixth method for measuring a component of a biological sample, the duration of the voltage application to the first Hct measurement system is any duration longer than 0 second and up to 0.7 second, preferably any duration longer than 0 second and up to 0.5 second, and further preferably any duration longer than 0 second and up to 0.1 second. Moreover, it is preferable that the voltage application to the first Hct measurement system be started at 0 second after detection of introduction of the biological sample.

In the sixth method for measuring a component of a biological sample, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the sixth method for measuring a component of a biological sample, the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the sixth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the sixth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the sixth method for measuring a component of a biological sample, the Hct value can be measured in a short time in the first Hct measurement system, and the Glu value corrected using the Hct value in the first Hct measurement system can be obtained with high accuracy.

<Seventh Method for Measuring Component of Biological Sample>

Furthermore, the present invention is:

the sixth method for measuring a component of a biological sample, further including: a step of applying a voltage to the first Hct measurement system after the step to obtain a first current value, to obtain a current value that depends on Glu, and a step of obtaining a Glu value of the biological sample based on the current value that depends on Glu and the Hct value of the biological sample (the seventh method for measuring a component of a biological sample).

In the seventh method for measuring a component of a biological sample, the duration of the voltage application to the first Hct measurement system in the step to obtain a current value that depends on Glu is preferably any duration between 0.01 and 10.0 seconds, more preferably any duration between 0.1 and 7.0 seconds, and further preferably any duration between 0.1 and 5.0 seconds.

In the seventh method for measuring a component of a biological sample, the voltage to be applied to the first Hct measurement system in the step to obtain a current value that depends on Glu is preferably any voltage in the range of 0.1 V to 1.4 V, more preferably any voltage in the range of 0.1 V to 1.0 V.

In the seventh method for measuring a component of a biological sample, it is preferable that the step to obtain a second current value be performed after the step to obtain a current value that depends on Glu.

According to the seventh method for measuring a component of a biological sample, since the current value that depends on Glu in the vicinity of the electrodes that are in contact with the reagent layer and the Hct value in the vicinity of the same electrodes are used to obtain a Glu value, the Glu value can be measured, with the properties of the biological sample in the vicinity of the electrodes being reflected with higher accuracy. Moreover, according to such a method, the Hct value can be measured in a short time in the first Hct measurement system, and the Glu value corrected using the Hct value can be obtained with high accuracy.

In the seventh method for measuring a component of a biological sample, the step of applying a voltage to the first Hct measurement system to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

The seventh method for measuring a component of a biological sample may further include a step of applying a voltage to the first Hct measurement system to obtain another Hct value based on the current value obtained thereby after the step to obtain a current value that depends on Glu. In this case, in the step of using the current value that depends on Glu and the Hct value to obtain a Glu value, the current value that depends on Glu and two Hct values are used to obtain a Glu value. When a voltage is applied to the second Hct measurement system to obtain another Hct value based on the current value obtained thereby after the step to obtain a current value that depends on Glu, the measurement accuracy can be further improved, which is preferable.

<Eighth Method for Measuring Component of Biological Sample>

Moreover, the present invention is:

a method for measuring a component of a biological sample, including a step of using the second biosensor to obtain a Hct value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value; and a step of obtaining the Hct value of the biological sample based on the first current value and the second current value (the eighth method for measuring a component of a biological sample).

In the eighth method for measuring a component of a biological sample, the duration of the voltage application to the first Hct measurement system is preferably any duration longer than 0 second and up to 0.5 second, further preferably any duration longer than 0 second and up to 0.1 second.

In the eighth method for measuring a component of a biological sample, it is preferable that the voltage application to the first Hct measurement system be started at 0 second after detection of introduction of the biological sample. Furthermore, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the eighth method for measuring a component of a biological sample, the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the eighth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the eighth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the eighth method for measuring a component of a biological sample, the Hct value can be measured in a short time in the first Hct measurement system, and the Glu value corrected using the Hct value can be obtained with high accuracy.

<Ninth Method for Measuring Component of Biological Sample>

Furthermore, the present invention is a method for measuring a component of a biological sample, further including, in the eighth method for measuring a component of a biological sample:

a step of applying a voltage to the electrode system for obtaining a current value that depends on Glu after the step to obtain a first current value, to obtain a current value that depends on Glu; and a step of obtaining a Glu value of the biological sample based on the current value that depends on Glu and the Hct value of the biological sample (the ninth method for measuring a component of a biological sample).

In the ninth method for measuring a component of a biological sample, the duration of the voltage application to the electrode system for obtaining a current value that depends on Glu is preferably any duration between 0.01 and 10.0 seconds, more preferably any duration between 0.1 and 7.0 seconds, and further preferably any duration between 0.1 and 5.0 seconds.

In the ninth method for measuring a component of a biological sample, the voltage to be applied to the electrode system for obtaining a current value that depends on Glu is preferably any voltage in the range of 0.1 V to 1.4 V, more preferably any voltage in the range of 0.1 V to 1.0 V.

In the ninth method for measuring a component of a biological sample, it is preferable that the step to obtain a second current value be performed after the step to obtain a current value that depends on Glu.

According to the ninth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the ninth method for measuring a component of a biological sample, the step of applying a voltage to the electrode system for obtaining a current value that depends on Glu to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

The ninth method for measuring a component of a biological sample may further include a step of applying a voltage to the second Hct measurement system to obtain another Hct value based on the current value obtained thereby after the step to obtain a current value that depends on Glu. In this case, in the step of using the current value that depends on Glu and the Hct value to obtain a Glu value, the current value that depends on Glu and two Hct values are used to obtain a Glu value. When a voltage is applied to the second Hct measurement system to obtain another Hct value based on the current value obtained thereby after the step to obtain a current value that depends on Glu, the measurement accuracy can be further improved, which is preferable.

<Tenth Method for Measuring Component of Biological Sample>

Moreover, the present invention is;

a method for measuring a component of a biological sample, including a step of using the first biosensor to obtain a Glu value of the biological sample, the method including;

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of applying a voltage to the first Hct measurement system after the step to obtain a first current value, to obtain a current value that depends on Glu; and a step of using the current value that depends on Glu, the first current value, and the second current value to obtain a Glu value of the biological sample (the tenth method for measuring a component of a biological sample).

In the tenth method for measuring a component of a biological sample, the duration of the voltage application to the first Hct measurement system in the step to obtain a first current value is preferably any duration longer than 0 second and up to 0.5 second, further preferably any duration longer than 0 second and up to 0.1 second.

In the tenth method for measuring a component of a biological sample, it is preferable that the voltage application to the first Hct measurement system in the step to obtain a first current value be started at 0 second after detection of introduction of the biological sample.

In the tenth method for measuring a component of a biological sample, the voltage application to the first Hct measurement system in the step to obtain a first current value is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the tenth method for measuring a component of a biological sample, the voltage to be applied to the first Hct measurement system in the step to obtain a first current value is preferably any voltage in the range of 1.5 to 4.0 V, more preferably any voltage in the range of 1.5 V to 3.0 V, and further preferably any voltage in the range of 1.5 V to 2.5 V.

In the tenth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the tenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

In the tenth method for measuring a component of a biological sample, the duration of the voltage application to the first Hct measurement system in the step to obtain a current value that depends on Glu is preferably any duration between 0.01 and 10.0 seconds, more preferably any duration between 0.1 and 7.0 seconds, and further preferably any duration between 0.1 and 5.0 seconds.

In the tenth method for measuring a component of a biological sample, the voltage to be applied to the first Hct measurement system in the step to obtain a current value that depends on Glu is preferably any voltage in the range of 0.1 V to 1.4 V, more preferably any voltage in the range of 0.1 V to 1.0 V.

In the tenth method for measuring a component of a biological sample, it is preferable that the step to obtain a second current value be performed after the step to obtain a current value that depends on Glu.

In the tenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the tenth method for measuring a component of a biological sample, the step of applying a voltage to the first Hct measurement system to obtain a current value that depends on Glu may be performed multiple times. In this case, a plurality of the current values that depend on Glu, the first current value, and the second current value (the current value that depends on Hct) are used to obtain a Glu value. When the step to obtain a current value that depends on Glu is performed multiple times, the measurement accuracy can be further improved, which is preferable.

<Eleventh Method for Measuring Component of Biological Sample>

Furthermore, the present invention is:

a method for measuring a component of a biological sample, including a step of using the second biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of applying a voltage to the electrode system for obtaining a current value that depends on Glu after the step to obtain a first current value, to obtain a current value that depends on Glu; and a step of using the current value that depends on Glu, the first current value, and the second current value to obtain a Glu value of the biological sample (the eleventh method for measuring a component of a biological sample).

In the eleventh method for measuring a component of a biological sample, the duration of the voltage application to the first Hct measurement system is preferably any duration longer than 0 second and up to 0.5 second, further preferably any duration longer than 0 second and up to 0.1 second. Moreover, it is preferable that the voltage application to the first Hct measurement system be started at 0 second after detection of introduction of the biological sample.

In the eleventh method for measuring a component of a biological sample, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the eleventh method for measuring a component of a biological sample, the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the eleventh method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the eleventh method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

In the eleventh method for measuring a component of a biological sample, the duration of the voltage application to the electrode system for obtaining a current value that depends on Glu is preferably any duration between 0.01 and 10.0 seconds, more preferably any duration between 0.1 and 7.0 seconds, and further preferably any duration between 0.1 and 5.0 seconds.

In the eleventh method for measuring a component of a biological sample, the voltage to be applied to the electrode system for obtaining a current value that depends on Glu is preferably any voltage in the range of 0.1 V to 1.4 V, more preferably any voltage in the range of 0.1 V to 1.0 V.

In the eleventh method for measuring a component of a biological sample, it is preferable that the step to obtain a second current value be performed after the step to obtain a current value that depends on Glu.

According to the eleventh method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the eleventh method for measuring a component of a biological sample, the step of applying a voltage to the electrode system for obtaining a current value that depends on Glu to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

<Twelfth Method for Measuring Component of Biological Sample>

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a current value that depends on Glu; and a step of obtaining the Glu value of the biological sample based on the current value that depends on Glu and the Hct value of the biological sample (the twelfth method for measuring a component of a biological sample).

In the twelfth method for measuring a component of a biological sample, the duration of the voltage application to the first Hct measurement system for obtaining a first current value is preferably any duration longer than 0 second and up to 0.5 second, further preferably any duration longer than 0 second and up to 0.1 second. Moreover, it is preferable that the voltage application to the first Hct measurement system be started at 0 second after detection of introduction of the biological sample.

In the twelfth method for measuring a component of a biological sample, the voltage application to the first Hct measurement system for obtaining a first current value is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the twelfth method for measuring a component of a biological sample, the voltage to be applied to the first Hct measurement system for obtaining a first current value is preferably any voltage in the range of 1.5 to 4.0 V, more preferably any voltage in the range of 1.5 V to 3.0 V, and further preferably any voltage in the range of 1.5 V to 2.5 V.

In the twelfth method for measuring a component of a biological sample,
the duration of the voltage application to the second Hct measurement system is preferably any duration between 0.01 and 5.0 seconds, more preferably any duration between 0.05 and 1.0 second, and further preferably any duration between 0.1 and 0.5 second.

In the twelfth method for measuring a component of a biological sample,
the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

In the twelfth method for measuring a component of a biological sample,
the duration of the voltage application to the first Hct measurement system for obtaining the current value that depends on Glu is preferably any duration between 0.01 and 10.0 seconds, more preferably any duration between 0.1 and 7.0 seconds, and further preferably any duration between 0.1 and 5.0 seconds.

In the twelfth method for measuring a component of a biological sample,
the voltage to be applied to the first Hct measurement system for obtaining the current value that depends on Glu is preferably any voltage in the range of 0.1 V to 1.4 V, more preferably any voltage in the range of 0.1 V to 1.0 V.

According to the twelfth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the twelfth method for measuring a component of a biological sample, the step of applying a voltage to the electrode system for obtaining a current value that depends on Glu to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

The twelfth method for measuring a component of a biological sample may further include a step of applying a voltage to the first Hct measurement system to obtain a third current value. It is preferable that the step to obtain a third current value be performed after the step to obtain a second current value.

<Thirteenth Method for Measuring Component of Biological Sample>

Furthermore, the present invention is:
a method for measuring a component of a biological sample, including a step of using the third biosensor to obtain a Glu value of the biological sample, the method including:
a step of starting voltage application for a duration longer than 0 second and up to 0.7 second to the first Hct measurement system within 0 second to 0.5 second after detection of introduction of the biological sample to obtain a first current value;
a step of applying a voltage to the second Hct measurement system after the step to obtain a first current value, to obtain a second current value;
a step of obtaining a Hct value of the biological sample based on the first current value and the second current value;
a step of applying a voltage to the electrode system for obtaining a current value that depends on Glu after the step to obtain a first current value, to obtain a current value that depends on Glu; and
a step of obtaining the Glu value of the biological sample based on the current value that depends on Glu and the Hct value of the biological sample (the thirteenth method for measuring a component of a biological sample).

In the thirteenth method for measuring a component of a biological sample,
the duration of the voltage application to the first Hct measurement system is preferably any duration longer than 0 second and up to 0.5 second, further preferably any duration longer than 0 second and up to 0.1 second.

In the thirteenth method for measuring a component of a biological sample,
it is preferable that the voltage application to the first Hct measurement system be started at 0 second after detection of introduction of the biological sample. Furthermore, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the thirteenth method for measuring a component of a biological sample,
the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the thirteenth method for measuring a component of a biological sample,
the duration of the voltage application to the second Hct measurement system is preferably any duration between 0.01 and 5.0 seconds, more preferably any duration between 0.05 and 1.0 second, and further preferably any duration between 0.1 and 0.5 second.

In the thirteenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the thirteenth method for measuring a component of a biological sample, the Hct value can be measured in a short time in the first Hct measurement system, and the Glu value corrected using the Hct value can be obtained with high accuracy.

In the thirteenth method for measuring a component of a biological sample, the duration of the voltage application to the electrode system for obtaining a current value that depends on Glu is preferably any duration between 0.01 and 10.0 seconds, more preferably any duration between 0.1 and 7.0 seconds, and further preferably any duration between 0.1 and 5.0 seconds.

In the thirteenth method for measuring a component of a biological sample, the voltage to be applied to the electrode system for obtaining a current value that depends on Glu is preferably any voltage in the range of 0.1 V to 1.4 V, more preferably any voltage in the range of 0.1 V to 1.0 V.

In the thirteenth method for measuring a component of a biological sample, it is preferable that the step to obtain a second current value be performed after the step to obtain a current value that depends on Glu.

According to the thirteenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the thirteenth method for measuring a component of a biological sample, the step of applying a voltage to the electrode system for obtaining a current value that depends on Glu to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

The thirteenth method for measuring a component of a biological sample may further include a step of applying a voltage to the second Hct measurement system to obtain another Hct value based on the current value obtained thereby after the step to obtain a current value that depends on Glu. In this case, in the step of using the current value that depends on Glu and the Hct value to obtain a Glu value, the current value that depends on Glu and two Hct values are used to obtain a Glu value. When a voltage is applied to the second Hct measurement system to obtain another Hct value based on the current value obtained thereby after the step to obtain a current value that depends on Glu, the measurement accuracy can be further improved, which is preferable.

<Fourteenth Method for Measuring Component of Biological Sample>

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a current value that depends on Glu;

a step of applying a voltage to an electrode system for obtaining a current value that depends on Int after the step to obtain a current value that depends on Glu, to obtain a current value that depends on an Int value of the biological sample; and a step of obtaining the Glu value of the biological sample based on the current value that depends on Glu, the Hct value of the biological sample, and the current value that depends on an Int value of the biological sample (the fourteenth method for measuring a component of a biological sample).

In the fourteenth method for measuring a component of a biological sample, the duration of the voltage application to the first Hct measurement system for obtaining a first current value is preferably any duration longer than 0 second and up to 0.5 second, further preferably any duration longer than 0 second and up to 0.1 second. Furthermore, it is preferable that the voltage application to the first Hct measurement system be started at 0 second after detection of introduction of the biological sample.

In the fourteenth method for measuring a component of a biological sample, the voltage application to the first Hct measurement system for obtaining a first current value is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the fourteenth method for measuring a component of a biological sample, the voltage to be applied to the first Hct measurement system for obtaining a first current value is preferably any voltage in the range of 1.5 to 4.0 V, more preferably any voltage in the range of 1.5 V to 3.0 V, and further preferably any voltage in the range of 1.5 V to 2.5 V.

In the fourteenth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the fourteenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

In the fourteenth method for measuring a component of a biological sample,
the duration of the voltage application to the first Hct measurement system for obtaining the current value that depends on Glu is preferably any duration between 0.01 and 10.0 seconds, more preferably any duration between 0.1 and 7.0 seconds, and further preferably any duration between 0.1 and 5.0 seconds.

In the fourteenth method for measuring a component of a biological sample,
the voltage to be applied to the first Hct measurement system for obtaining the current value that depends on Glu is preferably any voltage in the range of 0.1 V to 1.4 V, more preferably any voltage in the range of 0.1 V to 1.0 V.

According to the fourteenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the fourteenth method for measuring a component of a biological sample, the step of applying a voltage to the first Hct measurement system to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

The fourteenth method for measuring a component of a biological sample may further include a step of applying a voltage to the first Hct measurement system to obtain a third current value. It is preferable that the step to obtain a third current value be performed after the step to obtain a second current value.

In the fourteenth method for measuring a component of a biological sample, the duration of the voltage application to the electrode system for obtaining a current value that depends on Int is preferably any duration between 0.1 and 10.0 seconds, more preferably any duration between 0.1 and 7.0 seconds, and further preferably any duration between 0.1 and 5.0 seconds.

In the fourteenth method for measuring a component of a biological sample, the voltage to be applied to the electrode system for obtaining a current value that depends on Int is preferably any voltage in the range of 0.1 V to 1.4 V, more preferably any voltage in the range of 0.1 V to 1.0 V.

In the fourteenth method for measuring a component of a biological sample, it is preferable that the step to obtain a current value that depends on Int be performed after the step to obtain a current value that depends on Glu.

In the fourteenth method for measuring a component of a biological sample, it is preferable that the step to obtain a second current value be performed after the step to obtain a current value that depends on Int.

<Fifteenth Method for Measuring Component of Biological Sample>

Furthermore, the present invention is:
a method for measuring a component of a biological sample, including a step of using the third biosensor to obtain a Glu value of the biological sample, the method including:
a step of starting voltage application for a duration longer than 0 second and up to 0.7 second to the first Hct measurement system within 0 second to 0.5 second after detection of introduction of the biological sample to obtain a first current value;
a step of applying a voltage to the second Hct measurement system after the step to obtain a first current value, to obtain a second current value;
a step of obtaining a Hct value of the biological sample based on the first current value and the second current value;
a step of applying a voltage to the electrode system for obtaining a current value that depends on Glu after the step to obtain a first current value, to obtain a current value that depends on Glu;
a step of applying a voltage to an electrode system for obtaining a current value that depends on Int after the step to obtain a current value that depends on Glu, to obtain a current value that depends on an Int value of the biological sample; and
a step of obtaining the Glu value of the biological sample based on the current value that depends on Glu, the Hct value of the biological sample, and the current value that depends on an Int value of the biological sample (the fifteenth method for measuring a component of a biological sample).

In the fifteenth method for measuring a component of a biological sample,
the duration of the voltage application to the first Hct measurement system is preferably any duration longer than 0 second and up to 0.5 second, further preferably any duration longer than 0 second and up to 0.1 second.

In the fifteenth method for measuring a component of a biological sample,
it is preferable that the voltage application to the first Hct measurement system be started at 0 second after detection of introduction of the biological sample. Furthermore, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the fifteenth method for measuring a component of a biological sample,
the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the fifteenth method for measuring a component of a biological sample,
the duration of the voltage application to the second Hct measurement system is preferably any duration between 0.01 and 5.0 seconds, more preferably any duration between 0.05 and 1.0 second, and further preferably any duration between 0.1 and 0.5 second.

In the fifteenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the fifteenth method for measuring a component of a biological sample, the Hct value can be measured in a short time in the first Hct measurement system, and the Glu value corrected using the Hct value can be obtained with high accuracy.

In the fifteenth method for measuring a component of a biological sample,
the duration of the voltage application to the electrode system for obtaining a current value that depends on Glu is preferably any duration between 0.01 and 10.0 seconds, more preferably any duration between 0.1 and 7.0 seconds, and further preferably any duration between 0.1 and 5.0 seconds.

In the fifteenth method for measuring a component of a biological sample,
the voltage to be applied to the electrode system for obtaining a current value that depends on Glu is preferably any voltage in the range of 0.1 V to 1.4 V, more preferably any voltage in the range of 0.1 V to 1.0 V.

In the fifteenth method for measuring a component of a biological sample,
it is preferable that the step to obtain a second current value be performed after the step to obtain a current value that depends on Glu.

According to the fifteenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the fifteenth method for measuring a component of a biological sample, the step of applying a voltage to the electrode system for obtaining a current value that depends on Glu to obtain a current value that depends on Glu may be performed multiple times. In this case, a plurality of the current values that depend on Glu and the Hct value are used to obtain a Glu value. When the step to obtain a current value that depends on Glu is performed multiple times, the measurement accuracy can be further improved, which is preferable.

In the fifteenth method for measuring a component of a biological sample may further include a step of applying a voltage to the second Hct measurement system to obtain another Hct value based on the current value obtained thereby after the step to obtain a current value that depends on Glu. In this case, in the step of using the current value that depends on Glu and the Hct value to obtain a Glu value, the current value that depends on Glu and two Hct values are used to obtain a Glu value. When a voltage is applied to the second Hct measurement system to obtain another Hct value based on the current value obtained thereby after the step to obtain a current value that depends on Glu, the measurement accuracy can be further improved, which is preferable.

In the fifteenth method for measuring a component of a biological sample,
the duration of the voltage application to the electrode system for obtaining a current value that depends on Int is preferably any duration between 0.1 and 10.0 seconds, more preferably any duration between 0.1 and 7.0 seconds, and further preferably any duration between 0.1 and 5.0 seconds.

In the fifteenth method for measuring a component of a biological sample,
the voltage to be applied to the electrode system for obtaining a current value that depends on Int is preferably any voltage in the range of 0.1 V to 1.4 V, more preferably any voltage in the range of 0.1 V to 1.0 V.

In the fifteenth method for measuring a component of a biological sample,
it is preferable that the step to obtain a current value that depends on Int be performed after the step to obtain a current value that depends on Glu.

In the fifteenth method for measuring a component of a biological sample,
it is preferable that the step to obtain a second current value be performed after the step to obtain a current value that depends on Int.

<Sixteenth Method for Measuring Component of Biological Sample>

Moreover, the present invention is:
a method for measuring a component of a biological sample, including a step of using the third biosensor to obtain a Glu value of the biological sample, the method including:
a step of starting voltage application for a duration longer than 0 second and up to 0.7 second to the first Hct measurement system within 0 to 0.5 second after detection of introduction of the biological sample to obtain a first current value;
a step of applying a voltage to the second Hct measurement system after the step to obtain a first current value, to obtain a second current value;
a step of obtaining a Hct value of the biological sample based on the first current value and the second current value;
a step of applying a voltage to the first Hct measurement system after the step to obtain a first current value, to obtain a first current value that depends on Glu;
a step of applying a voltage to the electrode system for obtaining a second current value that depends on Glu after the step to obtain a first current value that depends on Glu, to obtain a second current value that depends on Glu;
a step of applying a voltage to an electrode system for obtaining a current value that depends on Int after the step to obtain a second current value that depends on Glu, to obtain a current value that depends on an Int value of the biological sample; and
a step of obtaining the Glu value of the biological sample based on the first current value that depends on Glu, the second current value that depends on Glu, the Hct value of the biological sample, and the current value that depends on an Int value of the biological sample (the sixteenth method for measuring a component of a biological sample).

In the sixteenth method for measuring a component of a biological sample,
the duration of the voltage application to the first Hct measurement system for obtaining a first current value is preferably any duration longer than 0 second and up to 0.5 second, further preferably any duration longer than 0 second and up to 0.1 second. Furthermore, it is preferable that the voltage application to the first Hct measurement system be started at 0 second after detection of introduction of the biological sample.

In the sixteenth method for measuring a component of a biological sample, the voltage application to the first Hct measurement system for obtaining a first current value is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the sixteenth method for measuring a component of a biological sample, the voltage to be applied to the first Hct measurement system for obtaining a first current value is preferably any voltage in the range of 1.5 to 4.0 V, more preferably any voltage in the range of 1.5 V to 3.0 V, and further preferably any voltage in the range of 1.5 V to 2.5 V.

In the sixteenth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the sixteenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

In the sixteenth method for measuring a component of a biological sample, the duration of the voltage application to the first Hct measurement system for obtaining the first current value that depends on Glu is preferably any duration between 0.01 and 10.0 seconds, more preferably any duration between 0.1 and 7.0 seconds, and further preferably any duration between 0.1 and 5.0 seconds.

In the sixteenth method for measuring a component of a biological sample, the voltage to be applied to the first Hct measurement system for obtaining the first current value that depends on Glu is preferably any voltage in the range of 0.1 V to 1.4 V, more preferably any voltage in the range of 0.1 V to 1.0 V.

In the sixteenth method for measuring a component of a biological sample, the duration of the voltage application to the electrode system for obtaining a second current value that depends on Glu is preferably any duration between 0.01 and 10.0 seconds, more preferably any duration between 0.1 and 7.0 seconds, and further preferably any duration between 0.1 and 5.0 seconds.

In the sixteenth method for measuring a component of a biological sample, the voltage to be applied to the electrode system for obtaining a second current value that depends on Glu is preferably any voltage in the range of 0.1 V to 1.4 V, more preferably any voltage in the range of 0.1 V to 1.0 V.

According to the sixteenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the sixteenth method for measuring a component of a biological sample, the step to obtain a first current value that depends on Glu and the step to obtain a second current value that depends on Glu may be performed multiple times. In this case, a plurality of the first current values that depend on Glu and the second current values that depend on Glu as well as the Hct value are used to obtain a Glu value. When the steps to obtain a current value that depends on Glu are performed multiple times, the measurement accuracy can be further improved, which is preferable.

The sixteenth method for measuring a component of a biological sample may further includes a step of applying a voltage to the first Hct measurement system to obtain a third current value. It is preferable that the step to obtain a third current value be performed after the step to obtain a second current value.

In the sixteenth method for measuring a component of a biological sample, the duration of the voltage application to the electrode system for obtaining a current value that depends on Int is preferably any duration between 0.1 and 10.0 seconds, more preferably any duration between 0.1 and 7.0 seconds, and further preferably any duration between 0.1 and 5.0 seconds.

In the sixteenth method for measuring a component of a biological sample, the voltage to be applied to the electrode system for obtaining a current value that depends on Int is preferably any voltage in the range of 0.1 V to 1.4 V, more preferably any voltage in the range of 0.1 V to 1.0 V.

In the sixteenth method for measuring a component of a biological sample, it is preferable that the step to obtain a current value that depends on Int be performed after the step to obtain a first current value that depends on Glu. Furthermore, it is preferable that the step to obtain a current value that depends on Int be performed after the step to obtain a second current value that depends on Glu.

In the sixteenth method for measuring a component of a biological sample, it is preferable that the step to obtain a second current value be performed after the step to obtain a current value that depends on Int.

In the sixteenth method for measuring a component of a biological sample, the duration of the voltage application to the electrode system for obtaining a second current value that depends on Glu is preferably any duration between 0.01 and 10.0 seconds, more preferably any duration between 0.1 and 7.0 seconds, and further preferably any duration between 0.1 and 5.0 seconds.

In the sixteenth method for measuring a component of a biological sample, the voltage to be applied to the electrode system for obtaining a second current value that depends on Glu is preferably any voltage in the range of 0.1 V to 1.4 V, more preferably any voltage in the range of 0.1 V to 1.0 V.

<Seventeenth Method for Measuring Component of Biological Sample>

Furthermore, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 second to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the electrode system for obtaining a first current value that depends on Glu after the step to obtain a first current value, to obtain a first current value that depends on Glu;

a step of applying a voltage to the electrode system for obtaining a second current value that depends on Glu after the step to obtain a first current value that depends on Glu, to obtain a second current value that depends on Glu;

a step of applying a voltage to an electrode system for obtaining a current value that depends on Int after the step to obtain a second current value that depends on Glu, to obtain a current value that depends on an Int value of the biological sample; and a step of obtaining the Glu value of the biological sample based on the first current value that depends on Glu, the second current value that depends on Glu, the Hct value of the biological sample, and the current value that depends on an Int value of the biological sample (the seventeenth method for measuring a component of a biological sample).

In the seventeenth method for measuring a component of a biological sample, the duration of the voltage application to the first Hct measurement system is preferably any duration longer than 0 second and up to 0.5 second, further preferably any duration longer than 0 second and up to 0.1 second.

In the seventeenth method for measuring a component of a biological sample, it is preferable that the voltage application to the first Hct measurement system be started at 0 second after detection of introduction of the biological sample. Furthermore, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the seventeenth method for measuring a component of a biological sample, the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the seventeenth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the seventeenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the seventeenth method for measuring a component of a biological sample, the Hct value can be measured in a short time in the first Hct measurement system, and the Glu value corrected using the Hct value can be obtained with high accuracy.

In the seventeenth method for measuring a component of a biological sample, the duration of the voltage application to the electrode system for obtaining the first current value that depends on Glu is preferably any duration between 0.01 and 10.0 seconds, more preferably any duration between 0.1 and 7.0 seconds, and further preferably any duration between 0.1 and 5.0 seconds.

In the seventeenth method for measuring a component of a biological sample, the voltage to be applied to the electrode system for obtaining a first current value that depends on Glu is preferably any voltage in the range of 0.1 V to 1.4 V, more preferably any voltage in the range of 0.1 V to 1.0 V.

In the seventeenth method for measuring a component of a biological sample, the duration of the voltage application to the electrode system for obtaining a second current value that depends on Glu is preferably any duration between 0.01 and 10.0 seconds, more preferably any duration between 0.1 and 7.0 seconds, and further preferably any duration between 0.1 and 5.0 seconds.

In the seventeenth method for measuring a component of a biological sample, the voltage to be applied to the electrode system for obtaining a second current value that depends on Glu is preferably any voltage in the range of 0.1 V to 1.4 V, more preferably any voltage in the range of 0.1 V to 1.0 V.

In the seventeenth method for measuring a component of a biological sample, it is preferable that the step to obtain a second current value be performed after the step to obtain a first current value that depends on Glu.

According to the seventeenth method for measuring a component of a biological sample, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy. Furthermore, according to such a method, the Hct value can be measured in a short time in the first Hct measurement system, and the Glu value corrected using the Hct value can be obtained with high accuracy.

In the seventeenth method for measuring a component of a biological sample, the step to obtain a first current value that depends on Glu and the step to obtain a second current value that depends on Glu may be performed multiple times. In this case, a plurality of the first current values that depend on Glu and the second current values that depend on Glu as well as the Hct value are used to obtain a Glu value. When the steps to obtain a current value that depends on Glu are performed multiple times, the measurement accuracy can be further improved, which is preferable.

The seventeenth method for measuring a component of a biological sample may further include a step of applying a voltage to the second Hct measurement system after the step to obtain a first current value that depends on Glu, to obtain another Hct value based on the current value obtained thereby. In this case, in the step of using the current values that depend on Glu and the Hct value to obtain a Glu value, the current values that depend on Glu and two Hct values are used to obtain a Glu value. When after the steps to obtain a current value that depends on Glu, a voltage is applied to the second Hct measurement system to obtain another Hct value based on the current value obtained thereby, the measurement accuracy can be further improved, which is preferable.

In the seventeenth method for measuring a component of a biological sample, the duration of the voltage application to the electrode system for obtaining a current value that depends on Int is preferably any duration between 0.1 and 10.0 seconds, more preferably any duration between 0.1 and 7.0 seconds, and further preferably any duration between 0.1 and 5.0 seconds.

In the seventeenth method for measuring a component of a biological sample, the voltage to be applied to the electrode system for obtaining a current value that depends on Int is preferably any voltage in the range of 0.1 V to 1.4 V, more preferably any voltage in the range of 0.1 V to 1.0 V.

In the seventeenth method for measuring a component of a biological sample, it is preferable that the step to obtain a current value that depends on Int be performed after the step to obtain a current value that depends on Glu.

In the seventeenth method for measuring a component of a biological sample, it is preferable that the step to obtain a second current value be performed after the step to obtain a current value that depends on Int.

Moreover, the present invention is:

a method for measuring a component of a biological sample, including a step of using the third biosensor to obtain a Glu value of the biological sample, the method including:

a step of starting voltage application for a duration longer than 0 second and up to 0.7 second to the first Hct measurement system within 0 to 0.5 second after detection of introduction of the biological sample to obtain a first current value;

a step of applying a voltage to the second Hct measurement system after the step to obtain a first current value, to obtain a second current value;

a step of obtaining a Hct value of the biological sample based on the first current value and the second current value;

a step of applying a voltage to the first Hct measurement system after the step to obtain a first current value, to obtain a first current value that depends on Glu;

a step of applying a voltage to the electrode system for obtaining a current value that depends on Glu after the step to obtain a first current value, to obtain a second current value that depends on Glu; and a step of obtaining the Glu value of the biological sample based on the first current value that depends on Glu, the second current value that depends on Glu, and the Hct value of the biological sample (the eighteenth method for measuring a component of a biological sample).

In the eighteenth method for measuring a component of a biological sample, the duration of the voltage application to the first Hct measurement system is preferably any duration longer than 0 second and up to 0.5 second, further preferably any duration longer than 0 second and up to 0.1 second.

In the eighteenth method for measuring a component of a biological sample, it is preferable that the voltage application to the first Hct measurement system be started at 0 second after detection of introduction of the biological sample. Furthermore, the voltage application to the first Hct measurement system is started at later than 0 second but within 0.5 second, preferably started at later than 0 second but within 0.3 second, more preferably started at later than 0 second but within 0.1 second, and further preferably started at later than 0 second but within 0.05 second after detection of introduction of the biological sample.

In the eighteenth method for measuring a component of a biological sample, the voltage to be applied to the first Hct measurement system is preferably any voltage in the range of 1.5 to 4.0 V, more preferably any voltage in the range of 1.5 V to 3.0 V, and further preferably any voltage in the range of 1.5 V to 2.5 V.

In the eighteenth method for measuring a component of a biological sample, the duration of the voltage application to the second Hct measurement system is preferably any duration between 0.01 and 5.0 seconds, more preferably any duration between 0.05 and 1.0 second, and further preferably any duration between 0.1 and 0.5 second.

In the eighteenth method for measuring a component of a biological sample, the voltage to be applied to the second Hct measurement system is preferably any voltage in the range of 1.0 V to 3.5 V, more preferably any voltage in the range of 1.5 V to 3.5 V, and further preferably any voltage in the range of 2.0 V to 3.0 V.

According to the eighteenth method for measuring a component of a biological sample, the Hct value can be measured in a short time in the first Hct measurement system, and the Glu value corrected using the Hct value can be obtained with high accuracy.

In the eighteenth method for measuring a component of a biological sample, the duration of the voltage application to the electrode system for obtaining a first current value that depends on Glu is preferably any duration between 0.01 and 10.0 seconds, more preferably any duration between 0.1 and 7.0 seconds, and further preferably any duration between 0.1 and 5.0 seconds.

In the eighteenth method for measuring a component of a biological sample, the voltage to be applied to the electrode system for obtaining a first current value that depends on Glu is preferably any voltage in the range of 0.1 V to 1.4 V, more preferably any voltage in the range of 0.1 V to 1.0 V.

In the eighteenth method for measuring a component of a biological sample, the duration of the voltage application to the electrode system for obtaining a second current value that depends on Glu is preferably any duration between 0.01 and 10.0 seconds, more preferably any duration between 0.1 and 7.0 seconds, and further preferably any duration between 0.1 and 5.0 seconds.

In the eighteenth method for measuring a component of a biological sample, the voltage to be applied to the electrode system for obtaining a second current value that depends on Glu is preferably any voltage in the range of 0.1 V to 1.4 V, more preferably any voltage in the range of 0.1 V to 1.0 V.

In the eighteenth method for measuring a component of a biological sample, it is preferable that the step to obtain a second current value be performed after the step to obtain a first current value that depends on Glu.

In the eighteenth method for measuring a component of a biological sample, the step to obtain a first current value that depends on Glu and the step to obtain a second current value that depends on Glu may be performed multiple times. In this case, a plurality of the first current values that depend on Glu and the second current values that depend on Glu as well as the Hct value are used to obtain a Glu value. When the steps to obtain a current value that depends on Glu are performed multiple times, the measurement accuracy can be further improved, which is preferable.

In the sixth method for measuring a component of a biological sample, the seventh method for measuring a component of a biological sample, the eighth method for measuring a component of a biological sample, the ninth method for measuring a component of a biological sample, the tenth method for measuring a component of a biological sample, the eleventh method for measuring a component of a biological sample, the twelfth method for measuring a component of a biological sample, the thirteenth method for measuring a component of a biological sample, the fourteenth method for measuring a component of a biological sample, the fifteenth method for measuring a component of a biological sample, the sixteenth method for measuring a component of a biological sample, the seventeenth method for measuring a component of a biological sample, or the eighteenth method for measuring a component of a biological sample, the biological sample may be, for example, blood, sweat, or urine and is preferably blood.

Next, embodiments of the method for measuring a component of a biological sample according to the present invention will be described with reference to the drawings.

Embodiment 1

Figure 9:
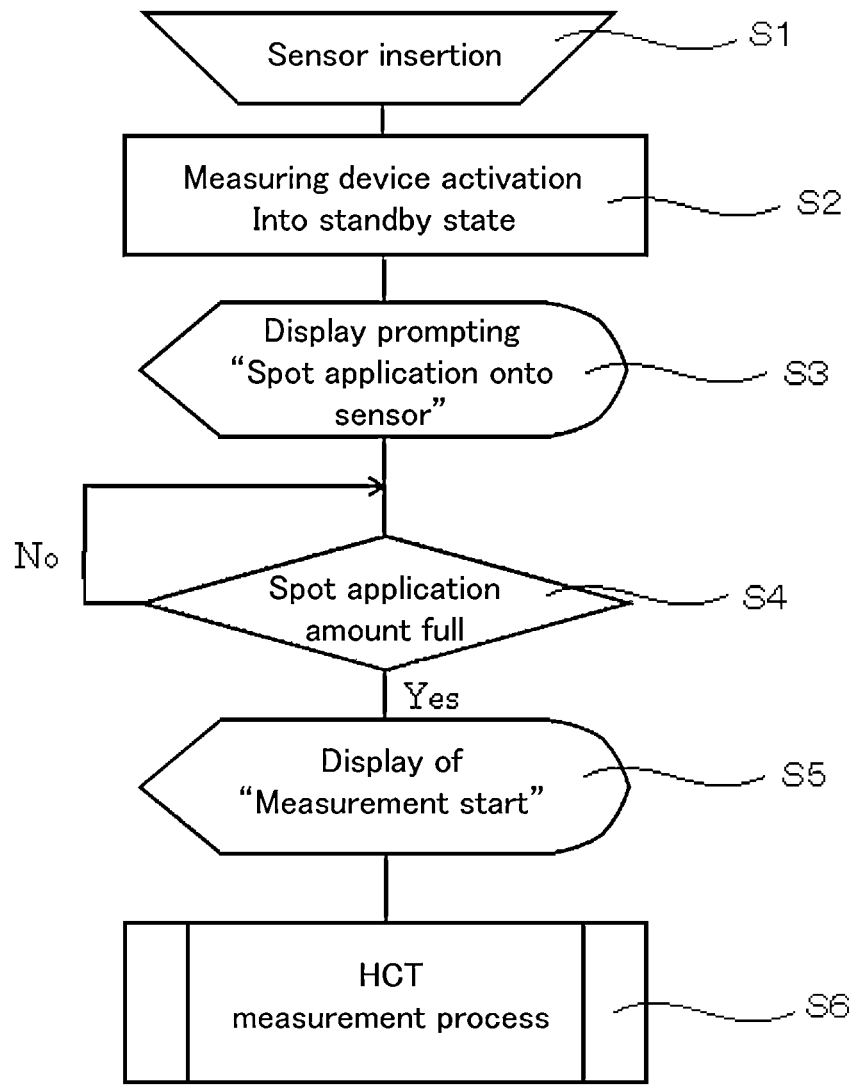
FIG. 9 is an operation flow chart according to Embodiment 1.

A method for measuring a component of a biological sample, in which a Hct value is obtained, will be described with reference to FIG. 9. FIG. 9 is an operation flow chart of the method according to this embodiment.

An example using blood as a biological sample will be described. First, for example, a fingertip is pricked with a dedicated lancet to cause bleeding. On the other hand, the biosensor 1 is set in a dedicated measuring apparatus (a meter) (S1), and the measuring device is activated and put into a standby state (S2). In the measuring device, a display prompting "spot application onto the sensor" is presented (S3), the biological sample supply port 12 of the sensor set in the measuring apparatus is brought into contact with the bleeding blood, and the blood is introduced into the sensor by a capillary phenomenon.

In this measuring method, for example, the biosensor 1 shown in FIG. 1 is used. In this case, the electrode A is used as a first working electrode and the electrode B is used as a first counter electrode.

<Step 1: Detection of Sample (Blood)>

A voltage is applied between the working electrode and the counter electrode, and the introduction of blood is detected by the change in the current value accompanying the introduction of blood. When the current value exceeds a threshold value, it is determined that the spot application amount is full (S4). After the spot application amount becomes full, "Measurement start" is displayed on the measuring device (S5).

<Step 2: Hct Measurement Process>

Figure 10:
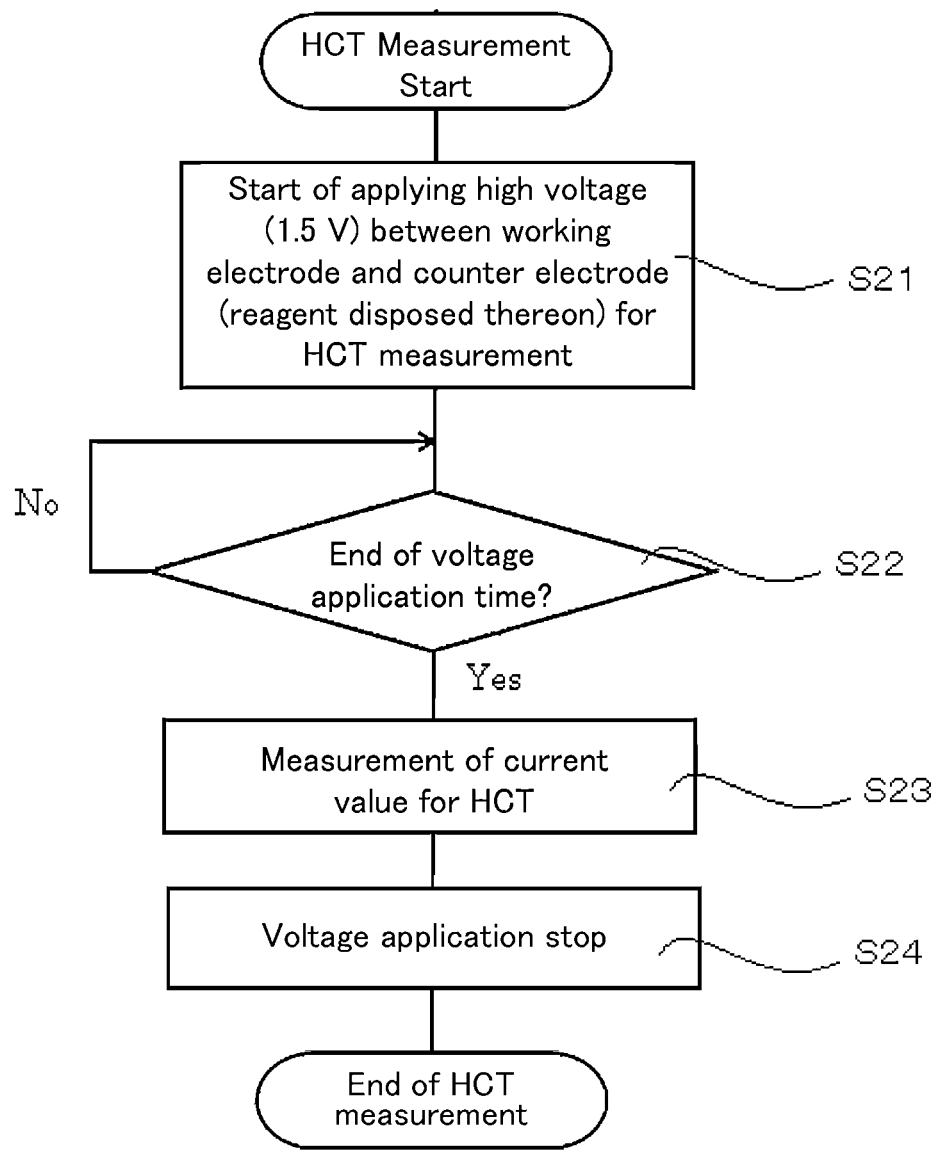
FIG. 10 is a flow chart of HCT measurement according to Embodiment 1.

After the introduction of blood is confirmed, the subsequent steps are started. The "Hct measurement process" shown in FIG. 9 will be described with reference to FIG. 10. A voltage is applied between the working electrode (the first working electrode) and the counter electrode (the first counter electrode) (S21). This voltage application is started within 0 second (i.e., immediately) to 0.5 second (i.e., after a very short time) after confirmation of the introduction of blood and is performed for a duration longer than 0 second and up to 0.7 second (i.e., a relatively short period of time) (S22). The voltage applied at this time is a high voltage, for example, 1.5 to 4.0 V. In the present invention, both the working electrode and the counter electrode are in contact with the reagent part containing an enzyme and a mediator. During this relatively short period of time, the reaction between Glu in the blood and the enzyme (for example, Glu oxidoreductase) hardly proceeds by voltage application alone. Therefore, such voltage application makes it possible to detect a current value that does not depend on the electrolytic oxidation reaction of Glu but depends on the Hct value (S23). Then, based on the current value thus obtained, the Hct value is obtained. In this case, conversion from the detected current value to the Hct value can be performed using a calibration curve or a calibration curve table that has been obtained beforehand. In this correction, the Hct value obtained from the calibration curve of the current value and the Hct value that has been prepared beforehand may be used, or the detected current value may be used as it is. In this step, since the mediator is disposed on both the working electrode and the counter electrode, the Hct value can be obtained under the same environment as that for measuring a Glu value. The voltage application is terminated (S24), and the Hct measurement process is terminated.

Embodiment 2

Figure 11:
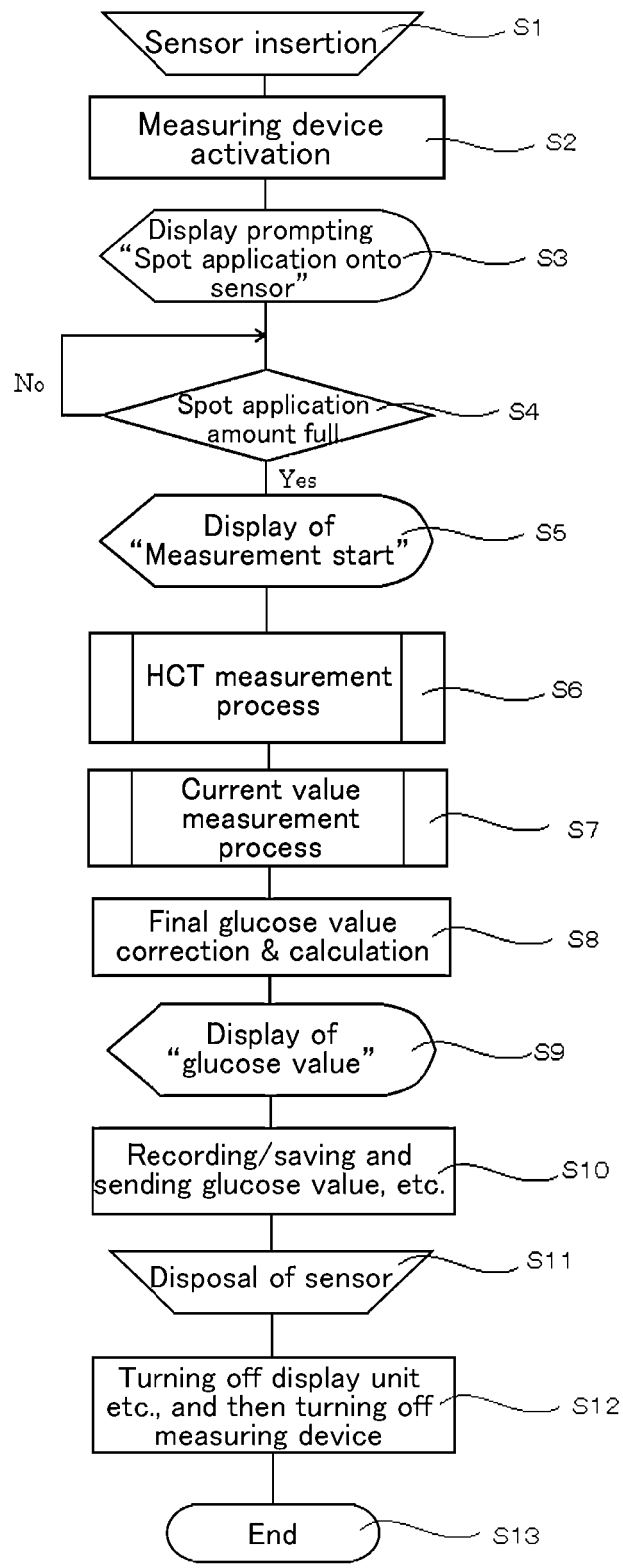
FIG. 11 is an operation flow chart according to Embodiment 2.

A method for measuring a component of a biological sample, in which a Glu value is obtained, will be described with reference to FIG. 11. FIG. 11 is an operation flow chart of the method according to this embodiment.

In this measuring method, for example, the biosensor (the first biosensor) shown in FIG. 4 may be used. In that case, for example, the electrode A is used as the working electrode in Step 2: Hct Measurement Process, the electrode B is used as the counter electrode in Step 2: Hct Measurement Process, the electrode A is used as the working electrode in Step 3: Measurement of Apparent Glu Amount, and the electrode B is used as the counter electrode in Step 3: Measurement of Apparent Glu Amount.

TABLE 22

| | Working Electrode | Counter Electrode |
|---|---|---|
| Step 2: Hct Measurement Process | A | B |
| Step 3: Measurement of Apparent Glu Amount | A | B |

Figure 12:
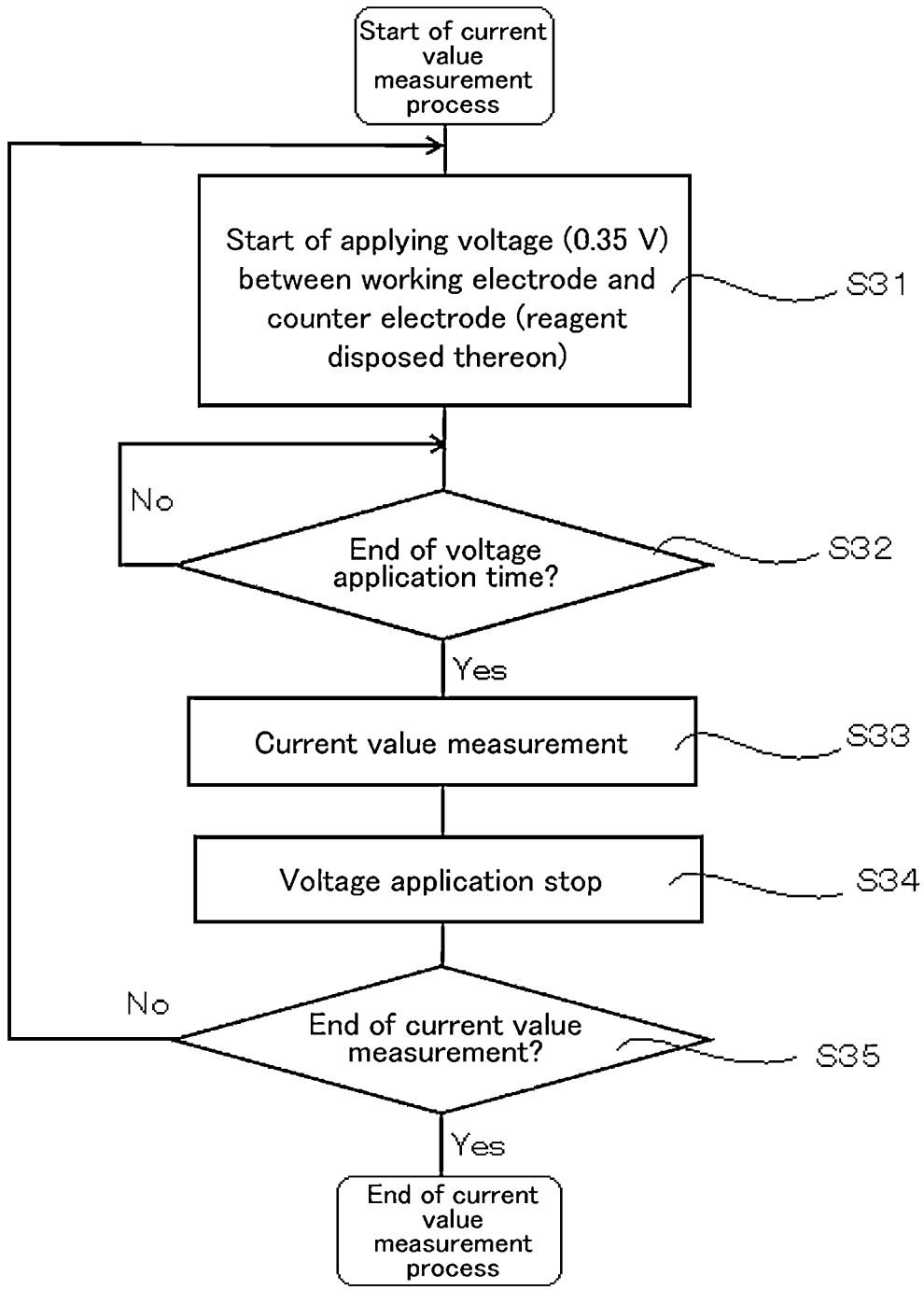
FIG. 12 is a flow chart of current value measurement according to Embodiment 2.

In the operation flow chart shown in FIG. 11, steps S1 to S6 are the same as steps S1 to S6 of Embodiment 1 shown in FIG. 9. The "current value measurement process"(S7) in FIG. 11 will be described with reference to FIG. 12.

<Step 3: Measurement of Apparent Glu Amount>

Figure 13:
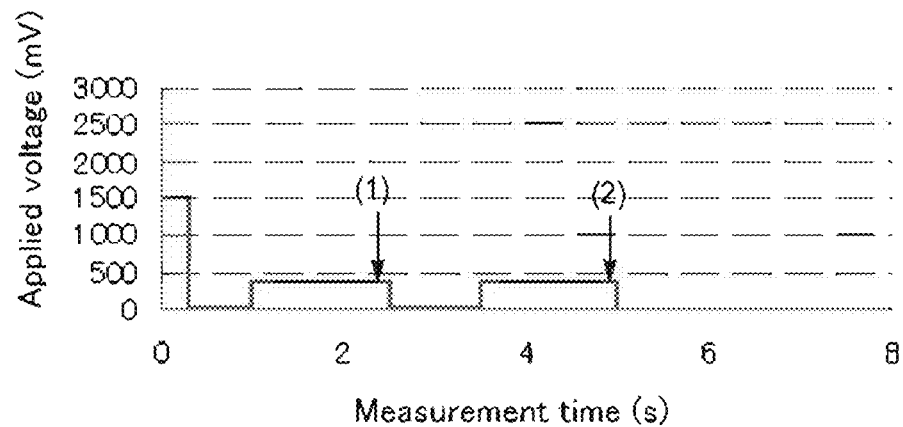
FIGS. 13 (a) and (b) each show an example of the relationship between voltage application time and applied voltage according to Embodiment 2.
Figure 13:
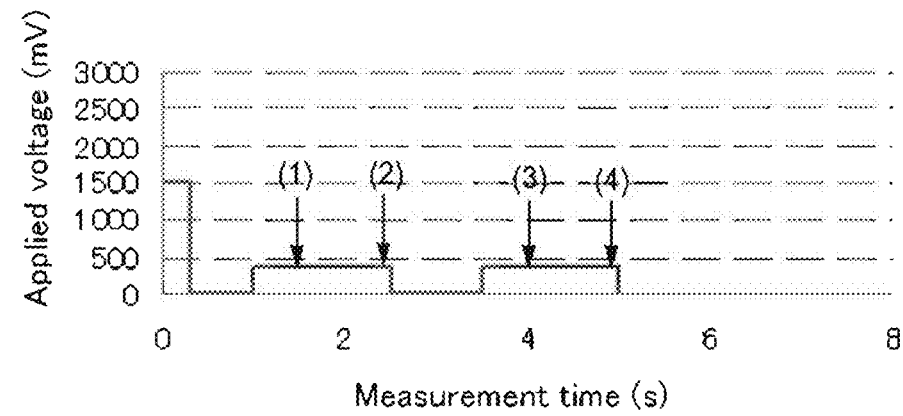

After Glu in the blood is reacted with the Glu oxidoreductase for a certain period of time, a voltage is applied between the working electrode A (the first working electrode) and the counter electrode B (the first counter electrode) (S 31). The voltage to be applied in this step is, for example, 0.1 to 1.4 V. Both the working electrode A and the counter electrode B are in contact with the reagent part 11 containing the enzyme and a mediator. Therefore, while a voltage is being applied, Glu in the blood and the enzyme (for example, Glu oxidoreductase) are reacted with each other for a certain period of time. By applying a voltage, a current value that depends on Glu based on the electrolytic oxidation reaction of Glu can be detected (S 33). The current value may be measured once or multiple times. For example, in the case of the relationship between voltage application time and applied voltage as shown in FIG. 13(*a*), the current value measured at the time point (1) may be used or the current value measured at the time point (2) may be used. Furthermore, in the case of the relationship between voltage application time and applied voltage as shown in FIG. 13(*b*), the current value measured at the time point (1), the current value measured at the time point (2), the current value measured at the time point (3), or the current value measured at the time point (4) may be used. Moreover, a plurality of parameters (x1, x2, x3, . . . , x10) are calculated based on, for example, the extracted current values measured at the plurality of predetermined time points and the extracted temperature information of the biological information measuring apparatus ("Calculate predetermined parameters"), a correction amount is calculated by a multiple regression equation (for example, Formula 1 below), and then a Glu value is calculated (S8).

[Mathematical Formula 1]

$$y = ax1 + bx2 + cx3 \ldots + kx10 + 1 \quad \text{(Formula 1)}$$

(y denotes the correction amount, x1, x2, x3 . . . , x10 denote parameters, and a, b, c, . . . 1 denote coefficients.)

After the current value is measured, if desired, current values are further measured. For example, in the case of the relationship between voltage application time and applied voltage as shown in FIG. 13(*a*), the current value may be measured at the time point (1) and then the current value may be measured again at the time point (2). After the current value is measured for a desired number of times, the voltage application is stopped (S34), the current value measurement is terminated (S35), and the current value measurement process is terminated.

<Step 4: Correction of Blood Component>

The Hct value obtained in Step 2 and the current value that depends on Glu obtained in Step 3 are used to obtain a Glu value (S8, FIG. 11). It is preferable that this be performed based on a calibration curve (including a calibration table) prepared beforehand. The Glu amount thus obtained is displayed or stored in the measuring apparatus (S9). Instead of correcting the Glu amount after the Hct value is obtained first as described above, the current value that depends on the Hct value detected in Step 2 and the current value that depends on Glu obtained in Step 3 may be used to obtain a Glu value. Thereafter, the sensor is discarded (S11). After the display unit, etc. are turned off, the measuring device is also turned off (S 12), and the measurement of the component of the biological sample is terminated (S13).

That is, in Embodiment 2, Step 1: Detection of Sample (Blood), Step 2: Hct Measurement Process, Step 3: Measurement of Apparent Glu Amount, and Step 4: Correction of Blood Component are performed in this order.

Figure 16A:
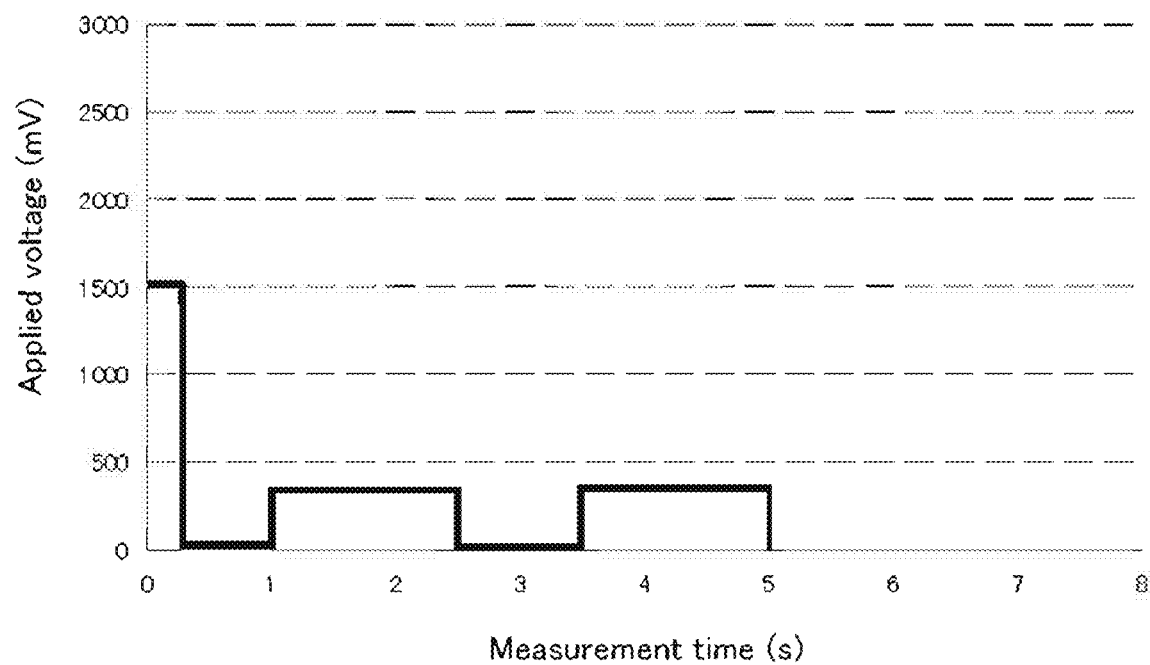
FIG. 16a shows an example of the relationship between applied voltage and voltage application time according to Embodiment 2.
Figure 16B:
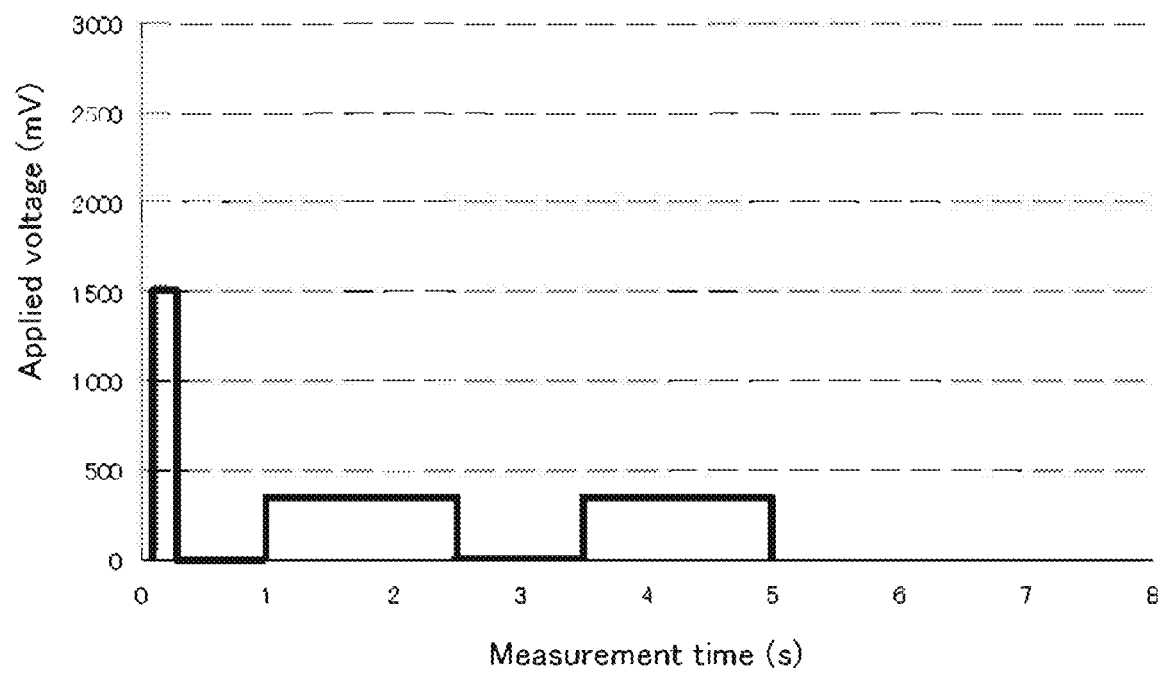
FIG. 16b shows another example of the relationship between applied voltage and voltage application time according to Embodiment 2.

FIGS. 16*a* and 16*b* show the relationship between applied voltage and voltage application time in Embodiment 2.

In FIG. 16*a*, the Hct measurement process in Step 2 is started at zero second after confirmation of the introduction of blood and is performed by applying a voltage, until 0.3 second thereafter, for 0.3 second. In this case, a voltage of 1.5 V is applied. Then, the voltage application for measuring the apparent Glu amount in Step 3 is performed twice. Specifically, a voltage of 0.35 V is applied for 1.5 seconds from 1 second to 2.5 seconds, and a voltage of 0.35 V is applied for 1.5 seconds from 3.5 seconds to 5 seconds.

In FIG. 16*b*, the Hct measurement process in Step 2 is started at 0.1 second after confirmation of the introduction of blood and is performed by applying a voltage, until 0.3 second thereafter, for 0.2 second. In this case, a voltage of 1.5 V is applied. Then, the voltage application for measuring the apparent Glu amount in Step 3 is performed twice. Specifically, a voltage of 0.35 V is applied for 1.5 seconds from 1 second to 2.5 seconds, and a voltage of 0.35 V is applied for 1.5 seconds from 3.5 seconds to 5 seconds.

Embodiment 3

Figure 14A:
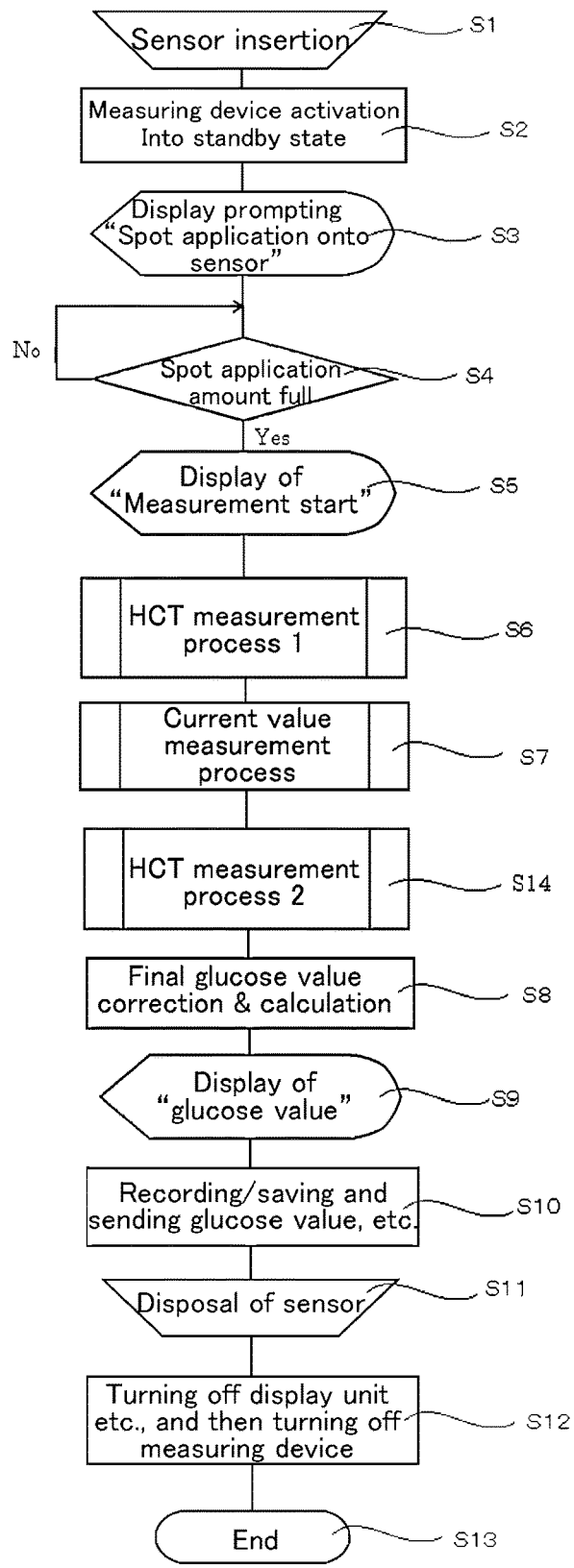
FIG. 14a is an operation flow chart according to Embodiment 3.

Another Method for Measuring a Component of a Biological Sample, in which a Glu value is obtained, will be described with reference to FIG. 14*a*. FIG. 14*a* is an operation flow chart of the method according to this embodiment.

In this measuring method, for example, the biosensor (the first biosensor) shown in FIG. 4 may be used. In this case, for example, the electrode A is used as the working electrode in Step 2: Hct Measurement Process and the counter electrode in Step 5: Second Hct Measurement Process, the electrode B is used as the counter electrode in Step 2: Hct Measurement Process, the electrode A is used as the working electrode in Step 3: Measurement of Apparent Glu Amount, the electrode B is used as the counter electrode in Step 3: Measurement of Apparent Glu Amount, and the electrode C is used as the working electrode in Step 5: Second Hct Measurement Process.

TABLE 23

|  | Working Electrode | Counter Electrode |
| --- | --- | --- |
| Step 2: Hct Measurement Process | A | B |
| Step 3: Measurement of Apparent Glu Amount | A | B |
| Step 5: Second Hct Measurement Process | C | A |

Figure 14B:
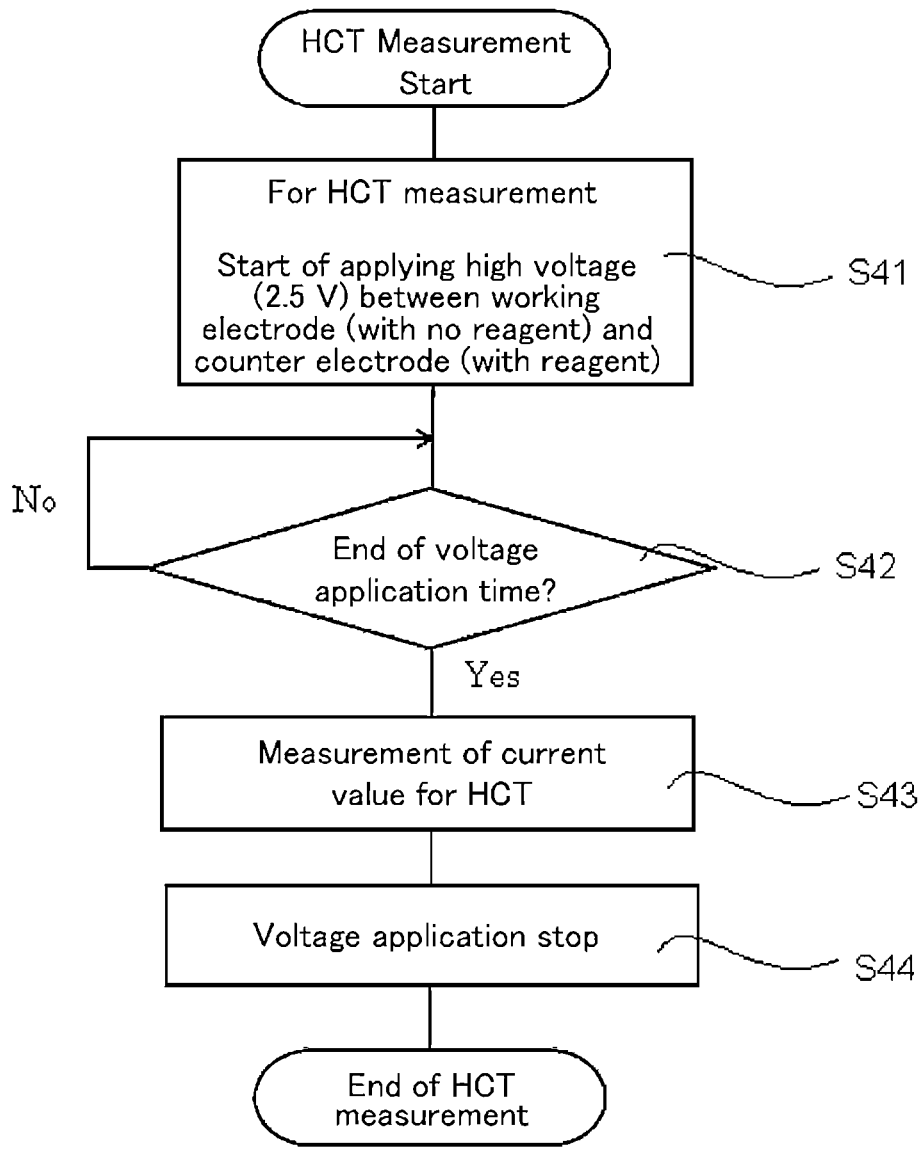
FIG. 14b is a flow chart of HCT measurement 2 according to Embodiment 3.

In the operation flow chart shown in FIG. 14*a*, steps S1 to S13 are the same as steps S1 to S13 of Embodiment 2 shown in FIG. 11. The "Hct measurement process 2" (S14 in FIG. 14*a*) in FIG. 14*a* will be described with reference to FIG. 14*b*.

<Step 5: Second Hct Measurement Process>

This step is a step arranged between Step 3: Measurement of Apparent Glu Amount and Step 4: Correction of Blood Component in Embodiment 2.

First, a voltage is applied between the working electrode C (the second working electrode) and the counter electrode A (the second counter electrode) (S41). In this case, the voltage is, for example, 1.5 to 3.5V. In the present invention, the counter electrode A is in contact with the reagent part containing an enzyme and a mediator. On the other hand, the working electrode C is not in contact with the reagent part. With this voltage application, the reaction between Glu in the blood and the enzyme (for example, Glu oxidoreductase) hardly proceeds (S42). Therefore, such voltage application makes it possible to detect a current value that does not depend on the electrolytic oxidation reaction of Glu but depends on the Hct value (S43). Then, based on the current value thus obtained, the Hct value is obtained. In this case, conversion from the detected current value to the Hct value can be performed using a calibration curve or a calibration curve table that has been obtained beforehand. In this correction, the Hct value obtained from the calibration curve of the current value and the Hct value that has been prepared beforehand may be used, or the detected current value may be used as it is. The voltage application is terminated (S44), and the Hct measurement process is terminated.

In this case, in Step 4: Correction of Blood Component, the Hct value obtained in Step 2, the Hct value obtained in Step 5, and the current value that depends on Glu obtained in Step 3 are used to obtain a Glu value (S8, FIG. 14a). When such Step 5 is added, it is possible to capture the Hct value of the blood of the entire capillary. Thus, it is possible to measure the Glu value with higher accuracy compared to the case where Step 5 is not added.

That is, in Embodiment 3, Step 1: Detection of Sample (Blood), Step 2: Hct Measurement Process, Step 3: Measurement of Apparent Glu Amount, Step 5: Second Hct Measurement Process, and Step 4: Correction of Blood Component are performed in this order.

Figure 17A:
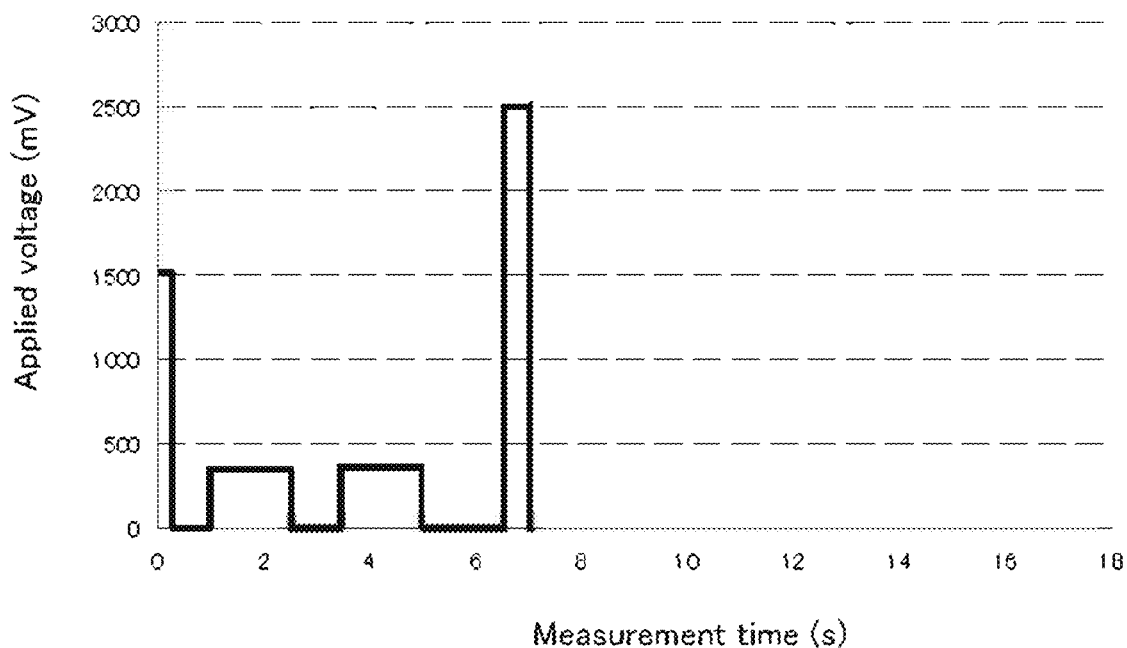
FIG. 17a shows an example of the relationship between applied voltage and voltage application time according to Embodiment 3.
Figure 17B:
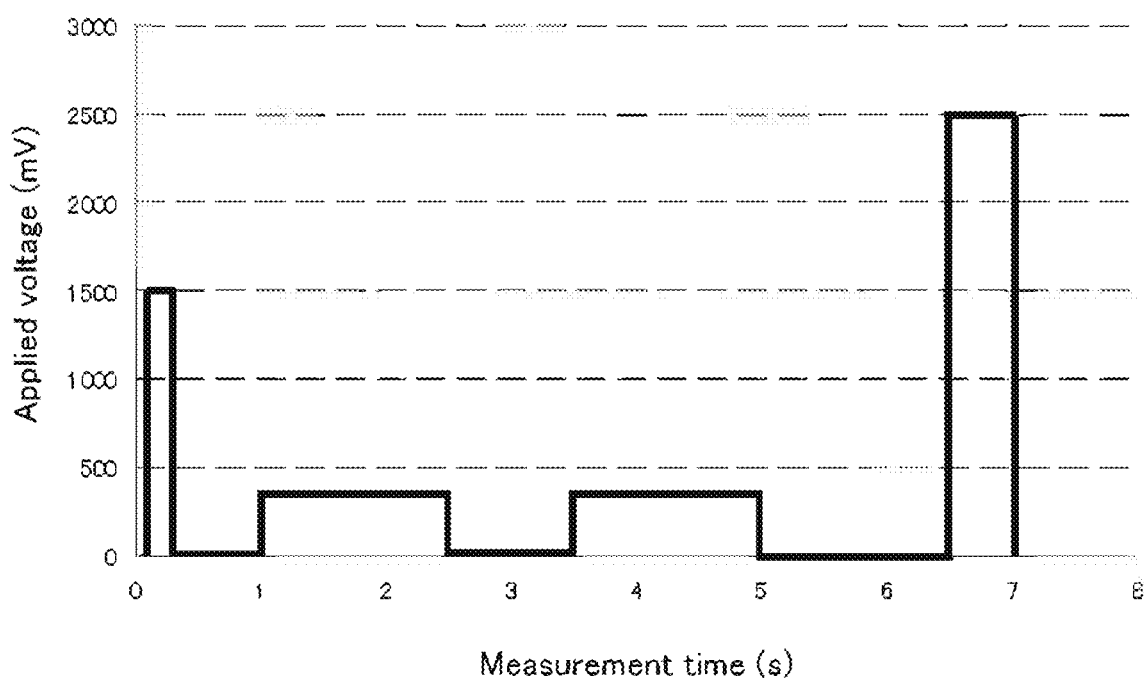
FIG. 17b shows another example of the relationship between applied voltage and voltage application time according to Embodiment 3.

FIGS. 17a and 17b show examples of the relationship between applied voltage and voltage application time in Embodiment 3.

In FIG. 17a, the Hct measurement process in Step 2 is started at zero second after confirmation of the introduction of blood and is performed by applying a voltage, until 0.3 second thereafter, for 0.3 second. In this case, a voltage of 1.5 V is applied. Then, the voltage application for measuring the apparent Glu amount in Step 3 is performed twice. Specifically, a voltage of 0.35 V is applied for 1.5 seconds from 1 second to 2.5 seconds, and a voltage of 0.35 Vis applied for 1.5 seconds from 3.5 seconds to 5 seconds. Then, in the second Hct measurement process in Step 5, a voltage of 2.5 V is applied for 0.5 second from 6.5 seconds to 7 seconds.

In FIG. 17b, the Hct measurement process in Step 2 is started at 0.1 second after confirmation of the introduction of blood and is performed by applying a voltage, until 0.3 second thereafter, for 0.2 second. In this case, a voltage of 1.5 V is applied. Then, the voltage application for measuring the apparent Glu amount in Step 3 is performed twice. Specifically, a voltage of 0.35 V is applied for 1.5 seconds from 1 second to 2.5 seconds, and a voltage of 0.35 Vis applied for 1.5 seconds from 3.5 seconds to 5 seconds. Then, in the second Hct measurement process in Step 5, a voltage of 2.5 Vis applied for 0.5 second from 6.5 seconds to 7 seconds.

Embodiment 4

Figure 15A:
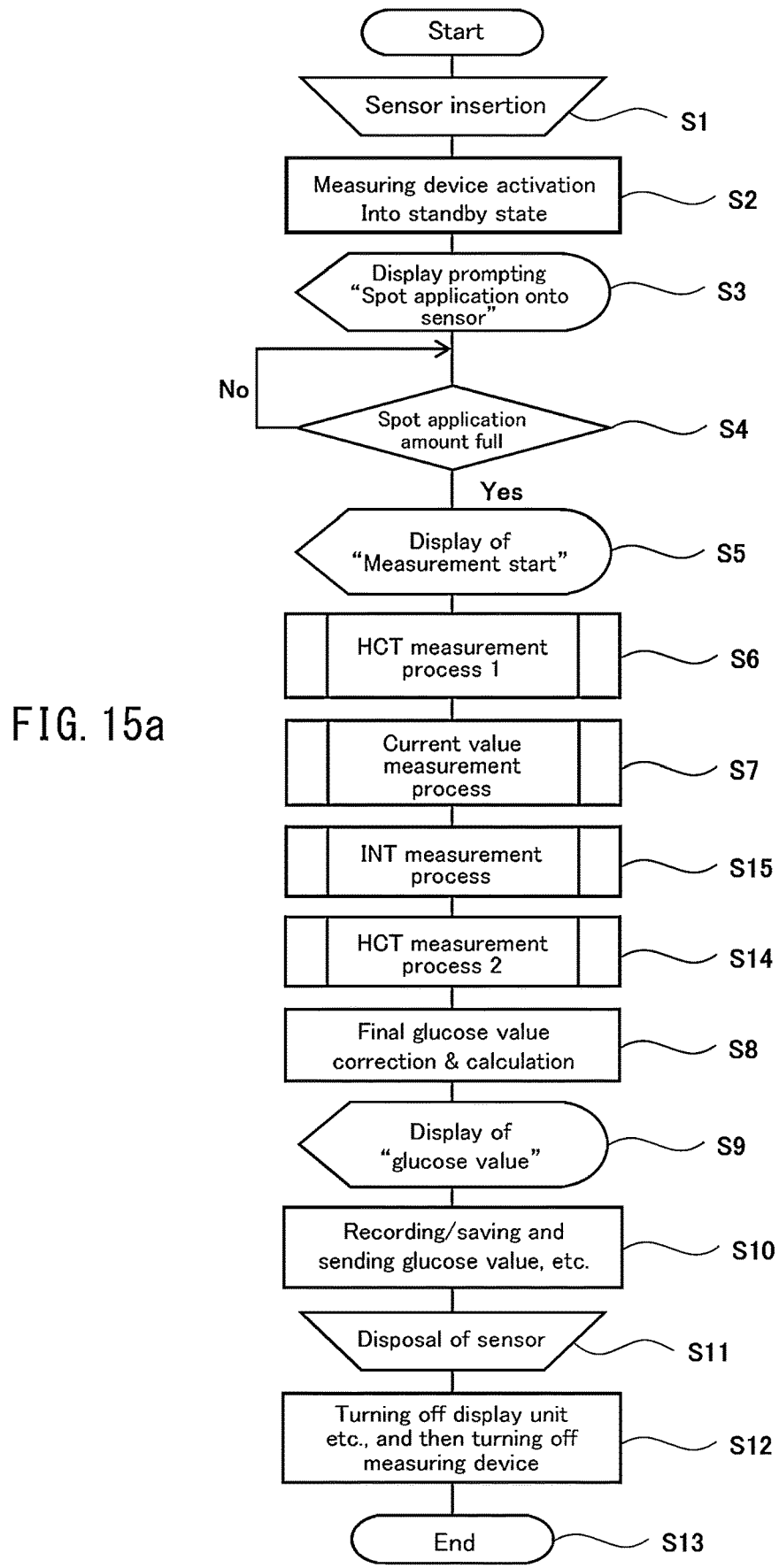
FIG. 15a is an operation flow chart according to Embodiment 4.

Another method for measuring a component of a biological sample, in which a Glu value is obtained, will be described with reference to FIG. 15a. FIG. 15a is an operation flow chart of the method according to this embodiment.

In this measuring method, for example, the biosensor (the third biosensor) shown in FIG. 6 may be used. In this case, for example, the electrode A is used as the working electrode in Step 2: Hct Measurement Process, the working electrode in Step 3: Measurement of Apparent Glu Amount, and the counter electrode in Step 5: Second Hct Measurement Process, the electrode B is used as the counter electrode in Step 2: Hct Measurement Process and the counter electrode in Step 3: Measurement of Apparent Glu Amount, the electrode C is used as the counter electrode in Step 3: Measurement of Apparent Glu Amount, the counter electrode in Step 6: Int Measurement Process, and the counter electrode in Step 5: Second Hct Measurement Process, the electrode E is used as the counter electrode in Step 3: Measurement of Apparent Glu Amount and the counter electrode in Step 6; Int Measurement Process, the electrode G is used as the counter electrode in Step 5: Second Hct Measurement Process, and the electrode F is used as the working electrode in Step 6; Int Measurement Process and the working electrode in Step 5: Second Hct Measurement Process.

In Step 6: Int Measurement Process described above, an electrode (for example, the electrode F) that is not in contact with the reagent layer can be used as the working electrode, and an electrode (for example, the electrode B, C, E) that is in contact with the reagent layer can be used as the counter electrode. Furthermore, it is preferable to use the same electrode for the counter electrode used in Step 6: Int Measurement Process and the counter electrode used in Step 3: Measurement of Apparent Glu Amount.

TABLE 24

|  | Working Electrode | Counter Electrode |
| --- | --- | --- |
| Step 2: Hct Measurement Process | A | B |
| Step 3: Measurement of Apparent Glu Amount | A or G | B, C, E |
| Step 6: Int Measurement Process | F | B, C, E |
| Step 5: Second Hct Measurement Process | F | A, B, C, G |

Figure 15B:
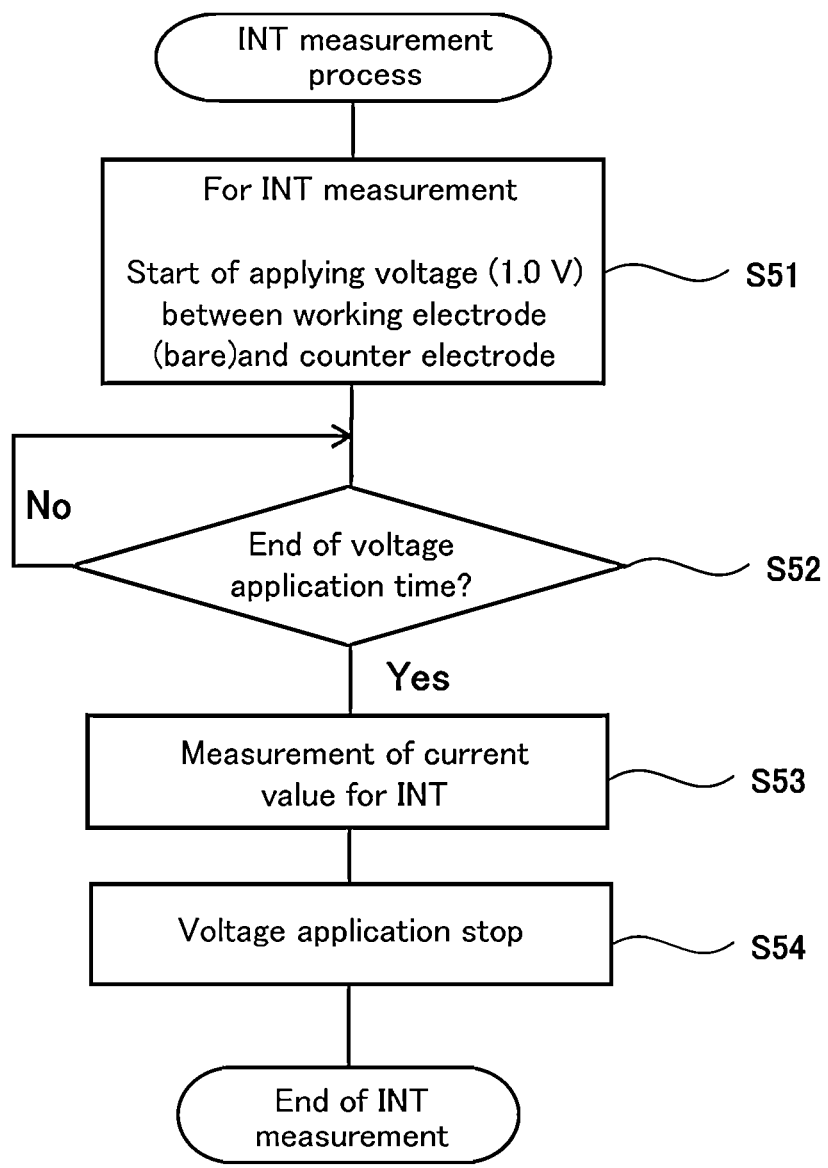
FIG. 15b is a flow chart of INT measurement according to Embodiment 4.

In the operation flow chart shown in FIG. 15a, steps S1 to S13 are the same as steps S1 to S13 of Embodiment 2 shown in FIG. 11. The "Hct measurement process 2" (S14 in FIG. 15a) in FIG. 15a is the same as step S14 of Embodiment 3 shown in FIG. 14b. The "INT measurement process" (S15 in FIG. 15a) in FIG. 15a will be described with reference to FIG. 15b.

<Step 6: Int Measurement Process>

This step is a step arranged between Step 3: Measurement of Apparent Glu Amount and Step 5: Hct Measurement Process 2 in Embodiment 3.

First, a voltage is applied between the working electrode F (the sixth working electrode) and the counter electrodes BA (the sixth counter electrode), C (the sixth counter electrode), E (the sixth counter electrode) (S51). In this case, the voltage is lower than the voltage used in the Hct measurement process such as S21 in Step 2 or S41 in Step 5, for example, 0.1 to 1.4 V. In the present invention, the counter electrode A is in contact with the reagent part containing an enzyme and a mediator. On the other hand, the working electrode C is not in contact with the reagent part. With this voltage application, a current value that depends on an interfering substance (uric acid, acetaminophen, etc.; abbreviated as Int) can be detected (S53). Then, based on the current value thus obtained, an Int value is obtained. In this case, conversion from the detected current value to the Int value can be performed using a calibration curve or a calibration curve table that has been obtained beforehand. In this correction, the Int value obtained from the calibration curve of the current value and the Int value that has been prepared beforehand may be used, or the detected current value may be used as it is. The voltage application is terminated (S54), and the Int measurement process is terminated.

In this case, in Step 4: Correction of Blood Component, the Hct value obtained in Step 2, the Hct value obtained in Step 5, the current value that depends on Glu obtained in Step 3, and the Int value obtained in Step 6 are used to obtain a Glu value (S8, FIG. 15a). When such Step 6 is added, it is possible to capture the Int value of the blood of the entire capillary. Thus, it is possible to measure the Glu value with higher accuracy compared to the case where Step 6 is not added.

That is, in Embodiment 4, Step 1: Detection of Sample (Blood), Step 2: Hct Measurement Process, Step 3: Measurement of Apparent Glu Amount, Step 6: Int Measurement Process, Step 5: Second Hct Measurement Process, and Step 4: Correction of Blood Component are performed in this order.

Figure 18A:
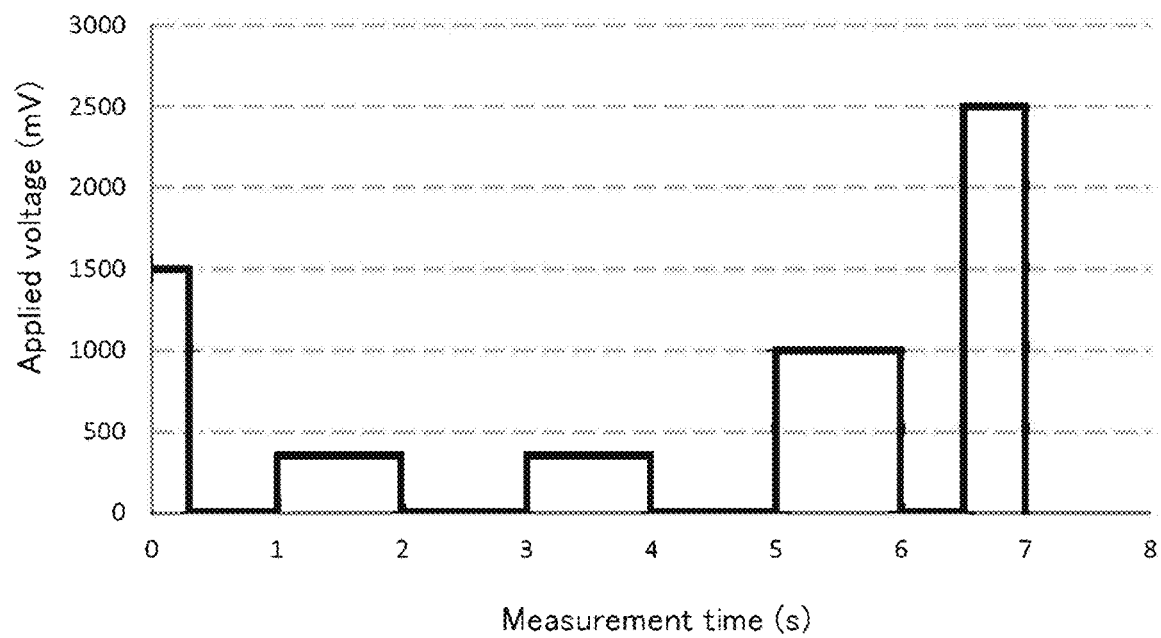
FIG. 18a shows an example of the relationship between applied voltage and voltage application time according to Embodiment 4.

FIG. 18a shows an example of the relationship between applied voltage and voltage application time in Embodiment 4.

In FIG. 18a, the Hct measurement process in Step 2 is started at zero second after confirmation of the introduction of blood and is performed by applying a voltage, until 0.3 second thereafter, for 0.3 second. In this case, a voltage of 1.5 V is applied. Then, the voltage application for measuring the apparent Glu amount in Step 3 is performed twice. Specifically, a voltage of 0.35 V is applied for 1 second from 1 second to 2 seconds, and a voltage of 0.35 V is applied for 1 second from 3 seconds to 4 seconds. Then, in the Int measurement process in Step 6, a voltage of 1.0 V is applied for 1 second from 5 seconds to 6 seconds. Finally, in the second Hct measurement process in Step 5, a voltage of 2.5 V is applied for 0.5 second from 6.5 seconds to 7 seconds.

Embodiment 5

Still another method for measuring a component of a biological sample, in which a Glu value is obtained, will be described with reference to FIG. 15a. FIG. 15a is an operation flow chart of the method according to Embodiment 4, but a Hct measurement process 1 (S 6) is further added between the Hct measurement process 2 (S14) and the final glucose value correction & calculation (S8) to perform the method of Embodiment 5.

In this measuring method, for example, the biosensor (the third biosensor) shown in FIG. 6 may be used. In this case, for example, the electrode A is used as the counter electrode in Step 2: Hct Measurement Process, the counter electrode in Step 3: Measurement of Apparent Glu Amount, the counter electrode in Step 5: Second Hct Measurement Process, and the counter electrode in Step 6; Int Measurement Process, the electrode B is used as the working electrode in Step 2: Hct Measurement Process, the working electrode in Step 3: Measurement of Apparent Glu Amount, and the counter electrode in Step 5: Second Hct Measurement Process, the electrode C is used as the counter electrode in Step 3: Measurement of Apparent Glu Amount, the counter electrode in Step 5: Second Hct Measurement Process, and the counter electrode in Step 6; Int Measurement Process, the electrode E is used as the counter electrode in Step 3: Measurement of Apparent Glu Amount and the counter electrode in Step 6; Int Measurement Process, the electrode G is used as the working electrode in Step 3: Measurement of Apparent Glu Amount and the counter electrode in Step 5: Second Hct Measurement Process, and the electrode F is used as the working electrode in Step 5: Second Hct Measurement Process and the working electrode in Step 6; Int Measurement Process.

In Step 6: Int Measurement Process described above, an electrode (for example, the electrode F) that is not in contact with the reagent layer can be used as the working electrode, and an electrode (for example, electrode A, C, E) that is in contact with the reagent layer can be used as the counter electrode. Furthermore, it is preferable to use the same electrode for the counter electrode used in Step 6: Int Measurement Process and the counter electrode used in Step 3: Measurement of Apparent Glu Amount.

In Step 3: Measurement of Apparent Glu Amount, voltage application can be performed multiple times. In this case, the same electrode (for example, the electrode A, the electrode C, the electrode E) is used as the counter electrode, and different electrodes (for example, the electrode B and the electrode G) among the electrodes that are in contact with the reagent layer each can be used as the working electrode. This makes it possible to obtain a current value for Glu of the whole biosensor, which is preferable.

TABLE 25

| | Working Electrode | Counter Electrode |
|---|---|---|
| Step 2: Hct Measurement Process | B | A |
| Step 3: Measurement of Apparent Glu Amount | B or G | A, C, E |
| Step 6: Int Measurement Process | F | A, C, E |
| Step 5: Second Hct Measurement Process | F | A, B, C, G |

In the operation flow chart shown in FIG. 15a, steps S1 to S13 are the same as steps S1 to S13 of Embodiment 2 shown in FIG. 11. The "Hct measurement process 2" (S14 in FIG. 15a) in FIG. 15a is the same as step S14 of Embodiment 3 shown in FIG. 14b. The Hct measurement process 1 (S6) further performed between the Hct measurement process 2 (S14) and the final glucose value correction & calculation (S8) is the same as the Hct measurement process (S6) in Embodiment 2 shown in FIG. 11.

In this case, in Step 4: Correction of Blood Component, the Hct values obtained in Step 2 performed twice, the Hct value obtained in Step 5, the current value that depends on Glu obtained in Step 3, and the Int value obtained in Step 6 are used to obtain a Glu value (S8, FIG. 15a). When such Step 6 is added, it is possible to capture the Int value of the blood of the entire capillary. Thus, it is possible to measure the Glu value with higher accuracy compared to the case where Step 6 is not added. Furthermore, Step 2 performed twice makes it possible to grasp the state of blood in the capillary more accurately, which can result in the effect that the Glu value can be measured with higher accuracy.

That is, in Embodiment 5, Step 1: Detection of Sample (Blood), Step 2: Hct Measurement Process, Step 3: Measurement of Apparent Glu Amount, Step 6: Int Measurement Process, and Step 5: Second Hct Measurement Process as well as additional Step 2: Hct Measurement Process and Step 4: Correction of Blood Component are performed in this order.

Figure 18B:
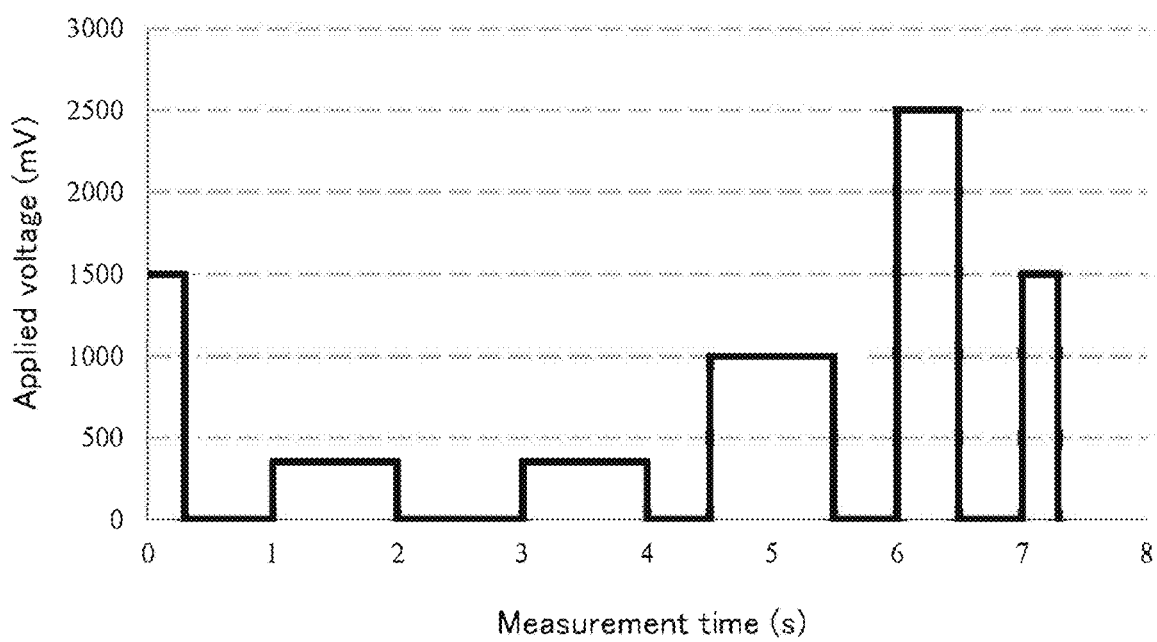
FIG. 18b shows another example of the relationship between applied voltage and voltage application time according to Embodiment 4.

FIG. 18b shows an example of the relationship between applied voltage and voltage application time in Embodiment 5.

In FIG. 18b, the Hct measurement process in Step 2 is started at zero second after confirmation of the introduction of blood and is performed by applying a voltage, until 0.3 second thereafter, for 0.3 second. In this case, a voltage of 1.5 V is applied. Then, the voltage application for measuring the apparent Glu amount in Step 3 is performed twice. Specifically, a voltage of 0.35 V is applied for 1 second from 1 second to 2 seconds, and a voltage of 0.35 V is applied for 1 second from 3 seconds to 4 seconds. Then, in the Int measurement process in Step 6, a voltage of 1.0 V is applied for 1 second from 4.5 seconds to 5.5 seconds. Furthermore, in the second Hct measurement process in Step 5, a voltage of 2.5 V is applied for 0.5 second from 6 seconds to 6.5 seconds. Finally, in the second Hct measurement process in Step 2, a voltage of 1.5 V is applied for 0.5 second from 7 seconds to 7.5 seconds.

Figure 20A:
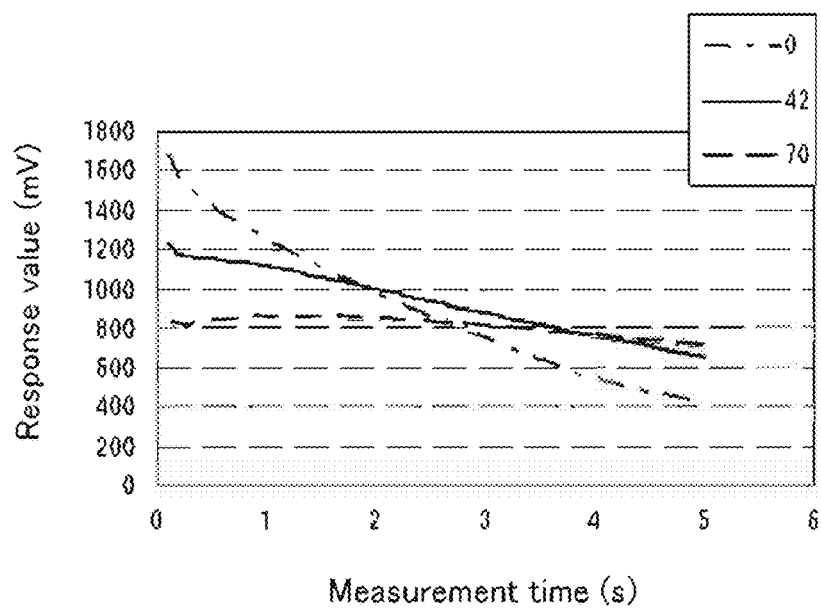
FIG. 20a is a graph showing the change with time in the response current value relative to an applied voltage with respect to each blood sample with a Glu concentration of 45 mg/dl (Hct value: 0%, 42%, and 70%) in Example 1.

Next, examples of the method for measuring a component of a biological sample according to the present invention will be described with reference to the drawings. In FIGS. 20a to 127b, the curve of "0" denotes a curve in the case of a Hct value of 0%, the curve of "42" denotes a curve in the case of a Hct value of 42%, the curve of "70" denotes a curve in the case of a Hct value of 70%, the curve of "45" denotes a curve in the case of a Glu value of 45 mg/dl, and the curve of "550" denotes a curve in the case of a Glu value of 550 mg/dl.

Example 1

FIGS. 1, 2, and 3 show an example of a sensor for measuring a blood component that is used in the measuring method of the present invention. FIG. 1 is an exploded perspective view of the sensor, FIG. 2 is a sectional view, and FIG. 3 is a plan view. In the above-mentioned three drawings, the same parts are indicated with the same reference signs. As an example, this sensor is a sensor for measuring Glu as a blood component.

As shown in the drawings, in this sensor 1, two electrodes A and B are formed on an insulating substrate 101. The space between these electrodes is 100 to 1600 μm and they can be switched between a working electrode and a counter electrode. The areas of the electrode A and the electrode B each are 0.055 to 1.1 mm². The surfaces of the electrodes A and B are coated with a polymer material such as CMC. A reagent layer 11 is disposed so as to cover part of the electrodes A and B. The reagent layer 11 contains an oxidoreductase such as glucose dehydrogenase and a mediator such as phenanthrenequinone (9,10-phenanthrenequinone), 3-phenylimino-3H-phenothiazine, or potassium ferricyanide, as well as, as an optional component, an enzyme stabilizer, a crystal homogenizing agent, a polymer, etc. A cover 103 is disposed above the insulating substrate 101 with a spacer 102 interposed therebetween, with one end (the right end in the drawings) being left uncovered. In this sensor 1, in order to introduce blood to each electrode (A and B), a channel 14 is formed of the insulating substrate 101, the spacer 102, and the cover 103. The end of the channel 14 extends to the other end (the left end in the drawings) of the sensor 1 and is open to the outside to serve as a biological sample supply port 12. The two electrodes (A and B) are connected to leads, respectively, and these leads extend to the one end side (the right end in the drawings), and the end of each lead is exposed without being covered with the cover 103. The cover 103 has an air hole 13 formed in a portion corresponding to the right end of the channel 14.

In the present invention, the material for the insulating substrate 101 is polyethylene terephthalate. The size of the insulating substrate 101 is an overall length of 10 to 30 mm, a width of 3 to 10 mm, and a thickness of 0.1 to 0.6 mm. With respect to the material and the size of the insulating substrate, the same applies to Examples 2 to 93 described later.

The electrodes and leads on the insulating substrate were formed by using palladium as a material to form a conductive layer by a sputtering method and processing it into a specific electrode pattern with a laser. The laser used herein was a green laser. The distance between the working electrode and the counter electrode was set at 1000 μm. This also applies to Examples 2 to 93 described later.

The reagent layer 11 is formed as follows. An aqueous solution containing 0.1 to 5 U/sensor of glucose dehydrogenase, 10 to 300 mM of phenanthrenequinone (9,10-phenanthrenequinone), 3-phenylimino-3H-phenothiazine, or potassium ferricyanide, 1 to 50 mM of maltitol, 20 to 200 mM of taurine, and 0.01 to 2% by weight of CMC is applied dropwise to a circular slit portion 20 (not shown in the drawings) and then is dried. With the slit portion 20 being provided, spreading of the aqueous solution applied dropwise can be suppressed, and the reagent layer 11 can be disposed at a more accurate position. Thus, the reagent layer 11 is formed so as to cover part of the electrode part formed of the electrode A and the electrode B. The above-mentioned drying was carried out using a dryer.

In the present invention, the material for the spacer 102 is the same as that used for the insulating substrate. The size of the spacer 102 is an overall length of 10 to 30 mm, a width of 3 to 10 mm, and a thickness of 0.05 to 0.25 mm. The spacer 102 of this example is formed with an I-shaped cutout portion that serves as a channel for blood introduction, and the size thereof is an overall length of 1.0 to 5.0 mm and a width of 0.5 to 2.0 mm. The cutout portion was formed using a mold. With respect to the material and size of the spacer 102 as well as the cutout portion, the same applies to Examples 2 to 93 described later.

In the present invention, the material for the cover 103 is the same as that used for the insulating substrate. The portion corresponding to the ceiling portion of the channel for introducing blood of the cover 103 was subjected to a hydrophilic treatment. The hydrophilic treatment was carried out by a method of applying a surfactant. The size of the cover 103 is an overall length of 15 to 30 mm, a width of 5 to 10 mm, and a thickness of 0.05 to 0.1 mm. The cover 103 has an air hole formed therein, and the shape thereof is circular. The size thereof is a maximum diameter of 0.1 to 2.0 mm. With respect to the material and size of the cover 103 as well as the air hole 13, the same applies to Examples 2 to 93 described later.

Furthermore, the sensor 1 was produced by stacking the insulating substrate, the spacer 102, and the cover 103 in this order to form one body. The three members are stuck together with a thermosetting adhesive to form one body. This also applies to Examples 2 to 108 described later.

Measurement of the blood component amount, for example, a blood glucose value using the sensor 1 is carried out as follows. Three types of blood samples having Hct values adjusted to 0%, 42%, and 70%, respectively, were prepared for two Glu concentrations, i.e., 45 mg/dL or 550 mg/dL. With respect to these six blood samples, a voltage of 1.5 V was applied with the sensor 1 between the electrode A and the electrode B for 0.1 second from 0 second to 0.1 second after detection of the introduction of a blood sample (see FIG. 19(a)). The current flowing between the working electrode and the counter electrode of each sensor was measured, and the response current value and the sensitivity difference were measured in the measurement of the Hct value (see FIGS. 20a to 20d). FIG. 20a is a graph showing the change with time in the response current value relative to the applied voltage with respect to each blood sample with a Glu concentration of 45 mg/dl (Hct value: 0%, 42%, and 70%) in Example 1. FIG. 20b is a graph showing the change with time in the response current value relative to the applied voltage with respect to each blood sample with a Glu concentration of 550 mg/dl (Hct value: 0%, 42%, and 70%) in Example 1. FIGS. 20a and 20b each are a graph showing the change with time in the response current value relative to the applied voltage in the case of applying a voltage of 1.5 V for 5 seconds between the electrode A and the electrode B that have the reagent disposed thereon. FIG. 20c is a graph showing the sensitivity difference (%) in each case of Glu values of 45 mg/dl and 550 mg/dl with reference to Hct 42% in Example 1. FIG. 20d is a graph showing the sensitivity difference (%) in each case of Hct values of 0%, 42%, and 70% with reference to Glu 45 mg/dl in Example 1. FIGS. 20c and 20d each are a graph showing the sensitivity difference in each case at 0 second to 0.1 second after the detection.

Example 2

Figure 19:
FIG. 19 (a) shows the relationship between voltage application time and applied voltage immediately (0 second) after detection of the introduction of a blood sample and (b) shows the relationship between voltage application time and applied voltage after a predetermined time from detection of the introduction of a blood sample.
Figure 19:
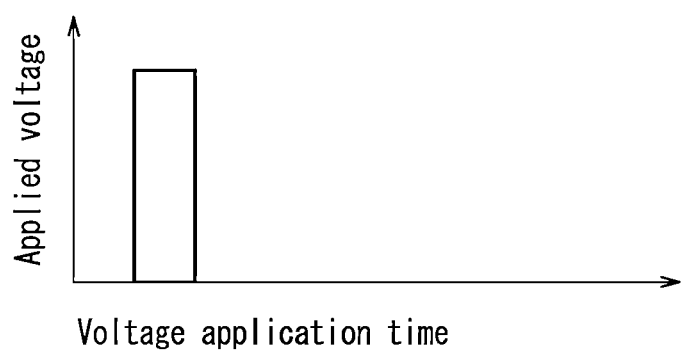
Figure 20B:
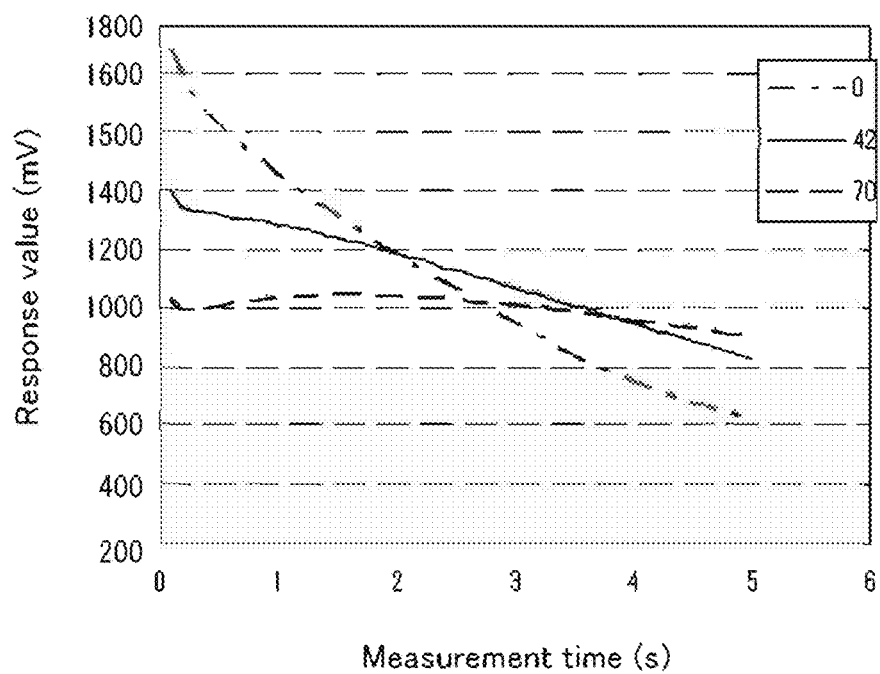
FIG. 20b is a graph showing the change with time in the response current value relative to an applied voltage with respect to each blood sample with a Glu concentration of 550 mg/dl (Hct value: 0%, 42%, and 70%) in Example 1.
Figure 20C:
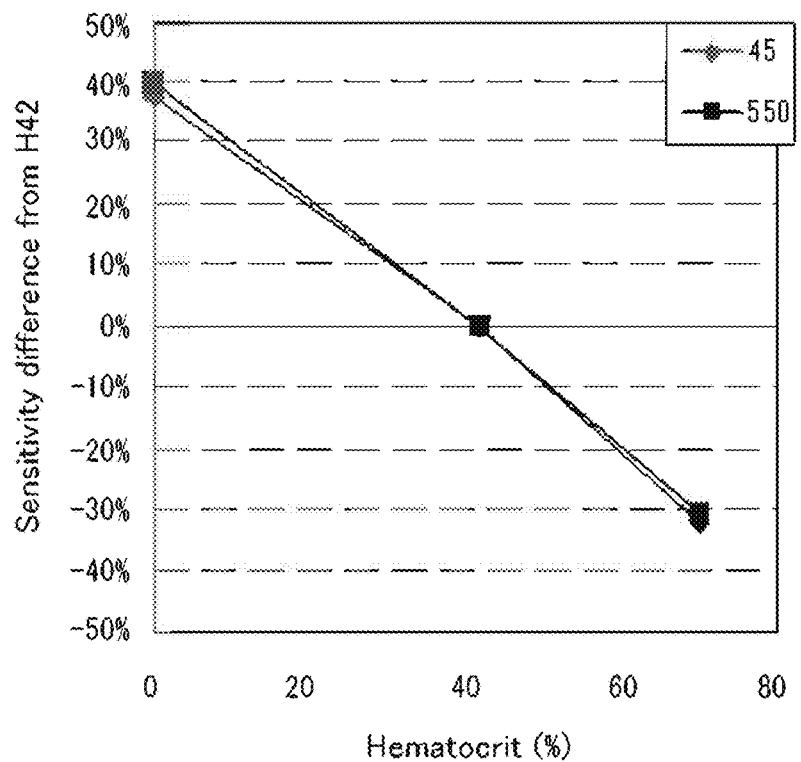
FIG. 20c is a graph showing the sensitivity difference (%) in each case of Glu values of 45 mg/dl and 550 mg/dl with reference to Hct 42% in Example 1.
Figure 20D:
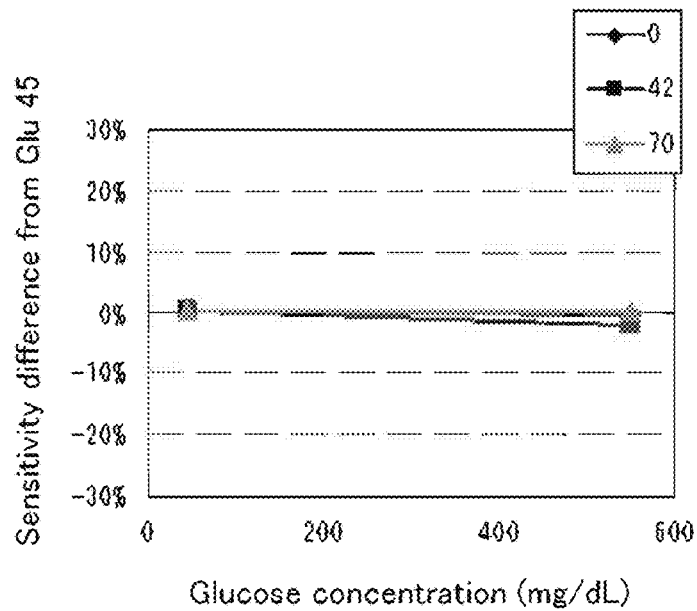
FIG. 20d is a graph showing the sensitivity difference (%) in each case of Hct values of 0%, 42%, and 70% with reference to Glu 45 mg/dl in Example 1.
Figure 21A:
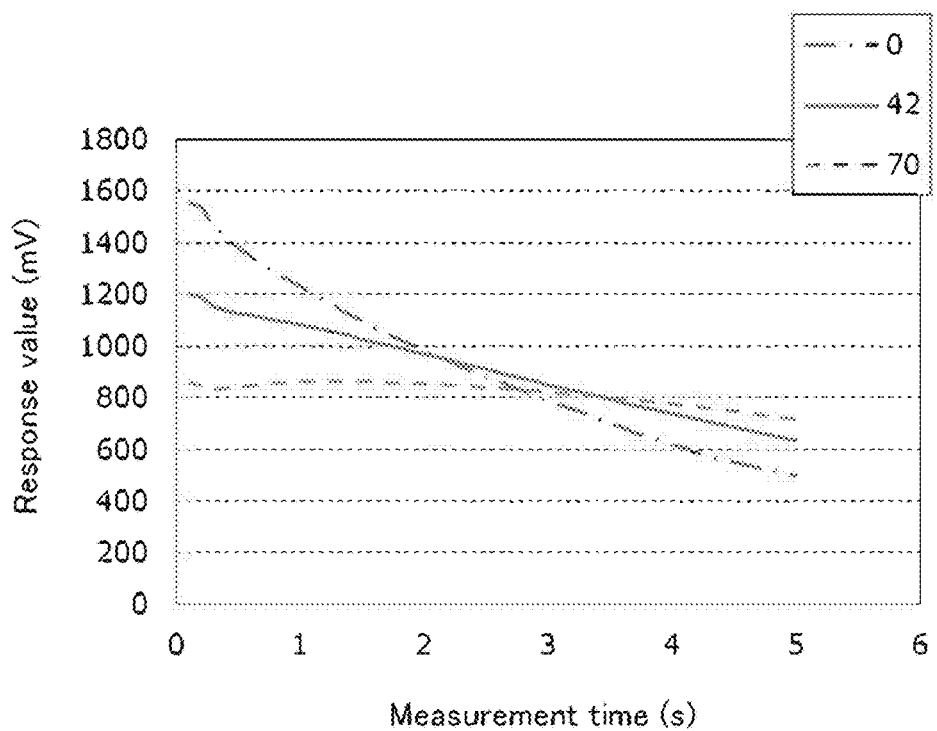
FIG. 21a is a graph showing the change with time in the response current value relative to an applied voltage with respect to each blood sample with a Glu concentration of 45 mg/dl (Hct value: 0%, 42%, and 70%) in Example 2.
Figure 21B:
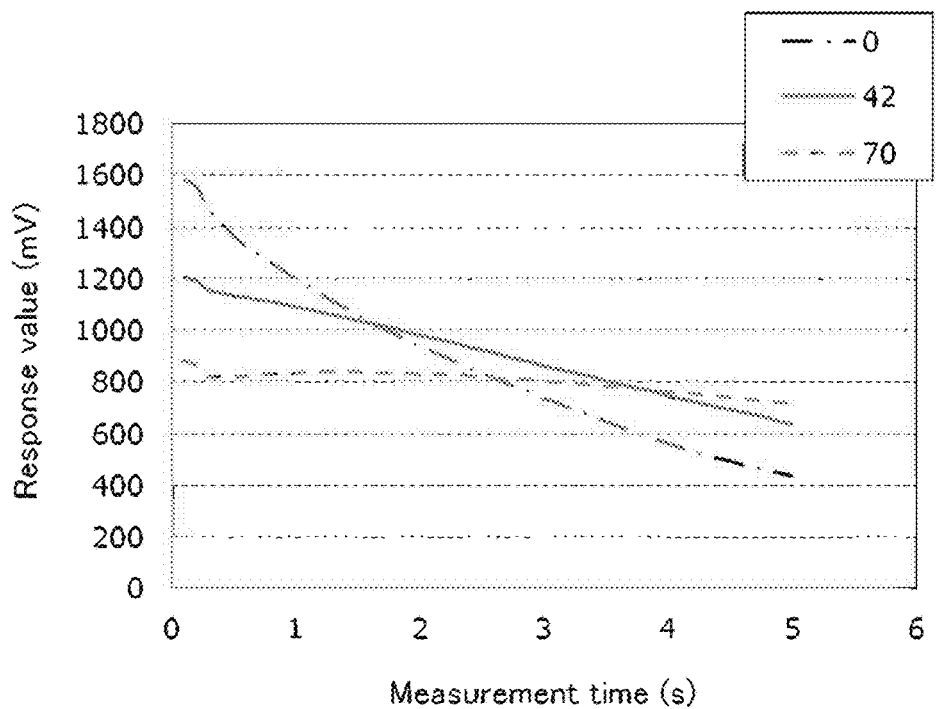
FIG. 21b is a graph showing the change with time in the response current value relative to an applied voltage with respect to each blood sample with a Glu concentration of 550 mg/dl (Hct value: 0%, 42%, and 70%) in Example 2.
Figure 21C:
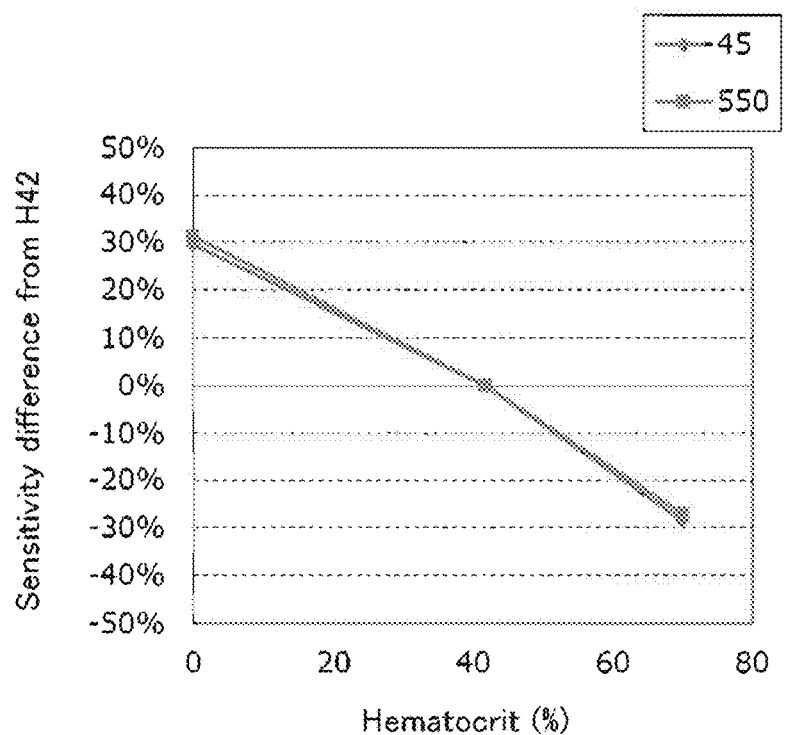
FIG. 21c is a graph showing the sensitivity difference (%) in each case of Glu values of 45 mg/dl and 550 mg/dl with reference to Hct 42% in Example 2.
Figure 21D:
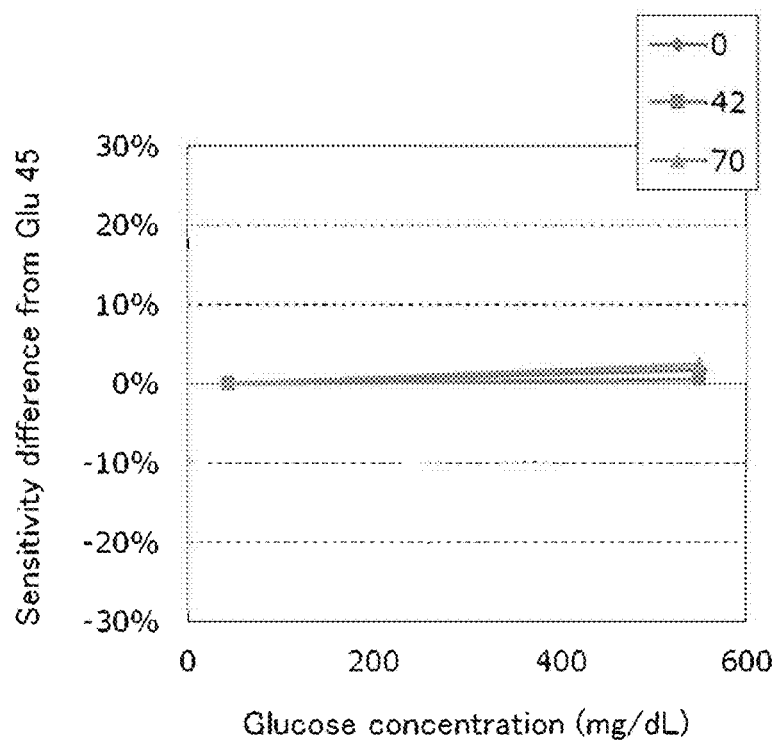
FIG. 21d is a graph showing the sensitivity difference (%) in each case of Hct values of 0%, 42%, and 70% with reference to Glu 45 mg/dl in Example 2.

The procedure was carried out in the same manner as in Example 1 except that voltage application was started at 0.05 second after detection of the introduction of a blood sample and a voltage of 1.5 V was applied between the electrode A and the electrode B, until 0.15 second, for 0.1 second (see FIG. 19 (b)). The current flowing between the working electrode and the counter electrode of each sensor 1 was measured, and the response current value and the sensitivity difference were measured in the measurement of the Hct value (see FIGS. 21a to 21d). FIG. 21a is a graph showing the change with time in the response current value relative to the applied voltage with respect to each blood sample with a Glu concentration of 45 mg/dl (Hct value: 0%, 42%, and 70%) in Example 2. FIG. 21b is a graph showing the change with time in the response current value relative to the applied voltage with respect to each blood sample with a Glu concentration of 550 mg/dl (Hct value: 0%, 42%, and 70%) in Example 2. FIGS. 21a and 21b each are a graph showing the change with time in the response current value relative to the applied voltage in the case of applying a voltage of 1.5 V for 5 seconds between the electrode A and the electrode B that have the reagent disposed thereon. FIG. 21c is a graph showing the sensitivity difference (%) in each case of Glu values of 45 mg/dl and 550 mg/dl with reference to Hct 42% in Example 2. FIG. 21d is a graph showing the sensitivity difference (%) in each case of Hct values of 0%, 42%, and 70% with reference to Glu 45 mg/dl in Example 2. FIGS. 21c and 21d each are a graph showing the sensitivity difference in each case at 0.05 second to 0.15 second after the detection.

Example 3

Figure 22A:
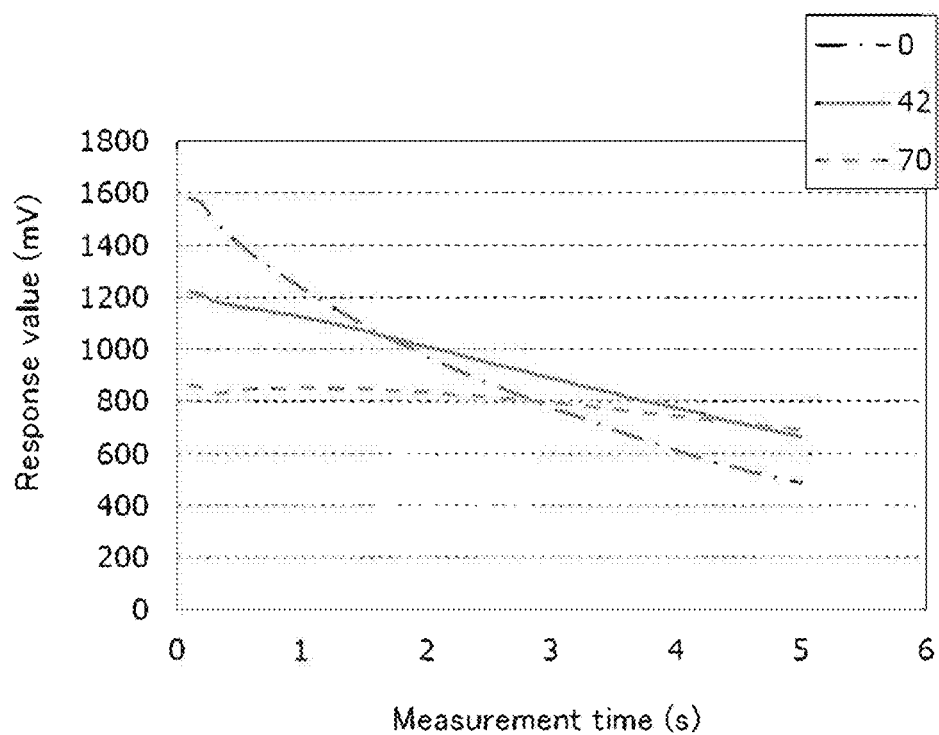
FIG. 22a is a graph showing the change with time in the response current value relative to an applied voltage with respect to each blood sample with a Glu concentration of 45 mg/dl (Hct value: 0%, 42%, and 70%) in Example 3.
Figure 22B:
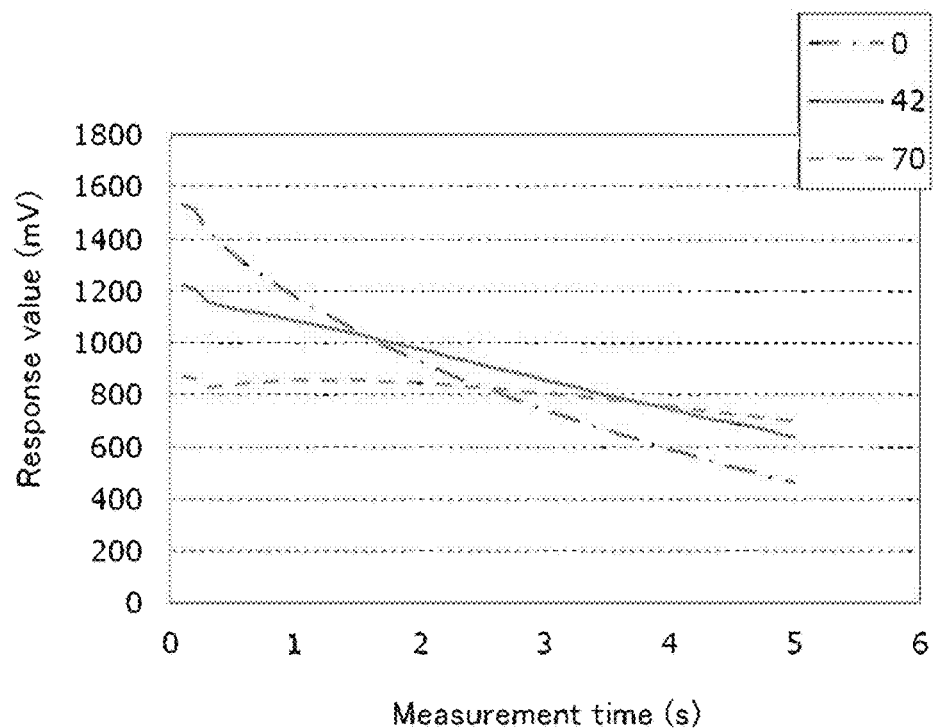
FIG. 22b is a graph showing the change with time in the response current value relative to an applied voltage with respect to each blood sample with a Glu concentration of 550 mg/dl (Hct value: 0%, 42%, and 70%) in Example 3.
Figure 22C:
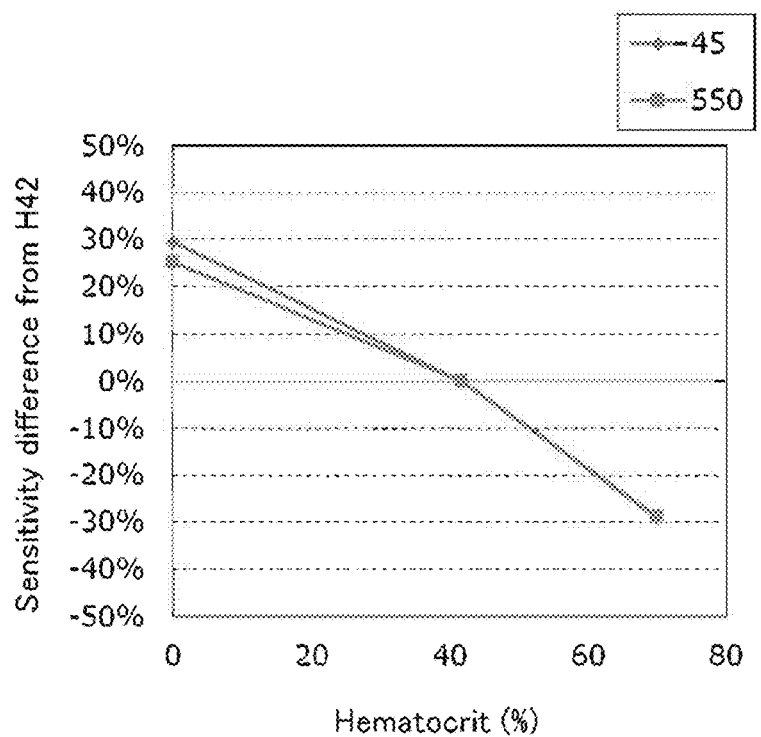
FIG. 22c is a graph showing the sensitivity difference (%) in each case of Glu values of 45 mg/dl and 550 mg/dl with reference to Hct 42% in Example 3.
Figure 22D:
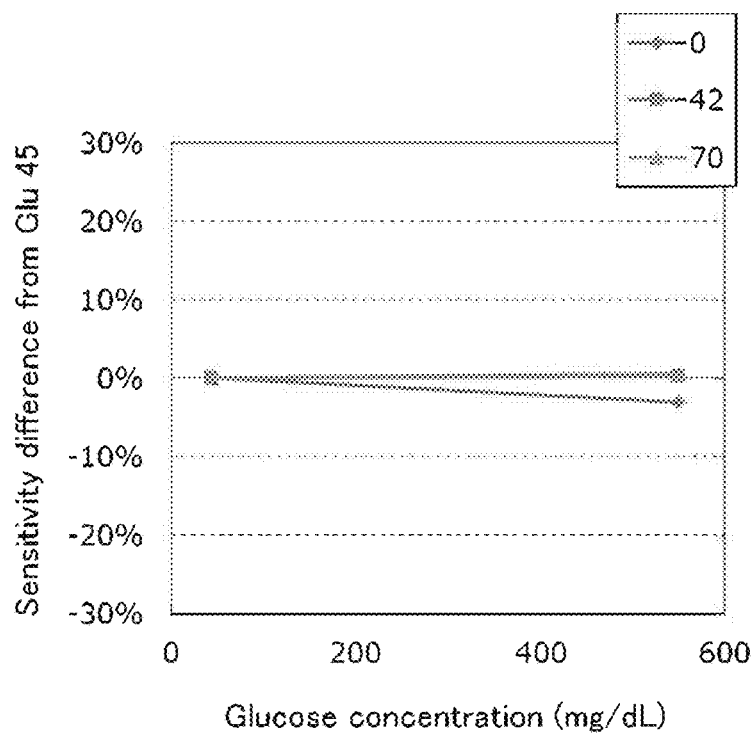
FIG. 22d is a graph showing the sensitivity difference (%) in each case of Hct values of 0%, 42%, and 70% with reference to Glu 45 mg/dl in Example 3.

The procedure was carried out in the same manner as in Example 1 except that voltage application was started at 0.1 second after detection of the introduction of a blood sample and a voltage of 1.5 V was applied between the electrode A and the electrode B, until 0.2 second, for 0.1 second. The current flowing between the working electrode and the counter electrode of each sensor 1 was measured, and the response current value and the sensitivity difference were measured in the measurement of the Hct value (see FIGS. 22a to 22d). FIG. 22a is a graph showing the change with time in the response current value relative to the applied voltage with respect to each blood sample with a Glu concentration of 45 mg/dl (Hct value: 0%, 42%, and 70%) in Example 3. FIG. 22b is a graph showing the change with time in the response current value relative to the applied voltage with respect to each blood sample with a Glu concentration of 550 mg/dl (Hct value: 0%, 42%, and 70%) in Example 3. FIGS. 22a and 22b each are a graph showing the change with time in the response current value relative to the applied voltage in the case of applying a voltage of 1.5 V for 5 seconds between the electrode A and the electrode B that have the reagent disposed thereon. FIG. 22c is a graph showing the sensitivity difference (%) in each case of Glu values of 45 mg/dl and 550 mg/dl with reference to Hct 42% in Example 3. FIG. 22d is a graph showing the sensitivity difference (%) in each case of Hct values of 0%, 42%, and 70% with reference to Glu 45 mg/dl in Example 3. FIGS. 22c and 22d each are a graph showing the sensitivity difference in each case at 0.1 second to 0.2 second after the detection.

Example 4

Figure 23A:
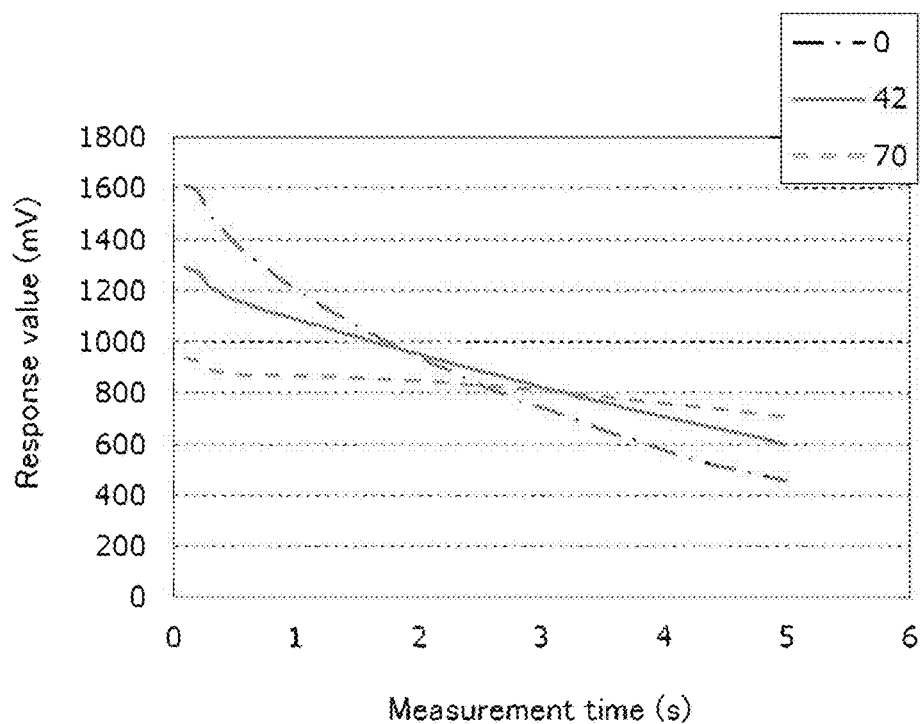
FIG. 23a is a graph showing the change with time in the response current value relative to an applied voltage with respect to each blood sample with a Glu concentration of 45 mg/dl (Hct value: 0%, 42%, and 70%) in Example 4.
Figure 23B:
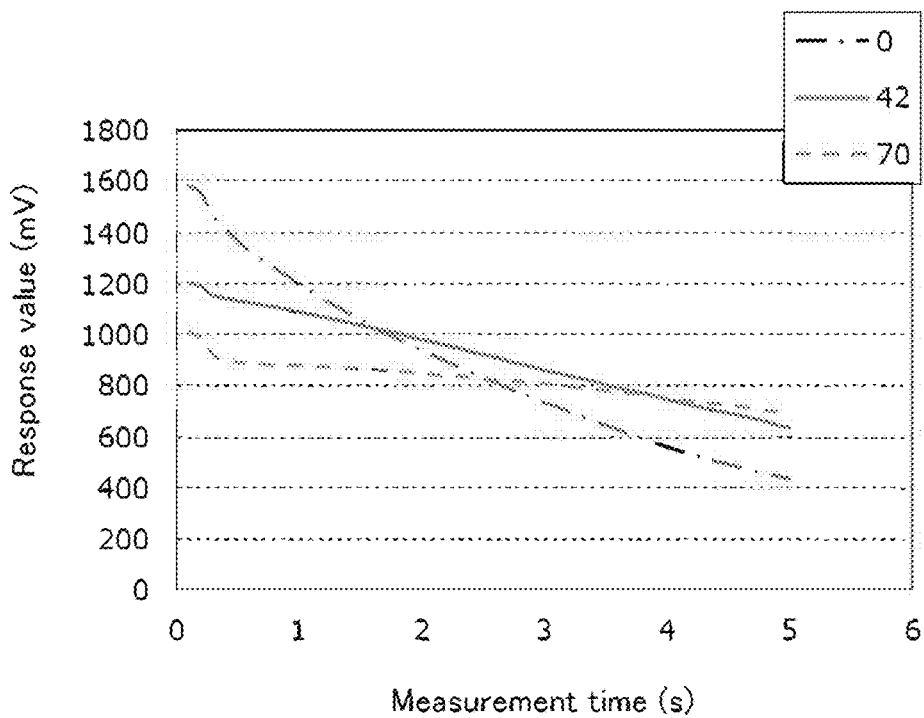
FIG. 23b is a graph showing the change with time in the response current value relative to an applied voltage with respect to each blood sample with a Glu concentration of 550 mg/dl (Hct value: 0%, 42%, and 70%) in Example 4.
Figure 23C:
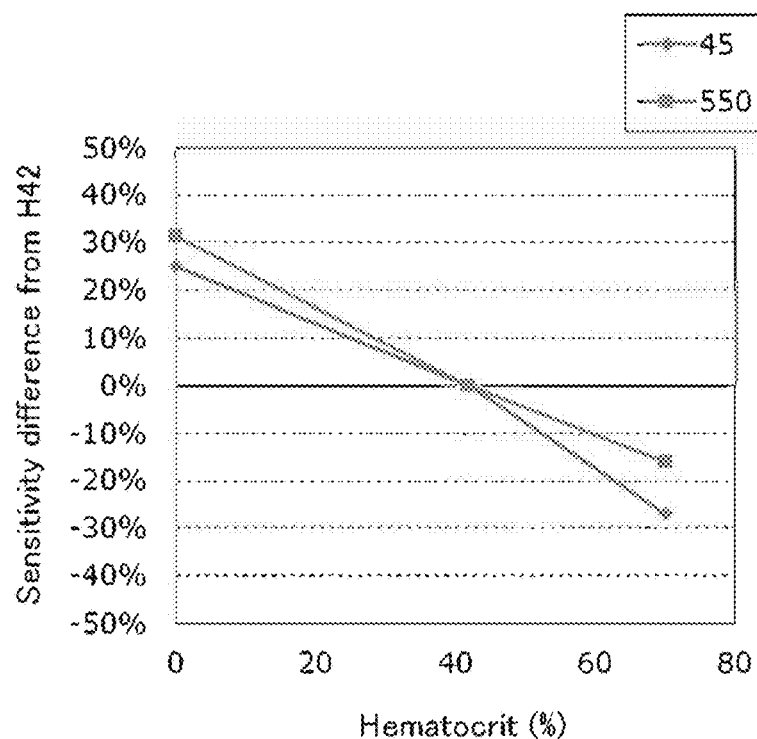
FIG. 23c is a graph showing the sensitivity difference (%) in each case of Glu values of 45 mg/dl and 550 mg/dl with reference to Hct 42% in Example 4.
Figure 23D:
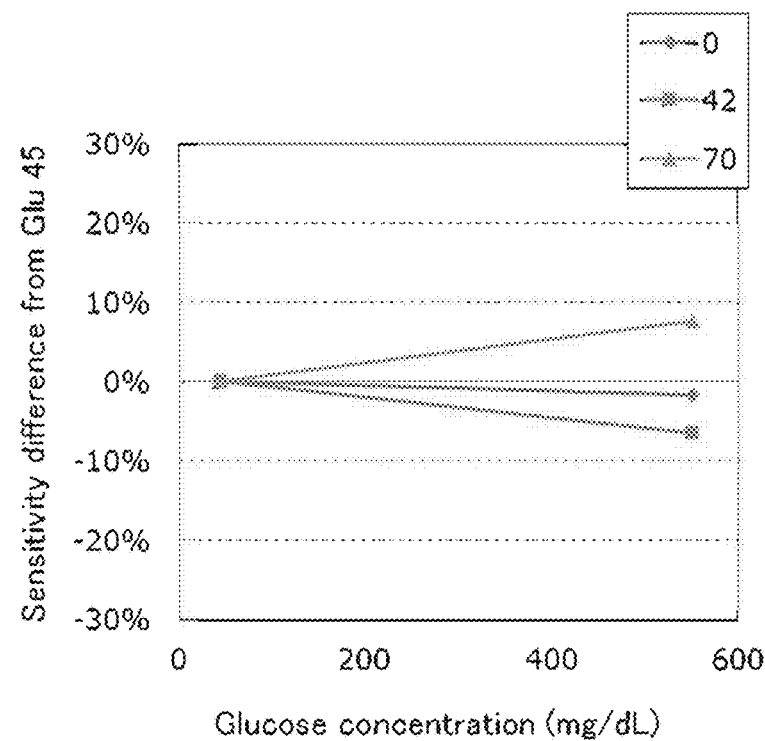
FIG. 23d is a graph showing the sensitivity difference (%) in each case of Hct values of 0%, 42%, and 70% with reference to Glu 45 mg/dl in Example 4.

The procedure was carried out in the same manner as in Example 1 except that voltage application was started at 0.5 second after detection of the introduction of a blood sample and a voltage of 1.5 V was applied between the electrode A and the electrode B, until 0.6 second, for 0.1 second. The current flowing between the working electrode and the counter electrode of each sensor 1 was measured, and the response current value and the sensitivity difference were measured in the measurement of the Hct value (see FIGS. 23a to 23d). FIG. 23a is a graph showing the change with time in the response current value relative to the applied voltage with respect to each blood sample with a Glu concentration of 45 mg/dl (Hct value: 0%, 42%, and 70%) in Example 4. FIG. 23b is a graph showing the change with time in the response current value relative to the applied voltage with respect to each blood sample with a Glu concentration of 550 mg/dl (Hct value: 0%, 42%, and 70%) in Example 4. FIGS. 23a and 23b each are a graph showing the change with time in the response current value relative to the applied voltage in the case of applying a voltage of 1.5 V for 5 seconds between the electrode A and the electrode B that have the reagent disposed thereon. FIG. 23c is a graph showing the sensitivity difference (%) in each case of Glu values of 45 mg/dl and 550 mg/dl with reference to Hct 42% in Example 4. FIG. 23d is a graph showing the sensitivity difference (%) in each case of Hct values of 0%, 42%, and 70% with reference to Glu 45 mg/dl in Example 4. FIGS. 23c and 23d each are a graph showing the sensitivity difference in each case at 0.5 second to 0.6 second after the detection.

Comparative Example 1

Figure 24A:
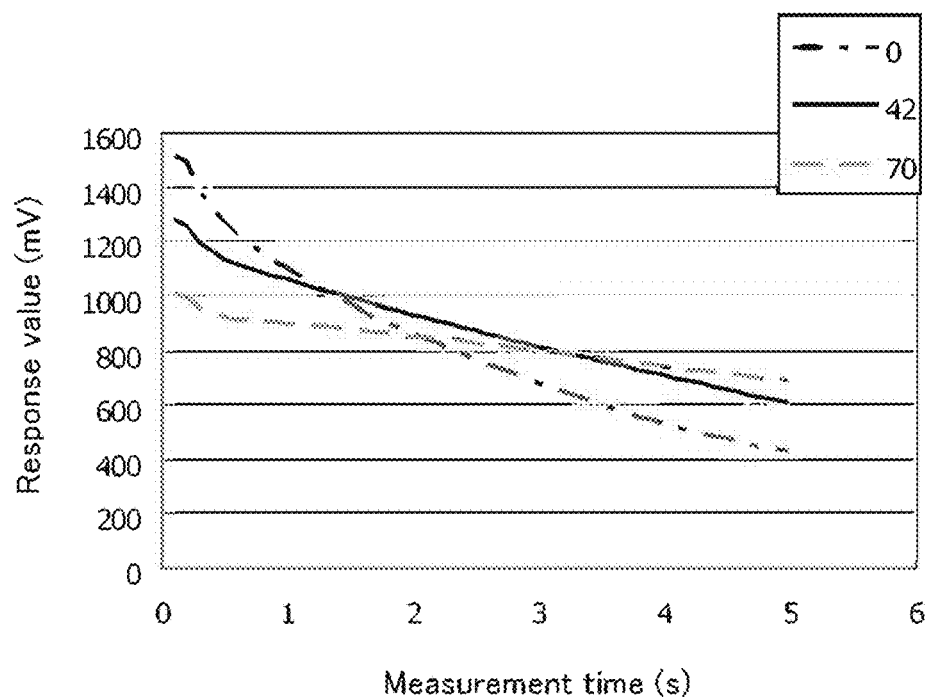
FIG. 24a is a graph showing the change with time in the response current value relative to an applied voltage with respect to each blood sample with a Glu concentration of 45 mg/dl (Hct value: 0%, 42%, and 70%) in Comparative Example 1.
Figure 24B:
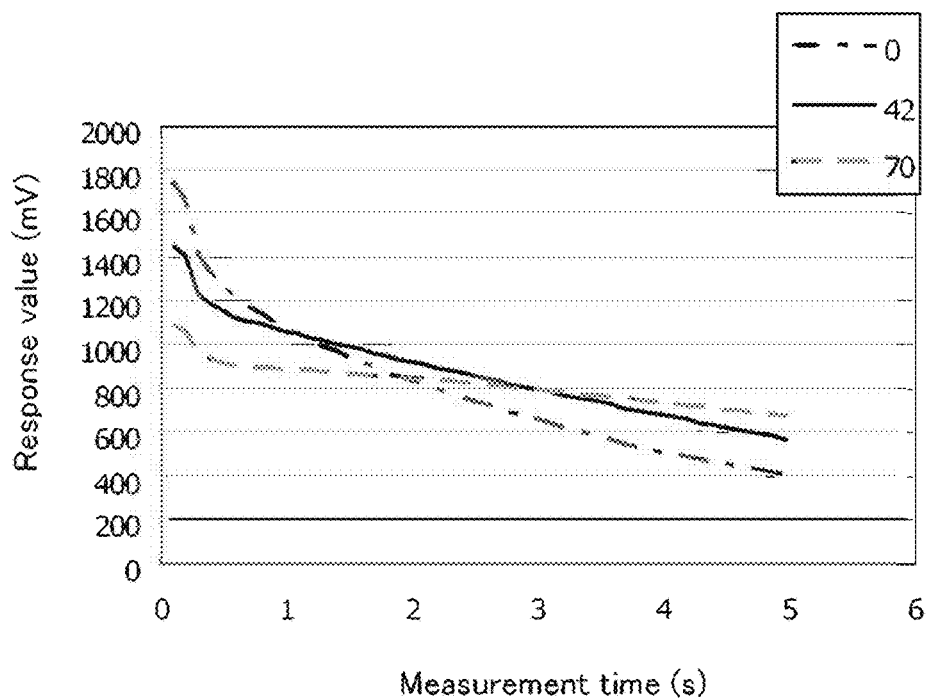
FIG. 24b is a graph showing the change with time in the response current value relative to an applied voltage with respect to each blood sample with a Glu concentration of 550 mg/dl (Hct value: 0%, 42%, and 70%) in Comparative Example 1.
Figure 24C:
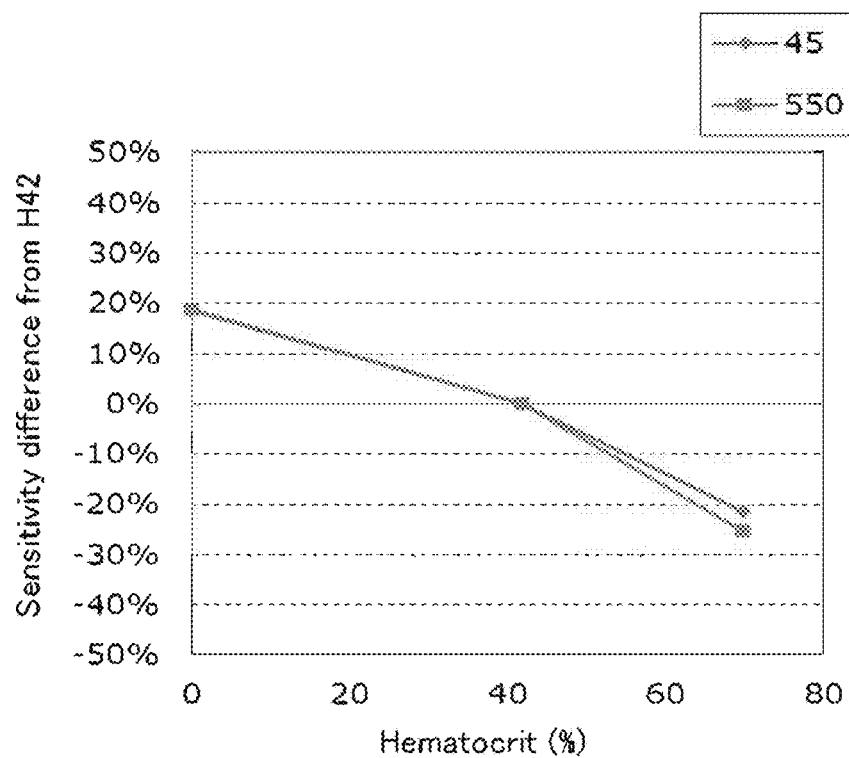
FIG. 24c is a graph showing the sensitivity difference (%) in each case of Glu values of 45 mg/dl and 550 mg/dl with reference to Hct 42% in Comparative Example 1.
Figure 24D:
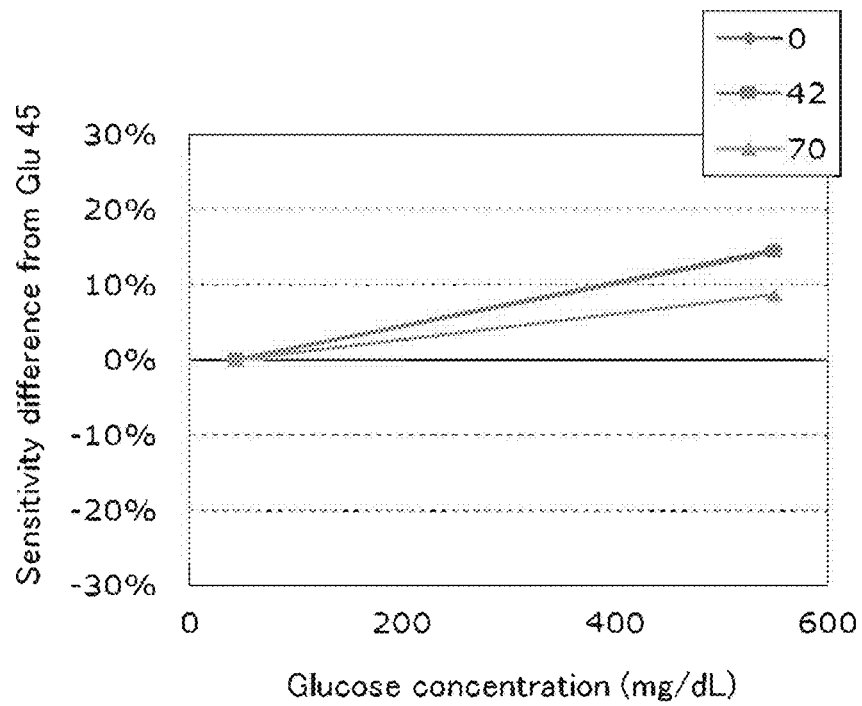
FIG. 24d is a graph showing the sensitivity difference (%) in each case of Hct values of 0%, 42%, and 70% with reference to Glu 45 mg/dl in Comparative Example 1.

The procedure was carried out in the same manner as in Example 1 except that voltage application was started at 1 second after detection of the introduction of a blood sample and a voltage of 1.5 V was applied between the electrode A and the electrode B, until 1.1 seconds, for 0.1 second. The current flowing between the working electrode and the counter electrode of each sensor 1 was measured, and the response current value and the sensitivity difference were measured in the measurement of the Hct value (see FIGS. 24a to 24d). FIG. 24a is a graph showing the change with time in the response current value relative to the applied voltage with respect to each blood sample with a Glu concentration of 45 mg/dl (Hct value: 0%, 42%, and 70%) in Comparative Example 1. FIG. 24b is a graph showing the change with time in the response current value relative to the applied voltage with respect to each blood sample with a Glu concentration of 550 mg/dl (Hct value: 0%, 42%, and 70%) in Comparative Example 1. FIGS. 24a and 24b each are a graph showing the change with time in the response current value relative to the applied voltage in the case of applying a voltage of 1.5 V for 5 seconds between the electrode A and the electrode B that have the reagent disposed thereon. FIG. 24c is a graph showing the sensitivity difference (%) in each case of Glu values of 45 mg/dl and 550 mg/dl with reference to Hct 42% in Comparative Example 1. FIG. 24d is a graph showing the sensitivity difference (%) in each case of Hct values of 0%, 42%, and 70% with reference to Glu 45 mg/dl in Comparative Example 1. FIGS. 24c and 24d each are a graph showing the sensitivity difference in each case at 1 second to 1.1 seconds after the detection.

Comparative Example 2

Figure 25A:
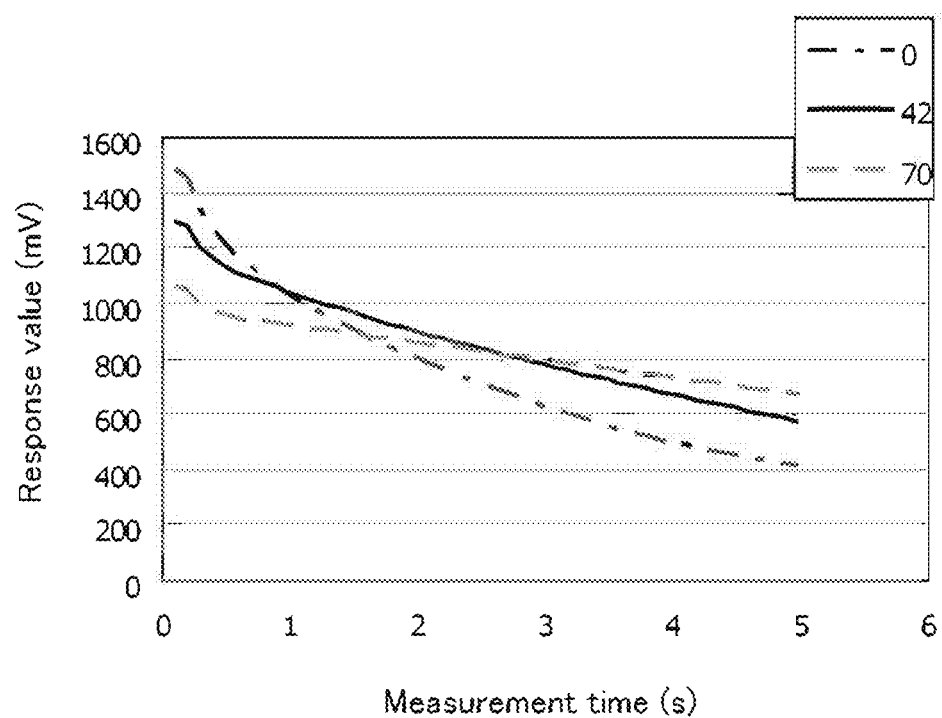
FIG. 25a is a graph showing the change with time in the response current value relative to an applied voltage with respect to each blood sample with a Glu concentration of 45 mg/dl (Hct value: 0%, 42%, and 70%) in Comparative Example 2.
Figure 25B:
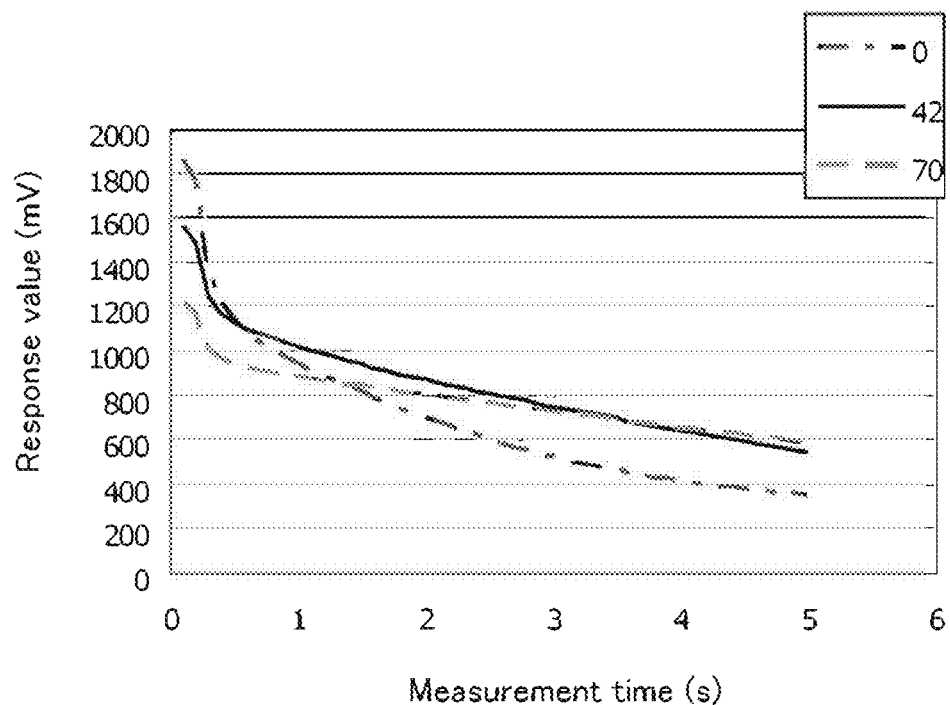
FIG. 25b is a graph showing the change with time in the response current value relative to an applied voltage with respect to each blood sample with a Glu concentration of 550 mg/dl (Hct value: 0%, 42%, and 70%) in Comparative Example 2.
Figure 25C:
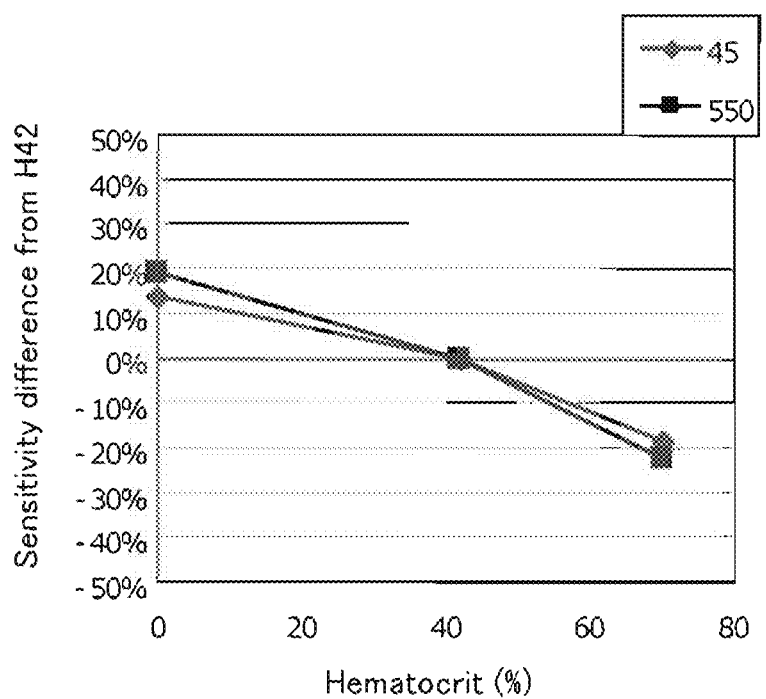
FIG. 25c is a graph showing the sensitivity difference (%) in each case of Glu values of 45 mg/dl and 550 mg/dl with reference to Hct 42% in Comparative Example 2.
Figure 25D:
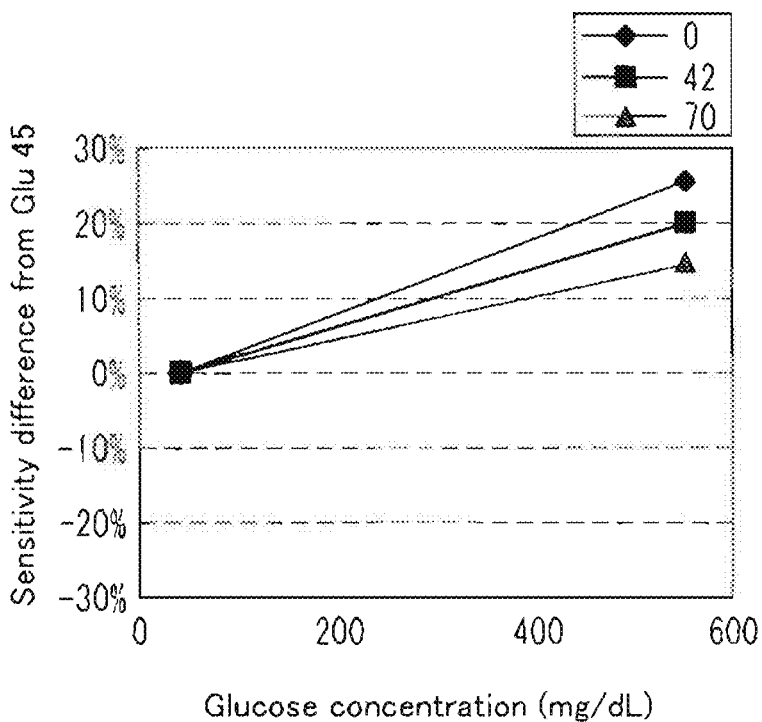
FIG. 25d is a graph showing the sensitivity difference (%) in each case of Hct values of 0%, 42%, and 70% with reference to Glu 45 mg/dl in Comparative Example 2.

The procedure was carried out in the same manner as in Example 1 except that voltage application was started at 2 seconds after detection of the introduction of a blood sample and a voltage of 1.5 V was applied between the electrode A and the electrode B, until 2.1 seconds, for 0.1 second. The current flowing between the working electrode and the counter electrode of each sensor 1 was measured, and the response current value and the sensitivity difference were measured in the measurement of the Hct value (see FIGS. 25a to 25d). FIG. 25a is a graph showing the change with time in the response current value relative to the applied voltage with respect to each blood sample with a Glu concentration of 45 mg/dl (Hct value: 0%, 42%, and 70%) in Comparative Example 2. FIG. 25b is a graph showing the change with time in the response current value relative to the applied voltage with respect to each blood sample with a Glu concentration of 550 mg/dl (Hct value: 0%, 42%, and 70%) in Comparative Example 2. FIGS. 25a and 25b each are a graph showing the change with time in the response current value relative to the applied voltage in the case of applying a voltage of 1.5 V for 5 seconds between the electrode A and the electrode B that have the reagent disposed thereon. FIG. 25c is a graph showing the sensitivity difference (%) in each case of Glu values of 45 mg/dl and 550 mg/dl with reference to Hct 42% in Comparative Example 2. FIG. 25d is a graph showing the sensitivity difference (%) in each case of Hct values of 0%, 42%, and 70% with reference to Glu 45 mg/dl in Comparative Example 2. FIGS. 25c and 25d each are a graph showing the sensitivity difference in each case at 2 seconds to 2.1 seconds after the detection.

From Examples 1 to 4 and Comparative Examples 1 and 2, it was confirmed that when a voltage of 1.5 V was applied for 0.1 second to the working electrode and the counter electrode within 0 second to 0.5 second after detection of the introduction of a biological sample, the current value obtained thereby had a high sensitivity and the Hct value obtained based on the current value had a high accuracy. The time from the start of blood introduction to the start of voltage application was changed between 0 and 2 seconds and the graphs showing the sensitivity difference were checked. As a result, it was found that the effect of the glucose concentration gradually increased as the time increased. Particularly, when the time until the start of voltage application was 2 seconds as in Comparative Example 2, a divergence was seen in the graph showing the sensitivity difference in each case of Hct values of 0%, 42%, and 70% particularly with reference to Glu 550 mg/dl as shown in FIG. 25d.

Example 5

Figure 26A:
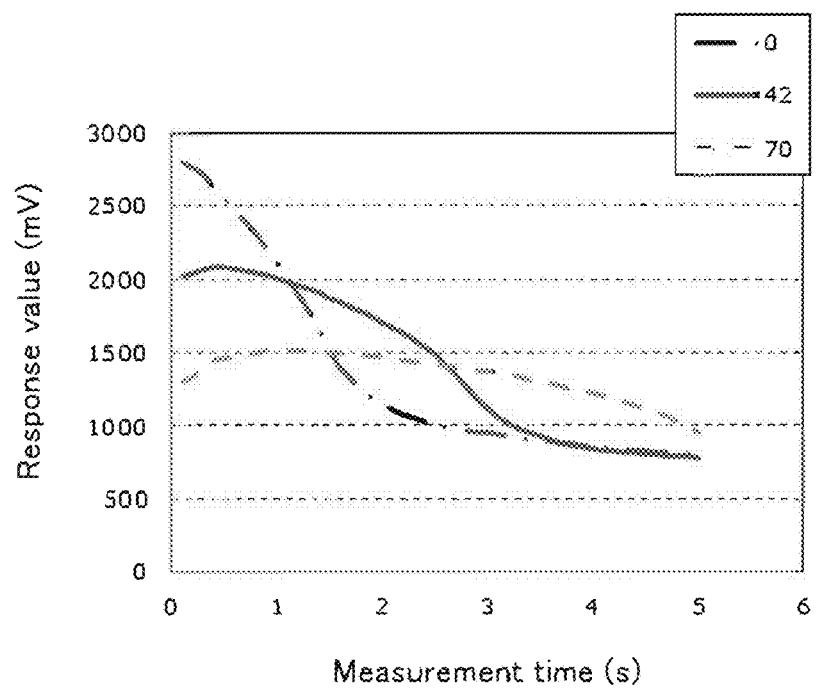
FIG. 26a is a graph showing the change with time in the response current value relative to an applied voltage with respect to each blood sample with a Glu concentration of 45 mg/dl (Hct value: 0%, 42%, and 70%) in Example 5.
Figure 26B:
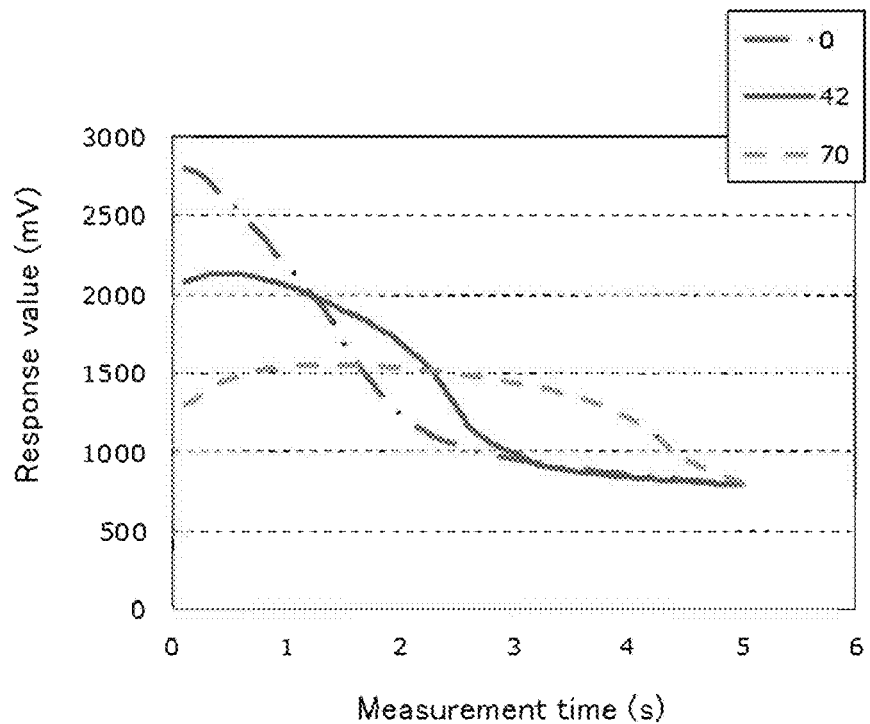
FIG. 26b is a graph showing the change with time in the response current value relative to an applied voltage with respect to each blood sample with a Glu concentration of 550 mg/dl (Hct value: 0%, 42%, and 70%) in Example 5.
Figure 26C:
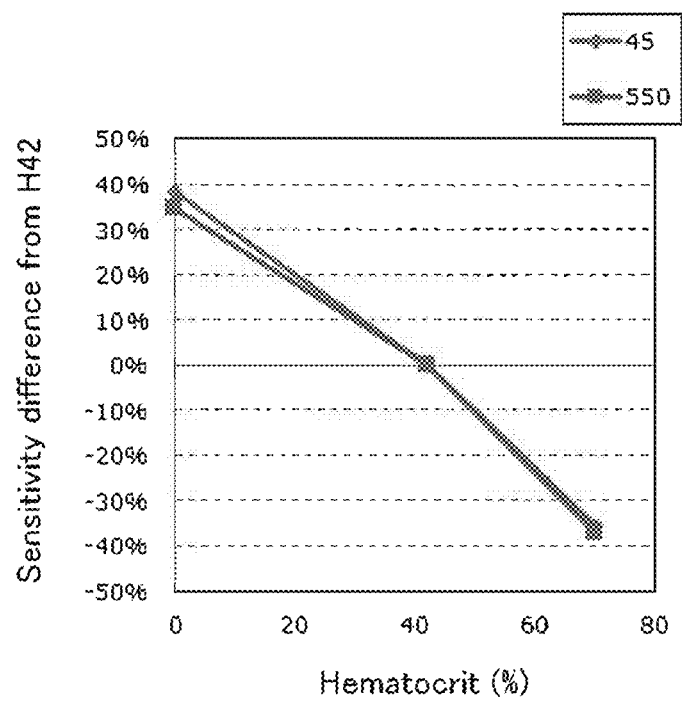
FIG. 26c is a graph showing the sensitivity difference (%) in each case of Glu values of 45 mg/dl and 550 mg/dl with reference to Hct 42% in Example 5.
Figure 26D:
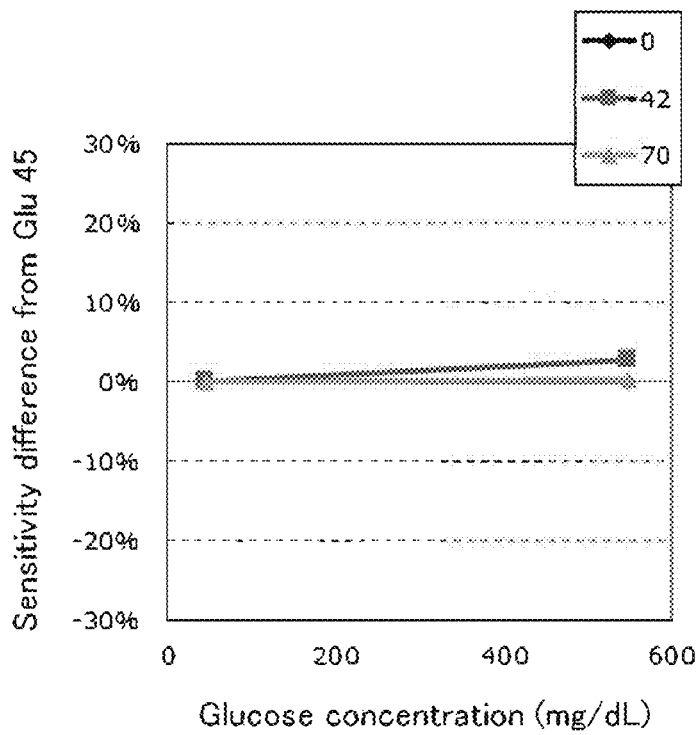
FIG. 26d is a graph showing the sensitivity difference (%) in each case of Hct values of 0%, 42%, and 70% with reference to Glu 45 mg/dl in Example 5.

The procedure was carried out in the same manner as in Example 1 except that a voltage of 2.0 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 26a to 26d). FIG. 26a is a graph showing the change with time in the response current value relative to the applied voltage with respect to each blood sample with a Glu concentration of 45 mg/dl (Hct value: 0%, 42%, and 70%) in Example 5. FIG. 26b is a graph showing the change with time in the response current value relative to the applied voltage with respect to each blood sample with a Glu concentration of 550 mg/dl (Hct value: 0%, 42%, and 70%) in Example 5. FIGS. 26a and 26b each are a graph showing the change with time in the response current value relative to the applied voltage in the case of applying a voltage of 2.0 V for 5 seconds between the electrode A and the electrode B that have the reagent disposed thereon. FIG. 26c is a graph showing the sensitivity difference (%) in each case of Glu values of 45 mg/dl and 550 mg/dl with reference to Hct 42% in Example 5. FIG. 26d is a graph showing the sensitivity difference (%) in each case of Hct values of 0%, 42%, and 70% with reference to Glu 45 mg/dl in Example 5. FIGS. 26c and 26d each are a graph showing the sensitivity difference in each case at 0 second to 0.1 second after the detection.

Example 6

Figure 27A:
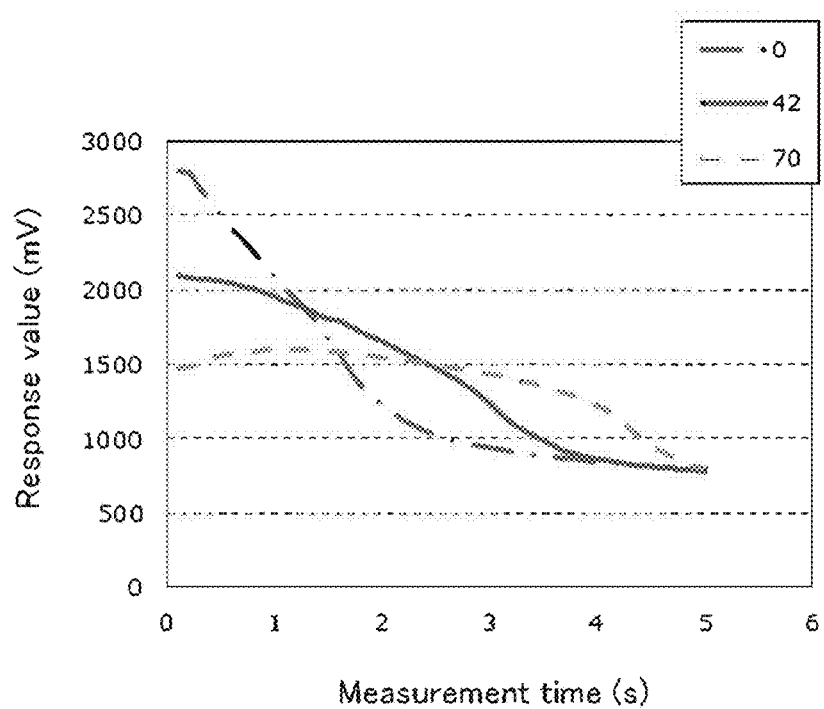
FIG. 27a is a graph showing the change with time in the response current value relative to an applied voltage with respect to each blood sample with a Glu concentration of 45 mg/dl (Hct value: 0%, 42%, and 70%) in Example 6.
Figure 27B:
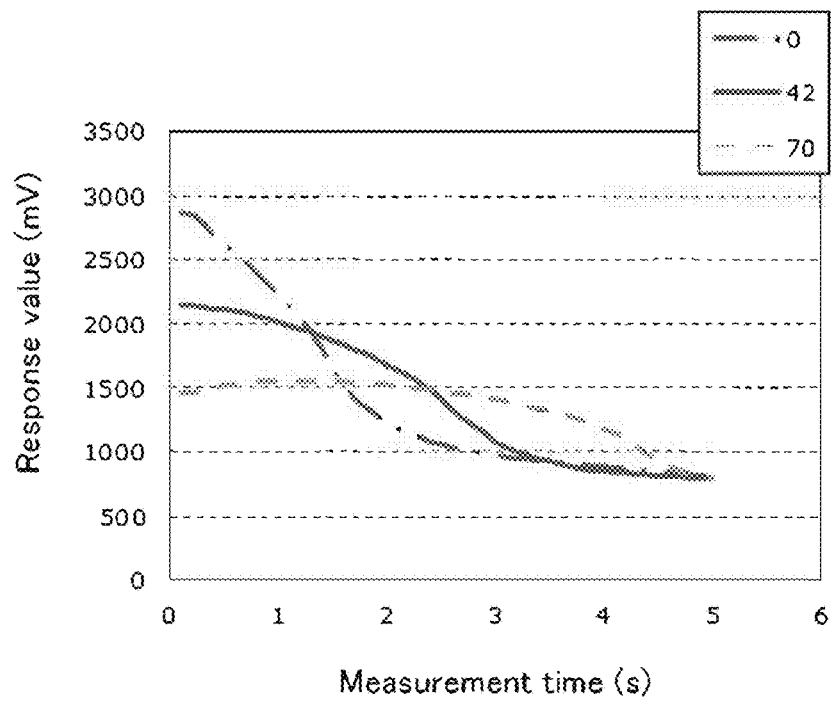
FIG. 27b is a graph showing the change with time in the response current value relative to an applied voltage with respect to each blood sample with a Glu concentration of 550 mg/dl (Hct value: 0%, 42%, and 70%) in Example 6.
Figure 27C:
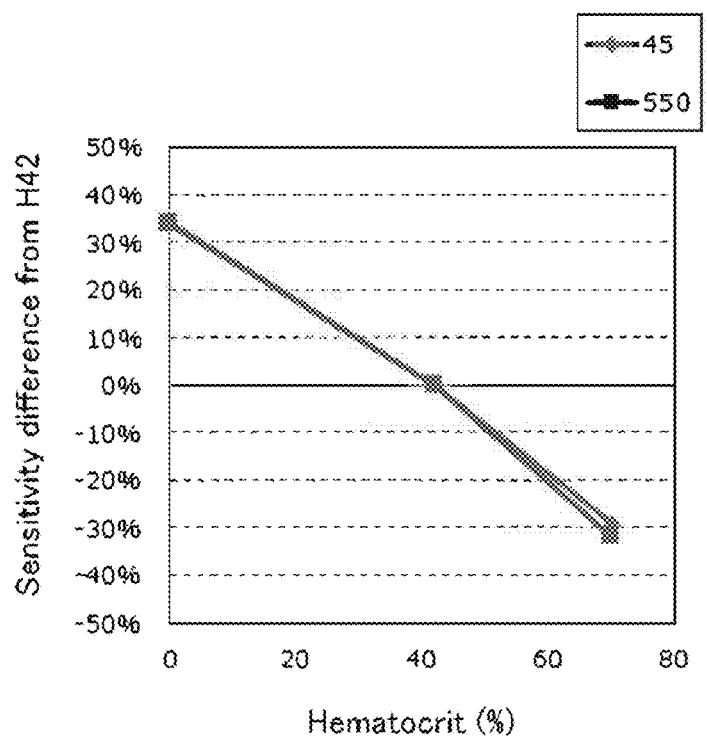
FIG. 27c is a graph showing the sensitivity difference (%) in each case of Glu values of 45 mg/dl and 550 mg/dl with reference to Hct 42% in Example 6.
Figure 27D:
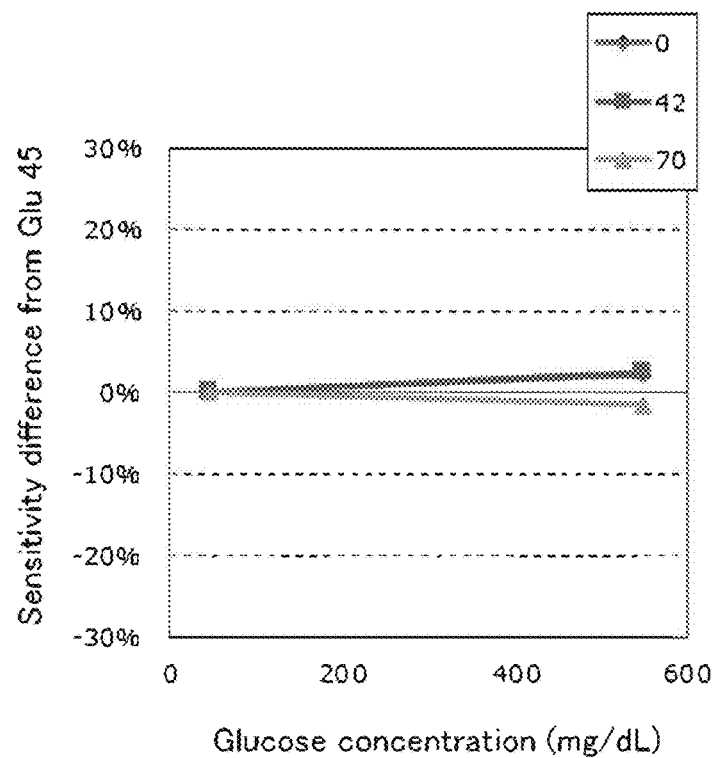
FIG. 27d is a graph showing the sensitivity difference (%) in each case of Hct values of 0%, 42%, and 70% with reference to Glu 45 mg/dl in Example 6.

The procedure was carried out in the same manner as in Example 5 except that voltage application was started at 0.05 second after detection of the introduction of a blood sample and a voltage of 2.0 V was applied between the electrode A and the electrode B, until 0.15 second, for 0.1 second. The current flowing between the working electrode and the counter electrode of each sensor 1 was measured, and the response current value and the sensitivity difference were measured in the measurement of the Hct value (see FIGS. 27a to 27d). FIG. 27a is a graph showing the change with time in the response current value relative to the applied voltage with respect to each blood sample with a Glu concentration of 45 mg/dl (Hct value: 0%, 42%, and 70%) in Example 6. FIG. 27b is a graph showing the change with time in the response current value relative to the applied voltage with respect to each blood sample with a Glu concentration of 550 mg/dl (Hct value: 0%, 42%, and 70%) in Example 6. FIGS. 27a and 27b each are a graph showing the change with time in the response current value relative to the applied voltage in the case of applying a voltage of 2.0 V for 5 seconds between the electrode A and the electrode B that have the reagent disposed thereon. FIG. 27c is a graph showing the sensitivity difference (%) in each case of Glu values of 45 mg/dl and 550 mg/dl with reference to Hct 42% in Example 6. FIG. 27d is a graph showing the sensitivity difference (%) in each case of Hct values of 0%, 42%, and 70% with reference to Glu 45 mg/dl in Example 6. FIGS.

27c and 27d each are a graph showing the sensitivity difference in each case at 0.05 second to 0.15 second after the detection.

Example 7

Figure 28A:
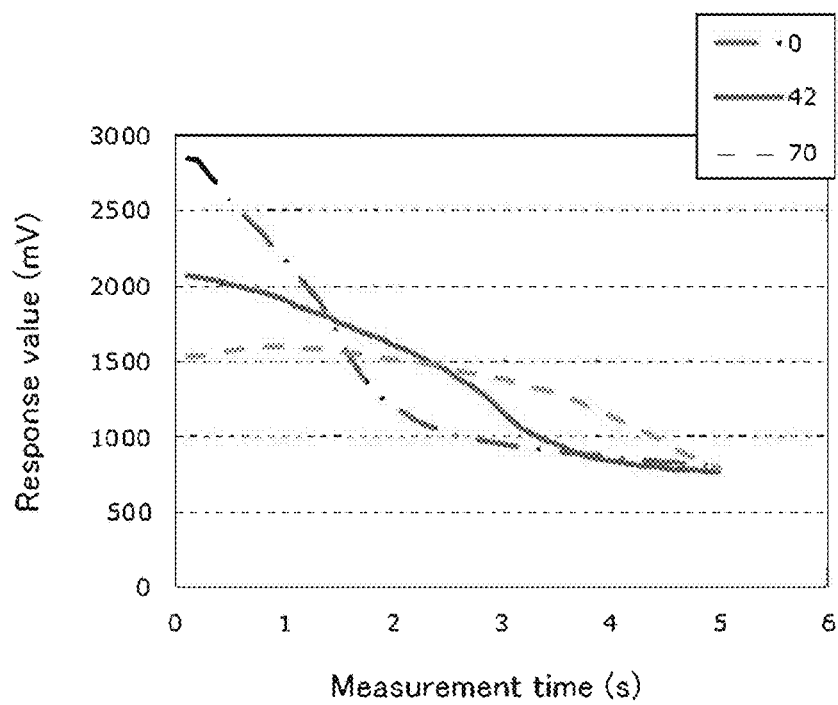
FIG. 28a is a graph showing the change with time in the response current value relative to an applied voltage with respect to each blood sample with a Glu concentration of 45 mg/dl (Hct value: 0%, 42%, and 70%) in Example 7.
Figure 28B:
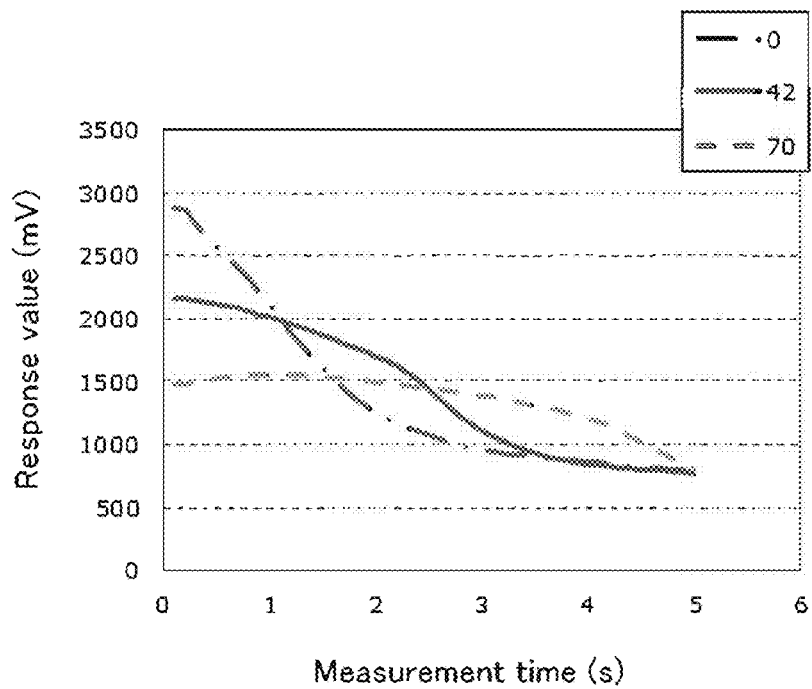
FIG. 28b is a graph showing the change with time in the response current value relative to an applied voltage with respect to each blood sample with a Glu concentration of 550 mg/dl (Hct value: 0%, 42%, and 70%) in Example 7.
Figure 28C:
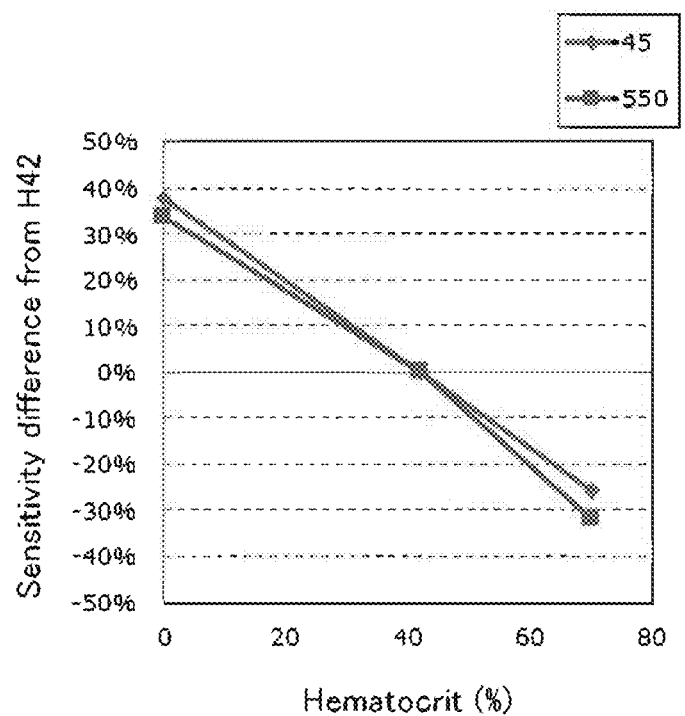
FIG. 28c is a graph showing the sensitivity difference (%) in each case of Glu values of 45 mg/dl and 550 mg/dl with reference to Hct 42% in Example 7.
Figure 28D:
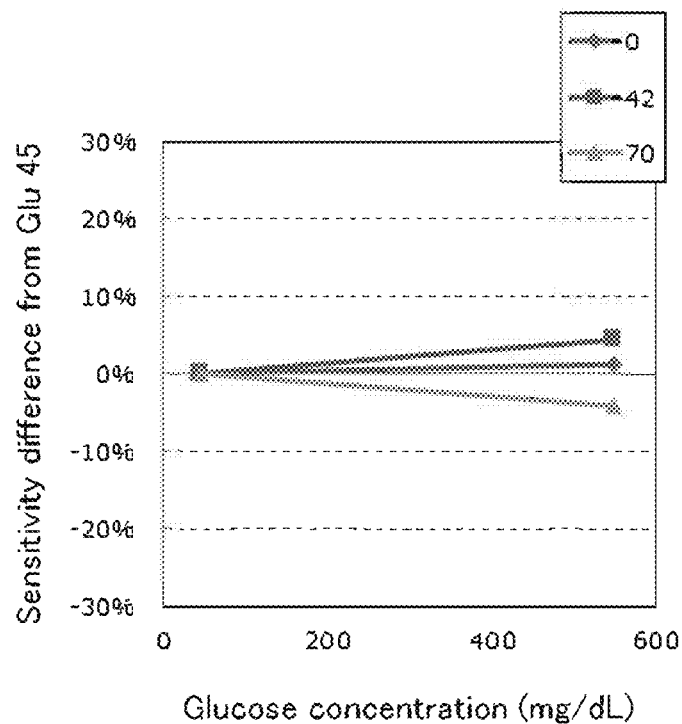
FIG. 28d is a graph showing the sensitivity difference (%) in each case of Hct values of 0%, 42%, and 70% with reference to Glu 45 mg/dl in Example 7.

The procedure was carried out in the same manner as in Example 5 except that voltage application was started at 0.1 second after detection of the introduction of a blood sample and a voltage of 2.0 V was applied between the electrode A and the electrode B, until 0.2 second, for 0.1 second. The current flowing between the working electrode and the counter electrode of each sensor 1 was measured, and the response current value and the sensitivity difference were measured in the measurement of the Hct value (see FIGS. 28a to 28d). FIG. 28a is a graph showing the change with time in the response current value relative to the applied voltage with respect to each blood sample with a Glu concentration of 45 mg/dl (Hct value: 0%, 42%, and 70%) in Example 7. FIG. 28b is a graph showing the change with time in the response current value relative to the applied voltage with respect to each blood sample with a Glu concentration of 550 mg/dl (Hct value: 0%, 42%, and 70%) in Example 7. FIGS. 28a and 28b each are a graph showing the change with time in the response current value relative to the applied voltage in the case of applying a voltage of 2.0 V for 5 seconds between the electrode A and the electrode B that have the reagent disposed thereon. FIG. 28c is a graph showing the sensitivity difference (%) in each case of Glu values of 45 mg/dl and 550 mg/dl with reference to Hct 42% in Example 7. FIG. 28d is a graph showing the sensitivity difference (%) in each case of Hct values of 0%, 42%, and 70% with reference to Glu 45 mg/dl in Example 7. FIGS. 28c and 28d each are a graph showing the sensitivity difference in each case at 0.1 second to 0.2 second after the detection.

Example 8

Figure 29A:
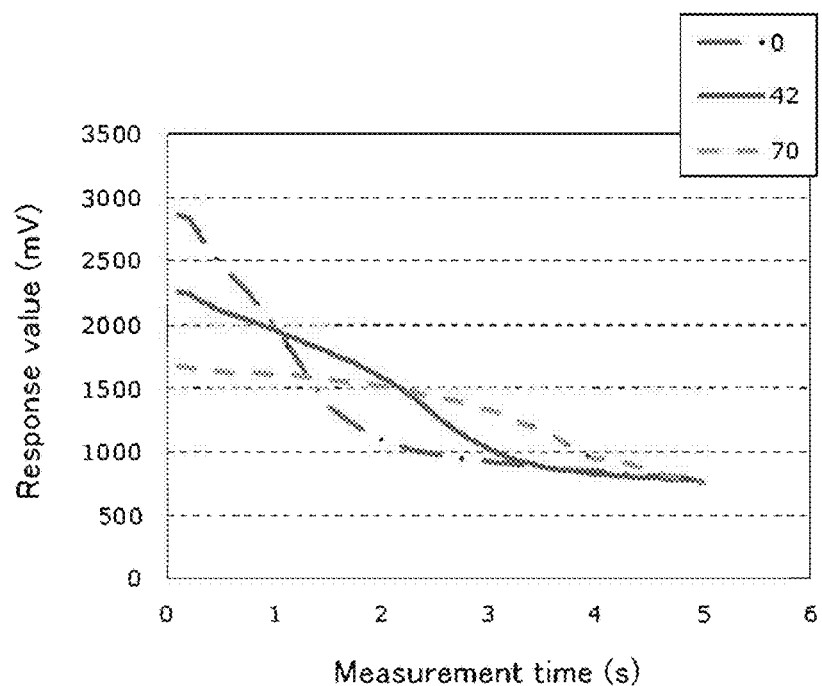
FIG. 29a is a graph showing the change with time in the response current value relative to an applied voltage with respect to each blood sample with a Glu concentration of 45 mg/dl (Hct value: 0%, 42%, and 70%) in Example 8.
Figure 29B:
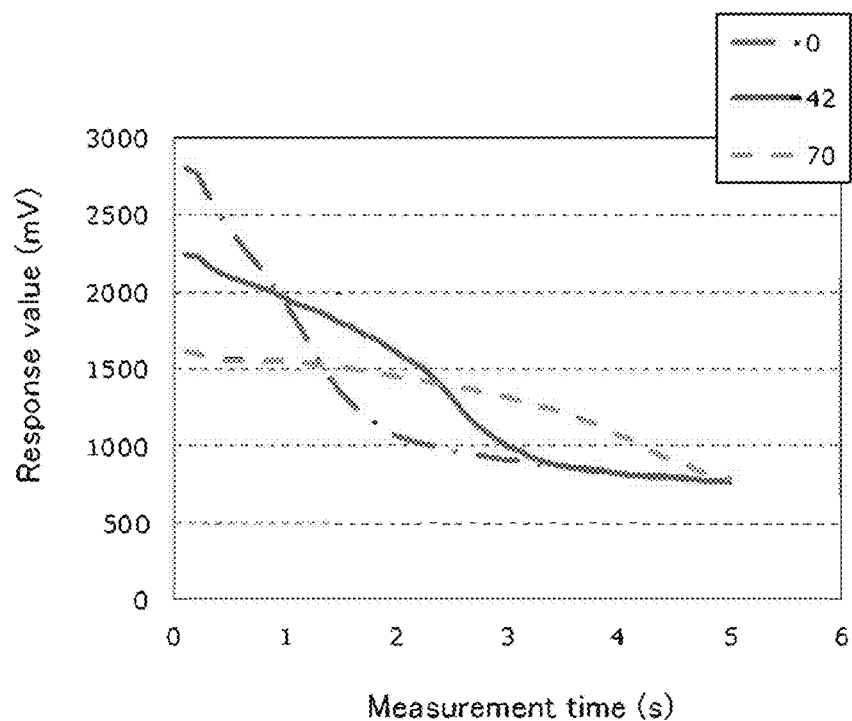
FIG. 29b is a graph showing the change with time in the response current value relative to an applied voltage with respect to each blood sample with a Glu concentration of 550 mg/dl (Hct value: 0%, 42%, and 70%) in Example 8.
Figure 29C:
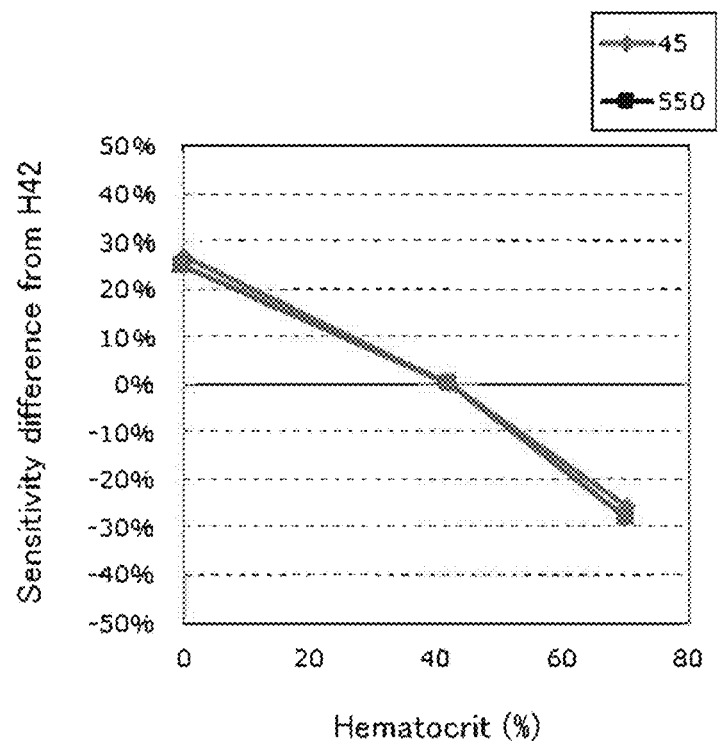
FIG. 29c is a graph showing the sensitivity difference (%) in each case of Glu values of 45 mg/dl and 550 mg/dl with reference to Hct 42% in Example 8.
Figure 29D:
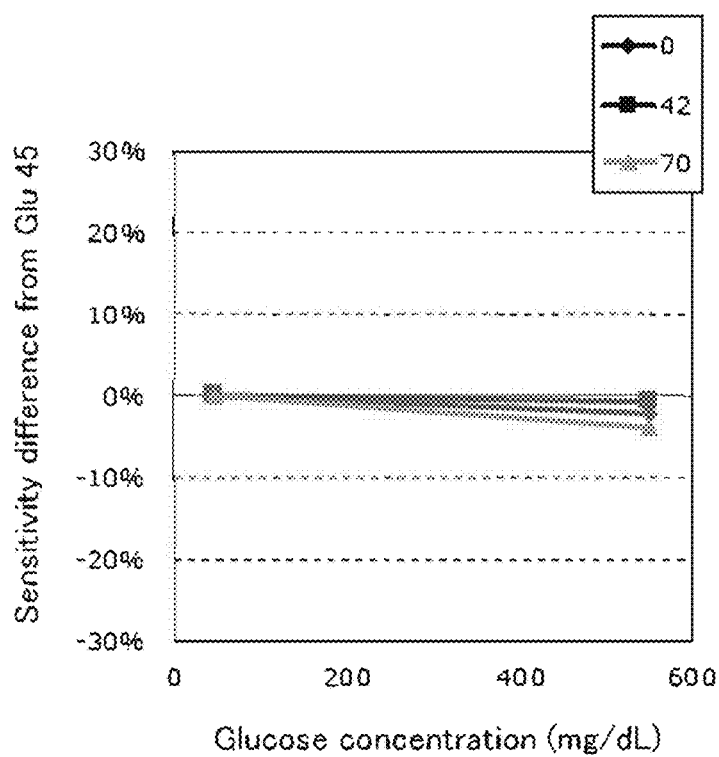
FIG. 29d is a graph showing the sensitivity difference (%) in each case of Hct values of 0%, 42%, and 70% with reference to Glu 45 mg/dl in Example 8.
Figure 30A:
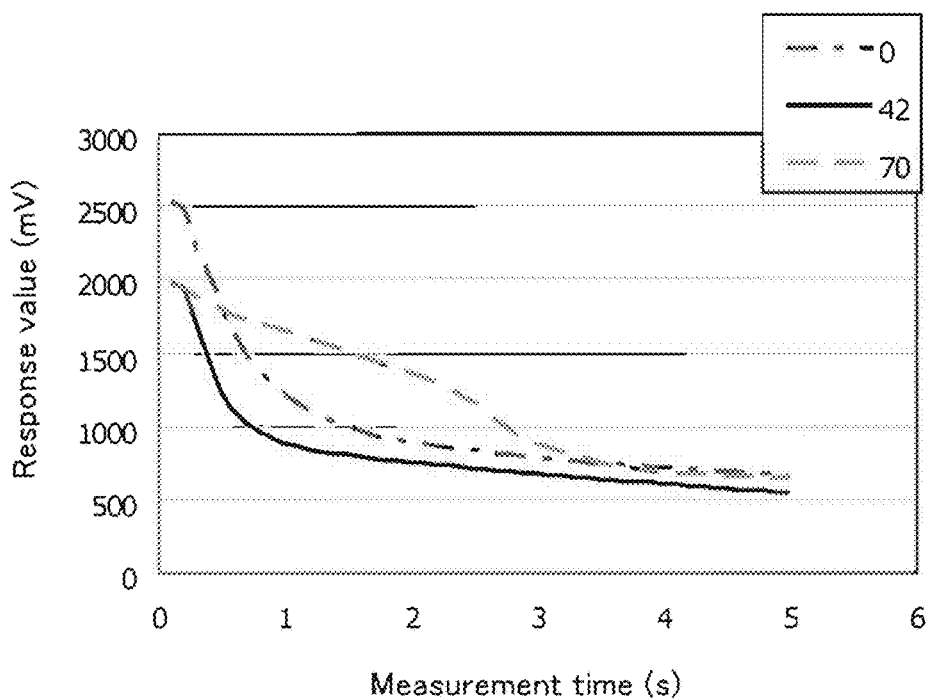
FIG. 30a is a graph showing the change with time in the response current value relative to an applied voltage with respect to each blood sample with a Glu concentration of 45 mg/dl (Hct value: 0%, 42%, and 70%) in Comparative Example 3.
Figure 30B:
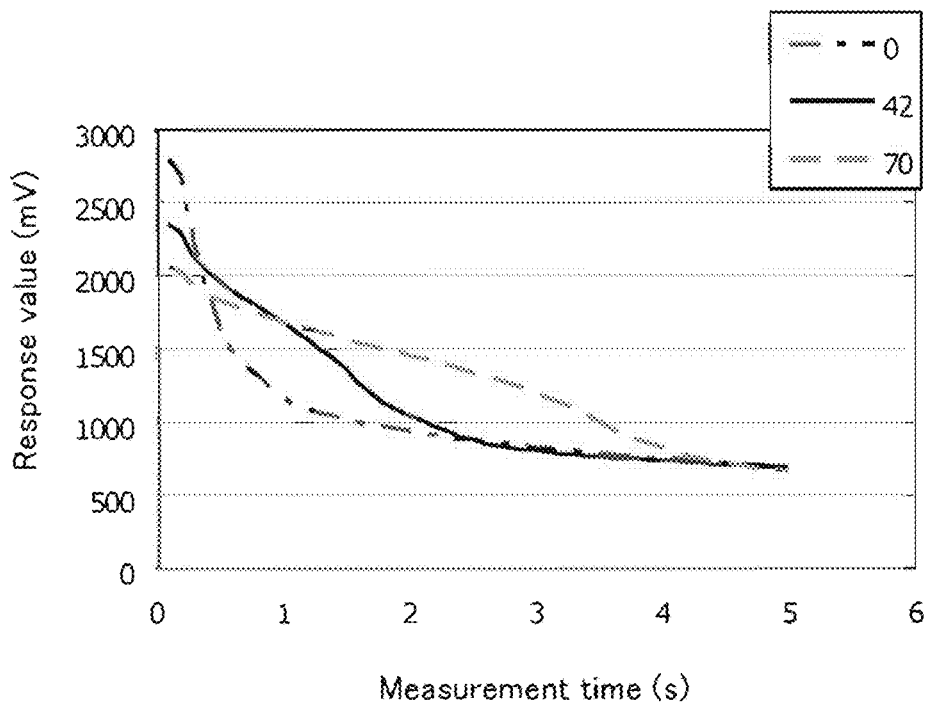
FIG. 30b is a graph showing the change with time in the response current value relative to an applied voltage with respect to each blood sample with a Glu concentration of 550 mg/dl (Hct value: 0%, 42%, and 70%) in Comparative Example 3.
Figure 30C:
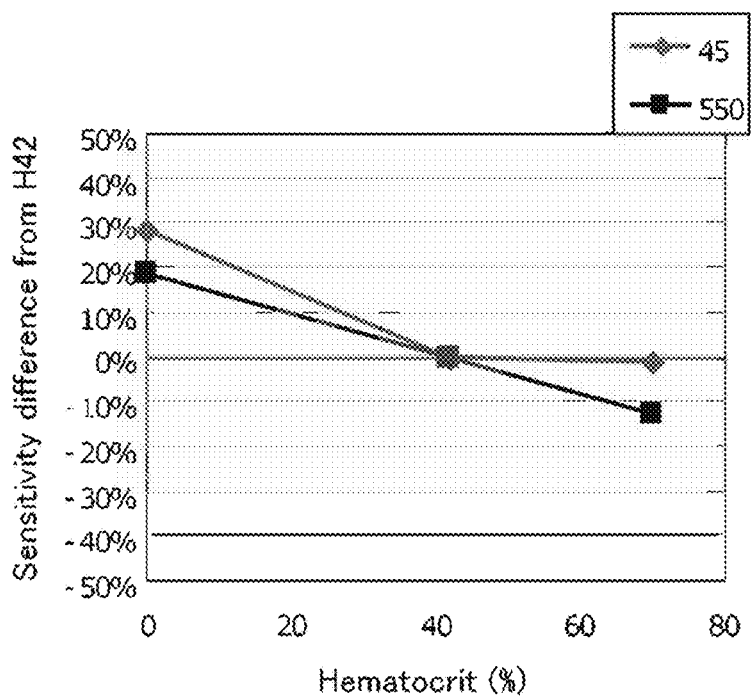
FIG. 30c is a graph showing the sensitivity difference (%) in each case of Glu values of 45 mg/dl and 550 mg/dl with reference to Hct 42% in Comparative Example 3.
Figure 30D:
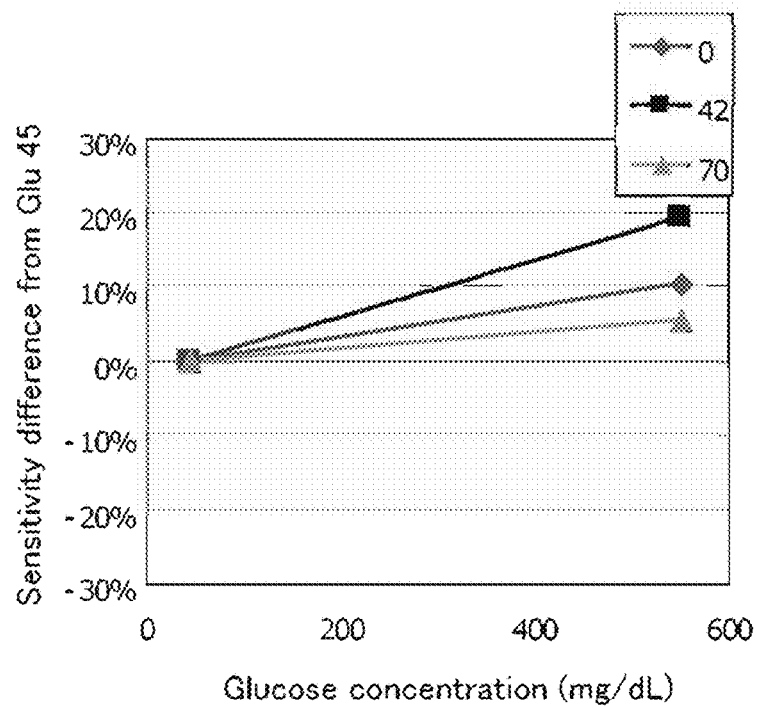
FIG. 30d is a graph showing the sensitivity difference (%) in each case of Hct values of 0%, 42%, and 70% with reference to Glu 45 mg/dl in Comparative Example 3.

The procedure was carried out in the same manner as in Example 5 except that voltage application was started at 0.5 second after detection of the introduction of a blood sample and a voltage of 2.0 V was applied between the electrode A and the electrode B, until 0.6 second, for 0.1 second. The current flowing between the working electrode and the counter electrode of each sensor 1 was measured, and the response current value and the sensitivity difference were measured in the measurement of the Hct value (see FIGS. 29a to 29d). FIG. 29a is a graph showing the change with time in the response current value relative to the applied voltage with respect to each blood sample with a Glu concentration of 45 mg/dl (Hct value: 0%, 42%, and 70%) in Example 8. FIG. 29b is a graph showing the change with time in the response current value relative to the applied voltage with respect to each blood sample with a Glu concentration of 550 mg/dl (Hct value: 0%, 42%, and 70%) in Example 8. FIGS. 29a and 29b each are a graph showing the change with time in the response current value relative to the applied voltage in the case of applying a voltage of 2.0 V for 5 seconds between the electrode A and the electrode B that have the reagent disposed thereon. FIG. 29c is a graph showing the sensitivity difference (%) in each case of Glu values of 45 mg/dl and 550 mg/dl with reference to Hct 42% in Example 8. FIG. 29d is a graph showing the sensitivity difference (%) in each case of Hct values of 0%, 42%, and 70% with reference to Glu 45 mg/dl in Example 8. FIGS. 29c and 29d each are a graph showing the sensitivity difference in each case at 0.5 second to 0.6 second after the detection.

Comparative Example 3

Figure 33A:
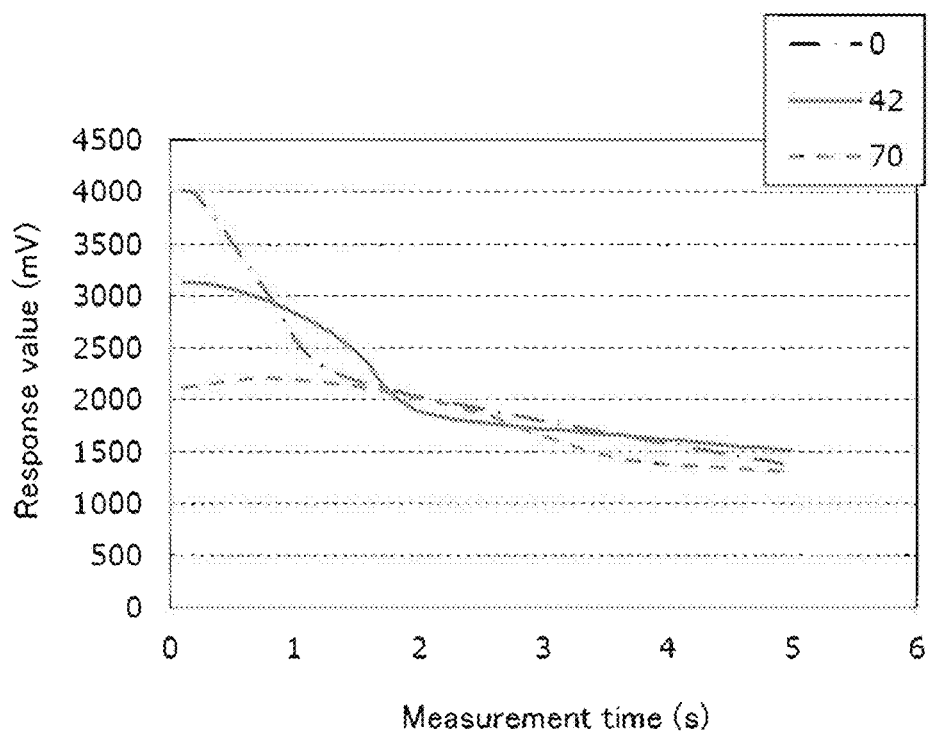
FIG. 33a is a graph showing the change with time in the response current value relative to an applied voltage with respect to each blood sample with a Glu concentration of 45 mg/dl (Hct value: 0%, 42%, and 70%) in Example 11.
Figure 33B:
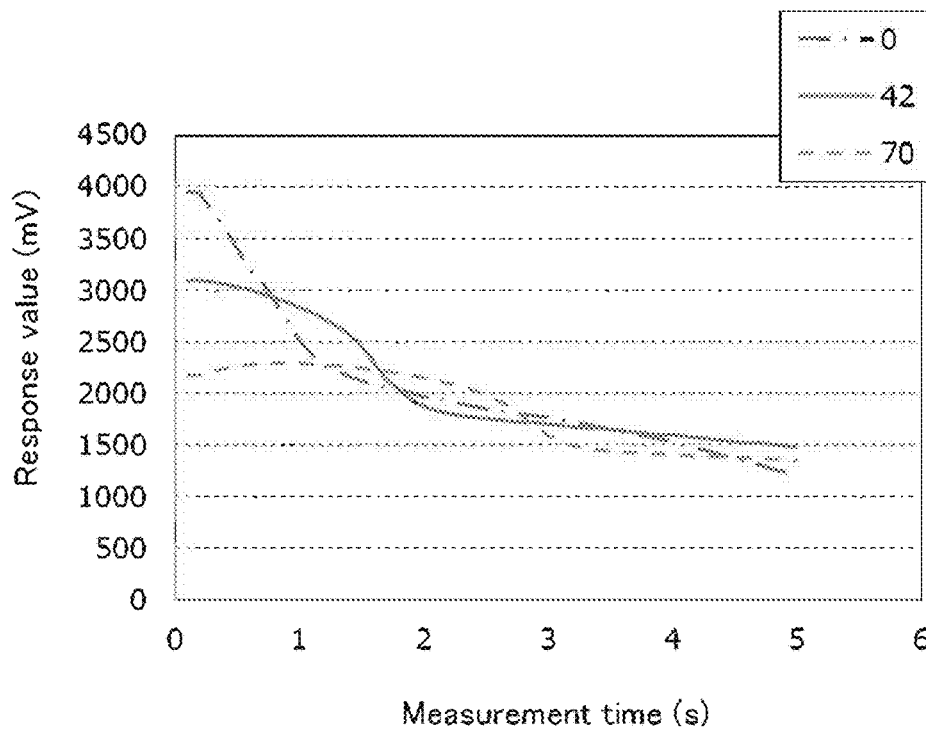
FIG. 33b is a graph showing the change with time in the response current value relative to an applied voltage with respect to each blood sample with a Glu concentration of 550 mg/dl (Hct value: 0%, 42%, and 70%) in Example 11.
Figure 33C:
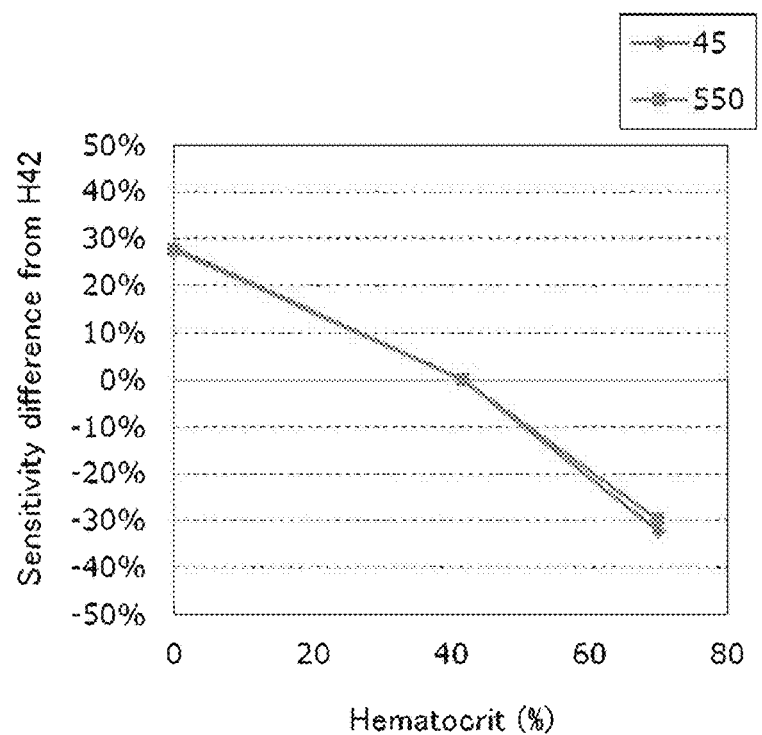
FIG. 33c is a graph showing the sensitivity difference (%) in each case of Glu values of 45 mg/dl and 550 mg/dl with reference to Hct 42% in Example 11.
Figure 33D:
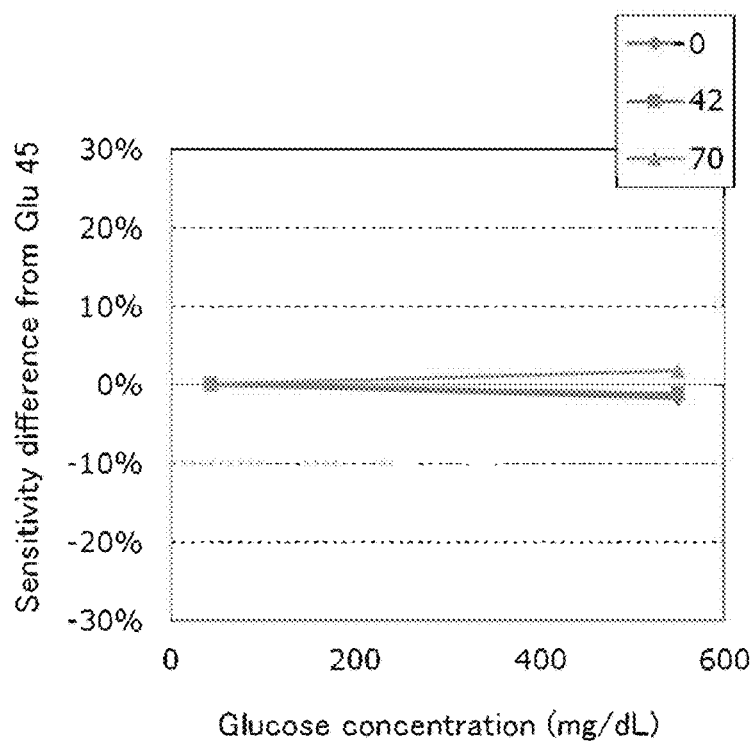
FIG. 33d is a graph showing the sensitivity difference (%) in each case of Hct values of 0%, 42%, and 70% with reference to Glu 45 mg/dl in Example 11.

The procedure was carried out in the same manner as in Example 5 except that voltage application was started at 4 seconds after detection of the introduction of a blood sample and a voltage of 2.0 V was applied between the electrode A and the electrode B, until 4.1 seconds, for 0.1 second. The current flowing between the working electrode and the counter electrode of each sensor 1 was measured, and the response current value and the sensitivity difference were measured in the measurement of the Hct value (see FIGS. 33a to 33d). FIG. 33a is a graph showing the change with time in the response current value relative to the applied voltage with respect to each blood sample with a Glu concentration of 45 mg/dl (Hct value: 0%, 42%, and 70%) in Comparative Example 3. FIG. 33b is a graph showing the change with time in the response current value relative to the applied voltage with respect to each blood sample with a Glu concentration of 550 mg/dl (Hct value: 0%, 42%, and 70%) in Comparative Example 3. FIGS. 33a and 33b each are a graph showing the change with time in the response current value relative to the applied voltage in the case of applying a voltage of 2.0 V for 5 seconds between the electrode A and the electrode B that have the reagent disposed thereon. FIG. 33c is a graph showing the sensitivity difference (%) in each case of Glu values of 45 mg/dl and 550 mg/dl with reference to Hct 42% in Comparative Example 3. FIG. 33d is a graph showing the sensitivity difference (%) in each case of Hct values of 0%, 42%, and 70% with reference to Glu 45 mg/dl in Comparative Example 3. FIGS. 33c and 33d each are a graph showing the sensitivity difference in each case at 4 seconds to 4.1 seconds after the detection.

From Examples 5 to 8 and Comparative Example 3, it was confirmed that when a voltage of 2.0 V was applied for 0.1 second to the working electrode and the counter electrode within 0 second to 0.5 second after detection of the introduction of a biological sample, the current value obtained thereby had a high sensitivity and the Hct value obtained based on the current value had a high accuracy. The time from the start of blood introduction to the start of voltage application was changed between 0 and 4 seconds and the graphs showing the sensitivity difference were checked. As a result, it was found that the effect of the glucose concentration gradually increased as the time increased. Particularly, when the time until the start of voltage application was 4 seconds as in Comparative Example 3, a divergence was seen in the graph showing the sensitivity difference in each case of Hct values of 0%, 42%, and 70% particularly with reference to Glu 550 mg/dl as shown in FIG. 33d.

Example 9

Figure 31A:
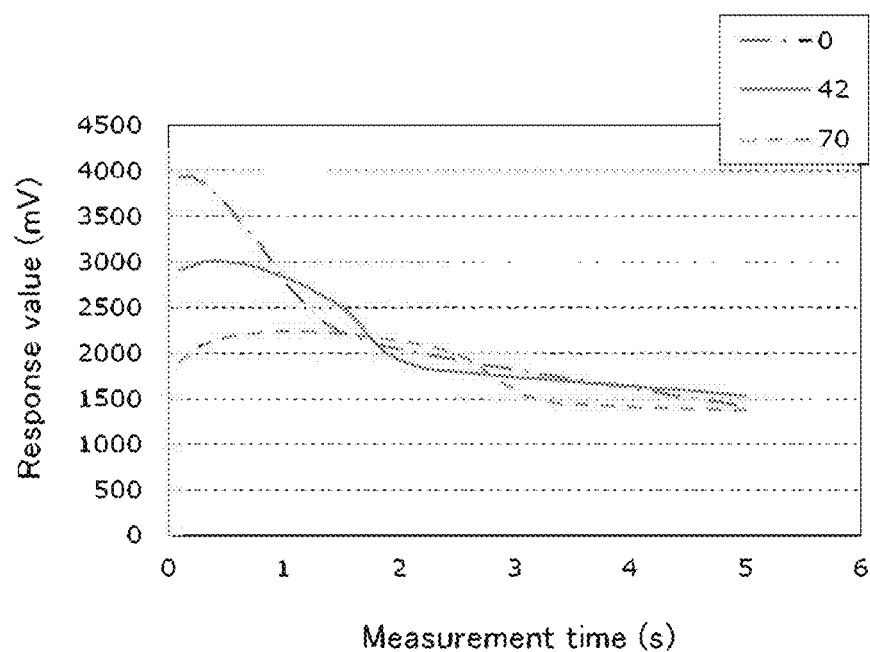
FIG. 31a is a graph showing the change with time in the response current value relative to an applied voltage with respect to each blood sample with a Glu concentration of 45 mg/dl (Hct value: 0%, 42%, and 70%) in Example 9.
Figure 31B:
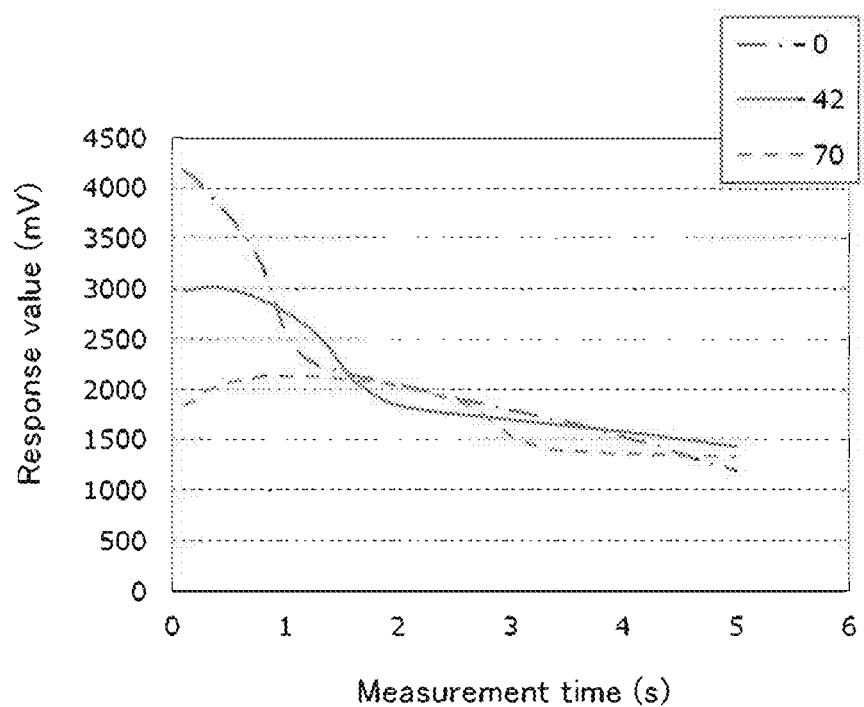
FIG. 31b is a graph showing the change with time in the response current value relative to an applied voltage with respect to each blood sample with a Glu concentration of 550 mg/dl (Hct value: 0%, 42%, and 70%) in Example 9.
Figure 31C:
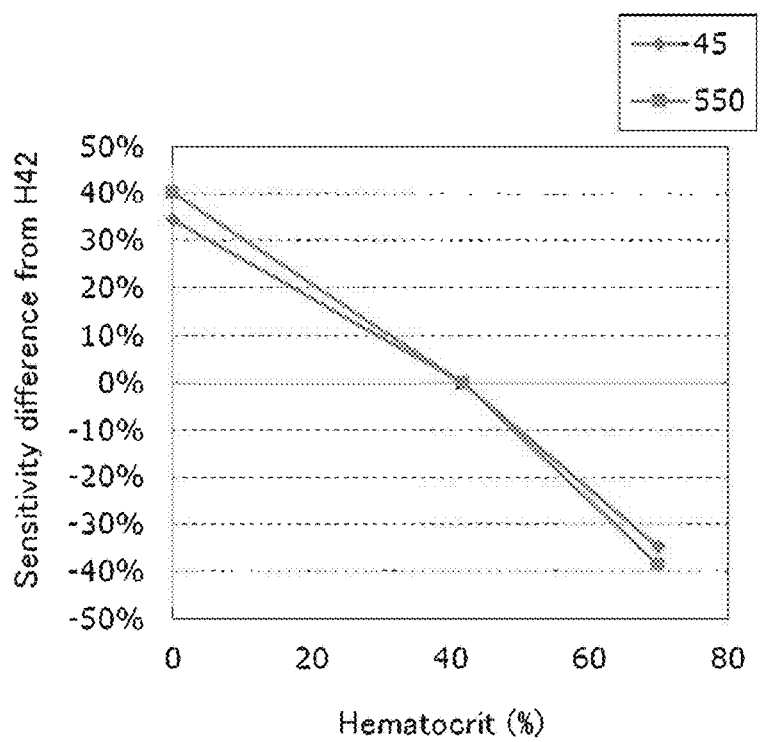
FIG. 31c is a graph showing the sensitivity difference (%) in each case of Glu values of 45 mg/dl and 550 mg/dl with reference to Hct 42% in Example 9.
Figure 31D:
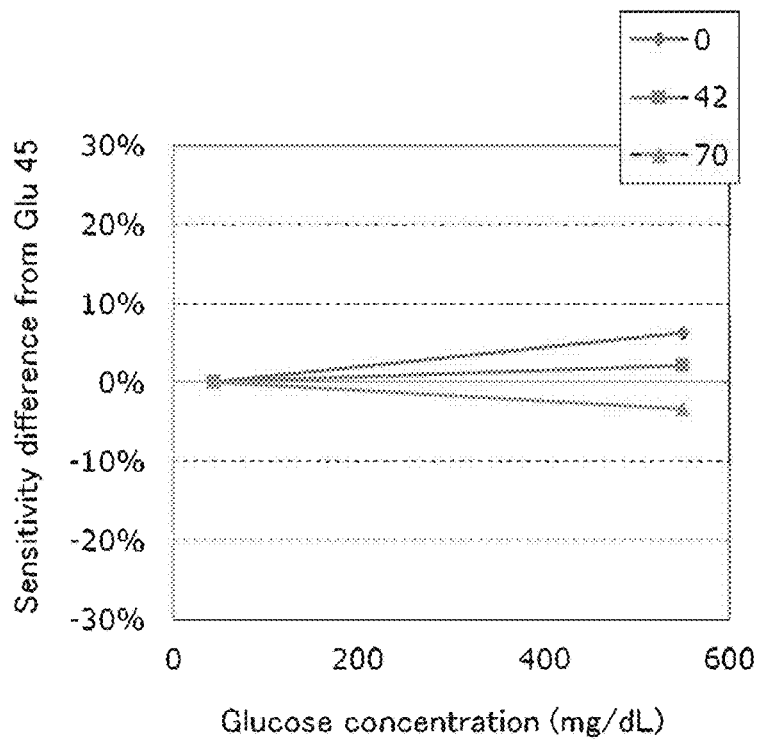
FIG. 31d is a graph showing the sensitivity difference (%) in each case of Hct values of 0%, 42%, and 70% with reference to Glu 45 mg/dl in Example 9.

The procedure was carried out in the same manner as in Example 1 except that a voltage of 2.5 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 31a to 31d). FIG. 31a is a graph showing the change with time in the response current value relative to the applied voltage with respect to each blood sample with a Glu concentration of 45 mg/dl (Hct value: 0%, 42%, and 70%) in Example 9. FIG. 31b is a graph showing the change with time in the response current value relative to the applied voltage with respect to each blood sample with a Glu concentration of 550 mg/dl (Hct value: 0%, 42%, and 70%) in Example 9. FIGS. 31a and 31b each are a graph showing the change with time in the response current value relative to the applied voltage in the case of applying a voltage of 2.5 V for 5 seconds between the electrode A and the electrode B that have the reagent disposed thereon. FIG. 31c is a graph showing the sensitivity difference (%) in each case of Glu values of 45 mg/dl and 550 mg/dl with reference to Hct 42% in Example 9. FIG. 31d is a graph showing the sensitivity difference (%) in each case of Hct values of 0%, 42%, and 70% with reference to Glu 45 mg/dl in Example 9. FIGS. 31c and 31d each are a graph showing the sensitivity difference in each case at 0 second to 0.1 second after the detection.

Example 10

Figure 32A:
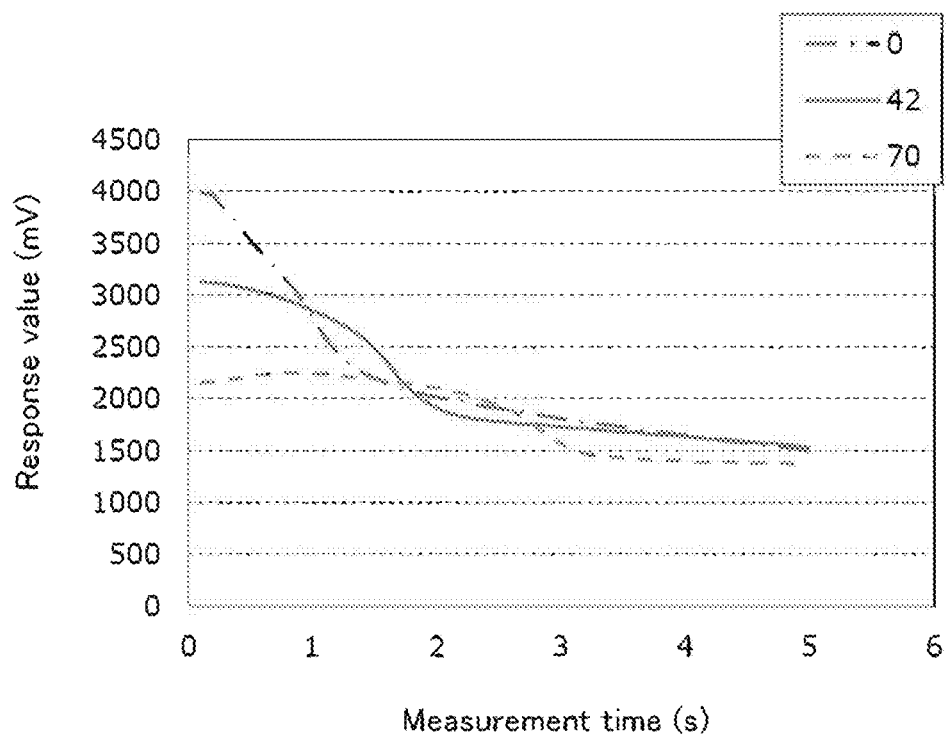
FIG. 32a is a graph showing the change with time in the response current value relative to an applied voltage with respect to each blood sample with a Glu concentration of 45 mg/dl (Hct value: 0%, 42%, and 70%) in Example 10.
Figure 32B:
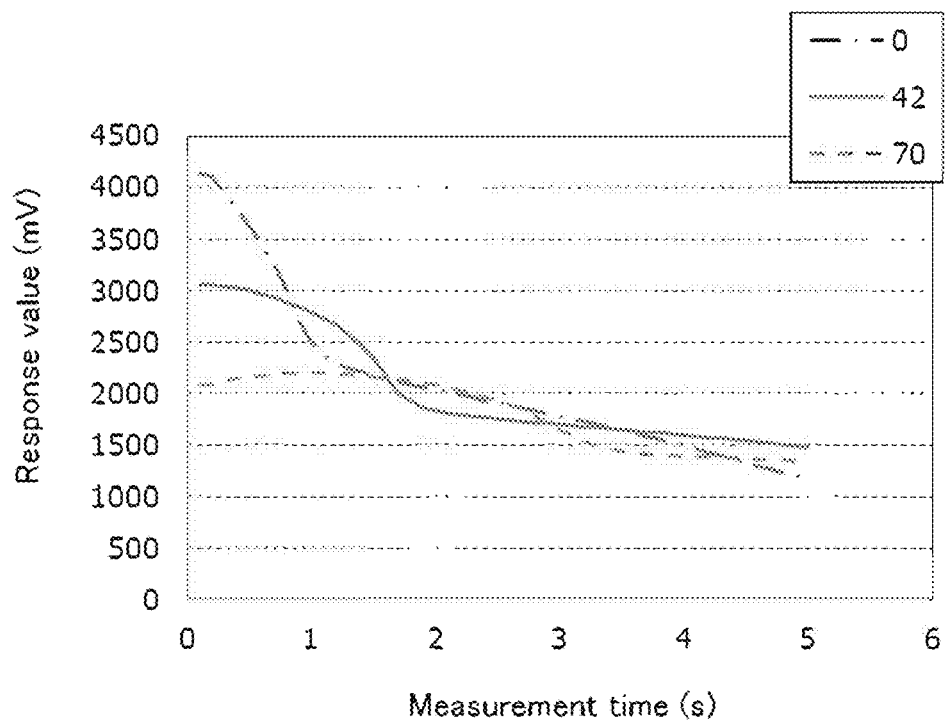
FIG. 32b is a graph showing the change with time in the response current value relative to an applied voltage with respect to each blood sample with a Glu concentration of 550 mg/dl (Hct value: 0%, 42%, and 70%) in Example 10.
Figure 32C:
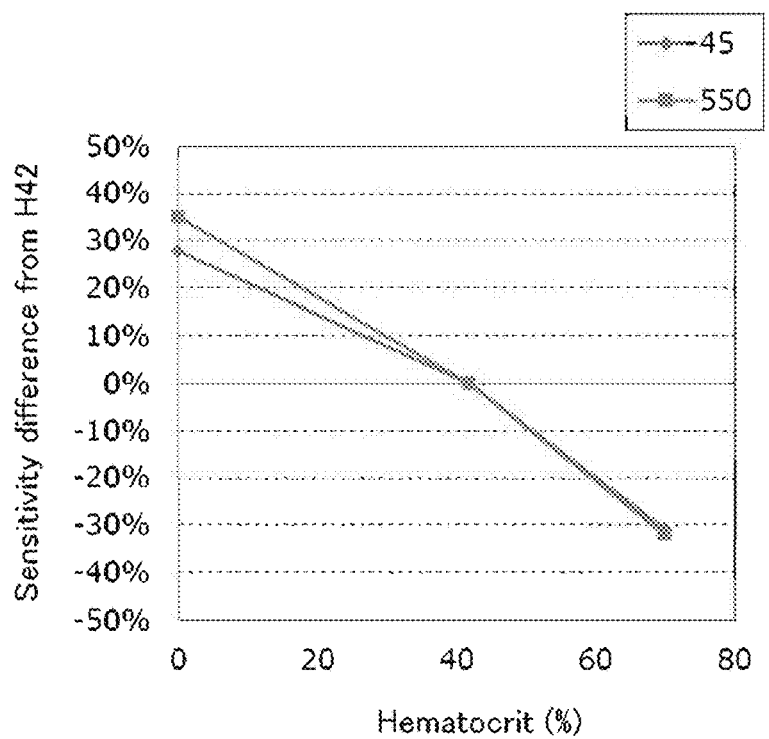
FIG. 32c is a graph showing the sensitivity difference (%) in each case of Glu values of 45 mg/dl and 550 mg/dl with reference to Hct 42% in Example 10.
Figure 32D:
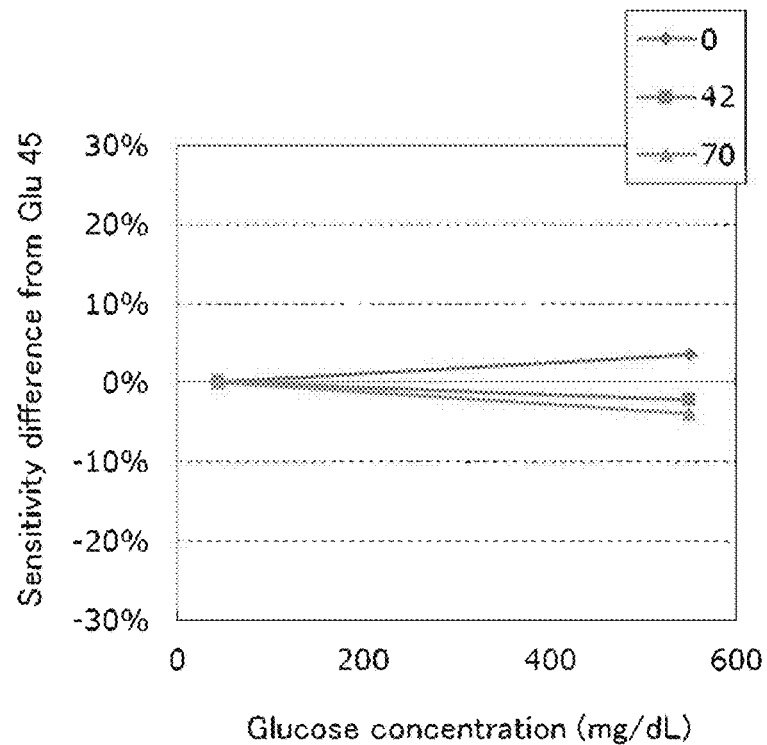
FIG. 32d is a graph showing the sensitivity difference (%) in each case of Hct values of 0%, 42%, and 70% with reference to Glu 45 mg/dl in Example 10.

The procedure was carried out in the same manner as in Example 9 except that voltage application was started at 0.05 second after detection of the introduction of a blood sample and a voltage of 2.5 V was applied between the electrode A and the electrode B, until 0.15 second, for 0.1 second. The current flowing between the working electrode and the counter electrode of each sensor 1 was measured, and the response current value and the sensitivity difference were measured in the measurement of the Hct value (see FIGS. 32a to 32d). FIG. 32a is a graph showing the change with time in the response current value relative to the applied voltage with respect to each blood sample with a Glu concentration of 45 mg/dl (Hct value: 0%, 42%, and 70%) in Example 10. FIG. 32b is a graph showing the change with time in the response current value relative to the applied voltage with respect to each blood sample with a Glu concentration of 550 mg/dl (Hct value: 0%, 42%, and 70%) in Example 10. FIGS. 32a and 32b each are a graph showing the change with time in the response current value relative to the applied voltage in the case of applying a voltage of 2.5 V for 5 seconds between the electrode A and the electrode B that have the reagent disposed thereon. FIG. 32c is a graph showing the sensitivity difference (%) in each case of Glu values of 45 mg/dl and 550 mg/dl with reference to Hct 42% in Example 10. FIG. 32d is a graph showing the sensitivity difference (%) in each case of Hct values of 0%, 42%, and 70% with reference to Glu 45 mg/dl in Example 10. FIGS. 32c and 32d each are a graph showing the sensitivity difference in each case at 0.05 second to 0.15 second after the detection.

Example 11

The procedure was carried out in the same manner as in Example 9 except that voltage application was started at 0.1 second after detection of the introduction of a blood sample and a voltage of 2.5 V was applied between the electrode A and the electrode B, until 0.2 second, for 0.1 second. The current flowing between the working electrode and the counter electrode of each sensor 1 was measured, and the response current value and the sensitivity difference were measured in the measurement of the Hct value (see FIGS. 33a to 33d). FIG. 33a is a graph showing the change with time in the response current value relative to the applied voltage with respect to each blood sample with a Glu concentration of 45 mg/dl (Hct value: 0%, 42%, and 70%) in Example 11. FIG. 33b is a graph showing the change with time in the response current value relative to the applied voltage with respect to each blood sample with a Glu concentration of 550 mg/dl (Hct value: 0%, 42%, and 70%) in Example 11. FIGS. 33a and 33b each are a graph showing the change with time in the response current value relative to the applied voltage in the case of applying a voltage of 2.5 V for 5 seconds between the electrode A and the electrode B that have the reagent disposed thereon. FIG. 33c is a graph showing the sensitivity difference (%) in each case of Glu values of 45 mg/dl and 550 mg/dl with reference to Hct 42% in Example 11. FIG. 33d is a graph showing the sensitivity difference (%) in each case of Hct values of 0%, 42%, and 70% with reference to Glu 45 mg/dl in Example 11. FIGS. 33c and 33d each are a graph showing the sensitivity difference in each case at 0.1 second to 0.2 second after the detection.

Example 12

Figure 34A:
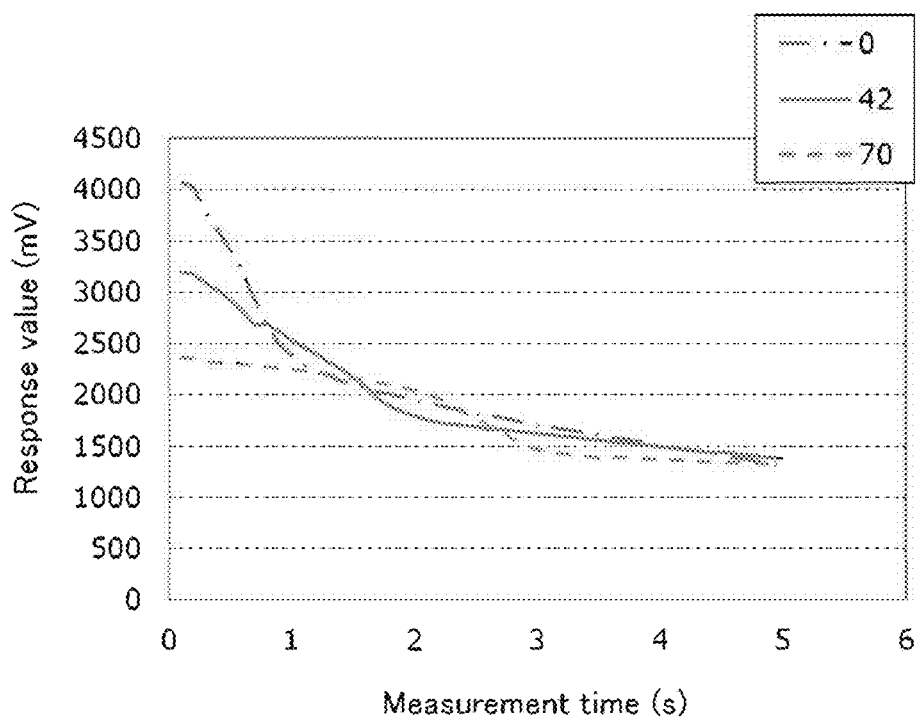
FIG. 34a is a graph showing the change with time in the response current value relative to an applied voltage with respect to each blood sample with a Glu concentration of 45 mg/dl (Hct value: 0%, 42%, and 70%) in Example 12.
Figure 34B:
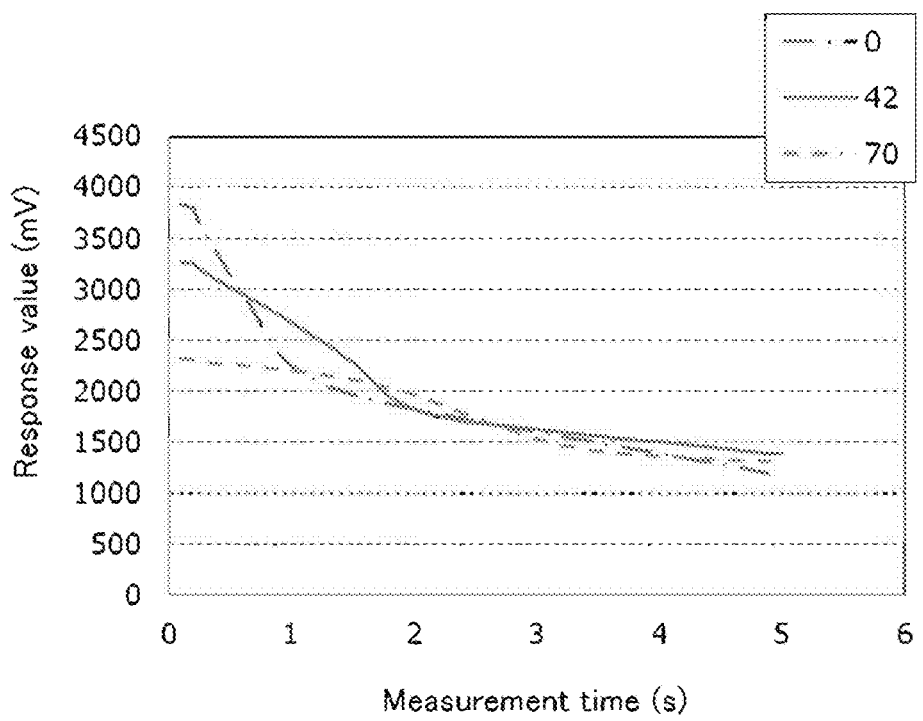
FIG. 34b is a graph showing the change with time in the response current value relative to an applied voltage with respect to each blood sample with a Glu concentration of 550 mg/dl (Hct value: 0%, 42%, and 70%) in Example 12.
Figure 34C:
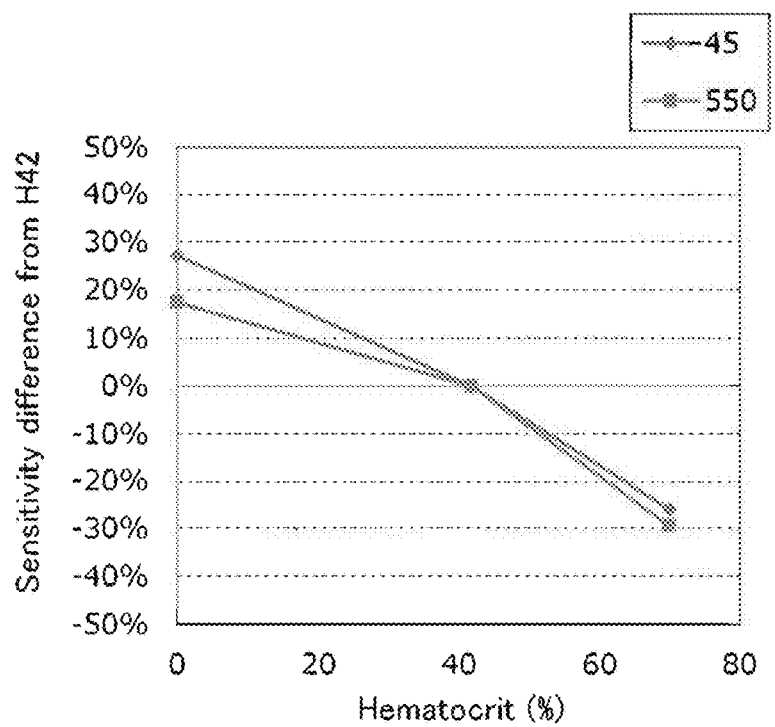
FIG. 34c is a graph showing the sensitivity difference (%) in each case of Glu values of 45 mg/dl and 550 mg/dl with reference to Hct 42% in Example 12.
Figure 34D:
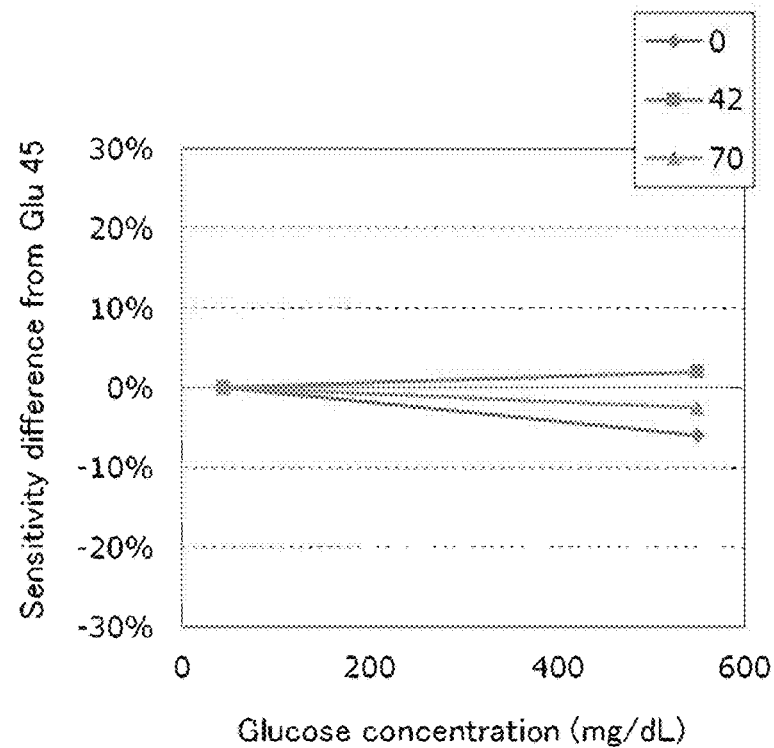
FIG. 34d is a graph showing the sensitivity difference (%) in each case of Hct values of 0%, 42%, and 70% with reference to Glu 45 mg/dl in Example 12.

The procedure was carried out in the same manner as in Example 9 except that voltage application was started at 0.5 second after detection of the introduction of a blood sample and a voltage of 2.5 V was applied between the electrode A and the electrode B, until 0.6 second, for 0.1 second. The current flowing between the working electrode and the counter electrode of each sensor 1 was measured, and the response current value and the sensitivity difference were measured in the measurement of the Hct value (see FIGS. 34a to 34d). FIG. 34a is a graph showing the change with time in the response current value relative to the applied voltage with respect to each blood sample with a Glu concentration of 45 mg/dl (Hct value: 0%, 42%, and 70%) in Example 12. FIG. 34b is a graph showing the change with time in the response current value relative to the applied voltage with respect to each blood sample with a Glu concentration of 550 mg/dl (Hct value: 0%, 42%, and 70%) in Example 12. FIGS. 34a and 34b each are a graph showing the change with time in the response current value relative to the applied voltage in the case of applying a voltage of 2.5 V for 5 seconds between the electrode A and the electrode B that have the reagent disposed thereon. FIG. 34c is a graph showing the sensitivity difference (%) in each case of Glu values of 45 mg/dl and 550 mg/dl with reference to Hct 42% in Example 12. FIG. 34d is a graph showing the sensitivity difference (%) in each case of Hct values of 0%, 42%, and 70% with reference to Glu 45 mg/dl in Example 12. FIGS. 34c and 34d each are a graph showing the sensitivity difference in each case at 0.5 second to 0.6 second after the detection.

From Examples 9 to 12, it was confirmed that when a voltage of 2.5 V was applied for 0.1 second to the working electrode and the counter electrode within 0 second to 0.5 second after detection of the introduction of a biological sample, the current value obtained thereby had a high sensitivity and the Hct value obtained based on the current value had a high accuracy.

Thus, according to the methods of the present invention, in Examples 1 to 12 in which a voltage was applied for 0.1 second from 0 second to 0.5 second after detection of the introduction of a blood sample, the divergence was small in the graphs of the sensitivity difference of Hct values of 0%, 42% and 70% regardless of the applied voltage, particularly with reference to Glu 550 mg/dl. Therefore, it was confirmed that the Hct measurement accuracy was improved. Furthermore, according to these methods of the present invention, it was also confirmed that Hct can be measured in a short time.

Example 13

Figure 35A:
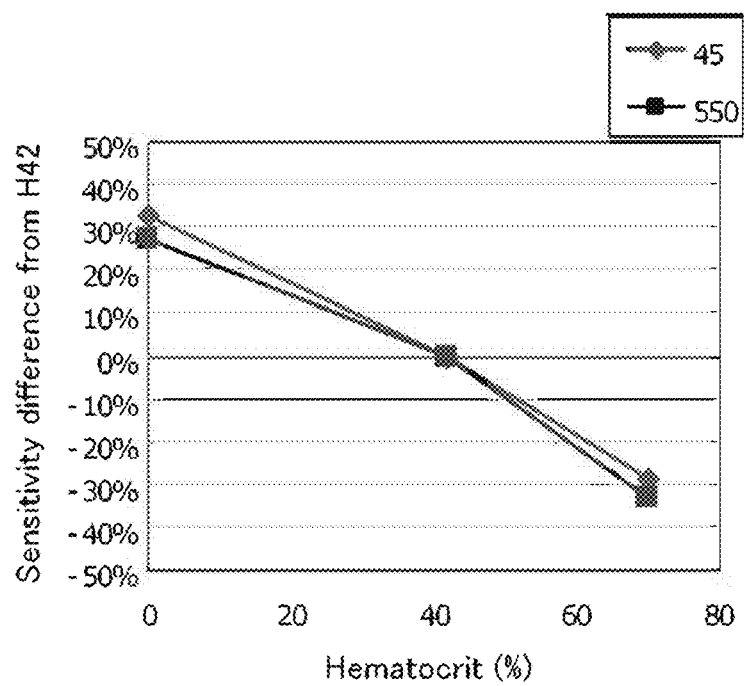
FIG. 35a is a graph showing the sensitivity difference (%) in each case of Glu values of 45 mg/dl and 550 mg/dl with reference to Hct 42% in Example 13.
Figure 35B:
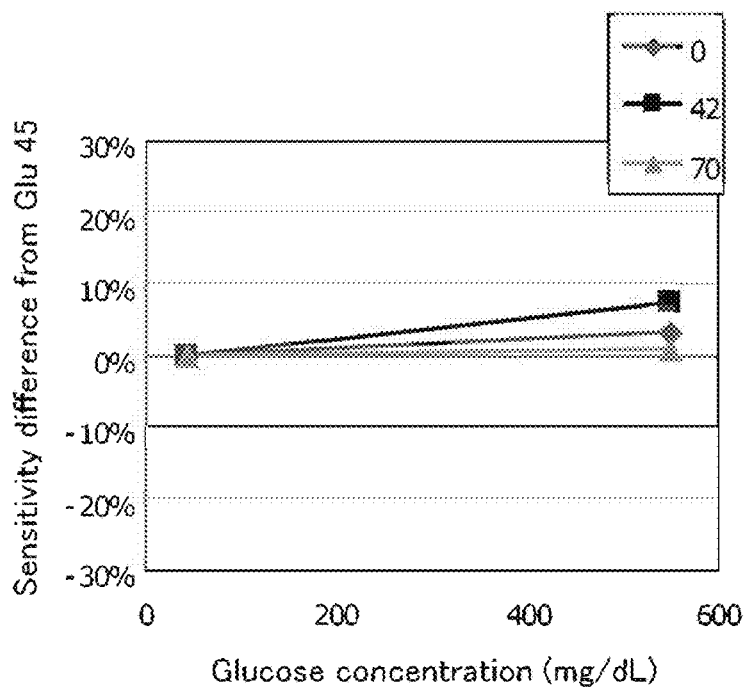
FIG. 35b is a graph showing the sensitivity difference (%) in each case of Hct values of 0%, 42%, and 70% with reference to Glu 45 mg/dl in Example 13.

Three types of blood samples having Hct values adjusted to 0%, 42%, and 70%, respectively, were prepared for two Glu concentrations, i.e., 45 mg/dl or 550 mg/dL. With respect to these six blood samples, a voltage of 1.5 V was applied for 0.1 second from 0 second to 0.1 second after detection of the introduction of a blood sample with the sensor 1 used in Example 1 (see FIG. 19 (a)). The current flowing between the working electrode and the counter electrode of each sensor 1 was measured, and the response current value and the sensitivity difference were measured in the measurement of the Hct value (see FIGS. 35a and 35b). FIG. 35a is a graph showing the sensitivity difference (%) in each case of Glu values of 45 mg/dl and 550 mg/dl with reference to Hct 42% in Example 13. FIG. 35b is a graph showing the sensitivity difference (%) in each case of Hct values of 0%, 42%, and 70% with reference to Glu 45 mg/dl in Example 13. FIGS. 35a and 35b each are a graph showing the sensitivity difference in each case at 0 second to 0.1 second after the detection.

Example 14

Figure 36A:
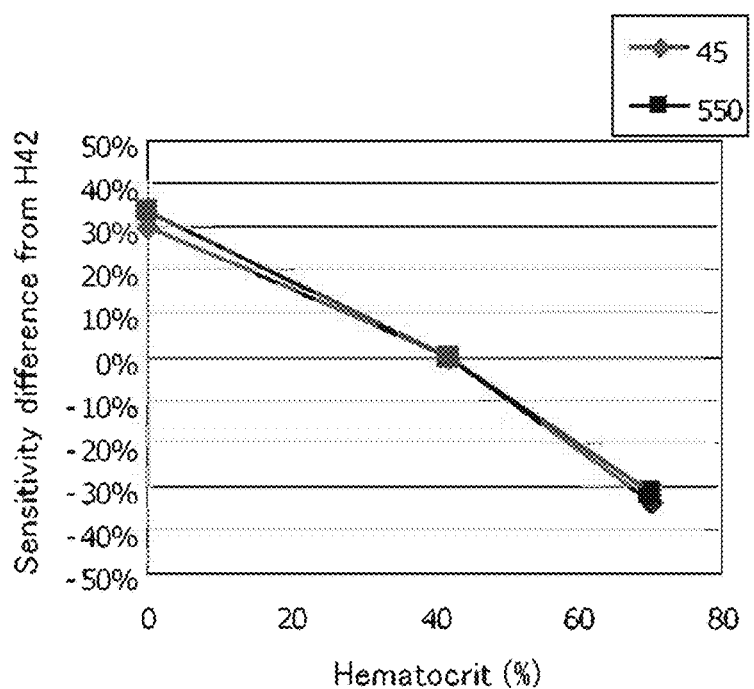
FIG. 36a is a graph showing the sensitivity difference (%) in each case of Glu values of 45 mg/dl and 550 mg/dl with reference to Hct 42% in Example 14.
Figure 36B:
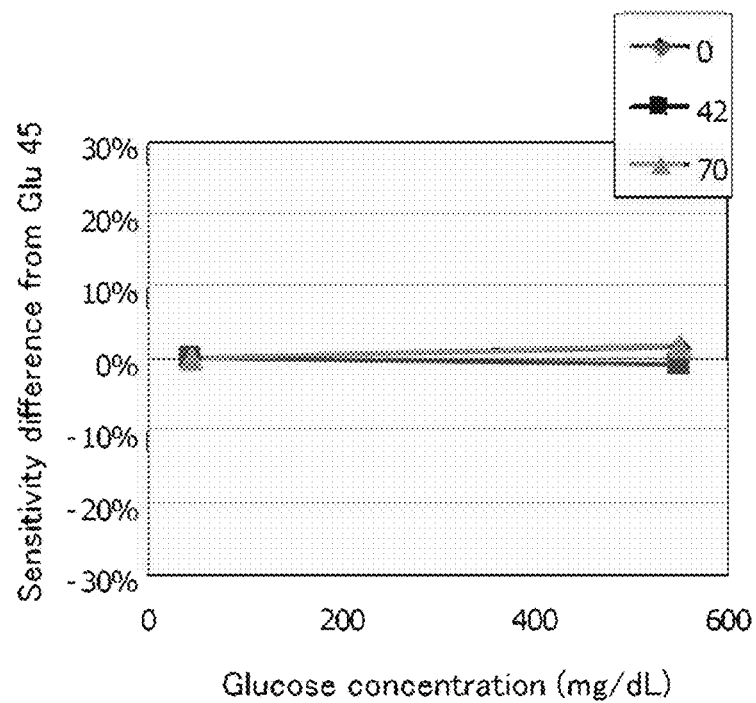
FIG. 36b is a graph showing the sensitivity difference (%) in each case of Hct values of 0%, 42%, and 70% with reference to Glu 45 mg/dl in Example 14.

The procedure was carried out in the same manner as in Example 13 except that a voltage of 1.6 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 36a and 36b). FIG. 36a is a graph showing the sensitivity difference (%) in each case of Glu values of 45 mg/dl and 550 mg/dl with reference to Hct 42% in Example 14. FIG. 36b is a graph showing the sensitivity difference (%) in each case of Hct values of 0%, 42%, and 70% with reference to Glu 45 mg/dl in Example 14. FIGS. 36a and 36b each are a graph showing the sensitivity difference in each case at 0 second to 0.1 second after the detection.

Example 15

Figure 37A:
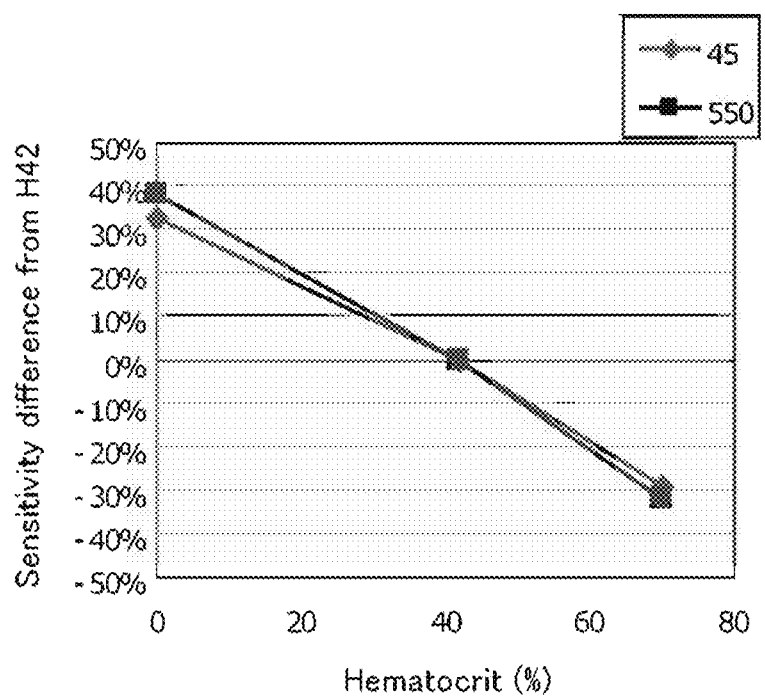
FIG. 37a is a graph showing the sensitivity difference (%) in each case of Glu values of 45 mg/dl and 550 mg/dl with reference to Hct 42% in Example 15.
Figure 37B:
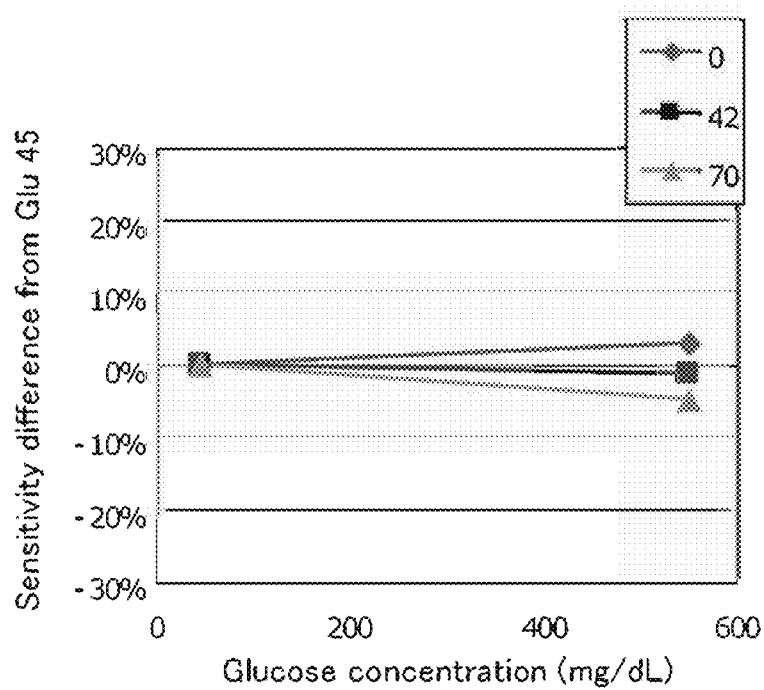
FIG. 37b is a graph showing the sensitivity difference (%) in each case of Hct values of 0%, 42%, and 70% with reference to Glu 45 mg/dl in Example 15.

The procedure was carried out in the same manner as in Example 13 except that a voltage of 1.7 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 37a and 37b). FIG. 37a is a graph showing the sensitivity difference (%) in each case of Glu values of 45 mg/dl and 550 mg/dl with reference to Hct 42% in Example 15. FIG. 37b is a graph showing the sensitivity difference (%) in each case of Hct values of 0%, 42%, and 70% with reference to Glu 45 mg/dl in Example 15. FIGS. 37a and 37b each are a graph showing the sensitivity difference in each case at 0 second to 0.1 second after the detection.

Example 16

Figure 38A:
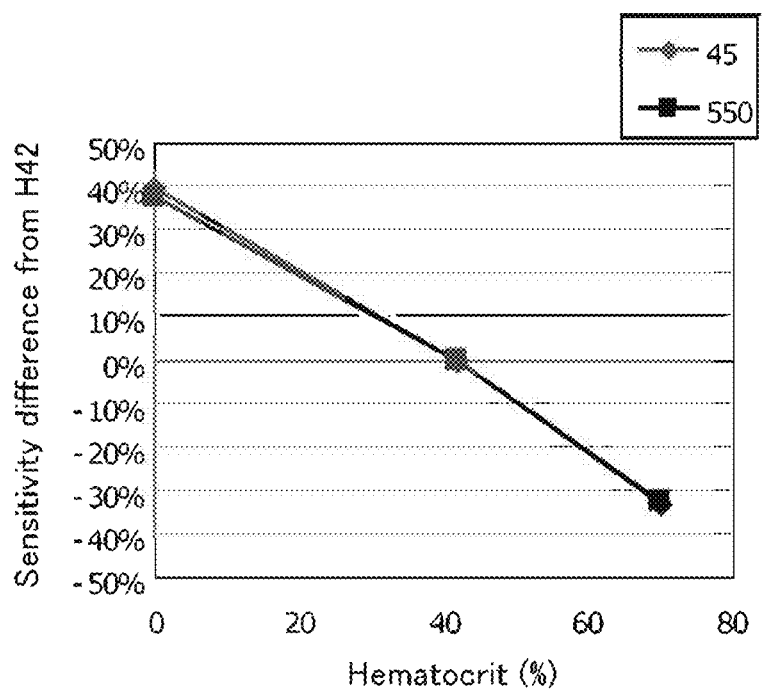
FIG. 38a is a graph showing the sensitivity difference (%) in each case of Glu values of 45 mg/dl and 550 mg/dl with reference to Hct 42% in Example 16.
Figure 38B:
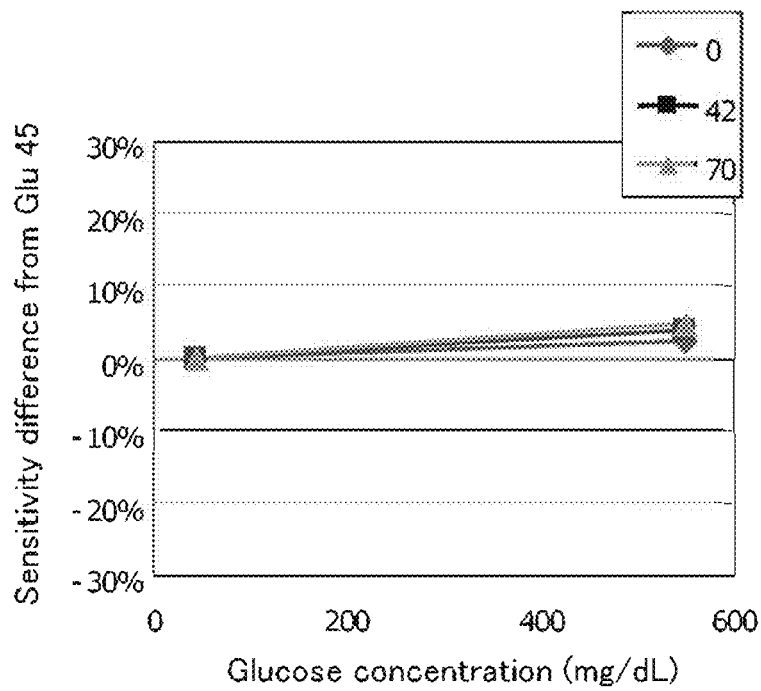
FIG. 38b is a graph showing the sensitivity difference (%) in each case of Hct values of 0%, 42%, and 70% with reference to Glu 45 mg/dl in Example 16.

The procedure was carried out in the same manner as in Example 13 except that a voltage of 1.8 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 38a and 38b). FIG. 38a is a graph showing the sensitivity difference (%) in each case of Glu values of 45 mg/dl and 550 mg/dl with reference to Hct 42% in Example 16. FIG. 38b is a graph showing the sensitivity difference (%) in each case of Hct values of 0%, 42%, and 70% with reference to Glu 45 mg/dl in Example 16. FIGS. 38a and 38b each are a graph showing the sensitivity difference in each case at 0 second to 0.1 second after the detection.

Example 17

Figure 39A:
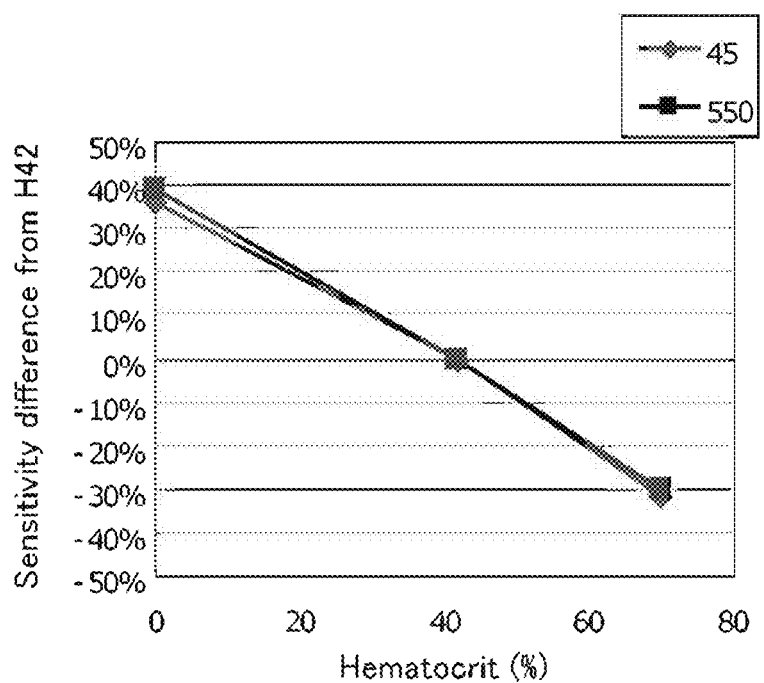
FIG. 39a is a graph showing the sensitivity difference (%) in each case of Glu values of 45 mg/dl and 550 mg/dl with reference to Hct 42% in Example 17.
Figure 39B:
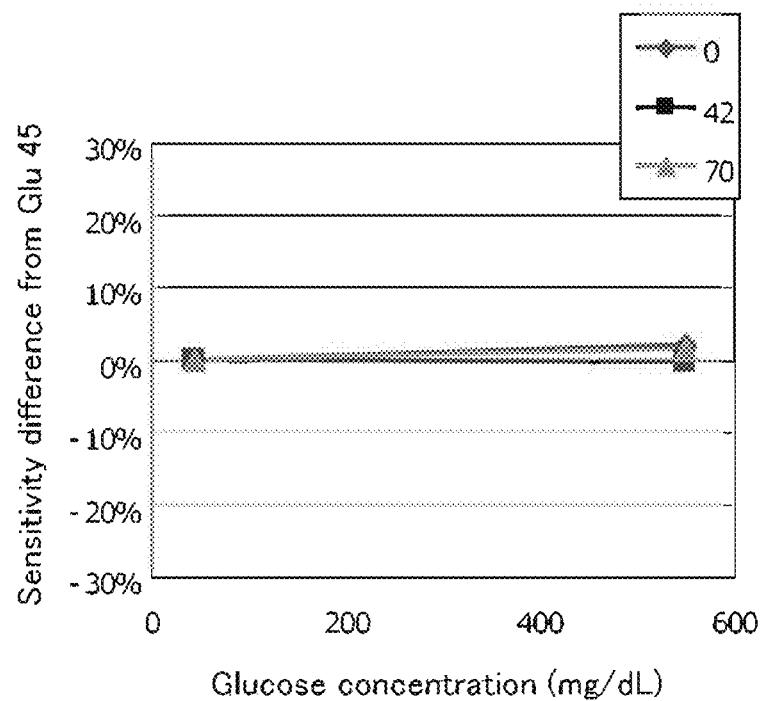
FIG. 39b is a graph showing the sensitivity difference (%) in each case of Hct values of 0%, 42%, and 70% with reference to Glu 45 mg/dl in Example 17.

The procedure was carried out in the same manner as in Example 13 except that a voltage of 1.9 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 39a and 39b). FIG. 39a is a graph showing the sensitivity difference (%) in each case of Glu values of 45 mg/dl and 550 mg/dl with reference to Hct 42% in Example 17. FIG. 39b is a graph showing the sensitivity difference (%) in each case of Hct values of 0%, 42%, and 70% with reference to Glu 45 mg/dl in Example 17. FIGS. 39a and 39b each are a graph showing the sensitivity difference in each case at 0 second to 0.1 second after the detection.

Example 18

Figure 40A:
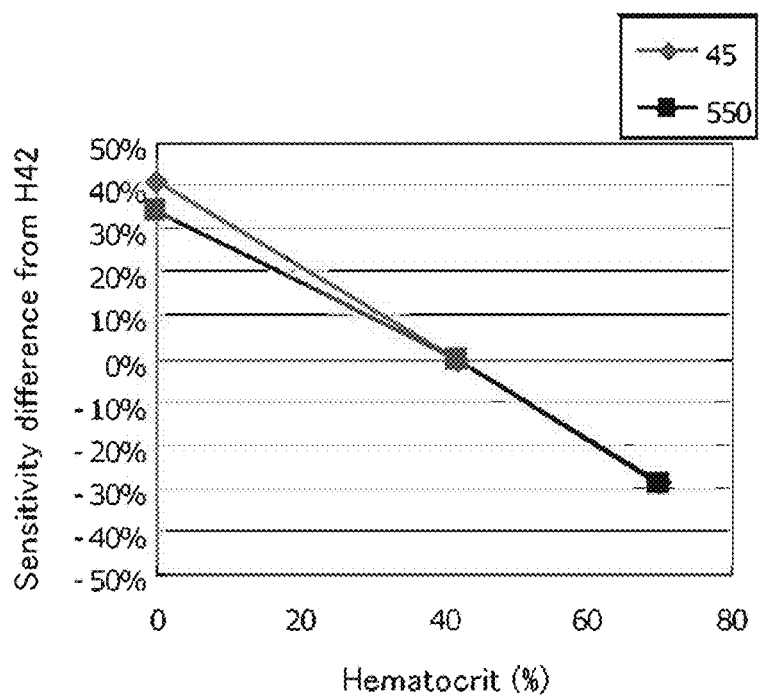
FIG. 40a is a graph showing the sensitivity difference (%) in each case of Glu values of 45 mg/dl and 550 mg/dl with reference to Hct 42% in Example 18.
Figure 40B:
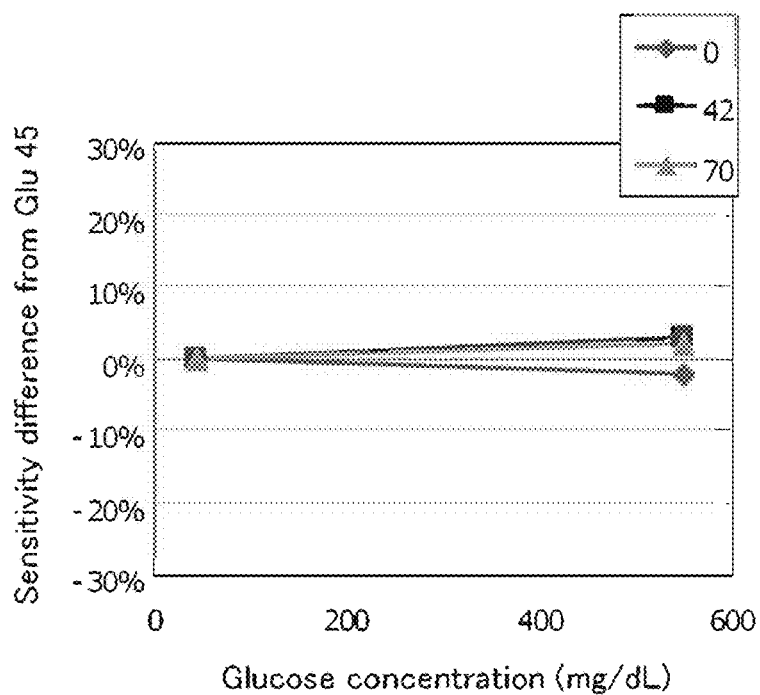
FIG. 40b is a graph showing the sensitivity difference (%) in each case of Hct values of 0%, 42%, and 70% with reference to Glu 45 mg/dl in Example 18.

The procedure was carried out in the same manner as in Example 13 except that a voltage of 2.0 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 40a and 40b). FIG. 40a is a graph showing the sensitivity difference (%) in each case of Glu values of 45 mg/dl and 550 mg/dl with reference to Hct 42% in Example 18. FIG. 40b is a graph showing the sensitivity difference (%) in each case of Hct values of 0%, 42%, and 70% with reference to Glu 45 mg/dl in Example 18. FIGS. 40a and 40b each are a graph showing the sensitivity difference in each case at 0 second to 0.1 second after the detection.

Example 19

Figure 41A:
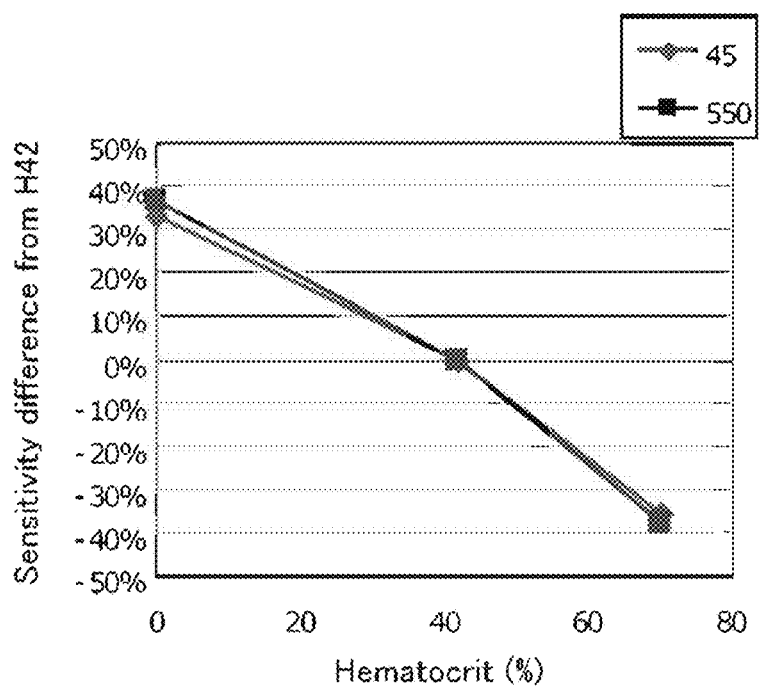
FIG. 41a is a graph showing the sensitivity difference (%) in each case of Glu values of 45 mg/dl and 550 mg/dl with reference to Hct 42% in Example 19.
Figure 41B:
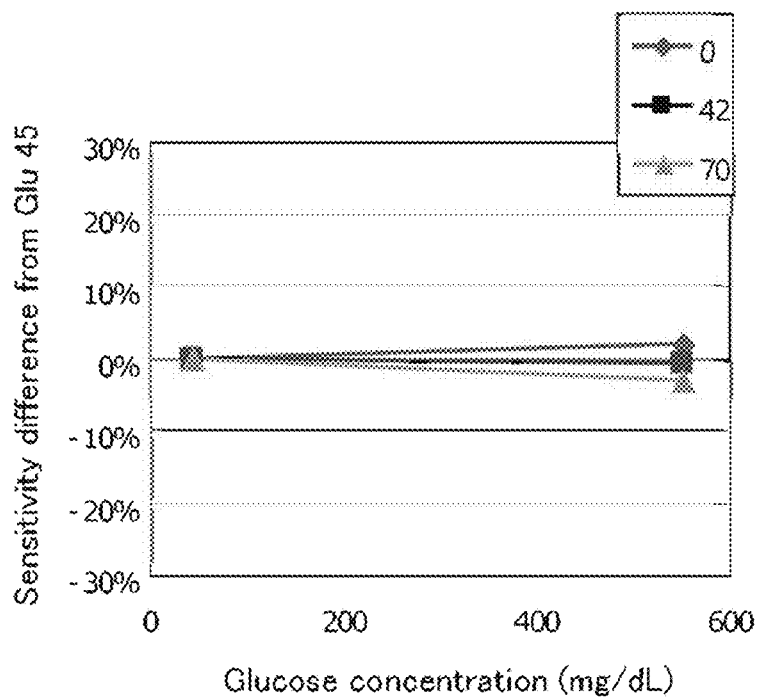
FIG. 41b is a graph showing the sensitivity difference (%) in each case of Hct values of 0%, 42%, and 70% with reference to Glu 45 mg/dl in Example 19.

The procedure was carried out in the same manner as in Example 13 except that a voltage of 2.5 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 41a and 41b). FIG. 41a is a graph showing the sensitivity difference (%) in each case of Glu values of 45 mg/dl and 550 mg/dl with reference to Hct 42% in Example 19. FIG. 41b is a graph showing the sensitivity difference (%) in each case of Hct values of 0%, 42%, and 70% with reference to Glu 45 mg/dl in Example 19. FIGS. 41a and 41b each are a graph showing the sensitivity difference in each case at 0 second to 0.1 second after the detection.

Example 20

Figure 42A:
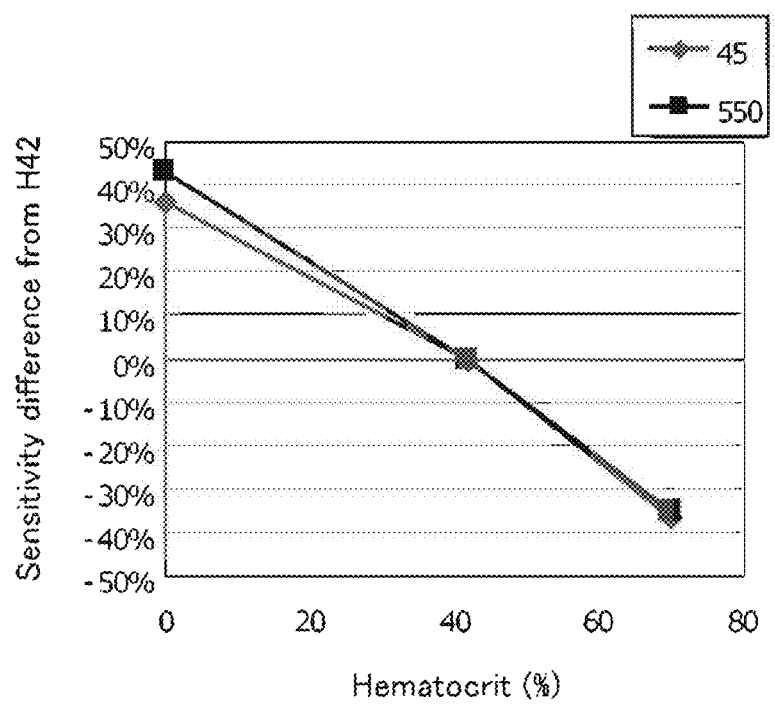
FIG. 42a is a graph showing the sensitivity difference (%) in each case of Glu values of 45 mg/dl and 550 mg/dl with reference to Hct 42% in Example 20.
Figure 42B:
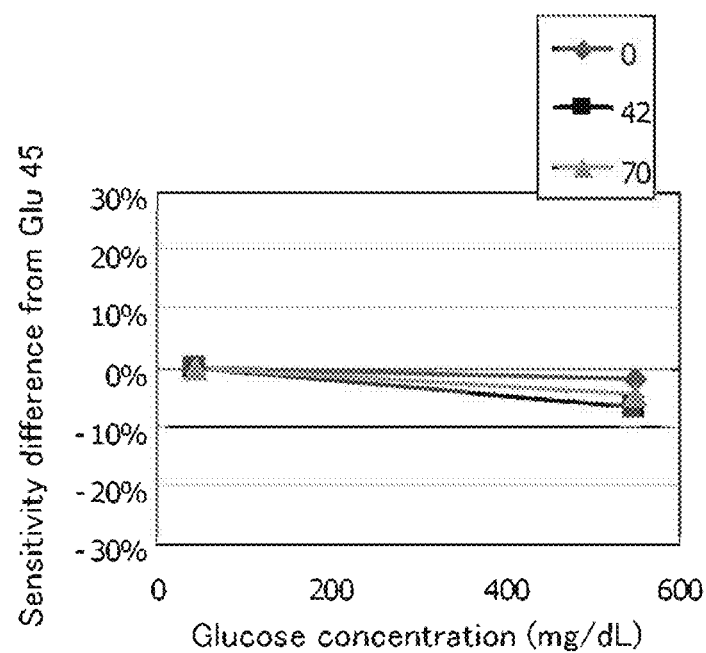
FIG. 42b is a graph showing the sensitivity difference (%) in each case of Hct values of 0%, 42%, and 70% with reference to Glu 45 mg/dl in Example 20.

The procedure was carried out in the same manner as in Example 13 except that a voltage of 3.0 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 42a and 42b). FIG. 42a is a graph showing the sensitivity difference (%) in each case of Glu values of 45 mg/dl and 550 mg/dl with reference to Hct 42% in Example 20. FIG. 42b is a graph showing the sensitivity difference (%) in each case of Hct values of 0%, 42%, and 70% with reference to Glu 45 mg/dl in Example 20. FIGS. 42a and 42b each are a graph showing the sensitivity difference in each case at 0 second to 0.1 second after the detection.

Example 21

Figure 43A:
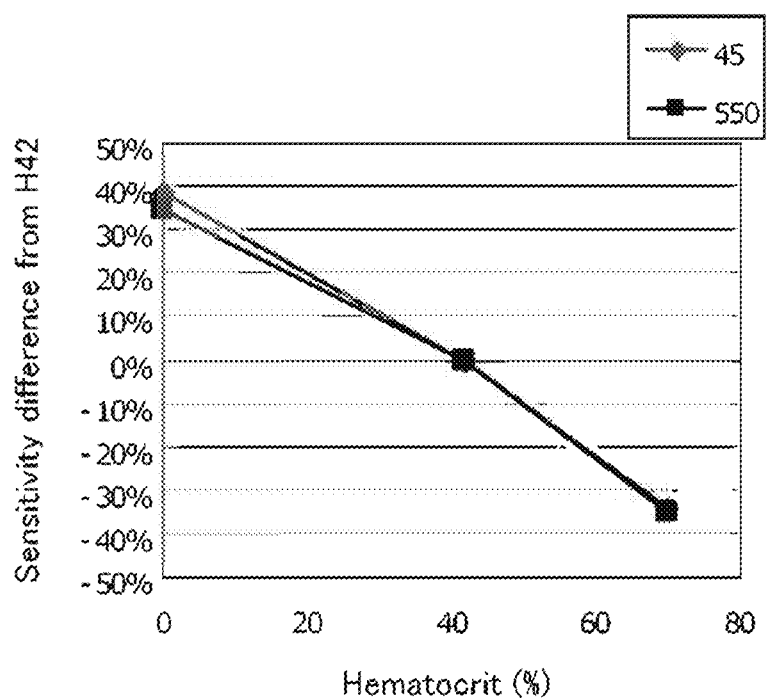
FIG. 43a is a graph showing the sensitivity difference (%) in each case of Glu values of 45 mg/dl and 550 mg/dl with reference to Hct 42% in Example 21.
Figure 43B:
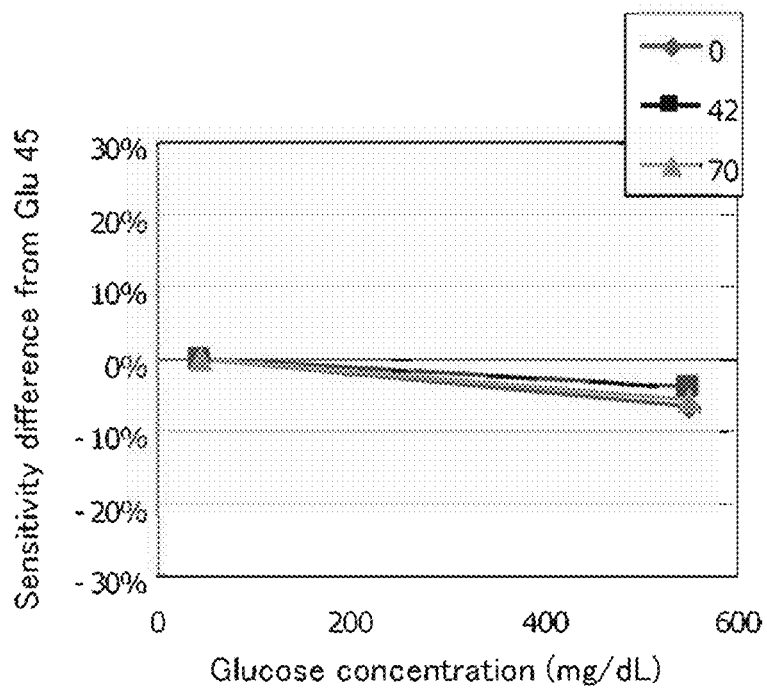
FIG. 43b is a graph showing the sensitivity difference (%) in each case of Hct values of 0%, 42%, and 70% with reference to Glu 45 mg/dl in Example 21.

The procedure was carried out in the same manner as in Example 13 except that a voltage of 3.5 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 43a and 43b). FIG. 43a is a graph showing the sensitivity difference (%) in each case of Glu values of 45 mg/dl and 550 mg/dl with reference to Hct 42% in Example 21. FIG. 43b is a graph showing the sensitivity difference (%) in each case of Hct values of 0%, 42%, and 70% with reference to Glu 45 mg/dl in Example 21. FIGS. 43a and 43b each are a graph showing the sensitivity difference in each case at 0 second to 0.1 second after the detection.

Example 22

Figure 44A:
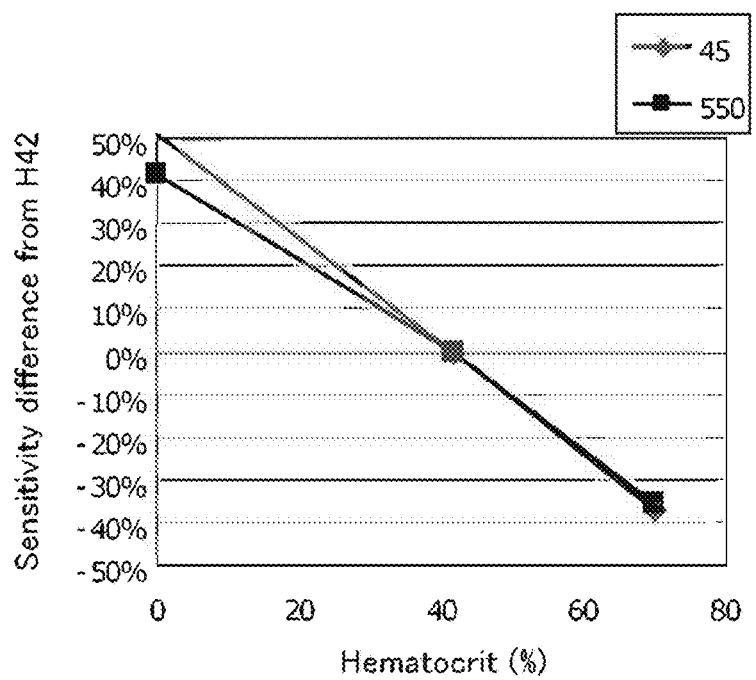
FIG. 44a is a graph showing the sensitivity difference (%) in each case of Glu values of 45 mg/dl and 550 mg/dl with reference to Hct 42% in Example 22.
Figure 44B:
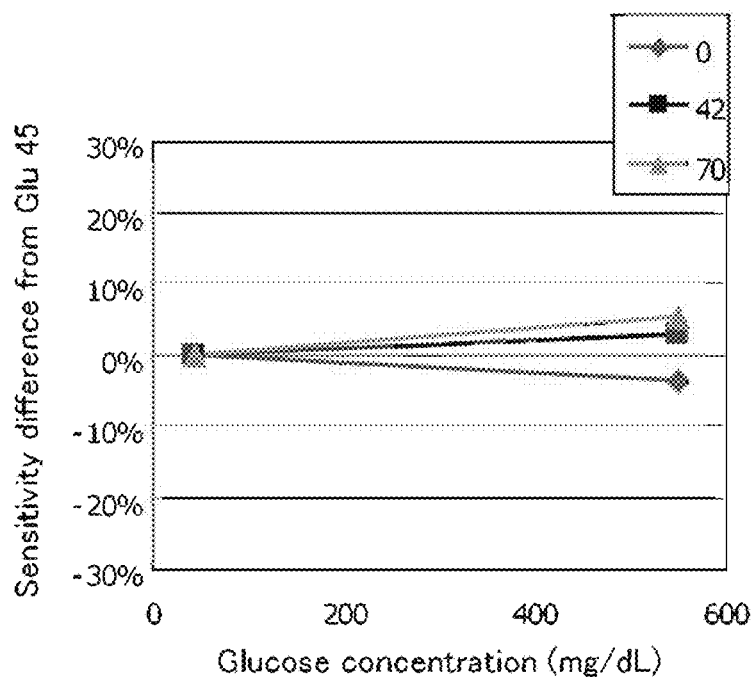
FIG. 44b is a graph showing the sensitivity difference (%) in each case of Hct values of 0%, 42%, and 70% with reference to Glu 45 mg/dl in Example 22.

The procedure was carried out in the same manner as in Example 13 except that a voltage of 4.0 V was applied between the electrode A and the electrode B for 0.1 second from 0 second to 0.1 second after detection of the introduction of a blood sample. The current flowing between the working electrode and the counter electrode of each sensor 1 was measured, and the response current value and the sensitivity difference were measured in the measurement of the Hct value (see FIGS. 44a and 44b). FIG. 44a is a graph showing the sensitivity difference (%) in each case of Glu values of 45 mg/dl and 550 mg/dl with reference to Hct 42% in Example 22. FIG. 44b is a graph showing the sensitivity difference (%) in each case of Hct values of 0%, 42%, and 70% with reference to Glu 45 mg/dl in Example 22. FIGS. 44a and 44b each are a graph showing the sensitivity difference in each case at 0 second to 0.1 second after the detection.

From Examples 13 to 22, it was confirmed that when a voltage of 1.5 to 4.0 V was applied to the working electrode and the counter electrode for 0.1 second immediately (0 second) after detection of the introduction of a biological sample, the current value obtained thereby had a high sensitivity, and the Hct value obtained based on the current value had a high accuracy.

Example 23

Figure 45A:
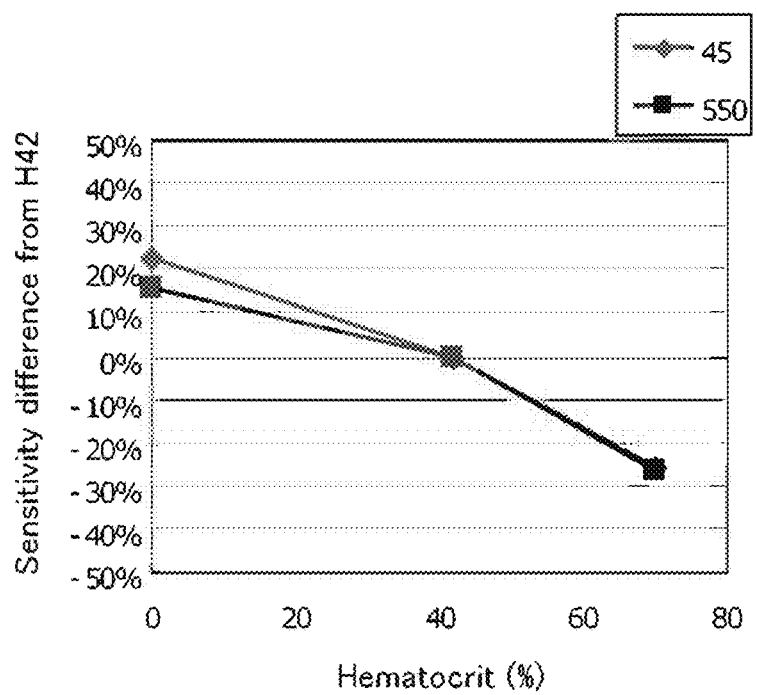
FIG. 45a is a graph showing the sensitivity difference (%) in each case of Glu values of 45 mg/dl and 550 mg/dl with reference to Hct 42% in Example 23.
Figure 45B:
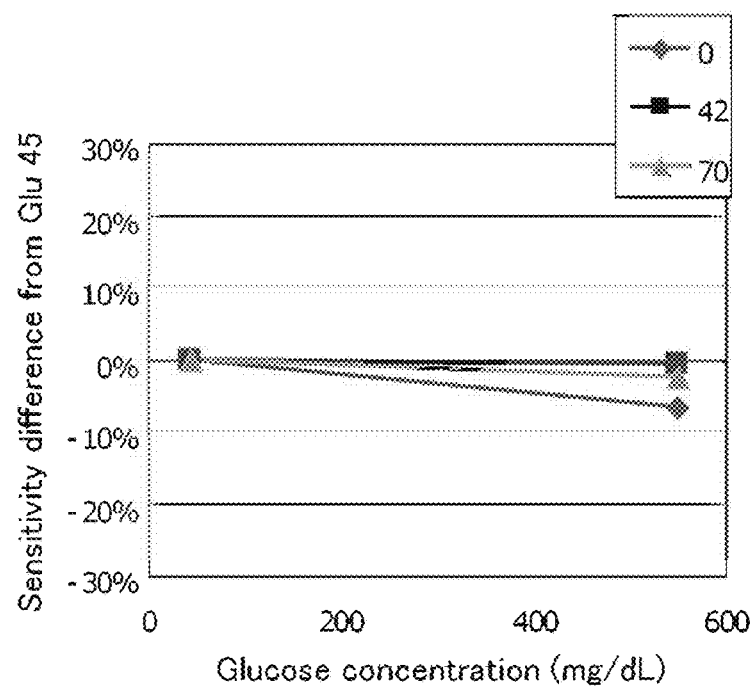
FIG. 45b is a graph showing the sensitivity difference (%) in each case of Hct values of 0%, 42%, and 70% with reference to Glu 45 mg/dl in Example 23.

A voltage of 1.5 V was applied between the electrode A and the electrode B for 0.5 second from 0 second to 0.5 second after detection of the introduction of a blood sample (see FIG. 19(a)). The current flowing between the working electrode and the counter electrode of each sensor 1 was measured, and the response current value and the sensitivity difference were measured in the measurement of the Hct value (see FIGS. 45a and 45b). FIG. 45a is a graph showing the sensitivity difference (%) in each case of Glu values of 45 mg/dl and 550 mg/dl with reference to Hct 42% in Example 23. FIG. 45b is a graph showing the sensitivity difference (%) in each case of Hct values of 0%, 42%, and 70% with reference to Glu 45 mg/dl in Example 23. FIGS. 45a and 45b each are a graph showing the sensitivity difference in each case at 0 second to 0.5 second after the detection.

Example 24

Figure 46A:
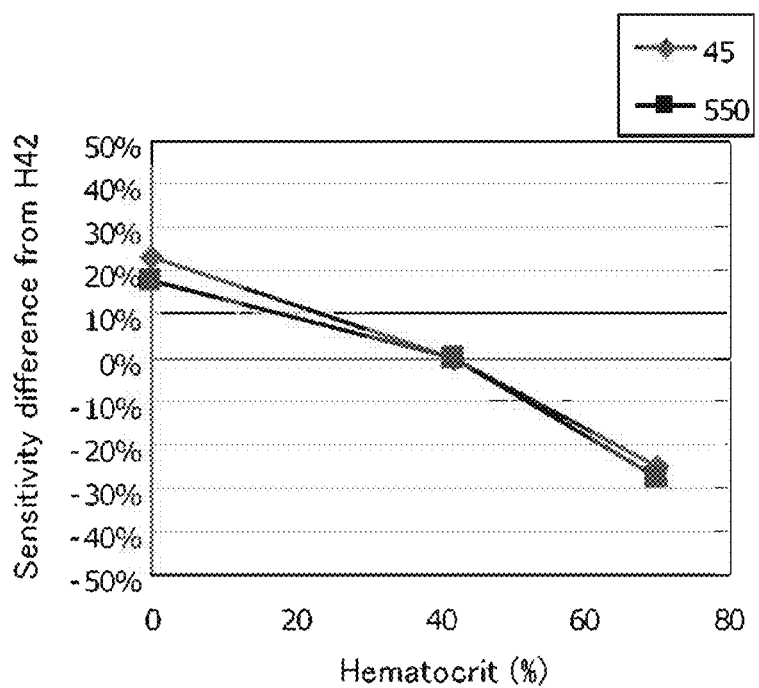
FIG. 46a is a graph showing the sensitivity difference (%) in each case of Glu values of 45 mg/dl and 550 mg/dl with reference to Hct 42% in Example 24.
Figure 46B:
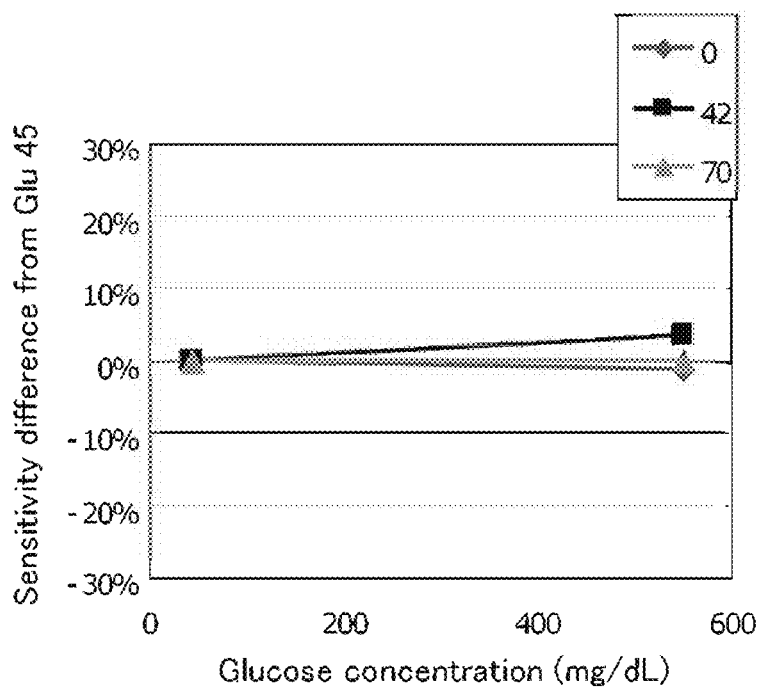
FIG. 46b is a graph showing the sensitivity difference (%) in each case of Hct values of 0%, 42%, and 70% with reference to Glu 45 mg/dl in Example 24.

The procedure was carried out in the same manner as in Example 23 except that a voltage of 1.6 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 46a and 46b). FIG. 46a is a graph showing the sensitivity difference (%) in each case of Glu values of 45 mg/dl and 550 mg/dl with reference to Hct 42% in Example 24. FIG. 46b is a graph showing the sensitivity difference (%) in each case of Hct values of 0%, 42%, and 70% with reference to Glu 45 mg/dl in Example 24. FIGS. 46a and 46b each are a graph showing the sensitivity difference in each case at 0 second to 0.5 second after the detection.

Example 25

Figure 47A:
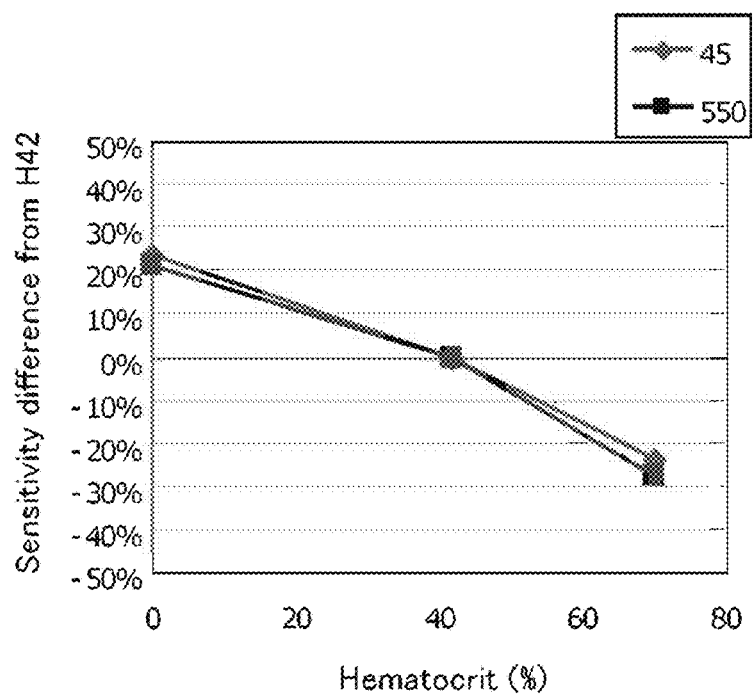
FIG. 47a is a graph showing the sensitivity difference (%) in each case of Glu values of 45 mg/dl and 550 mg/dl with reference to Hct 42% in Example 25.
Figure 47B:
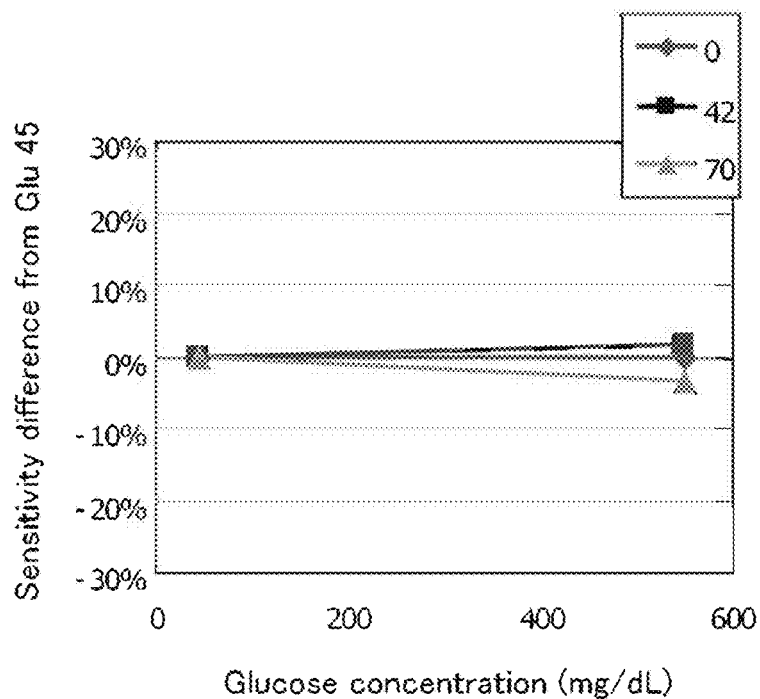
FIG. 47b is a graph showing the sensitivity difference (%) in each case of Hct values of 0%, 42%, and 70% with reference to Glu 45 mg/dl in Example 25.

The procedure was carried out in the same manner as in Example 23 except that a voltage of 1.7 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 47a and 47b). FIG. 47a is a graph showing the sensitivity difference (%) in each case of Glu values of 45 mg/dl and 550 mg/dl with reference to Hct 42% in Example 25. FIG. 47b is a graph showing the sensitivity difference (%) in each case of Hct values of 0%, 42%, and 70% with reference to Glu 45 mg/dl in Example 25. FIGS.

47*a* and 47*b* each are a graph showing the sensitivity difference in each case at 0 second to 0.5 second after the detection.

Example 26

Figure 48A:
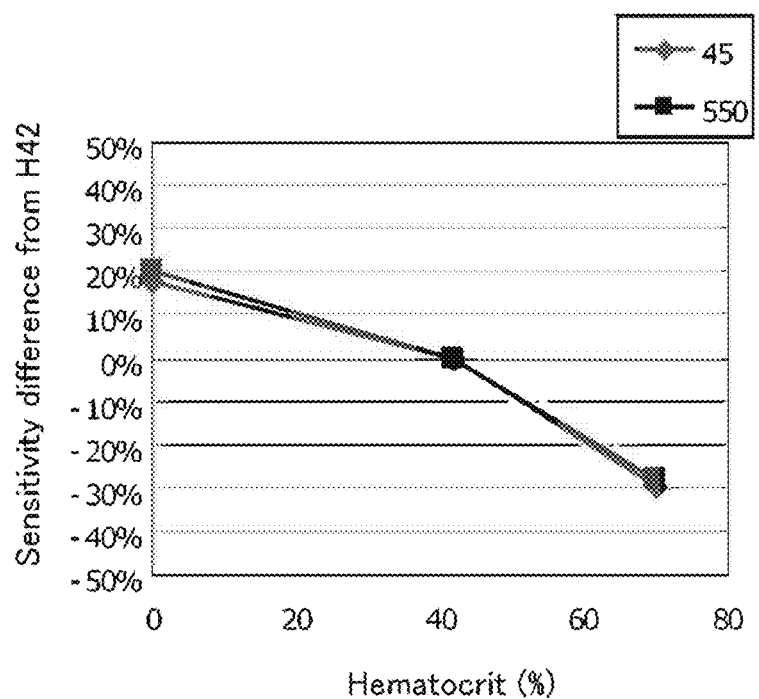
FIG. 48a is a graph showing the sensitivity difference (%) in each case of Glu values of 45 mg/dl and 550 mg/dl with reference to Hct 42% in Example 26.
Figure 48B:
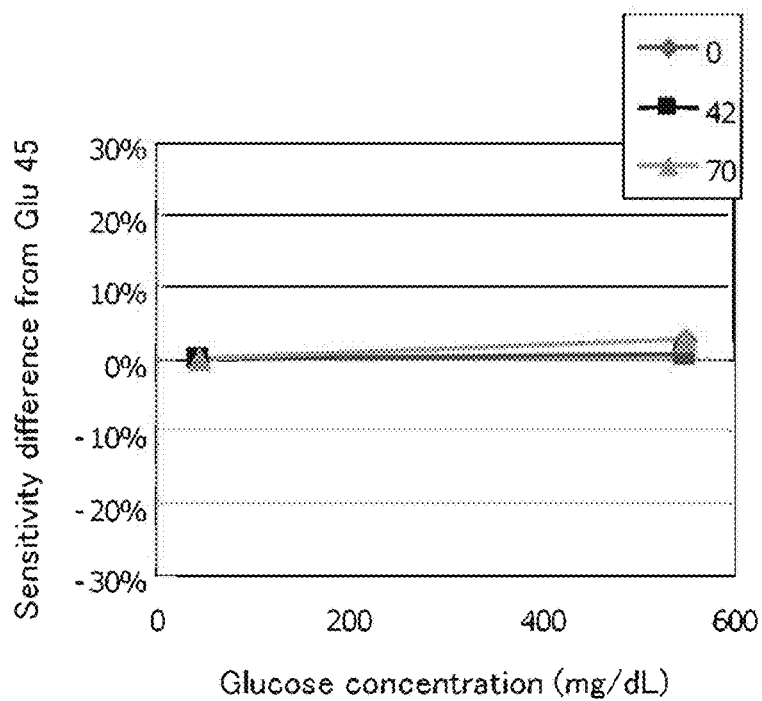
FIG. 48b is a graph showing the sensitivity difference (%) in each case of Hct values of 0%, 42%, and 70% with reference to Glu 45 mg/dl in Example 26.

The procedure was carried out in the same manner as in Example 23 except that a voltage of 1.8 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 48*a* and 48*b*). FIG. 48*a* is a graph showing the sensitivity difference (%) in each case of Glu values of 45 mg/dl and 550 mg/dl with reference to Hct 42% in Example 26. FIG. 48*b* is a graph showing the sensitivity difference (%) in each case of Hct values of 0%, 42%, and 70% with reference to Glu 45 mg/dl in Example 26. FIGS. 48*a* and 48*b* each are a graph showing the sensitivity difference in each case at 0 second to 0.5 second after the detection.

Example 27

Figure 49A:
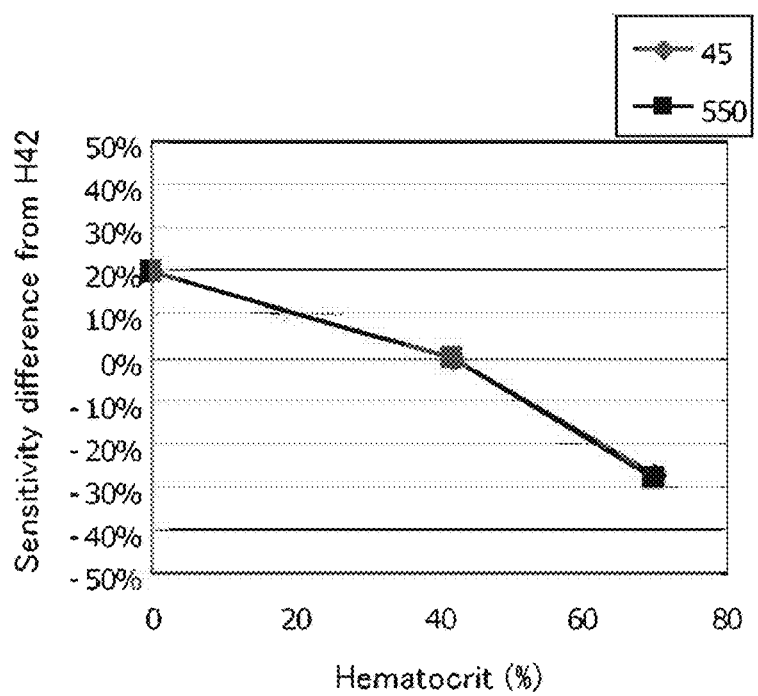
FIG. 49a is a graph showing the sensitivity difference (%) in each case of Glu values of 45 mg/dl and 550 mg/dl with reference to Hct 42% in Example 27.
Figure 49B:
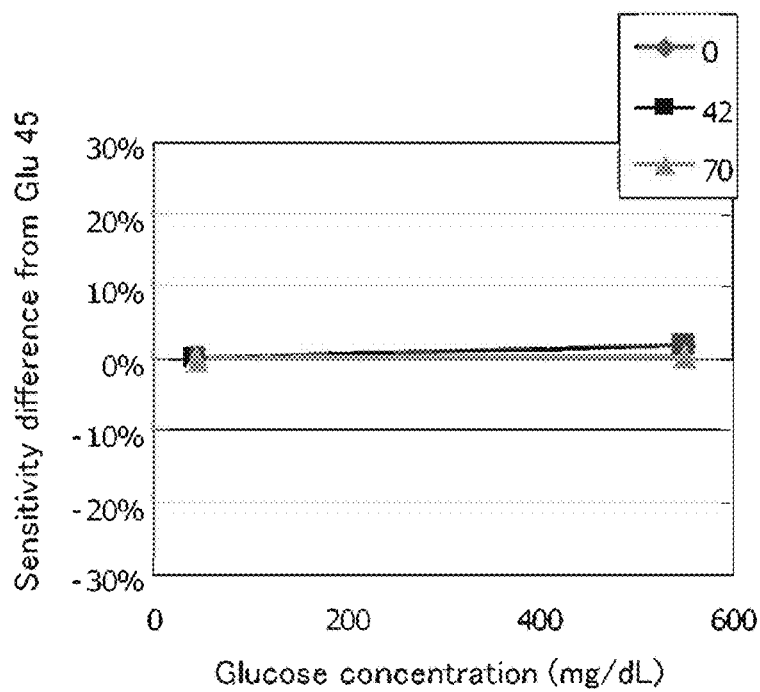
FIG. 49b is a graph showing the sensitivity difference (%) in each case of Hct values of 0%, 42%, and 70% with reference to Glu 45 mg/dl in Example 27.

The procedure was carried out in the same manner as in Example 23 except that a voltage of 1.9 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 49*a* and 49*b*). FIG. 49*a* is a graph showing the sensitivity difference (%) in each case of Glu values of 45 mg/dl and 550 mg/dl with reference to Hct 42% in Example 27. FIG. 49*b* is a graph showing the sensitivity difference (%) in each case of Hct values of 0%, 42%, and 70% with reference to Glu 45 mg/dl in Example 27. FIGS. 49*a* and 49*b* each are a graph showing the sensitivity difference in each case at 0 second to 0.5 second after the detection.

Example 28

Figure 50A:
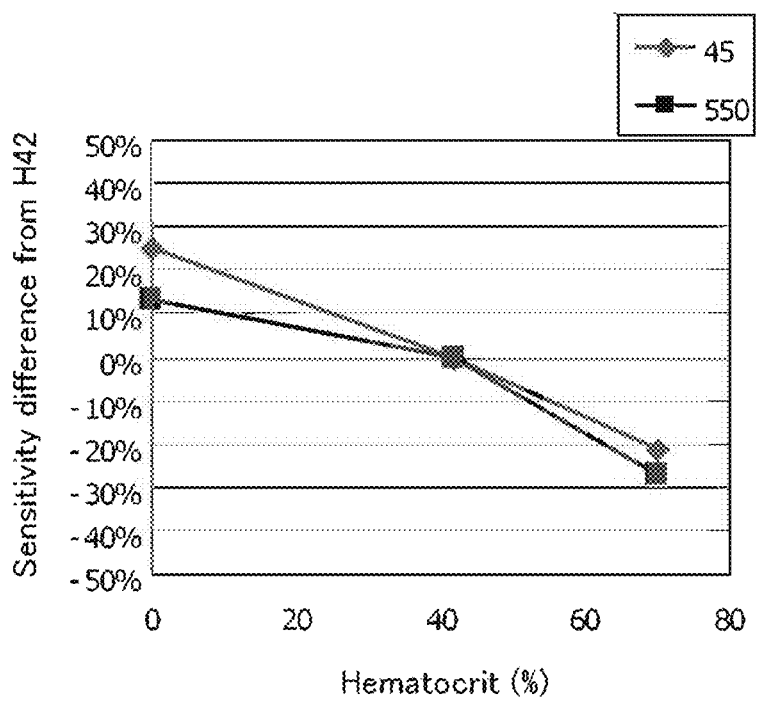
FIG. 50a is a graph showing the sensitivity difference (%) in each case of Glu values of 45 mg/dl and 550 mg/dl with reference to Hct 42% in Example 28.
Figure 50B:
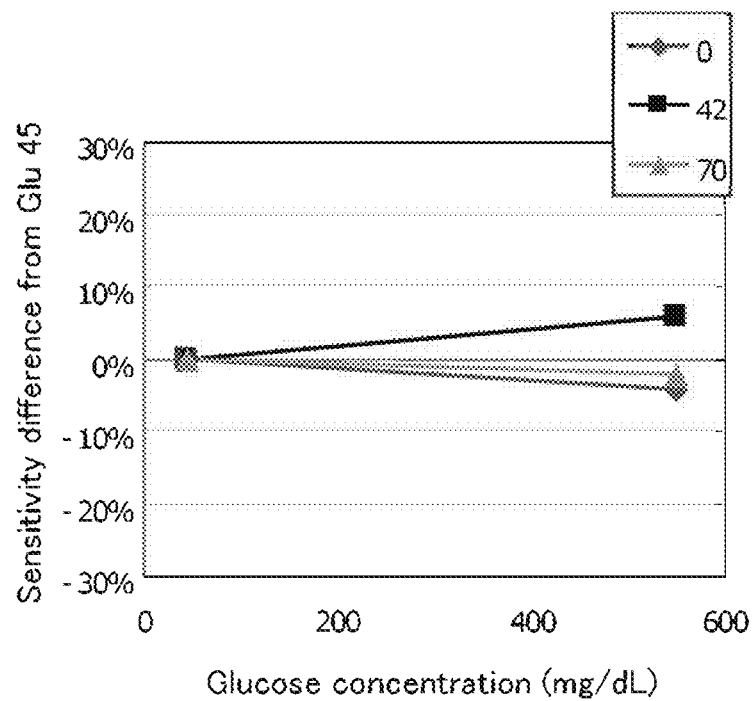
FIG. 50b is a graph showing the sensitivity difference (%) in each case of Hct values of 0%, 42%, and 70% with reference to Glu 45 mg/dl in Example 28.

The procedure was carried out in the same manner as in Example 23 except that a voltage of 2.0 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 50*a* and 50*b*). FIG. 50*a* is a graph showing the sensitivity difference (%) in each case of Glu values of 45 mg/dl and 550 mg/dl with reference to Hct 42% in Example 28. FIG. 50*b* is a graph showing the sensitivity difference (%) in each case of Hct values of 0%, 42%, and 70% with reference to Glu 45 mg/dl in Example 28. FIGS. 50*a* and 50*b* each are a graph showing the sensitivity difference in each case at 0 second to 0.5 second after the detection.

Example 29

Figure 51A:
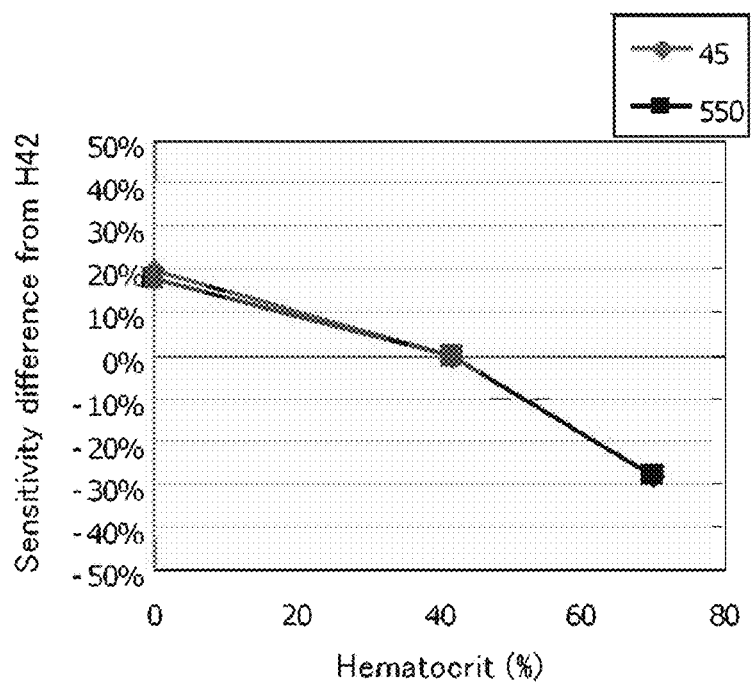
FIG. 51a is a graph showing the sensitivity difference (%) in each case of Glu values of 45 mg/dl and 550 mg/dl with reference to Hct 42% in Example 29.
Figure 51B:
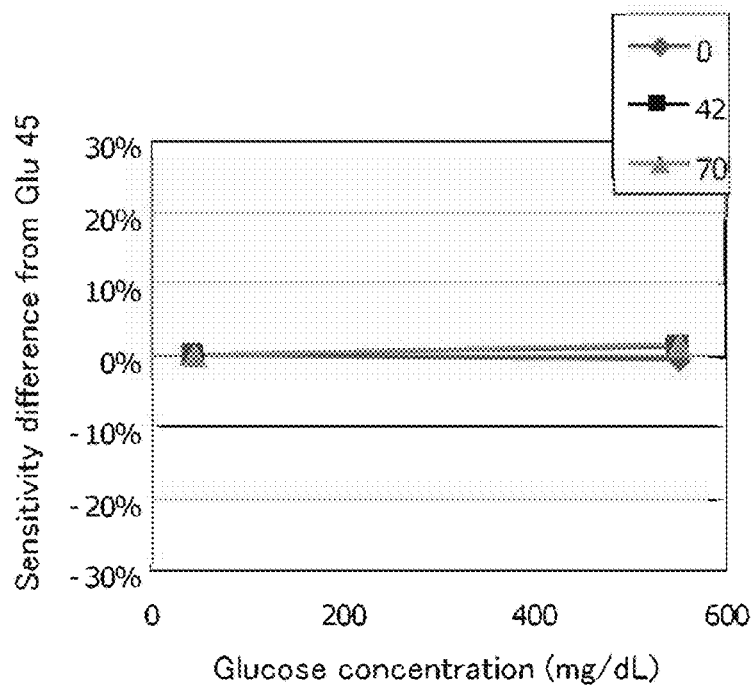
FIG. 51b is a graph showing the sensitivity difference (%) in each case of Hct values of 0%, 42%, and 70% with reference to Glu 45 mg/dl in Example 29.

The procedure was carried out in the same manner as in Example 23 except that a voltage of 2.5 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 51*a* and 51*b*). FIG. 51*a* is a graph showing the sensitivity difference (%) in each case of Glu values of 45 mg/dl and 550 mg/dl with reference to Hct 42% in Example 29. FIG. 51*b* is a graph showing the sensitivity difference (%) in each case of Hct values of 0%, 42%, and 70% with reference to Glu 45 mg/dl in Example 29. FIGS. 51*a* and 51*b* each are a graph showing the sensitivity difference in each case at 0 second to 0.5 second after the detection.

Example 30

Figure 52A:
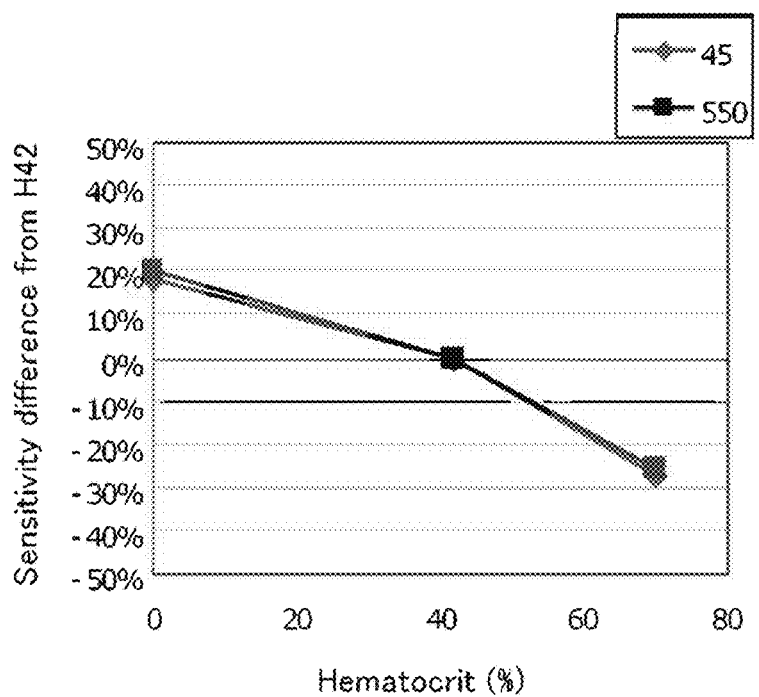
FIG. 52a is a graph showing the sensitivity difference (%) in each case of Glu values of 45 mg/dl and 550 mg/dl with reference to Hct 42% in Example 30.
Figure 52B:
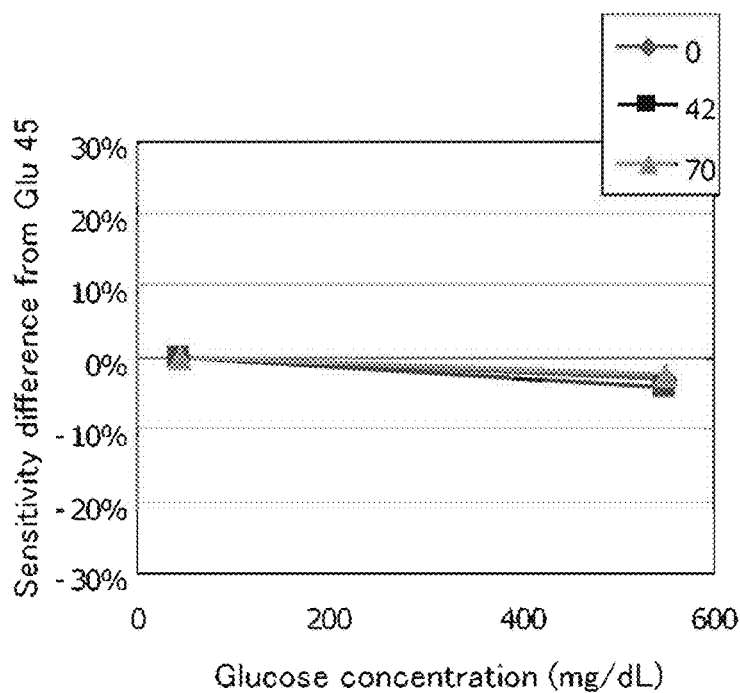

The procedure was carried out in the same manner as in Example 23 except that a voltage of 3.0 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 52*a* and 52*b*). FIG. 52*a* is a graph showing the sensitivity difference (%) in each case of Glu values of 45 mg/dl and 550 mg/dl with reference to Hct 42% in Example 30. FIG. 52*b* is a graph showing the sensitivity difference (%) in each case of Hct values of 0%, 42%, and 70% with reference to Glu 45 mg/dl in Example 30. FIGS. 52*a* and 52*b* each are a graph showing the sensitivity difference in each case at 0 second to 0.5 second after the detection.

Example 31

Figure 53A:
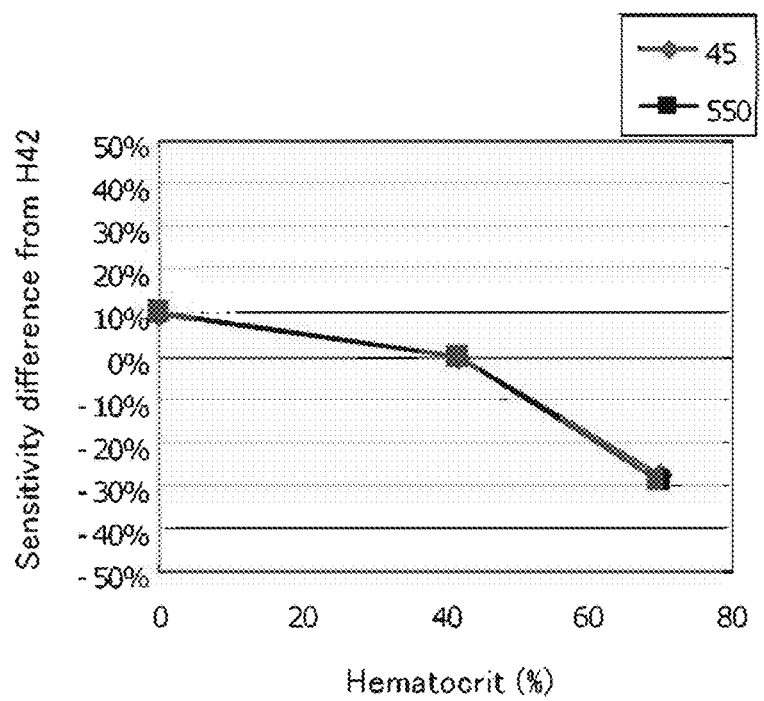
Figure 53B:
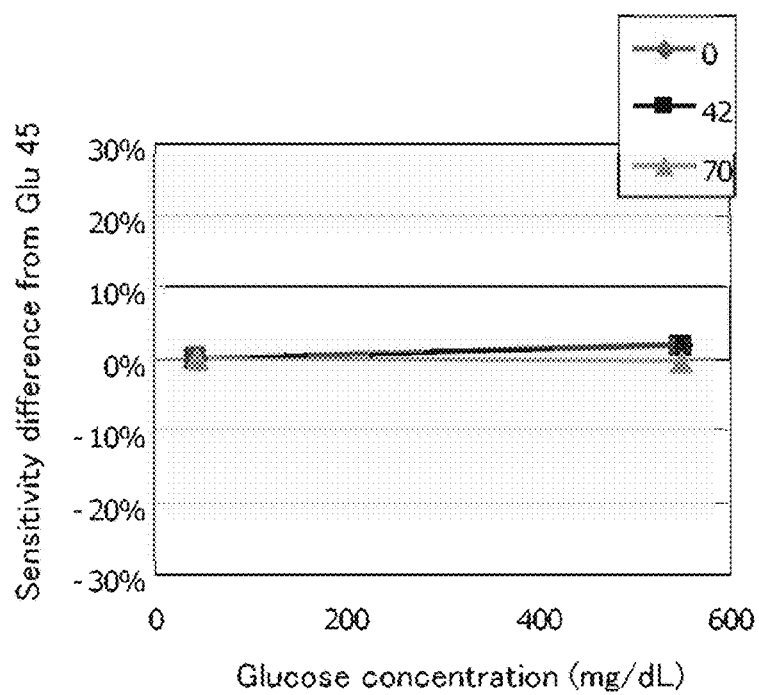

The procedure was carried out in the same manner as in Example 23 except that a voltage of 3.5 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 53*a* and 53*b*). FIG. 53*a* is a graph showing the sensitivity difference (%) in each case of Glu values of 45 mg/dl and 550 mg/dl with reference to Hct 42% in Example 31. FIG. 53*b* is a graph showing the sensitivity difference (%) in each case of Hct values of 0%, 42%, and 70% with reference to Glu 45 mg/dl in Example 31. FIGS. 53*a* and 53*b* each are a graph showing the sensitivity difference in each case at 0 second to 0.5 second after the detection.

Example 32

Figure 54A:
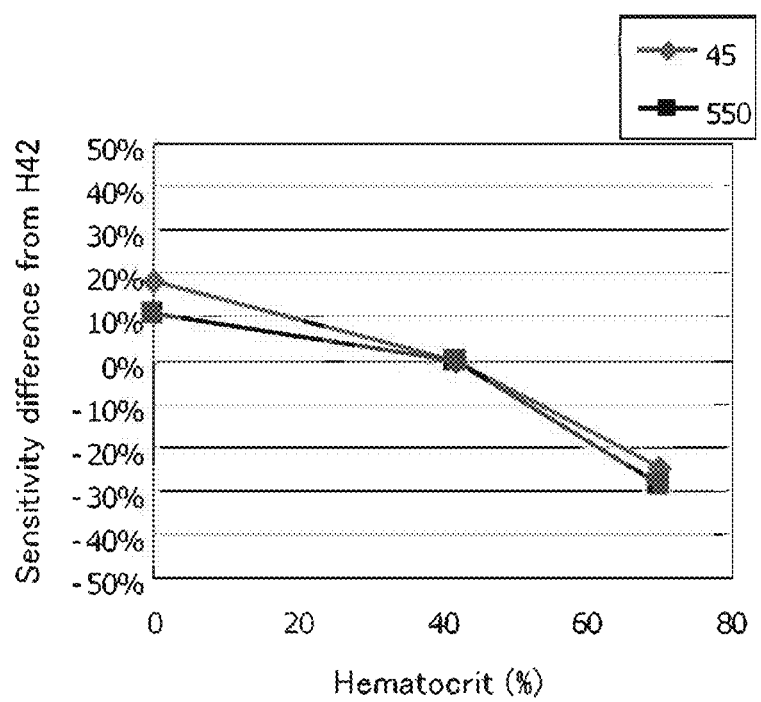
Figure 54B:
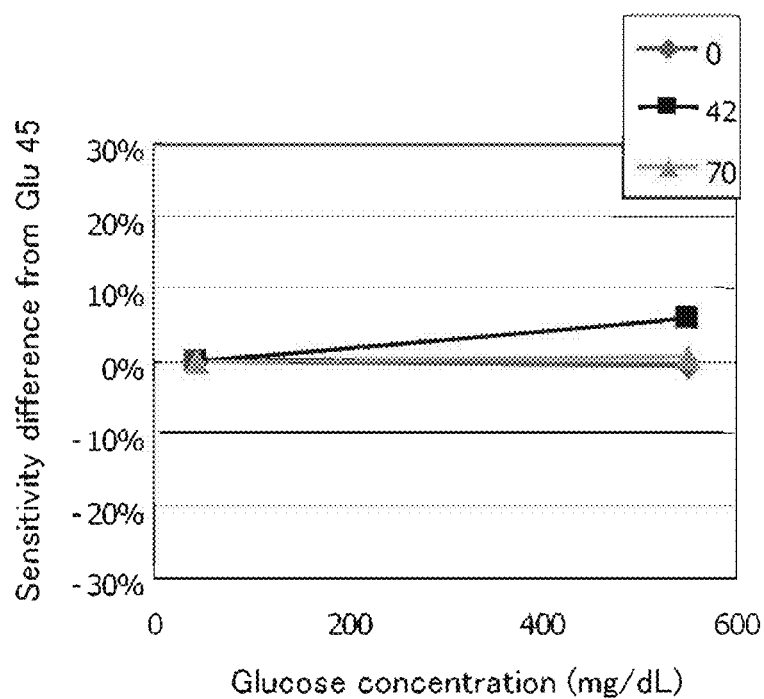

The procedure was carried out in the same manner as in Example 23 except that a voltage of 4.0 V was applied between the electrode A and the electrode B for 0.5 second from 0 second to 0.5 second after detection of the introduction of a blood sample. The current flowing between the working electrode and the counter electrode of each sensor 1 was measured, and the response current value and the sensitivity difference were measured in the measurement of the Hct value (see FIGS. 54*a* and 54*b*). FIG. 54*a* is a graph showing the sensitivity difference (%) in each case of Glu values of 45 mg/dl and 550 mg/dl with reference to Hct 42% in Example 32. FIG. 54b is a graph showing the sensitivity difference (%) in each case of Hct values of 0%, 42%, and 70% with reference to Glu 45 mg/dl in Example 32. FIGS. 54a and 54b each are a graph showing the sensitivity difference in each case at 0 second to 0.5 second after the detection.

From Examples 23 to 32, it was confirmed that when a voltage of 1.5 to 4.0 V was applied to the working electrode and the counter electrode for 0.5 second immediately (0 second) after detection of the introduction of a biological sample, the current value obtained thereby had a high sensitivity, and the Hct value obtained based on the current value had a high accuracy.

Comparative Example 4

Figure 55A:
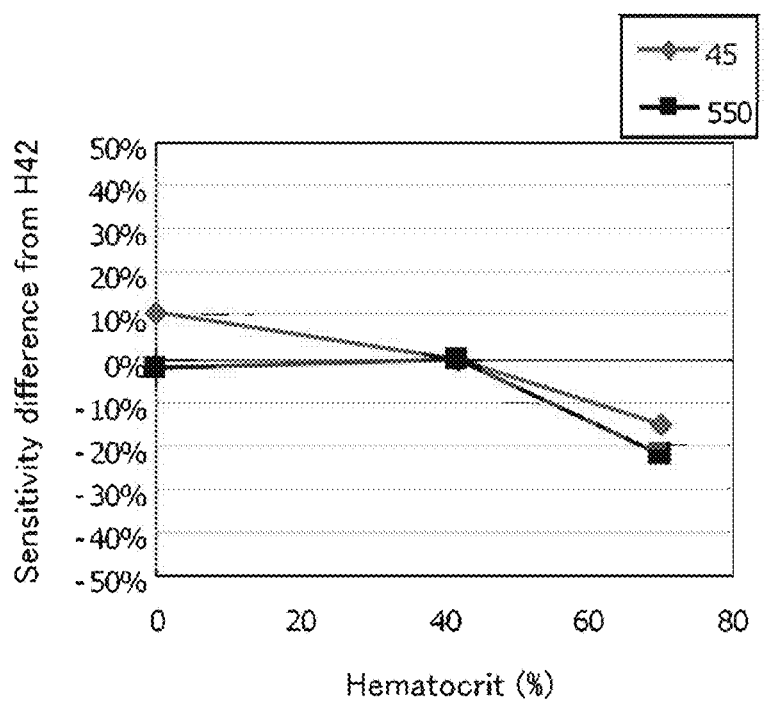
Figure 55B:
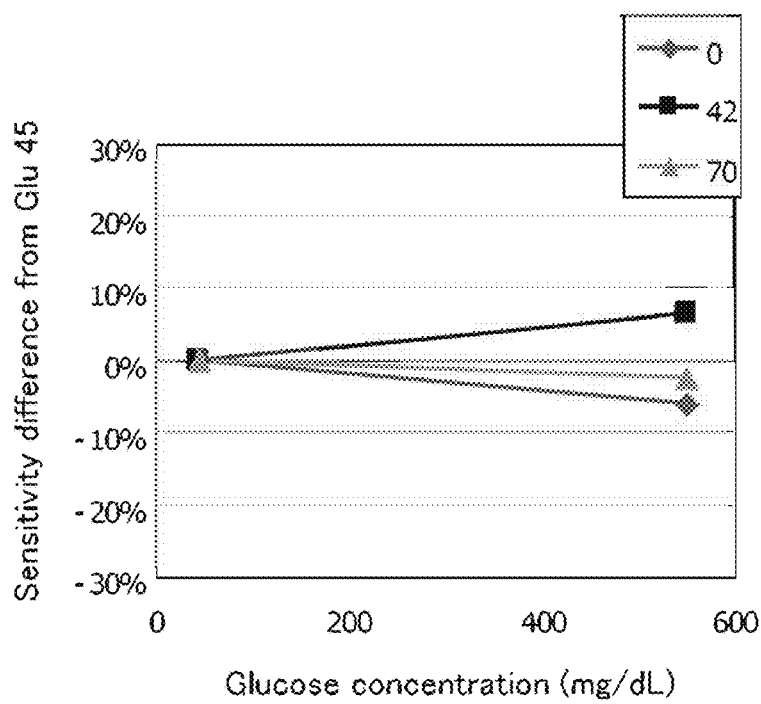

A voltage of 2.0 V was applied between the electrode A and the electrode B for 1.0 second from 0 second to 1.0 second after detection of the introduction of a blood sample (see FIG. 19(a)). The current flowing between the working electrode and the counter electrode of each sensor 1 was measured, and the response current value and the sensitivity difference were measured in the measurement of the Hct value (see FIGS. 55a and 55b). FIG. 55a is a graph showing the sensitivity difference (%) in each case of Glu values of 45 mg/dl and 550 mg/dl with reference to Hct 42% in Comparative Example 4. FIG. 55b is a graph showing the sensitivity difference (%) in each case of Hct values of 0%, 42%, and 70% with reference to Glu 45 mg/dl in Comparative Example 4. FIGS. 55a and 55b each are a graph showing the sensitivity difference in each case at 0 second to 1.0 second after the detection.

Comparative Example 5

Figure 56A:
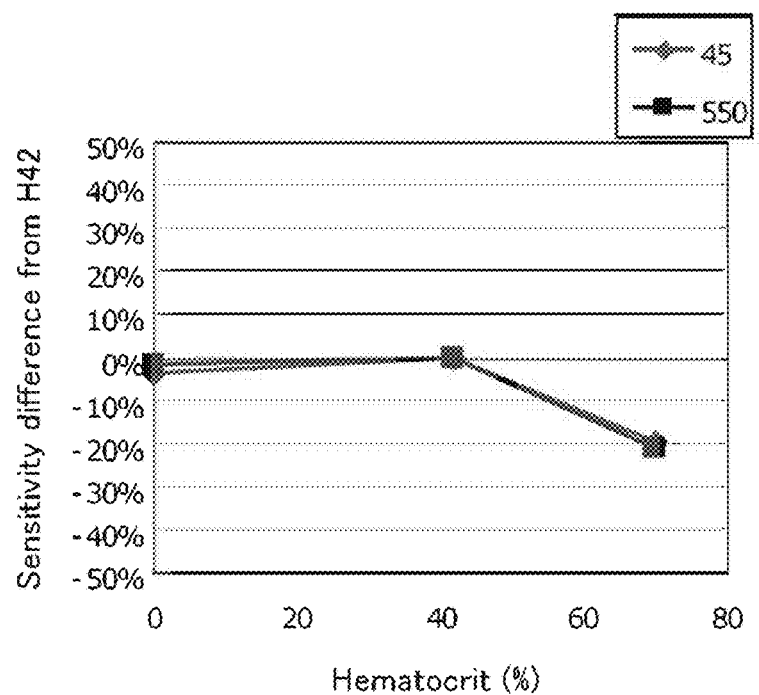
Figure 56B:
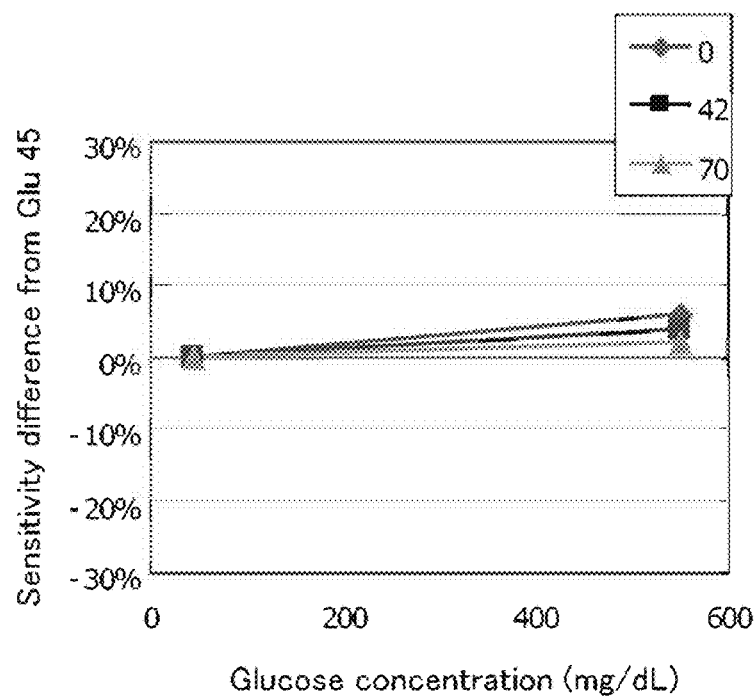

The procedure was carried out in the same manner as in Comparative Example 4 except that a voltage of 2.5 V was applied between the electrode A and the electrode B for 1.0 second from 0 second to 1.0 second after detection of the introduction of a blood sample. The current flowing between the working electrode and the counter electrode of each sensor was measured, and the response current value and the sensitivity difference were measured in the measurement of the Hct value (see FIGS. 56a and 56b). FIG. 56a is a graph showing the sensitivity difference (%) in each case of Glu values of 45 mg/dl and 550 mg/dl with reference to Hct 42% in Comparative Example 5. FIG. 56b is a graph showing the sensitivity difference (%) in each case of Hct values of 0%, 42%, and 70% with reference to Glu 45 mg/dl in Comparative Example 5. FIGS. 56a and 56b each are a graph showing the sensitivity difference in each case at 0 second to 1.0 second after the detection.

Comparative Example 6

Figure 57A:
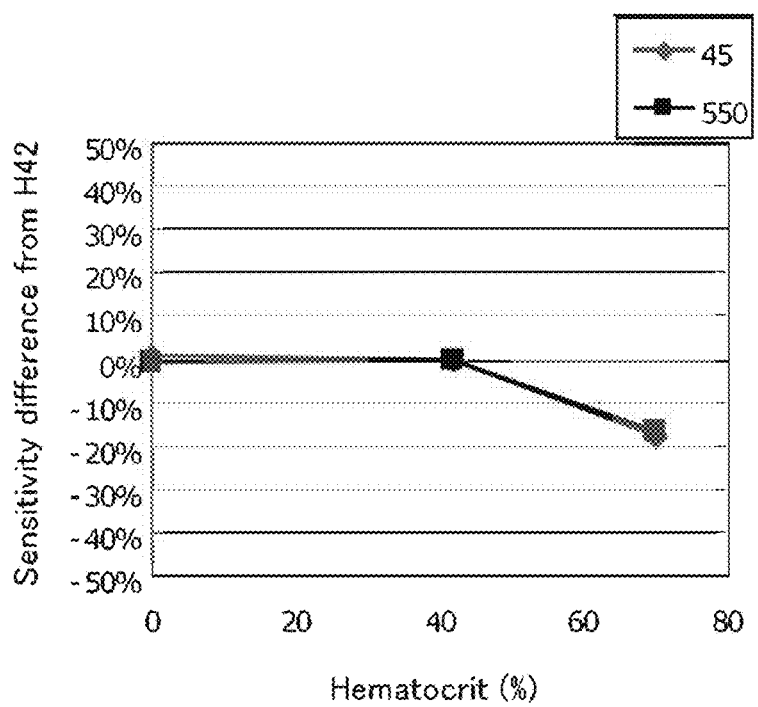
Figure 57B:
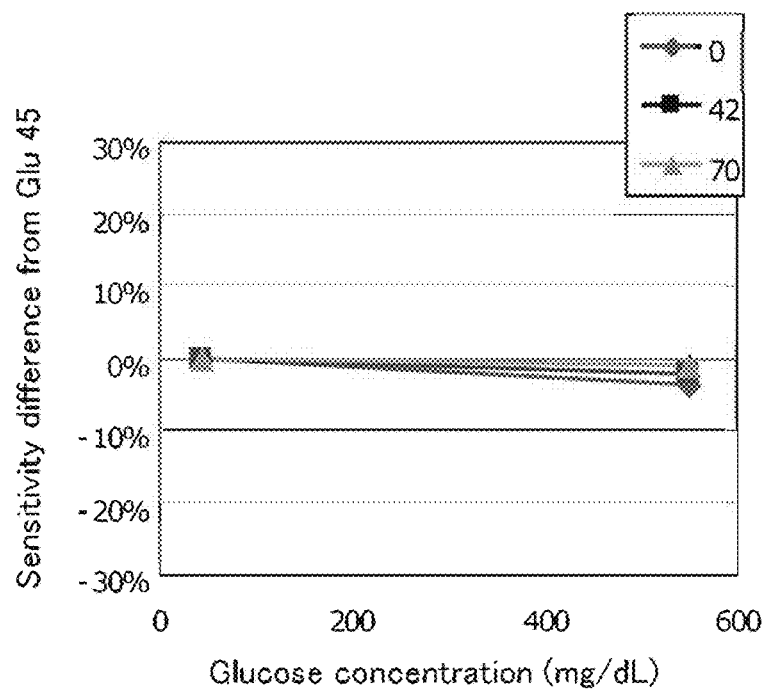

The procedure was carried out in the same manner as in Comparative Example 4 except that a voltage of 3.0 V was applied between the electrode A and the electrode B for 1.0 second from 0 second to 1.0 second after detection of the introduction of a blood sample. The current flowing between the working electrode and the counter electrode of each sensor was measured, and the response current value and the sensitivity difference were measured in the measurement of the Hct value (see FIGS. 57a and 57b). FIG. 57a is a graph showing the sensitivity difference (%) in each case of Glu values of 45 mg/dl and 550 mg/dl with reference to Hct 42% in Comparative Example 6. FIG. 57b is a graph showing the sensitivity difference (%) in each case of Hct values of 0%, 42%, and 70% with reference to Glu 45 mg/dl in Comparative Example 6. FIGS. 57a and 57b each are a graph showing the sensitivity difference in each case at 0 second to 1.0 second after the detection.

From Comparative Examples 4 to 6, when the voltage application time was changed to 1.0 second after the start of blood introduction and then the graphs showing the sensitivity difference were checked, it was found that the effect of the glucose concentration increased. Particularly, as in Comparative Example 4, when the voltage application time was 1 second, a divergence was seen in the graph of the sensitivity difference of Hct values of 0%, 42% and 70% particularly with reference to Glu 550 mg/dl as shown in FIG. 55b.

Example 33

A voltage of 1.5 V was applied between the electrode A and the electrode B for 0.1 second from 0.05 second to 0.15 second after detection of the introduction of a blood sample (see FIG. 19(b)). The current flowing between the working electrode and the counter electrode of each sensor 1 was measured, and the response current value and the sensitivity difference were measured in the measurement of the Hct value (see FIGS. 58a to 58d). FIG. 58a is a graph showing the change with time in the response current value relative to the applied voltage with respect to each blood sample with a Glu concentration of 45 mg/dl (Hct value: 0%, 42%, and 70%) in Example 33. FIG. 58b is a graph showing the change with time in the response current value relative to the applied voltage with respect to each blood sample with a Glu concentration of 550 mg/dl (Hct value: 0%, 42%, and 70%) in Example 33. FIGS. 58a and 58b each are a graph showing the change with time in the response current value relative to the applied voltage in the case of applying a voltage of 1.5 V for 5 seconds between the electrode A and the electrode B that have the reagent disposed thereon. FIG. 58c is a graph showing the sensitivity difference (%) in each case of Glu values of 45 mg/dl and 550 mg/dl with reference to Hct 42% in Example 33. FIG. 58d is a graph showing the sensitivity difference (%) in each case of Hct values of 0%, 42%, and 70% with reference to Glu 45 mg/dl in Example 33. FIGS. 58c and 58d each are a graph showing the sensitivity difference in each case at 0.05 second to 0.15 second after the detection.

Example 34

The procedure was carried out in the same manner as in Example 33 except that a voltage of 1.6 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 59a to 59d). FIG. 59a is a graph showing the change with time in the response current value relative to the applied voltage with respect to each blood sample with a Glu concentration of 45 mg/dl (Hct value: 0%, 42%, and 70%) in Example 34. FIG. 59b is a graph showing the change with time in the response current value relative to the applied voltage with respect to each blood sample with a Glu concentration of 550 mg/dl (Hct value: 0%, 42%, and 70%) in Example 34. FIGS. 59*a* and 59*b* each are a graph showing the change with time in the response current value relative to the applied voltage in the case of applying a voltage of 1.6 V for 5 seconds between the electrode A and the electrode B that have the reagent disposed thereon. FIG. 59*c* is a graph showing the sensitivity difference (%) in each case of Glu values of 45 mg/dl and 550 mg/dl with reference to Hct 42% in Example 34. FIG. 59*d* is a graph showing the sensitivity difference (%) in each case of Hct values of 0%, 42%, and 70% with reference to Glu 45 mg/dl in Example 34. FIGS. 59*c* and 59*d* each are a graph showing the sensitivity difference in each case at 0.05 second to 0.15 second after the detection.

Example 35

The procedure was carried out in the same manner as in Example 33 except that a voltage of 1.7 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 60*a* to 60*d*). FIG. 60*a* is a graph showing the change with time in the response current value relative to the applied voltage with respect to each blood sample with a Glu concentration of 45 mg/dl (Hct value: 0%, 42%, and 70%) in Example 35. FIG. 60*b* is a graph showing the change with time in the response current value relative to the applied voltage with respect to each blood sample with a Glu concentration of 550 mg/dl (Hct value: 0%, 42%, and 70%) in Example 35. FIGS. 60*a* and 60*b* each are a graph showing the change with time in the response current value relative to the applied voltage in the case of applying a voltage of 1.7 V for 5 seconds between the electrode A and the electrode B that have the reagent disposed thereon. FIG. 60*c* is a graph showing the sensitivity difference (%) in each case of Glu values of 45 mg/dl and 550 mg/dl with reference to Hct 42% in Example 35. FIG. 60*d* is a graph showing the sensitivity difference (%) in each case of Hct values of 0%, 42%, and 70% with reference to Glu 45 mg/dl in Example 35. FIGS. 60*c* and 60*d* each are a graph showing the sensitivity difference in each case at 0.05 second to 0.15 second after the detection.

Example 36

The procedure was carried out in the same manner as in Example 33 except that a voltage of 1.8 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 61*a* to 61*d*). FIG. 61*a* is a graph showing the change with time in the response current value relative to the applied voltage with respect to each blood sample with a Glu concentration of 45 mg/dl (Hct value: 0%, 42%, and 70%) in Example 36. FIG. 61*b* is a graph showing the change with time in the response current value relative to the applied voltage with respect to each blood sample with a Glu concentration of 550 mg/dl (Hct value: 0%, 42%, and 70%) in Example 36. FIGS. 61*a* and 61*b* each are a graph showing the change with time in the response current value relative to the applied voltage in the case of applying a voltage of 1.8 V for 5 seconds between the electrode A and the electrode B that have the reagent disposed thereon. FIG. 61*c* is a graph showing the sensitivity difference (%) in each case of Glu values of 45 mg/dl and 550 mg/dl with reference to Hct 42% in Example 36. FIG. 61*d* is a graph showing the sensitivity difference (%) in each case of Hct values of 0%, 42%, and 70% with reference to Glu 45 mg/dl in Example 36. FIGS. 61*c* and 61*d* each are a graph showing the sensitivity difference in each case at 0.05 second to 0.15 second after the detection.

Example 37

The procedure was carried out in the same manner as in Example 33 except that a voltage of 1.9 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 62*a* to 62*d*). FIG. 62*a* is a graph showing the change with time in the response current value relative to the applied voltage with respect to each blood sample with a Glu concentration of 45 mg/dl (Hct value: 0%, 42%, and 70%) in Example 37. FIG. 62*b* is a graph showing the change with time in the response current value relative to the applied voltage with respect to each blood sample with a Glu concentration of 550 mg/dl (Hct value: 0%, 42%, and 70%) in Example 37. FIGS. 62*a* and 62*b* each are a graph showing the change with time in the response current value relative to the applied voltage in the case of applying a voltage of 1.9 V for 5 seconds between the electrode A and the electrode B that have the reagent disposed thereon. FIG. 62*c* is a graph showing the sensitivity difference (%) in each case of Glu values of 45 mg/dl and 550 mg/dl with reference to Hct 42% in Example 37. FIG. 62*d* is a graph showing the sensitivity difference (%) in each case of Hct values of 0%, 42%, and 70% with reference to Glu 45 mg/dl in Example 37. FIGS. 62*c* and 62*d* each are a graph showing the sensitivity difference in each case at 0.05 second to 0.15 second after the detection.

Example 38

The procedure was carried out in the same manner as in Example 33 except that a voltage of 2.0 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 63*a* to 63*d*). FIG. 63*a* is a graph showing the change with time in the response current value relative to the applied voltage with respect to each blood sample with a Glu concentration of 45 mg/dl (Hct value: 0%, 42%, and 70%) in Example 38. FIG. 63*b* is a graph showing the change with time in the response current value relative to the applied voltage with respect to each blood sample with a Glu concentration of 550 mg/dl (Hct value: 0%, 42%, and 70%) in Example 38. FIGS. 63*a* and 63*b* each are a graph showing the change with time in the response current value relative to the applied voltage in the case of applying a voltage of 2.0 V for 5 seconds between the electrode A and the electrode B that have the reagent disposed thereon. FIG. 63*c* is a graph showing the sensitivity difference (%) in each case of Glu values of 45 mg/dl and 550 mg/dl with reference to Hct 42% in Example 38. FIG. 63*d* is a graph showing the sensitivity difference (%) in each case of Hct values of 0%, 42%, and 70% with reference to Glu 45 mg/dl in Example 38. FIGS. 63*c* and 63*d* each are a graph showing the sensitivity difference in each case at 0.05 second to 0.15 second after the detection.

Example 39

The procedure was carried out in the same manner as in Example 33 except that a voltage of 2.5 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 64*a* to 64*d*). FIG. 64*a* is a graph showing the change with time in the response current value relative to the applied voltage with respect to each blood sample with a Glu concentration of 45 mg/dl (Hct value: 0%, 42%, and 70%) in Example 39. FIG. 64*b* is a graph showing the change with time in the response current value relative to the applied voltage with respect to each blood sample with a Glu concentration of 550 mg/dl (Hct value: 0%, 42%, and 70%) in Example 39. FIGS. 64*a* and 64*b* each are a graph showing the change with time in the response current value relative to the applied voltage in the case of applying a voltage of 2.5 V for 5 seconds between the electrode A and the electrode B that have the reagent disposed thereon. FIG. 64*c* is a graph showing the sensitivity difference (%) in each case of Glu values of 45 mg/dl and 550 mg/dl with reference to Hct 42% in Example 39. FIG. 64*d* is a graph showing the sensitivity difference (%) in each case of Hct values of 0%, 42%, and 70% with reference to Glu 45 mg/dl in Example 39. FIGS. 64*c* and 64*d* each are a graph showing the sensitivity difference in each case at 0.05 second to 0.15 second after the detection.

Example 40

The procedure was carried out in the same manner as in Example 33 except that a voltage of 3.0 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 65*a* to 65*d*). FIG. 65*a* is a graph showing the change with time in the response current value relative to the applied voltage with respect to each blood sample with a Glu concentration of 45 mg/dl (Hct value: 0%, 42%, and 70%) in Example 40. FIG. 65*b* is a graph showing the change with time in the response current value relative to the applied voltage with respect to each blood sample with a Glu concentration of 550 mg/dl (Hct value: 0%, 42%, and 70%) in Example 40. FIGS. 65*a* and 65*b* each are a graph showing the change with time in the response current value relative to the applied voltage in the case of applying a voltage of 3.0 V for 5 seconds between the electrode A and the electrode B that have the reagent disposed thereon. FIG. 65*c* is a graph showing the sensitivity difference (%) in each case of Glu values of 45 mg/dl and 550 mg/dl with reference to Hct 42% in Example 40. FIG. 65*d* is a graph showing the sensitivity difference (%) in each case of Hct values of 0%, 42%, and 70% with reference to Glu 45 mg/dl in Example 40. FIGS. 65*c* and 65*d* each are a graph showing the sensitivity difference in each case at 0.05 second to 0.15 second after the detection.

Example 41

The procedure was carried out in the same manner as in Example 33 except that a voltage of 3.5 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 66*a* to 66*d*). FIG. 66*a* is a graph showing the change with time in the response current value relative to the applied voltage with respect to each blood sample with a Glu concentration of 45 mg/dl (Hct value: 0%, 42%, and 70%) in Example 41. FIG. 66*b* is a graph showing the change with time in the response current value relative to the applied voltage with respect to each blood sample with a Glu concentration of 550 mg/dl (Hct value: 0%, 42%, and 70%) in Example 41. FIGS. 66*a* and 66*b* each are a graph showing the change with time in the response current value relative to the applied voltage in the case of applying a voltage of 3.5 V for 5 seconds between the electrode A and the electrode B that have the reagent disposed thereon. FIG. 66*c* is a graph showing the sensitivity difference (%) in each case of Glu values of 45 mg/dl and 550 mg/dl with reference to Hct 42% in Example 41. FIG. 66*d* is a graph showing the sensitivity difference (%) in each case of Hct values of 0%, 42%, and 70% with reference to Glu 45 mg/dl in Example 41. FIGS. 66*c* and 66*d* each are a graph showing the sensitivity difference in each case at 0.05 second to 0.15 second after the detection.

Example 42

The procedure was carried out in the same manner as in Example 33 except that a voltage of 4.0 V was applied between the electrode A and the electrode B for 0.1 second from 0.05 second to 0.15 second after detection of the introduction of a blood sample. The current flowing between the working electrode and the counter electrode of each sensor 1 was measured, and the response current value and the sensitivity difference were measured in the measurement of the Hct value (see FIGS. 67*a* to 67*d*). FIG. 67*a* is a graph showing the change with time in the response current value relative to the applied voltage with respect to each blood sample with a Glu concentration of 45 mg/dl (Hct value: 0%, 42%, and 70%) in Example 42. FIG. 67*b* is a graph showing the change with time in the response current value relative to the applied voltage with respect to each blood sample with a Glu concentration of 550 mg/dl (Hct value: 0%, 42%, and 70%) in Example 42. FIGS. 67*a* and 67*b* each are a graph showing the change with time in the response current value relative to the applied voltage in the case of applying a voltage of 4.0 V for 5 seconds between the electrode A and the electrode B that have the reagent disposed thereon. FIG. 67*c* is a graph showing the sensitivity difference (%) in each case of Glu values of 45 mg/dl and 550 mg/dl with reference to Hct 42% in Example 42. FIG. 67*d* is a graph showing the sensitivity difference (%) in each case of Hct values of 0%, 42%, and 70% with reference to Glu 45 mg/dl in Example 42. FIGS. 67*c* and 67*d* each are a graph showing the sensitivity difference in each case at 0.05 second to 0.15 second after the detection.

From Examples 33 to 42, it was confirmed that when a voltage of 1.5 to 4.0 V was applied to the working electrode and the counter electrode for 0.05 second to 0.15 second after detection of the introduction of a biological sample, the current value obtained thereby had a high sensitivity and the Hct value obtained based on the current value had a high accuracy.

Example 43

A voltage of 1.5 V was applied between the electrode A and the electrode B for 0.5 second from 0.05 second to 0.55 second after detection of the introduction of a blood sample (see FIG. 19(*b*)). The current flowing between the working electrode and the counter electrode of each sensor 1 was measured, and the response current value and the sensitivity difference were measured in the measurement of the Hct value (see FIGS. 68*a* and 68*b*). FIG. 68*a* is a graph showing the sensitivity difference (%) in each case of Glu values of 45 mg/dl and 550 mg/dl with reference to Hct 42% in Example 43. FIG. 68*b* is a graph showing the sensitivity difference (%) in each case of Hct values of 0%, 42%, and 70% with reference to Glu 45 mg/dl in Example 43. FIGS. 68*a* and 68*b* each are a graph showing the sensitivity difference in each case at 0.05 second to 0.55 second after the detection.

Example 44

The procedure was carried out in the same manner as in Example 43 except that a voltage of 1.6 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 69*a* and 69*b*). FIG. 69*a* is a graph showing the sensitivity difference (%) in each case of Glu values of 45 mg/dl and 550 mg/dl with reference to Hct 42% in Example 44. FIG. 69*b* is a graph showing the sensitivity difference (%) in each case of Hct values of 0%, 42%, and 70% with reference to Glu 45 mg/dl in Example 44. FIGS. 69*a* and 69*b* each are a graph showing the sensitivity difference in each case at 0.05 second to 0.55 second after the detection.

Example 45

The procedure was carried out in the same manner as in Example 43 except that a voltage of 1.7 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 70*a* and 70*b*). FIG. 70*a* is a graph showing the sensitivity difference (%) in each case of Glu values of 45 mg/dl and 550 mg/dl with reference to Hct 42% in Example 45. FIG. 70*b* is a graph showing the sensitivity difference (%) in each case of Hct values of 0%, 42%, and 70% with reference to Glu 45 mg/dl in Example 45. FIGS. 70*a* and 70*b* each are a graph showing the sensitivity difference in each case at 0.05 second to 0.55 second after the detection.

Example 46

The procedure was carried out in the same manner as in Example 43 except that a voltage of 1.8 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 71*a* and 71*b*). FIG. 71*a* is a graph showing the sensitivity difference (%) in each case of Glu values of 45 mg/dl and 550 mg/dl with reference to Hct 42% in Example 46. FIG. 71*b* is a graph showing the sensitivity difference (%) in each case of Hct values of 0%, 42%, and 70% with reference to Glu 45 mg/dl in Example 46. FIGS. 71*a* and 71*b* each are a graph showing the sensitivity difference in each case at 0.05 second to 0.55 second after the detection.

Example 47

The procedure was carried out in the same manner as in Example 43 except that a voltage of 1.9 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 72*a* and 72*b*). FIG. 72*a* is a graph showing the sensitivity difference (%) in each case of Glu values of 45 mg/dl and 550 mg/dl with reference to Hct 42% in Example 47. FIG. 72*b* is a graph showing the sensitivity difference (%) in each case of Hct values of 0%, 42%, and 70% with reference to Glu 45 mg/dl in Example 47. FIGS. 72*a* and 72*b* each are a graph showing the sensitivity difference in each case at 0.05 second to 0.55 second after the detection.

Example 48

The procedure was carried out in the same manner as in Example 43 except that a voltage of 2.0 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 73*a* and 73*b*). FIG. 73*a* is a graph showing the sensitivity difference (%) in each case of Glu values of 45 mg/dl and 550 mg/dl with reference to Hct 42% in Example 48. FIG. 73*b* is a graph showing the sensitivity difference (%) in each case of Hct values of 0%, 42%, and 70% with reference to Glu 45 mg/dl in Example 48. FIGS. 73*a* and 73*b* each are a graph showing the sensitivity difference in each case at 0.05 second to 0.55 second after the detection.

Example 49

The procedure was carried out in the same manner as in Example 43 except that a voltage of 2.5 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 74*a* and 74*b*). FIG. 74*a* is a graph showing the sensitivity difference (%) in each case of Glu values of 45 mg/dl and 550 mg/dl with reference to Hct 42% in Example 49. FIG. 74*b* is a graph showing the sensitivity difference (%) in each case of Hct values of 0%, 42%, and 70% with reference to Glu 45 mg/dl in Example 49. FIGS. 74*a* and 74*b* each are a graph showing the sensitivity difference in each case at 0.05 second to 0.55 second after the detection.

Example 50

The procedure was carried out in the same manner as in Example 43 except that a voltage of 3.0 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 75*a* and 75*b*). FIG. 75*a* is a graph showing the sensitivity difference (%) in each case of Glu values of 45 mg/dl and 550 mg/dl with reference to Hct 42% in Example 50. FIG. 75*b* is a graph showing the sensitivity difference (%) in each case of Hct values of 0%, 42%, and 70% with reference to Glu 45 mg/dl in Example 50. FIGS. 75*a* and 75*b* each are a graph showing the sensitivity difference in each case at 0.05 second to 0.55 second after the detection.

Example 51

The procedure was carried out in the same manner as in Example 43 except that a voltage of 3.5 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 76*a* and 76*b*). FIG. 76*a* is a graph showing the sensitivity difference (%) in each case of Glu values of 45 mg/dl and 550 mg/dl with reference to Hct 42% in Example 51. FIG. 76*b* is a graph showing the sensitivity difference (%) in each case of Hct values of 0%, 42%, and 70% with reference to Glu 45 mg/dl in Example 51. FIGS. 76*a* and 76*b* each are a graph showing the sensitivity difference in each case at 0.05 second to 0.55 second after the detection.

Example 52

The procedure was carried out in the same manner as in Example 43 except that a voltage of 4.0 V was applied between the electrode A and the electrode B for 0.5 second from 0.05 second to 0.55 second after detection of the introduction of a blood sample. The current flowing between the working electrode and the counter electrode of each sensor 1 was measured, and the response current value and the sensitivity difference were measured in the measurement of the Hct value (see FIGS. 77*a* and 77*b*). FIG. 77*a* is a graph showing the sensitivity difference (%) in each case of Glu values of 45 mg/dl and 550 mg/dl with reference to Hct 42% in Example 52. FIG. 77*b* is a graph showing the sensitivity difference (%) in each case of Hct values of 0%, 42%, and 70% with reference to Glu 45 mg/dl in Example 52. FIGS. 77*a* and 77*b* each are a graph showing the sensitivity difference in each case at 0.05 second to 0.55 second after the detection.

From Examples 43 to 52, it was confirmed that when a voltage of 1.5 to 4.0 V was applied to the working electrode and the counter electrode for 0.5 second at 0.05 second after detection of the introduction of a biological sample, the current value obtained thereby had a high sensitivity, and the Hct value obtained based on the current value had a high accuracy.

Comparative Example 7

A voltage of 2.5 V was applied between the electrode A and the electrode B for 1.0 second from 0.05 second to 1.05 seconds after detection of the introduction of a blood sample (see FIG. 19(*b*)). The current flowing between the working electrode and the counter electrode of each sensor 1 was measured, and the response current value and the sensitivity difference were measured in the measurement of the Hct value (see FIGS. 78*a* and 78*b*). FIG. 78*a* is a graph showing the sensitivity difference (%) in each case of Glu values of 45 mg/dl and 550 mg/dl with reference to Hct 42% in Comparative Example 7. FIG. 78*b* is a graph showing the sensitivity difference (%) in each case of Hct values of 0%, 42%, and 70% with reference to Glu 45 mg/dl in Comparative Example 7. FIGS. 78*a* and 78*b* each are a graph showing the sensitivity difference in each case at 0.05 second to 1.05 seconds after the detection.

Comparative Example 8

The procedure was carried out in the same manner as in Comparative Example 7 except that a voltage of 3.0 V was applied between the electrode A and the electrode B for 1.0 second from 0.05 second to 1.05 seconds after detection of the introduction of a blood sample. The current flowing between the working electrode and the counter electrode of each sensor 1 was measured, and the response current value and the sensitivity difference were measured in the measurement of the Hct value (see FIGS. 79*a* and 79*b*). FIG. 79*a* is a graph showing the sensitivity difference (%) in each case of Glu values of 45 mg/dl and 550 mg/dl with reference to Hct 42% in Comparative Example 8. FIG. 79*b* is a graph showing the sensitivity difference (%) in each case of Hct values of 0%, 42%, and 70% with reference to Glu 45 mg/dl in Comparative Example 8. FIGS. 79*a* and 79*b* each are a graph showing the sensitivity difference in each case at 0.05 second to 1.05 seconds after the detection.

From Comparative Examples 7 and 8, the voltage application time after the start of blood introduction was changed to 1 second and the graph showing the sensitivity difference was checked. As a result, it was found that the effect of the glucose concentration gradually increased as the time increased. Particularly, when the voltage application time was 1 second as in Comparative Example 7, a divergence was seen in the graph showing the sensitivity difference in each case of Hct values of 0%, 42%, and 70% particularly with reference to Glu 550 mg/dl as shown in FIG. 78*b*.

According to the method of the present invention, the sensitivity difference (%) in Examples 33 to 52 in which the applied voltage was 1.5 V to 2.0 V was small as compared with Comparative Examples 7 and 8. Therefore, it was confirmed that the Hct measurement accuracy was improved. Furthermore, it was also confirmed that Hct can be measured in a short time according to these methods of the present invention.

Furthermore, it was confirmed that an effect similar to that described above was obtained in Examples 39 to 42 and Examples 49 to 52 if the voltage application time was less than 1.0 second also at an applied voltage of 2.5 V to 4.0 V.

Example 53

A biosensor (first biosensor) was produced in the same manner as in Example 1 except that the plan view of FIG. 4 was followed instead of the plan view of FIG. 3. A voltage of 1.5 V was applied between the electrode A and the electrode B for 0.1 second from 0 second to 0.1 second after detection of the introduction of a blood sample (see FIG. 80(a)). Next, a voltage of 0.1 to 1.0 V was applied multiple times between the electrode A and the electrode B from 0.1 second to 7.0 seconds after the detection of the introduction of a blood sample (see FIG. 80(a), voltage application for Glu). Finally, then, a voltage of 2.5 V was applied between the electrode C and the electrode A from 7.1 seconds to 7.5 seconds after the detection of the introduction of a blood sample (see FIG. 80(a), voltage application for the second Hct). The current flowing between the working electrode and the counter electrode of each sensor 1 was measured, and the response current value and the sensitivity difference were measured in the measurement of the Hct value. FIG. 81a is a graph showing the sensitivity difference (%) in each case of Glu values of 45 mg/dl and 550 mg/dl with reference to Hct 42% in Example 53. FIG. 81b is a graph showing the sensitivity difference (%) in each case of Hct values of 0%, 42%, and 70% with reference to Glu 45 mg/dl in Example 53. FIGS. 81a and 81b each are a graph showing the sensitivity difference in each case at 0 second to 0.1 second after the detection.

Example 54

The procedure was carried out in the same manner as in Example 53 except that a voltage of 1.5 V was applied between the electrode A and the electrode B for 0.2 second from 0 second to 0.2 second after detection of the introduction of a blood sample, then a voltage of 0.1 to 1.0 V was applied multiple times between the electrode A and the electrode B from 0.2 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 82a and 82b). FIG. 82a is a graph showing the sensitivity difference (%) in each case of Glu values of 45 mg/dl and 550 mg/dl with reference to Hct 42% in Example 54. FIG. 82b is a graph showing the sensitivity difference (%) in each case of Hct values of 0%, 42%, and 70% with reference to Glu 45 mg/dl in Example 54. FIGS. 82a and 82b each are a graph showing the sensitivity difference in each case at 0 second to 0.2 second after the detection.

Example 55

The procedure was carried out in the same manner as in Example 53 except that a voltage of 1.5 V was applied between the electrode A and the electrode B for 0.3 second from 0 second to 0.3 second after detection of the introduction of a blood sample, then a voltage of 0.1 to 1.0 V was applied multiple times between the electrode A and the electrode B from 0.3 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 83a and 83b). FIG. 83a is a graph showing the sensitivity difference (%) in each case of Glu values of 45 mg/dl and 550 mg/dl with reference to Hct 42% in Example 55. FIG. 83b is a graph showing the sensitivity difference (%) in each case of Hct values of 0%, 42%, and 70% with reference to Glu 45 mg/dl in Example 55. FIGS. 83a and 83b each are a graph showing the sensitivity difference in each case at 0 second to 0.3 second after the detection.

Example 56

The procedure was carried out in the same manner as in Example 53 except that a voltage of 1.5 V was applied between the electrode A and the electrode B for 0.4 second from 0 second to 0.4 second after detection of the introduction of a blood sample, then a voltage of 0.1 to 1.0 V was applied multiple times between the electrode A and the electrode B from 0.4 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 84a and 84b). FIG. 84a is a graph showing the sensitivity difference (%) in each case of Glu values of 45 mg/dl and 550 mg/dl with reference to Hct 42% in Example 56. FIG. 84b is a graph showing the sensitivity difference (%) in each case of Hct values of 0%, 42%, and 70% with reference to Glu 45 mg/dl in Example 56. FIGS. 84a and 84b each are a graph showing the sensitivity difference in each case at 0 second to 0.4 second after the detection.

Example 57

The procedure was carried out in the same manner as in Example 53 except that a voltage of 1.5 V was applied between the electrode A and the electrode B for 0.5 second from 0 second to 0.5 second after detection of the introduction of a blood sample, then a voltage of 0.1 to 1.0 V was applied multiple times between the electrode A and the electrode B from 0.5 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 85a and 85b). FIG. 85a is a graph showing the sensitivity difference (%) in each case of Glu values of 45 mg/dl and 550 mg/dl with reference to Hct 42% in Example 57. FIG. 85(b) is a graph showing the sensitivity difference (%) in each case of Hct values of 0%, 42%, and 70% with reference to Glu 45 mg/dl in Example 57. FIGS. 85a and 85b each are a graph showing the sensitivity difference in each case at 0 second to 0.5 second after the detection.

Example 58

The procedure was carried out in the same manner as in Example 53 except that a voltage of 1.5 V was applied between the electrode A and the electrode B for 0.6 second from 0 second to 0.6 second after detection of the introduction of a blood sample, then a voltage of 0.1 to 1.0 V was applied multiple times between the electrode A and the electrode B from 0.6 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 86a and 86b). FIG. 86a is a graph showing the sensitivity difference (%) in each case of Glu values of 45 mg/dl and 550 mg/dl with reference to Hct 42% in Example 58. FIG. 86b is a graph showing the sensitivity difference (%) in each case of Hct values of 0%, 42%, and 70% with reference to Glu 45 mg/dl in Example 58. FIGS. 86a and 86b each are a graph showing the sensitivity difference in each case at 0 second to 0.6 second after the detection.

Example 59

The procedure was carried out in the same manner as in Example 53 except that a voltage of 1.5 V was applied between the electrode A and the electrode B for 0.7 second from 0 second to 0.7 second after detection of the introduction of a blood sample, then a voltage of 0.1 to 1.0 V was applied multiple times between the electrode A and the electrode B from 0.7 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 87a and 87b). FIG. 87a is a graph showing the sensitivity difference (%) in each case of Glu values of 45 mg/dl and 550 mg/dl with reference to Hct 42% in Example 59. FIG. 87b is a graph showing the sensitivity difference (%) in each case of Hct values of 0%, 42%, and 70% with reference to Glu 45 mg/dl in Example 59. FIGS. 87a and 87b each are a graph showing the sensitivity difference in each case at 0 second to 0.7 second after the detection.

From Examples 53 to 59, it was confirmed that when a voltage of 1.5 V was applied to the working electrode and the counter electrode for 0.1 to 0.7 second immediately (0 second) after detection of the introduction of a biological sample, the current value obtained thereby had a high sensitivity, and the Hct value and the Glu value obtained based on the current value had a high accuracy.

Example 60

The procedure was carried out in the same manner as in Example 53 except that a voltage of 2.0 V was applied between the electrode A and the electrode B for 0.1 second from 0 second to 0.1 second after detection of the introduction of a blood sample, then a voltage of 0.1 to 1.0 V was applied multiple times between the electrode A and the electrode B from 0.1 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 88a and 88b). FIG. 88a is a graph showing the sensitivity difference (%) in each case of Glu values of 45 mg/dl and 550 mg/dl with reference to Hct 42% in Example 60. FIG. 88b is a graph showing the sensitivity difference (%) in each case of Hct values of 0%, 42%, and 70% with reference to Glu 45 mg/dl in Example 60. FIGS. 88a and 88b each are a graph showing the sensitivity difference in each case at 0 second to 0.1 second after the detection.

Example 61

The procedure was carried out in the same manner as in Example 60 except that a voltage of 2.0 V was applied between the electrode A and the electrode B for 0.2 second from 0 second to 0.2 second after detection of the introduction of a blood sample, then a voltage of 0.1 to 1.0 V was applied multiple times between the electrode A and the electrode B from 0.2 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 89a and 89b). FIG. 89a is a graph showing the sensitivity difference (%) in each case of Glu values of 45 mg/dl and 550 mg/dl with reference to Hct 42% in Example 61. FIG. 89b is a graph showing the sensitivity difference (%) in each case of Hct values of 0%, 42%, and 70% with reference to Glu 45 mg/dl in Example 61. FIGS. 89a and 89b each are a graph showing the sensitivity difference in each case at 0 second to 0.2 second after the detection.

Example 62

The procedure was carried out in the same manner as in Example 60 except that a voltage of 2.0 V was applied between the electrode A and the electrode B for 0.3 second from 0 second to 0.3 second after detection of the introduction of a blood sample, then a voltage of 0.1 to 1.0 V was applied multiple times between the electrode A and the electrode B from 0.3 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 90a and 90b). FIG. 90a is a graph showing the sensitivity difference (%) in each case of Glu values of 45 mg/dl and 550 mg/dl with reference to Hct 42% in Example 62. FIG. 90*b* is a graph showing the sensitivity difference (%) in each case of Hct values of 0%, 42%, and 70% with reference to Glu 45 mg/dl in Example 62. FIGS. 90*a* and 90*b* each are a graph showing the sensitivity difference in each case at 0 second to 0.3 second after the detection.

Example 63

The procedure was carried out in the same manner as in Example 60 except that a voltage of 2.0 V was applied between the electrode A and the electrode B for 0.4 second from 0 second to 0.4 second after detection of the introduction of a blood sample, then a voltage of 0.1 to 1.0 V was applied multiple times between the electrode A and the electrode B from 0.4 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 91*a* and 91*b*). FIG. 91*a* is a graph showing the sensitivity difference (%) in each case of Glu values of 45 mg/dl and 550 mg/dl with reference to Hct 42% in Example 63. FIG. 91*b* is a graph showing the sensitivity difference (%) in each case of Hct values of 0%, 42%, and 70% with reference to Glu 45 mg/dl in Example 63. FIGS. 91*a* and 91*b* each are a graph showing the sensitivity difference in each case at 0 second to 0.4 second after the detection.

Example 64

The procedure was carried out in the same manner as in Example 60 except that a voltage of 2.0 V was applied between the electrode A and the electrode B for 0.5 second from 0 second to 0.5 second after detection of the introduction of a blood sample, then a voltage of 0.1 to 1.0 V was applied multiple times between the electrode A and the electrode B from 0.5 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 92*a* and 92*b*). FIG. 92*a* is a graph showing the sensitivity difference (%) in each case of Glu values of 45 mg/dl and 550 mg/dl with reference to Hct 42% in Example 64. FIG. 92*b* is a graph showing the sensitivity difference (%) in each case of Hct values of 0%, 42%, and 70% with reference to Glu 45 mg/dl in Example 64. FIGS. 92*a* and 92*b* each are a graph showing the sensitivity difference in each case at 0 second to 0.5 second after the detection.

Example 65

The procedure was carried out in the same manner as in Example 60 except that a voltage of 2.0 V was applied between the electrode A and the electrode B for 0.6 second from 0 second to 0.6 second after detection of the introduction of a blood sample, then a voltage of 0.1 to 1.0 V was applied multiple times between the electrode A and the electrode B from 0.6 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 93*a* and 93*b*). FIG. 93*a* is a graph showing the sensitivity difference (%) in each case of Glu values of 45 mg/dl and 550 mg/dl with reference to Hct 42% in Example 65. B FIG. 93*b* is a graph showing the sensitivity difference (%) in each case of Hct values of 0%, 42%, and 70% with reference to Glu 45 mg/dl in Example 65. FIGS. 93*a* and 93*b* each are a graph showing the sensitivity difference in each case at 0 second to 0.6 second after the detection.

Example 66

The procedure was carried out in the same manner as in Example 60 except that a voltage of 2.0 V was applied between the electrode A and the electrode B for 0.7 second from 0 second to 0.7 second after detection of the introduction of a blood sample, then a voltage of 0.1 to 1.0 V was applied multiple times between the electrode A and the electrode B from 0.7 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 94*a* and 94*b*). FIG. 94*a* is a graph showing the sensitivity difference (%) in each case of Glu values of 45 mg/dl and 550 mg/dl with reference to Hct 42% in Example 66. FIG. 94*b* is a graph showing the sensitivity difference (%) in each case of Hct values of 0%, 42%, and 70% with reference to Glu 45 mg/dl in Example 66. FIGS. 94*a* and 94*b* each are a graph showing the sensitivity difference in each case at 0 second to 0.7 second after the detection.

Comparative Example 9

The procedure was carried out in the same manner as in Example 60 except that a voltage of 2.0 V was applied between the electrode A and the electrode B for 0.8 second from 0 second to 0.8 second after detection of the introduction of a blood sample, then a voltage of 0.1 to 1.0 V was applied multiple times between the electrode A and the electrode B from 0.8 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 95*a* and 95*b*). FIG. 95*a* is a graph showing the sensitivity difference (%) in each case of Glu values of 45 mg/dl and 550 mg/dl with reference to Hct 42% in Comparative Example 9. FIG. 95*b* is a graph showing the sensitivity difference (%) in each case of Hct values of 0%, 42%, and 70% with reference to Glu 45 mg/dl in Comparative Example 9. FIGS. 95*a* and 95*b* each are a graph showing the sensitivity difference in each case at 0 second to 0.8 second after the detection.

Comparative Example 10

The procedure was carried out in the same manner as in Example 60 except that a voltage of 2.0 V was applied between the electrode A and the electrode B for 0.9 second from 0 second to 0.9 second after detection of the introduction of a blood sample, then a voltage of 0.1 to 1.0 V was applied multiple times between the electrode A and the electrode B from 0.9 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 96a and 96b). FIG. 96a is a graph showing the sensitivity difference (%) in each case of Glu values of 45 mg/dl and 550 mg/dl with reference to Hct 42% in Comparative Example 10. FIG. 96b is a graph showing the sensitivity difference (%) in each case of Hct values of 0%, 42%, and 70% with reference to Glu 45 mg/dl in Comparative Example 10. FIGS. 96a and 96b each are a graph showing the sensitivity difference in each case at 0 second to 0.9 second after the detection.

Comparative Example 11

The procedure was carried out in the same manner as in Example 78 except that a voltage of 2.0 V was applied between the electrode A and the electrode B for 1.0 second from 0 second to 1.0 second after detection of the introduction of a blood sample, then a voltage of 0.1 to 1.0 V was applied multiple times between the electrode A and the electrode B from 1.0 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 97a and 97b). FIG. 97a is a graph showing the sensitivity difference (%) in each case of Glu values of 45 mg/dl and 550 mg/dl with reference to Hct 42% in Comparative Example 11. FIG. 97b is a graph showing the sensitivity difference (%) in each case of Hct values of 0%, 42%, and 70% with reference to Glu 45 mg/dl in Comparative Example 11. FIGS. 97a and 97b each are a graph showing the sensitivity difference in each case at 0 second to 1.0 second after the detection.

From Examples 60 to 66 and Comparative Examples 9 to 11, it was confirmed that when a voltage of 2.0 V was applied to the working electrode and the counter electrode for 0.1 to 0.7 second immediately (0 second) after detection of the introduction of a biological sample, the current value obtained thereby had a high sensitivity, and the Hct value and the Glu value obtained based on the current value had a high accuracy.

Example 67

The procedure was carried out in the same manner as in Example 53 except that a voltage of 2.5 V was applied between the electrode A and the electrode B for 0.1 second from 0 second to 0.1 second after detection of the introduction of a blood sample, then a voltage of 0.1 to 1.0 V was applied multiple times between the electrode A and the electrode B from 0.1 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 98a and 98b). FIG. 98a is a graph showing the sensitivity difference (%) in each case of Glu values of 45 mg/dl and 550 mg/dl with reference to Hct 42% in Example 67. FIG. 98b is a graph showing the sensitivity difference (%) in each case of Hct values of 0%, 42%, and 70% with reference to Glu 45 mg/dl in Example 67. FIGS. 98a and 98b each are a graph showing the sensitivity difference in each case at 0 second to 0.1 second after the detection.

Example 68

The procedure was carried out in the same manner as in Example 67 except that a voltage of 2.5 V was applied between the electrode A and the electrode B for 0.2 second from 0 second to 0.2 second after detection of the introduction of a blood sample, then a voltage of 0.1 to 1.0 V was applied multiple times between the electrode A and the electrode B from 0.2 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 99a and 99b). FIG. 99a is a graph showing the sensitivity difference (%) in each case of Glu values of 45 mg/dl and 550 mg/dl with reference to Hct 42% in Example 68. FIG. 99b is a graph showing the sensitivity difference (%) in each case of Hct values of 0%, 42%, and 70% with reference to Glu 45 mg/dl in Example 68. FIGS. 99a and 99b each are a graph showing the sensitivity difference in each case at 0 second to 0.2 second after the detection.

Example 69

The procedure was carried out in the same manner as in Example 67 except that a voltage of 2.5 V was applied between the electrode A and the electrode B for 0.3 second from 0 second to 0.3 second after detection of the introduction of a blood sample, then a voltage of 0.1 to 1.0 V was applied multiple times between the electrode A and the electrode B from 0.3 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 100a and 100b). FIG. 100a is a graph showing the sensitivity difference (%) in each case of Glu values of 45 mg/dl and 550 mg/dl with reference to Hct 42% in Example 69. FIG. 100b is a graph showing the sensitivity difference (%) in each case of Hct values of 0%, 42%, and 70% with reference to Glu 45 mg/dl in Example 69. FIGS. 100a and 100b each are a graph showing the sensitivity difference in each case at 0 second to 0.3 second after the detection.

Example 70

The procedure was carried out in the same manner as in Example 67 except that a voltage of 2.5 V was applied between the electrode A and the electrode B for 0.4 second from 0 second to 0.4 second after detection of the introduction of a blood sample, then a voltage of 0.1 to 1.0 V was applied multiple times between the electrode A and the electrode B from 0.4 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 101a and 101b). FIG. 101a is a graph showing the sensitivity difference (%) in each case of Glu values of 45 mg/dl and 550 mg/dl with reference to Hct 42% in Example 70. FIG. 101b is a graph showing the sensitivity difference (%) in each case of Hct values of 0%, 42%, and 70% with reference to Glu 45 mg/dl in Example 70. FIGS. 101a and 101b each are a graph showing the sensitivity difference in each case at 0 second to 0.4 second after the detection.

Example 71

The procedure was carried out in the same manner as in Example 67 except that a voltage of 2.5 V was applied between the electrode A and the electrode B for 0.5 second from 0 second to 0.5 second after detection of the introduction of a blood sample, then a voltage of 0.1 to 1.0 V was applied multiple times between the electrode A and the electrode B from 0.5 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 102a and 102b). FIG. 102a is a graph showing the sensitivity difference (%) in each case of Glu values of 45 mg/dl and 550 mg/dl with reference to Hct 42% in Example 71. FIG. 102b is a graph showing the sensitivity difference (%) in each case of Hct values of 0%, 42%, and 70% with reference to Glu 45 mg/dl in Example 71. FIGS. 102a and 102b each are a graph showing the sensitivity difference in each case at 0 second to 0.5 second after the detection.

Example 72

The procedure was carried out in the same manner as in Example 67 except that a voltage of 2.5 V was applied between the electrode A and the electrode B for 0.6 second from 0 second to 0.6 second after detection of the introduction of a blood sample, then a voltage of 0.1 to 1.0 V was applied multiple times between the electrode A and the electrode B from 0.6 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 103a and 103b). FIG. 103a is a graph showing the sensitivity difference (%) in each case of Glu values of 45 mg/dl and 550 mg/dl with reference to Hct 42% in Example 72. FIG. 103b is a graph showing the sensitivity difference (%) in each case of Hct values of 0%, 42%, and 70% with reference to Glu 45 mg/dl in Example 72. FIGS. 103a and 103b each are a graph showing the sensitivity difference in each case at 0 second to 0.6 second after the detection.

Example 73

The procedure was carried out in the same manner as in Example 67 except that a voltage of 2.5 V was applied between the electrode A and the electrode B for 0.7 second from 0 second to 0.7 second after detection of the introduction of a blood sample, then a voltage of 0.1 to 1.0 V was applied multiple times between the electrode A and the electrode B from 0.7 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 104a and 104b). FIG. 104a is a graph showing the sensitivity difference (%) in each case of Glu values of 45 mg/dl and 550 mg/dl with reference to Hct 42% in Example 73. FIG. 104b is a graph showing the sensitivity difference (%) in each case of Hct values of 0%, 42%, and 70% with reference to Glu 45 mg/dl in Example 73. FIGS. 104a and 104b each are a graph showing the sensitivity difference in each case at 0 second to 0.7 second after the detection.

Comparative Example 12

The procedure was carried out in the same manner as in Example 67 except that a voltage of 2.5 V was applied between the electrode A and the electrode B for 0.9 second from 0 second to 0.9 second after detection of the introduction of a blood sample, then a voltage of 0.1 to 1.0 V was applied multiple times between the electrode A and the electrode B from 0.9 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 105a and 105b). FIG. 105a is a graph showing the change with time in the sensitivity difference (%) relative to the applied voltage with reference to Hct 42% in Comparative Example 12. FIG. 105b is a graph showing the change with time in the sensitivity difference (%) relative to the applied voltage with reference to Glu 45% in Comparative Example 12. FIGS.

105*a* and 105*b* each are a graph showing the sensitivity difference in each case at 0 second to 0.9 second after the detection.

Comparative Example 13

The procedure was carried out in the same manner as in Example 67 except that a voltage of 2.5 V was applied between the electrode A and the electrode B for 1.0 second from 0 second to 1.0 second after detection of the introduction of a blood sample, then a voltage of 0.1 to 1.0 V was applied multiple times between the electrode A and the electrode B from 1.0 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (FIGS. 106*a* and 106*b*). FIG. 106*a* is a graph showing the sensitivity difference (%) in each case of Glu values of 45 mg/dl and 550 mg/dl with reference to Hct 42% in Comparative Example 13. FIG. 106*b* is a graph showing the sensitivity difference (%) in each case of Hct values of 0%, 42%, and 70% with reference to Glu 45 mg/dl in Comparative Example 13. FIGS. 106*a* and 106*b* each are a graph showing the sensitivity difference in each case at 0 second to 1.0 second after the detection.

From Examples 67 to 73 and Comparative Examples 12 and 13, it was confirmed that when a voltage of 2.5 V was applied to the working electrode and the counter electrode for 0.1 to 0.7 second immediately (0 second) after detection of the introduction of a biological sample, the current value obtained thereby had a high sensitivity, and the Hct value and the Glu value obtained based on the current value had a high accuracy. After the start of blood introduction, the voltage application time was changed between 0.1 and 1.0 second and the graphs showing the sensitivity difference were checked. As a result, it was found that the effect of the glucose concentration gradually increased as the time increased. Particularly, when the voltage application time was 0.9 second as in Comparative Example 12, a divergence was seen in the graph showing the sensitivity difference in each case of Hct values of 0%, 42%, and 70% particularly with reference to Glu 550 mg/dl as shown in FIG. 105*b*.

Example 74

A biosensor (first biosensor) was produced in the same manner as in Example 1 except that the plan view of FIG. 4 was followed instead of the plan view of FIG. 3. A voltage of 1.5 V was applied between the electrode A and the electrode B for 0.1 second from 0.05 second to 0.15 second after detection of the introduction of a blood sample (see FIG. 80(*b*)). Next, a voltage of 0.1 to 1.0 V was applied multiple times from 0.15 second to 7.05 seconds after the detection of the introduction of a blood sample (see FIG. 80(*b*), voltage application for Glu). Finally, then, a voltage of 2.5 V was applied from 7.15 seconds to 7.55 seconds after the detection of the introduction of a blood sample (see FIG. 80(*b*), voltage application for the second Hct). The current flowing between the working electrode and the counter electrode of each sensor 1 was measured, and the response current value and the sensitivity difference were measured in the measurement of the Hct value. FIG. 107*a* is a graph showing the sensitivity difference (%) in each case of Glu values of 45 mg/dl and 550 mg/dl with reference to Hct 42% in Example 74. FIG. 107*b* is a graph showing the sensitivity difference (%) in each case of Hct values of 0%, 42%, and 70% with reference to Glu 45 mg/dl in Example 74. FIGS. 107*a* and 107*b* each are a graph showing the sensitivity difference in each case at 0.05 second to 0.15 second after the detection.

Example 75

The procedure was carried out in the same manner as in Example 74 except that a voltage of 1.5 V was applied between the electrode A and the electrode B for 0.2 second from 0.05 second to 0.25 second after detection of the introduction of a blood sample, then a voltage of 0.1 to 1.0 V was applied multiple times between the electrode A and the electrode B from 0.25 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 108*a* and 108*b*). FIG. 108*a* is a graph showing the sensitivity difference (%) in each case of Glu values of 45 mg/dl and 550 mg/dl with reference to Hct 42% in Example 75. FIG. 108*b* is a graph showing the sensitivity difference (%) in each case of Hct values of 0%, 42%, and 70% with reference to Glu 45 mg/dl in Example 75. FIGS. 108*a* and 108*b* each are a graph showing the sensitivity difference in each case at 0.05 second to 0.25 second after the detection.

Example 76

The procedure was carried out in the same manner as in Example 74 except that a voltage of 1.5 V was applied between the electrode A and the electrode B for 0.3 second from 0.05 second to 0.35 second after detection of the introduction of a blood sample, then a voltage of 0.1 to 1.0 V was applied multiple times between the electrode A and the electrode B from 0.3 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 109*a* and 109*b*). FIG. 109*a* is a graph showing the sensitivity difference (%) in each case of Glu values of 45 mg/dl and 550 mg/dl with reference to Hct 42% in Example 76. FIG. 109*b* is a graph showing the sensitivity difference (%) in each case of Hct values of 0%, 42%, and 70% with reference to Glu 45 mg/dl in Example 76. FIGS. 109*a* and 109*b* each are a graph showing the sensitivity difference in each case at 0.05 second to 0.35 second after the detection.

Example 77

The procedure was carried out in the same manner as in Example 74 except that a voltage of 1.5 V was applied between the electrode A and the electrode B for 0.4 second from 0.05 second to 0.45 second after detection of the introduction of a blood sample, then a voltage of 0.1 to 1.0

V was applied multiple times between the electrode A and the electrode B from 0.45 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 110a and 110b). FIG. 110a is a graph showing the sensitivity difference (%) in each case of Glu values of 45 mg/dl and 550 mg/dl with reference to Hct 42% in Example 77. FIG. 110b is a graph showing the sensitivity difference (%) in each case of Hct values of 0%, 42%, and 70% with reference to Glu 45 mg/dl in Example 77. FIGS. 110a and 110b each are a graph showing the sensitivity difference in each case at 0.05 second to 0.45 second after the detection.

Example 78

The procedure was carried out in the same manner as in Example 74 except that a voltage of 1.5 V was applied between the electrode A and the electrode B for 0.5 second from 0.05 second to 0.55 second after detection of the introduction of a blood sample, then a voltage of 0.1 to 1.0 V was applied multiple times between the electrode A and the electrode B from 0.55 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 111a and 111b). FIG. 111a is a graph showing the sensitivity difference (%) in each case of Glu values of 45 mg/dl and 550 mg/dl with reference to Hct 42% in Example 78. FIG. 111b is a graph showing the sensitivity difference (%) in each case of Hct values of 0%, 42%, and 70% with reference to Glu 45 mg/dl in Example 78. FIGS. 111a and 111b each are a graph showing the sensitivity difference in each case at 0.05 second to 0.55 second after the detection.

Example 79

The procedure was carried out in the same manner as in Example 74 except that a voltage of 1.5 V was applied between the electrode A and the electrode B for 0.6 second from 0.05 second to 0.65 second after detection of the introduction of a blood sample, then a voltage of 0.1 to 1.0 V was applied multiple times between the electrode A and the electrode B from 0.65 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 112a and 112b). FIG. 112a is a graph showing the sensitivity difference (%) in each case of Glu values of 45 mg/dl and 550 mg/dl with reference to Hct 42% in Example 79. FIG. 112b is a graph showing the sensitivity difference (%) in each case of Hct values of 0%, 42%, and 70% with reference to Glu 45 mg/dl in Example 79. FIGS. 112a and 112b each are a graph showing the sensitivity difference in each case at 0.05 second to 0.65 second after the detection.

Example 80

The procedure was carried out in the same manner as in Example 74 except that a voltage of 1.5 V was applied between the electrode A and the electrode B for 0.7 second from 0.05 second to 0.75 second after detection of the introduction of a blood sample, then a voltage of 0.1 to 1.0 V was applied multiple times between the electrode A and the electrode B from 0.75 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 113a and 113b). FIG. 113a is a graph showing the sensitivity difference (%) in each case of Glu values of 45 mg/dl and 550 mg/dl with reference to Hct 42% in Example 80. FIG. 113b is a graph showing the sensitivity difference (%) in each case of Hct values of 0%, 42%, and 70% with reference to Glu 45 mg/dl in Example 80. FIGS. 113a and 113b each are a graph showing the sensitivity difference in each case at 0.05 second to 0.75 second after the detection.

From Examples 74 to 80, it was confirmed that when a voltage of 1.5 V was applied to the working electrode and the counter electrode for 0.1 to 0.7 second at 0.05 second after detection of the introduction of a biological sample, the current value obtained thereby had a high sensitivity, and the Hct value and the Glu value obtained based on the current value had a high accuracy.

Example 81

The procedure was carried out in the same manner as in Example 74 except that a voltage of 2.0 V was applied between the electrode A and the electrode B for 0.1 second from 0.05 second to 0.15 second after detection of the introduction of a blood sample, then a voltage of 0.1 to 1.0 V was applied multiple times between the electrode A and the electrode B from 0.15 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 114a and 114b). FIG. 114a is a graph showing the sensitivity difference (%) in each case of Glu values of 45 mg/dl and 550 mg/dl with reference to Hct 42% in Example 81. FIG. 114b is a graph showing the sensitivity difference (%) in each case of Hct values of 0%, 42%, and 70% with reference to Glu 45 mg/dl in Example 81. FIGS. 114a and 114b each are a graph showing the sensitivity difference in each case at 0.05 second to 0.15 second after the detection.

Example 82

The procedure was carried out in the same manner as in Example 81 except that a voltage of 2.0 V was applied between the electrode A and the electrode B for 0.2 second from 0.05 second to 0.25 second after detection of the introduction of a blood sample, then a voltage of 0.1 to 1.0 V was applied multiple times between the electrode A and the electrode B from 0.25 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 115a and 115b). FIG. 115a is a graph showing the sensitivity difference (%) in each case of Glu values of 45 mg/dl and 550 mg/dl with reference to Hct 42% in Example 82. FIG. 115b is a graph showing the sensitivity difference (%) in each case of Hct values of 0%, 42%, and 70% with reference to Glu 45 mg/dl in Example 82. FIGS. 115a and 115b each are a graph showing the sensitivity difference in each case at 0.05 second to 0.25 second after the detection.

Example 83

The procedure was carried out in the same manner as in Example 81 except that a voltage of 2.0 V was applied between the electrode A and the electrode B for 0.3 second from 0.05 second to 0.35 second after detection of the introduction of a blood sample, then a voltage of 0.1 to 1.0 V was applied multiple times between the electrode A and the electrode B from 0.35 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see 116a and 116b). FIG. 116a is a graph showing the sensitivity difference (%) in each case of Glu values of 45 mg/dl and 550 mg/dl with reference to Hct 42% in Example 83. FIG. 116b is a graph showing the sensitivity difference (%) in each case of Hct values of 0%, 42%, and 70% with reference to Glu 45 mg/dl in Example 83. FIGS. 116a and 116b each are a graph showing the sensitivity difference in each case at 0.05 second to 0.35 second after the detection.

Example 84

The procedure was carried out in the same manner as in Example 81 except that a voltage of 2.0 V was applied between the electrode A and the electrode B for 0.4 second from 0.05 second to 0.45 second after detection of the introduction of a blood sample, then a voltage of 0.1 to 1.0 V was applied multiple times between the electrode A and the electrode B from 0.45 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 117a and 117b). FIG. 117a is a graph showing the sensitivity difference (%) in each case of Glu values of 45 mg/dl and 550 mg/dl with reference to Hct 42% in Example 84. FIG. 117b is a graph showing the sensitivity difference (%) in each case of Hct values of 0%, 42%, and 70% with reference to Glu 45 mg/dl in Example 84. FIGS. 117a and 117b each are a graph showing the sensitivity difference in each case at 0.05 second to 0.45 second after the detection.

Example 85

The procedure was carried out in the same manner as in Example 81 except that a voltage of 2.0 V was applied between the electrode A and the electrode B for 0.5 second from 0.05 second to 0.55 second after detection of the introduction of a blood sample, then a voltage of 0.1 to 1.0 V was applied multiple times between the electrode A and the electrode B from 0.55 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 118a and 118b). FIG. 118a is a graph showing the sensitivity difference (%) in each case of Glu values of 45 mg/dl and 550 mg/dl with reference to Hct 42% in Example 85. FIG. 118b is a graph showing the sensitivity difference (%) in each case of Hct values of 0%, 42%, and 70% with reference to Glu 45 mg/dl in Example 85. FIGS. 118a and 118b each are a graph showing the sensitivity difference in each case at 0.05 second to 0.55 second after the detection.

Example 86

The procedure was carried out in the same manner as in Example 81 except that a voltage of 2.0 V was applied between the electrode A and the electrode B for 0.6 second from 0.05 second to 0.65 second after detection of the introduction of a blood sample, then a voltage of 0.1 to 1.0 V was applied multiple times between the electrode A and the electrode B from 0.65 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 119a and 119b). FIG. 119a is a graph showing the sensitivity difference (%) in each case of Glu values of 45 mg/dl and 550 mg/dl with reference to Hct 42% in Example 86. FIG. 119b is a graph showing the sensitivity difference (%) in each case of Hct values of 0%, 42%, and 70% with reference to Glu 45 mg/dl in Example 86. FIGS. 119a and 119b each are a graph showing the sensitivity difference in each case at 0.05 second to 0.65 second after the detection.

Example 87

The procedure was carried out in the same manner as in Example 81 except that a voltage of 2.0 V was applied between the electrode A and the electrode B for 0.7 second from 0.05 second to 0.75 second after detection of the introduction of a blood sample, then a voltage of 0.1 to 1.0 V was applied multiple times between the electrode A and the electrode B from 0.75 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 120a and 120b). FIG. 120a is a graph showing the sensitivity difference (%) in each case of Glu values of 45 mg/dl and 550 mg/dl with reference to Hct 42% in Example 87. FIG. 120b is a graph showing the sensitivity difference (%) in each case of Hct values of 0%, 42%, and 70% with reference to Glu 45 mg/dl in Example 87. FIGS. 120a and 120b each are a graph showing the sensitivity difference in each case at 0.05 second to 0.75 second after the detection.

From Example 81 to 87, it was confirmed that when a voltage of 2.0 V was applied to the working electrode and the counter electrode for 0.1 to 0.7 second at 0.05 second after detection of the introduction of a biological sample, the current value obtained thereby had a high sensitivity, and the Hct value and the Glu value obtained based on the current value had a high accuracy.

Example 88

The procedure was carried out in the same manner as in Example 74 except that a voltage of 2.5 V was applied between the electrode A and the electrode B for 0.1 second from 0.05 second to 0.15 second after detection of the introduction of a blood sample, then a voltage of 0.1 to 1.0 V was applied multiple times between the electrode A and the electrode B from 0.15 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 121a and 121b). FIG. 121a is a graph showing the sensitivity difference (%) in each case of Glu values of 45 mg/dl and 550 mg/dl with reference to Hct 42% in Example 88. FIG. 121b is a graph showing the sensitivity difference (%) in each case of Hct values of 0%, 42%, and 70% with reference to Glu 45 mg/dl in Example 88. FIGS. 121a and 121b each are a graph showing the sensitivity difference in each case at 0.05 second to 0.15 second after the detection.

Example 89

The procedure was carried out in the same manner as in Example 88 except that a voltage of 2.5 V was applied between the electrode A and the electrode B for 0.2 second from 0.05 second to 0.25 second after detection of the introduction of a blood sample, then a voltage of 0.1 to 1.0 V was applied multiple times between the electrode A and the electrode B from 0.25 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 122a and 122b). FIG. 122a is a graph showing the sensitivity difference (%) in each case of Glu values of 45 mg/dl and 550 mg/dl with reference to Hct 42% in Example 89. FIG. 122b is a graph showing the sensitivity difference (%) in each case of Hct values of 0%, 42%, and 70% with reference to Glu 45 mg/dl in Example 89. FIGS. 122a and 122b each are a graph showing the sensitivity difference in each case at 0.05 second to 0.25 second after the detection.

Example 90

The procedure was carried out in the same manner as in Example 88 except that a voltage of 2.5 V was applied between the electrode A and the electrode B for 0.3 second from 0.05 second to 0.35 second after detection of the introduction of a blood sample, then a voltage of 0.1 to 1.0 V was applied multiple times between the electrode A and the electrode B from 0.35 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 123a and 123b). FIG. 123a is a graph showing the sensitivity difference (%) in each case of Glu values of 45 mg/dl and 550 mg/dl with reference to Hct 42% in Example 90. FIG. 123b is a graph showing the sensitivity difference (%) in each case of Hct values of 0%, 42%, and 70% with reference to Glu 45 mg/dl in Example 90. FIGS. 123a and 123b each are a graph showing the sensitivity difference in each case at 0.05 second to 0.35 second after the detection.

Example 91

The procedure was carried out in the same manner as in Example 88 except that a voltage of 2.5 V was applied between the electrode A and the electrode B for 0.4 second from 0.05 second to 0.45 second after detection of the introduction of a blood sample, then a voltage of 0.1 to 1.0 V was applied multiple times between the electrode A and the electrode B from 0.45 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 124a and 124b). FIG. 124a is a graph showing the sensitivity difference (%) in each case of Glu values of 45 mg/dl and 550 mg/dl with reference to Hct 42% in Example 91. FIG. 124b is a graph showing the sensitivity difference (%) in each case of Hct values of 0%, 42%, and 70% with reference to Glu 45 mg/dl in Example 91. FIGS. 124a and 124b each are a graph showing the sensitivity difference in each case at 0.05 second to 0.45 second after the detection.

Example 92

The procedure was carried out in the same manner as in Example 88 except that a voltage of 2.5 V was applied between the electrode A and the electrode B for 0.5 second from 0.05 second to 0.55 second after detection of the introduction of a blood sample, then a voltage of 0.1 to 1.0 V was applied multiple times between the electrode A and the electrode B from 0.55 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 125a and 125b). FIG. 125a is a graph showing the sensitivity difference (%) in each case of Glu values of 45 mg/dl and 550 mg/dl with reference to Hct 42% in Example 92. FIG. 125b is a graph showing the sensitivity difference (%) in each case of Hct values of 0%, 42%, and 70% with reference to Glu 45 mg/dl in Example 92. FIGS. 125a and 125b each are a graph showing the sensitivity difference in each case at 0.05 second to 0.55 second after the detection.

Example 93

The procedure was carried out in the same manner as in Example 88 except that a voltage of 2.5 V was applied between the electrode A and the electrode B for 0.6 second from 0.05 second to 0.65 second after detection of the introduction of a blood sample, then a voltage of 0.1 to 1.0 V was applied multiple times between the electrode A and the electrode B from 0.65 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 126a and 126b). FIG. 126a is a graph showing the sensitivity difference (%) in each case of Glu values of 45 mg/dl and 550 mg/dl with reference to Hct 42% in Example 93. FIG. 126b is a graph showing the sensitivity difference (%) in each case of Hct values of 0%, 42%, and 70% with reference to Glu 45 mg/dl in Example 93. FIGS. 126a and 126b each are a graph showing the sensitivity difference in each case at 0.05 second to 0.65 second after the detection.

Comparative Example 14

The procedure was carried out in the same manner as in Example 88 except that a voltage of 2.5 V was applied between the electrode A and the electrode B for 0.8 second from 0.05 second to 0.85 second after detection of the introduction of a blood sample, then a voltage of 0.1 to 1.0 V was applied multiple times between the electrode A and the electrode B from 0.85 second to 7.0 seconds after the detection of the introduction of a blood sample, and finally a voltage of 2.5 V was applied between the electrode C and the electrode A from 7.1 seconds to 7.5 seconds after the detection of the introduction of a blood sample. The current flowing between the working electrode and the counter electrode of each sensor 1 was measured, and the response current value and the sensitivity difference were measured in the measurement of the Hct value (see FIGS. 127a and 127b). FIG. 127a is a graph showing the sensitivity difference (%) in each case of Glu values of 45 mg/dl and 550 mg/dl with reference to Hct 42% in Comparative Example 14. FIG. 127b is a graph showing the sensitivity difference (%) in each case of Hct values of 0%, 42%, and 70% with reference to Glu 45 mg/dl in Comparative Example 14. FIGS. 127a and 127b each are a graph showing the sensitivity difference in each case at 0.05 second to 0.85 second after the detection.

From Examples 88 to 93 and Comparative Example 14, it was confirmed that when a voltage of 2.5 V was applied to the working electrode and the counter electrode for 0.1 to 0.6 second at 0.05 second after detection of the introduction of a biological sample, the current value obtained thereby had a high sensitivity, and the Hct value and the Glu value obtained based on the current value had a high accuracy. The voltage application time after the start of blood introduction was changed between 0 and 0.8 second and the graphs showing the sensitivity difference were checked. As a result, it was found that the effect of the glucose concentration gradually increased as the time increased. Particularly, when the voltage application time was 0.8 second as in Comparative Example 14, a divergence was seen in the graph showing the sensitivity difference in each case of Hct values of 0%, 42%, and 70% particularly with reference to Glu 550 mg/dl as shown in FIG. 127b.

According to the present invention, in the examples in which the voltage application time was longer than 0 second and up to 0.6 second, the sensitivity difference (%) was small. Therefore, it was confirmed that the Hct measurement accuracy was improved. Furthermore, it was confirmed that according to the present invention, Hct can be measured in a short time. Thus, by obtaining such Hct values, it was possible to obtain a corrected Glu value in a short time. Furthermore, according to the present invention, since the current value that depends on Glu in the vicinity of the electrodes that are in contact with the reagent part and the current value that depends on Hct in the vicinity of the same electrodes are used to obtain a Glu value, the Glu value can be measured, with the properties of the biological sample in the vicinity of the electrodes being reflected with higher accuracy.

INDUSTRIAL APPLICABILITY

As described above, in the method for measuring a component of a biological sample according to the present invention, a Hct value can be measured in a short time with an electrode system having a reagent layer disposed thereon and the accuracy of the Glu value calculated under the same reagent layer is improved. Accordingly, the method of the present invention can be preferably used in all fields of measuring blood components such as biology, biochemistry, and medicine, and is particularly suitable for the field of clinical examinations.

REFERENCE SIGNS LIST

A Electrode A
B Electrode B
C Electrode C
D Electrode D
E Electrode E
F Electrode F
11 Reagent Layer
12 Biological Sample Supply Port
13 Air Hole
14 Channel
101 Insulating Substrate
102 Spacer 103 Cover
1 Sensor
2 Measuring Apparatus
4 Display Unit
5 Insertion Port
6 Input Terminal Area
30 A/D Conversion Unit
31 Determination Means
32 Display Unit
33 Power Supply Unit
34 Memory
35 Clock
36 Correction Means
37 Voltage Applying Unit
38 Current-Voltage Conversion Unit
39 Control Unit

The invention claimed is:

1. A biosensor for obtaining a hematocrit value of a biological sample, comprising:
   a capillary for introducing the biological sample;
   a reagent part containing an enzyme and a mediator in the capillary;
   a first hematocrit measurement system for measuring a hematocrit value, the first hematocrit measurement system being disposed so as to be in contact with the reagent part in the capillary and comprising a first working electrode and a first counter electrode; and
   a second hematocrit measurement system for measuring a hematocrit value, the second hematocrit measurement system comprising a second working electrode at a place where the reagent part is not disposed and a second counter electrode disposed so as to be in contact with the reagent part,
   wherein the first hematocrit measuring system is configured to start a first voltage application for a duration longer than 0 second and up to 0.7 second within 0 to 0.5 second after detecting introduction of the biological sample so as to obtain a first current value,
   the second hematocrit measurement system is configured to apply a second voltage to the second hematocrit measurement system after the first current value is obtained, so as to obtain a second current value, and
   the biosensor is configured to obtain the hematocrit value of the biological sample based on the first current value and the second current value.

2. The biosensor according to claim 1, further comprising:
   an electrode system for obtaining a current value that depends on glucose, the electrode system being disposed so as to be in contact with the reagent part in the capillary and comprising a third working electrode and a third counter electrode; and
   an electrode system for obtaining a current value that depends on glucose, the electrode system being disposed so as to be in contact with the reagent part in the capillary and comprising a fourth working electrode and a fourth counter electrode.

3. A method for obtaining a hematocrit value of a biological sample using the biosensor according to claim 1, the method comprising:
   starting voltage application for a duration longer than 0 second and up to 0.7 second to the first hematocrit measurement system within 0 to 0.5 second after detection of introduction of the biological sample to obtain the first current value;
   applying the second voltage to the second hematocrit measurement system after obtaining the first current value, to obtain the second current value; and
   obtaining the hematocrit value of the biological sample based on the first current value and the second current value.

4. The method for measuring a component of a biological sample according to claim 3, wherein the duration of the voltage application to the first hematocrit measurement system is any duration longer than 0 second and up to 0.5 second.

5. The method for measuring a component of a biological sample according to claim 3, wherein the voltage application to the first hematocrit measurement system is started at 0 second after the detection of introduction of the biological sample.

6. The method for measuring a component of a biological sample according to claim 3, wherein the voltage application to the first hematocrit measurement system is started at later than 0 second but within 0.1 second after the detection of introduction of the biological sample.

7. The method for measuring a component of a biological sample according to claim 3, wherein the voltage to be applied to the first hematocrit measurement system is any voltage in a range of 1.5 V to 4.0 V.

8. The method for measuring a component of a biological sample according to claim 3, wherein the duration of applying the second voltage to the second hematocrit measurement system is any duration between 0.01 and 5.0 seconds.

9. The method for measuring a component of a biological sample according to claim 3, wherein the second voltage to be applied to the second hematocrit measurement system is any voltage in a range of 1.0 V to 3.5 V.

* * * * *